(12) United States Patent
Martinson et al.

US009980986B2

(10) Patent No.: US 9,980,986 B2
(45) Date of Patent: *May 29, 2018

(54) METHODS OF PRODUCING PANCREATIC HORMONES

(71) Applicant: ViaCyte, Inc., San Diego, CA (US)

(72) Inventors: Laura Martinson, San Diego, CA (US); Evert Kroon, San Diego, CA (US); Kevin D'Amour, San Diego, CA (US); Emmanuel Edward Baetge, Encinitas, CA (US)

(73) Assignee: ViaCyte, Inc., San Diego, CA (US)

( * ) Notice: Subject to any disclaimer, the term of this patent is extended or adjusted under 35 U.S.C. 154(b) by 28 days.

This patent is subject to a terminal disclaimer.

(21) Appl. No.: 14/670,249

(22) Filed: Mar. 26, 2015

(65) Prior Publication Data

US 2015/0265657 A1    Sep. 24, 2015

Related U.S. Application Data

(63) Continuation of application No. 13/205,511, filed on Aug. 8, 2011, now Pat. No. 9,585,917, which is a continuation of application No. 12/758,734, filed on Apr. 12, 2010, now Pat. No. 7,993,920, which is a continuation of application No. 11/773,944, filed on Jul. 5, 2007, now Pat. No. 7,695,965, which is a continuation-in-part of application No. 11/681,687, filed on Mar. 2, 2007, now Pat. No. 8,129,182.

(60) Provisional application No. 60/852,878, filed on Oct. 18, 2006, provisional application No. 60/833,633, filed on Jul. 26, 2006, provisional application No. 60/778,649, filed on Mar. 2, 2006.

(51) Int. Cl.
| | |
|---|---|
| *A61K 35/39* | (2015.01) |
| *C12N 5/071* | (2010.01) |
| *A61K 38/26* | (2006.01) |
| *A61K 38/28* | (2006.01) |
| *A61K 35/12* | (2015.01) |

(52) U.S. Cl.
CPC ............ *A61K 35/39* (2013.01); *A61K 38/26* (2013.01); *A61K 38/28* (2013.01); *C12N 5/0676* (2013.01); *C12N 5/0678* (2013.01); *A61K 35/12* (2013.01); *C12N 2500/38* (2013.01); *C12N 2501/10* (2013.01); *C12N 2501/105* (2013.01); *C12N 2501/113* (2013.01); *C12N 2501/115* (2013.01); *C12N 2501/119* (2013.01); *C12N 2501/12* (2013.01); *C12N 2501/16* (2013.01); *C12N 2501/33* (2013.01); *C12N 2501/385* (2013.01); *C12N 2501/41* (2013.01); *C12N 2501/415* (2013.01); *C12N 2501/42* (2013.01); *C12N 2501/58* (2013.01); *C12N 2501/999* (2013.01); *C12N 2506/02* (2013.01)

(58) Field of Classification Search
CPC ...................................................... A61K 35/39
See application file for complete search history.

(56) References Cited

U.S. PATENT DOCUMENTS

| | | | |
|---|---|---|---|
| 5,453,357 | A | 9/1995 | Hogan |
| 5,670,372 | A | 9/1997 | Hogan |
| 5,690,926 | A | 11/1997 | Hogan |
| 5,817,637 | A | 10/1998 | Weiner et al. |
| 5,830,876 | A | 11/1998 | Weiner et al. |
| 5,843,780 | A | 12/1998 | Thomson |
| 5,942,435 | A | 8/1999 | Wheeler |
| 5,964,261 | A | 10/1999 | Neuenfeldt |
| 6,015,671 | A | 1/2000 | Field |
| 6,090,622 | A | 7/2000 | Gearhart et al. |
| 6,165,993 | A | 12/2000 | Herrmann et al. |
| 6,200,806 | B1 | 3/2001 | Thomson |
| 6,251,671 | B1 | 6/2001 | Hogan et al. |
| 6,261,281 | B1 | 7/2001 | Mathiesen et al. |
| 6,326,201 | B1 | 12/2001 | Fung et al. |
| 6,458,589 | B1 | 10/2002 | Rambhatla et al. |
| 6,506,574 | B1 | 1/2003 | Rambhatla et al. |
| 6,872,389 | B1 | 3/2005 | Faris |
| 6,921,811 | B2 | 7/2005 | Zamora et al. |
| 7,033,831 | B2 | 4/2006 | Fisk et al. |
| 7,153,684 | B1 | 12/2006 | Hogan |
| 7,157,278 | B2 | 1/2007 | Jin |
| 7,256,042 | B2 | 8/2007 | Rambhatla et al. |
| 7,326,572 | B2 | 2/2008 | Fisk et al. |
| 7,510,876 | B2 | 3/2009 | D'Amour et al. |

(Continued)

FOREIGN PATENT DOCUMENTS

| | | |
|---|---|---|
| EP | 1298201 A1 | 4/2003 |
| EP | 1627912 A1 | 2/2006 |

(Continued)

OTHER PUBLICATIONS

Lee et al. (2002, Diabetes, vol. 51, pp. 2546-2551).*
Cai et al. (2010, J. Molecular Cell Biology, vol. 2, pp. 50-60).*
2006, D'Amour et al., Nature Biotech., vol. 24(11), pp. 1392-1401.*
2007, Moody SA, Principles of Developmental Genetics, 2nd Ed., Elsevier, 3 pages total.*
Piran et al. (2014, Cell Death and Disease, vol. 5, e1357, 36 pages).*
Abe, et al., "Endoderm-Specific Gene Expression in Embryonic Stem Cells Differentiated to Embryoid Bodies." *Experimental Cell Research.* (1996) 229(1): 27-34.

(Continued)

*Primary Examiner* — Thaian N Ton
*Assistant Examiner* — David A. Montanari
(74) *Attorney, Agent, or Firm* — Klarquist Sparkman, LLP

(57) ABSTRACT

Disclosed herein are methods of producing pancreatic hormone-expressing cells by first differentiating pluripotent cells in cell culture so as to produce endodermal cells, the endodermal cells being competent to further differentiate into hormone-expressing cells capable of secreting at least one pancreatic hormone in response to a physiological signal, and then, transplanting the cultured endodermal cells into an organism, such as an organism in need of an endocrine cell therapy.

30 Claims, 74 Drawing Sheets

(56) References Cited

U.S. PATENT DOCUMENTS

| | | |
|---|---|---|
| 7,534,608 B2 | 5/2009 | Martinson et al. |
| 7,541,185 B2 | 6/2009 | D'Amour et al. |
| 7,695,963 B2 | 4/2010 | Agulnick et al. |
| 7,695,965 B2 | 4/2010 | Martinson et al. |
| 7,993,920 B2 | 8/2011 | Martinson et al. |
| 8,129,182 B2 | 3/2012 | D'Amour et al. |
| 8,603,811 B2 | 12/2013 | D'Amour et al. |
| 2002/0072117 A1 | 6/2002 | Xu et al. |
| 2002/0090723 A1 | 7/2002 | Carpenter et al. |
| 2002/0187548 A1 | 12/2002 | Keller et al. |
| 2003/0138948 A1 | 7/2003 | Fisk et al. |
| 2003/0138949 A1 | 7/2003 | Bhushan et al. |
| 2003/0175956 A1 | 9/2003 | Bodnar et al. |
| 2003/0190748 A1 | 10/2003 | Thomson |
| 2003/0224411 A1 | 12/2003 | Stanton et al. |
| 2004/0127406 A1 | 7/2004 | Presnell et al. |
| 2004/0229350 A1 | 11/2004 | Strelchenko et al. |
| 2005/0079159 A1 | 4/2005 | Shastri et al. |
| 2005/0158853 A1 | 7/2005 | D'Amour et al. |
| 2005/0266554 A1 | 12/2005 | D'Amour et al. |
| 2006/0003313 A1 | 1/2006 | D'Amour et al. |
| 2006/0003446 A1 | 1/2006 | Keller et al. |
| 2006/0019387 A1 | 1/2006 | Faris |
| 2006/0040385 A1 | 2/2006 | Itskovitz-Eldor et al. |
| 2006/0040387 A1 | 2/2006 | Fisk et al. |
| 2006/0128018 A1 | 6/2006 | Zwaka et al. |
| 2006/0148081 A1 | 7/2006 | Kelly et al. |
| 2006/0276420 A1 | 12/2006 | Keller et al. |
| 2007/0004038 A1 | 1/2007 | D'Amour et al. |
| 2007/0122905 A1 | 5/2007 | D'Amour et al. |
| 2007/0154984 A1 | 7/2007 | D'Amour et al. |
| 2007/0259421 A1 | 11/2007 | D'Amour et al. |
| 2007/0281355 A1 | 12/2007 | Dalton et al. |
| 2008/0241250 A1 | 10/2008 | Emans et al. |
| 2009/0004152 A1 | 1/2009 | Martinson et al. |
| 2009/0093372 A1 | 4/2009 | Agulnick et al. |
| 2009/0220959 A1 | 9/2009 | D'Amour et al. |
| 2009/0253202 A1 | 10/2009 | D'Amour et al. |
| 2012/0009675 A1 | 1/2012 | Martinson et al. |
| 2014/0154801 A1 | 6/2014 | D'Amour et al. |

FOREIGN PATENT DOCUMENTS

| | | |
|---|---|---|
| EP | 1627912 A4 | 2/2006 |
| WO | WO-98/30679 A1 | 7/1998 |
| WO | WO-99/13915 A1 | 3/1999 |
| WO | WO-00/29442 A1 | 5/2000 |
| WO | WO-2002/010347 A2 | 2/2002 |
| WO | WO-2002/010347 A3 | 2/2002 |
| WO | WO-02/034880 A2 | 5/2002 |
| WO | WO-02/034880 A3 | 5/2002 |
| WO | WO-02/059278 A2 | 8/2002 |
| WO | WO-02/059278 A3 | 8/2002 |
| WO | WO-03/050249 A2 | 6/2003 |
| WO | WO-03/050249 A3 | 6/2003 |
| WO | WO-03/050249 B1 | 6/2003 |
| WO | WO-03/100026 A2 | 12/2003 |
| WO | WO-03/100026 A3 | 12/2003 |
| WO | WO-2004/098490 A2 | 11/2004 |
| WO | WO-2004/098490 A3 | 11/2004 |
| WO | WO-2005/017131 A2 | 2/2005 |
| WO | WO-2005/017131 A3 | 2/2005 |
| WO | WO-2005/033294 A2 | 4/2005 |
| WO | WO-2005/033294 A3 | 4/2005 |
| WO | WO-2005/045001 A2 | 5/2005 |
| WO | WO-2005/045001 A3 | 5/2005 |
| WO | WO-2005/063971 A2 | 7/2005 |
| WO | WO-2005/063971 A3 | 7/2005 |
| WO | WO-2005/086860 A2 | 9/2005 |
| WO | WO-2005/086860 A3 | 9/2005 |
| WO | WO-2005/097977 A2 | 10/2005 |
| WO | WO-2005/097977 A3 | 10/2005 |
| WO | WO-2005/097980 A2 | 10/2005 |
| WO | WO-2005/097980 A3 | 10/2005 |
| WO | WO-2005/116073 A2 | 12/2005 |
| WO | WO-2005/116073 A3 | 12/2005 |
| WO | WO-2006/016999 A1 | 2/2006 |
| WO | WO-2006/017134 A2 | 2/2006 |
| WO | WO-2006/017134 A3 | 2/2006 |
| WO | WO-2006/020919 A2 | 2/2006 |
| WO | WO-2006/020919 A3 | 2/2006 |
| WO | WO-2006/034873 A1 | 4/2006 |
| WO | WO-2006/083782 A2 | 8/2006 |
| WO | WO-2006/083782 A3 | 8/2006 |
| WO | WO-2006/108361 A1 | 10/2006 |
| WO | WO-2006/108361 A8 | 10/2006 |
| WO | WO-2007/002210 A2 | 1/2007 |
| WO | WO-2007/002210 A3 | 1/2007 |
| WO | WO-2007/051038 A2 | 5/2007 |
| WO | WO-2007/051038 A3 | 5/2007 |
| WO | WO-2007/088372 A2 | 8/2007 |
| WO | WO-2007/088372 A3 | 8/2007 |
| WO | WO-2007/103282 A2 | 9/2007 |
| WO | WO-2007/103282 A3 | 9/2007 |

OTHER PUBLICATIONS

Alexander, J., and Stainier, D. Y., "A Molecular Pathway Leading to Endoderm Formation in Zebrafish" *Curr Biol* (1999) 9: 1147-1157.
Alexander, et al., "Casanova Plays an Early and Essential Role in Endoderm Formation in Zebrafish" *Dev Biol* (1999) 215: 343-357.
Ang, et al. "The Formation and Maintenance of the Definitive Endoderm Lineage in the Mouse: Involvement of HNF3/Forkhead Proteins" *Development* (1993) 119: 1301-1315.
Ang et al., "HNF-3beta is essential for node and notochord formation in mouse development," *Cell*, (1994) 78:561-574.
Aoki, et al., "Regulation of Nodal Signalling and Mesendoderm Formation by TARAM-A, A Tgfbeta-Related Type I Receptor" *Dev Biol* (2002) 241: 273-288.
Apelqvist et al., 1999, Nature, vol. 400, pp. 877-881.
Arnold et al., "Brachyury is a target gene of the Wnt/beta-catenin signaling pathway," *Mech. Dev.*, (2000) 91:249-258.
Assady et al. "Insulin Production by Human Embryonic Stem Cells" *Diabetes* (2001) 50(8): 1691-1697.
Bachiller et al., "The organizer factors chordin and noggin are required for mouse forebrain development," *Nature*, (2000) 403:658-661.
Baertschiger et al., "Mesenchymal Stem Cells Derived from Human Exocrine Pancreas Express Transcription Factors Implicated in Beta-Cell Development," (2008) Pancreas, 37:75-84.
Bain, et al., "Embryonic Stem Cells Express Neuronal Properties in Vitro." *Developmental Biology* (1995) 168: 342-357.
Barbacci, et al. "Variant Hepatocyte Nuclear Factor 1 Is Required for Visceral Endoderm Specification" *Development* (1999) 126: 4795-4805.
Barry, et al., "The Production of Monoclonal Antibodies by Genetic Immunization" *Biotechniques* (1994) 16: 616-620.
Batlle et al., "The transcription factor snail is a repressor of E-cadherin gene expression in epithelial tumour cells," *Nat. Cell. Biol.*, (2000) 2:84-89.
Beck, et al., "Extra-Embryonic Proteases Regulate Nodal Signalling During Gastrulation" *Nat Cell Biol* (2002) 4: 981-985.
Beddington, et al. "Brachyury—A Gene Affecting Mouse Gastrulation and Early Organogenesis" *Dev Suppl*, (1992) 157-165.
Bendall, et al., "IGF and FGF Cooperatively Establish Regulatory Stem Cell Niche of Pluripotent Human Cells In Vitro" *Nature* (2007), 448: 1015-1021.
Blum et al., "Gastrulation in the mouse: the role of the homebox gene goosecoid," Cell, (1992) 69:1097-1106.
Bongso, et al., "Isolation and Culture of Inner Cell Mass Cells From Human Blastocysts" *Hum Reprod* (1994) 9: 2110-2117.
Bordonaro et al., "Cell type—a promoter—dependent modulation of the Wnt signaling pathway by sodium butyrate," *Int. J. Cancer* (2002) 97(1):42-51.
Bost, et al., "Retinoic Acid Activation of the ERK Pathway is Required for Embryonic Stem Cell Commitment into the Adipocyte Lineage." *Biochem. J.* (2002) 361: 621-627.
Brennan et al., "*Nodal* signalling in the epiblast patterns the early mouse embryo," *Nature*, (2001) 411:965-969.
Brevini et al., 2010, Theriogenology, vol. 74, pp. 544-550.

(56) References Cited

OTHER PUBLICATIONS

Cai, et al., "Directed Differentiation of Human Embryonic Stem Cells into Functional Hepatic Cells" *Hepatology* (2007) 45(5): 1229-1239.
Candia et al., "Differential localization of mox-1 and mox-2 proteins indicates distinct roles during development," *Int. J. Dev. Biol.* (1996), 40:1179-1184.
Candia et al., "*Mox-1* and *Mox-2* define a novel homeobox gene subfamily and are differentially expressed during early mesodermal patterning in mouse embryos," *Development* (1992), 116:783-797.
Cereghini, et al. "Expression Patterns of vHNF1 and HNF1 Homeoproteins in Early Postimplantation Embryos Suggest Distinct and Sequential Developmental Roles" *Development* (1992) 116: 783-797.
Chang, et al., "Genetic Analysis of the Mammalian Transforming Growth Factor-Beta Superfamily" *Endocr Rev* (2002) 23: 787-823.
Chen, et al., "Retinoic acid signaling is essential for pancreas development and promotes endocrine at the expense of exocrine cell differentiation in Xenopus" *Developmental Biology* (2004) 271: 144-160.
Chen et al., "Suppression of ES cell differentiation by retinol (vitamin A) via the overexpression of Nanog," *Differentiation* (2007) 75(8):682-93.
Chin et al., "Induced pluripotent stem cells and embryonic stem cells are distinguished by gene expression signatures," *Cell Stem Cell* (2009) 5(1):111-23.
Ciani et al., "WNTs in the vertebrate nervous system: from patterning to neuronal connectivity," *Nat. Rev. Neurosci.* (2005) 6(5):351-62.
Ciruna et al., "Chimeric analysis of *fibroblast growth factor receptor-1* (*Fgfr1*) Function: a role for FGFR1 in morphogenetic movement through the primitive streak," *Development*, (1997) 124:2829-2841.
Ciruna et al., "FGF signaling regulates mesoderm cell fate specification and morphogenetic movement at the primitive streak," *Development*, (1997) 124:2829-2841.
Collombat, et al., "Specifying Pancreatic Endocrine Cell Fates" *Mechanisms of Development* (2006) 123(7): 501-512.
Conley, et al. "BMPs Regulate Differentiation of a Putative Visceral Endoderm Layer Within Human Embryonic Stem-Cell-Derived Embryoid Bodies" *Biochem Cell Biol* (2007) 85: 121-132.
Conlon, et al., "A primary requirement for nodal in the formation and maintenance of the primitive streak in the mouse" *Development* (1994) 120: 1919-1928.
Costaglia, et al., "Genetic Immunization Against The Human Thyrotropin Receptor Causes Thyroiditis and Allows Production of Monoclonal Antibodies Recognizing the Native Receptor" *J. Immunol.* (1998) 160: 1458-1465.
Czyz et al. "Embryonic Stem Cell Differentiation: The Role of Extracellular Factors" *Differentiation* (2001) 68(4-5): 167-174.
Daheron et al. "LIF/STAT3 Signaling Fails to Maintain Self-Renewal of Human Embryonic Stem Cells" *Stem Cells* (2004) 22: 770-778.
D'Amour, et al., "Efficient Differentiation of Human Embryonic Stem Cells to Definitive Endoderm" *Nature Biotechnology* (2005) 23(12): 1534-1541.
D'Amour et al. "Production of Pancreatic Hormone-Expressing Endocrine Cells From Human Embryonic Stem Cells" (Nov. 1, 2006) Nature Biotechnology 24(11): 1392-1401.
Dani, et al., "Differentiation of Embryonic Stem Cells into Adipocytes in Vitro." *J. Cell Science* (1997) 110: 1279-1285.
Database UniProt, "1-acyl-sn-glycerol-3-phosphate acyltransferase gmma (EC 2.3.1.51) (1-AGP acyltransferase 3) (1-AGPAT 3) (Lyspohosphatidic acid acyltransfearse gamma) (LPAAT-gamma) (1-acylglycerol-3-phosphate 0-acyltransfearse 3)" retrieved from EBI accession No. UNIPROT: Q9NRZ7 on Oct. 1, 2000.
de Caestecker, "The transforming growth factor-beta superfamily of receptors," *Cytokine Growth Factor* (2004) Rev 15:1-11.

Defelice, et al., "TTF-1 Phosphorylation is Required for Peripheral Lung Morphogenesis, Perinatal Survival, and Tissue-Specific Gene Expression" *J. Biological Chemistry* (2003) 278(37): 35574-35583.
DeSilva, et al., "Gene Expression Changes During Step-Wise Differentiation of Embryonic Stem Cells Along the Inner Ear Hair Cell Pathway" *Acta Otolaryngol.* (2006) 126(11): 1148-1157.— Abstract Only.
Docherty et al., "Embryonic stem cell therapy for diabetes mellitus", *Semin Cell Dev Biol.* (2007) 18(6):827-38.
Dougan, et al., "The Role of the Zebrafish Nodal-Related Genes Squint and Cyclops in Patterning of Mesendoderm" *Development* (2003) 130: 1837-1851.
Dovey et al., 2001, J. Neurochemistry, vol. 76, pp. 173-181.
Dudas, et al., "The Homebox Transcription Factor Prox1 is Highly Conserved in Embryonic Hepatoblasts and in Adult and Transformed Hepatocytes, but is Absent from Bile Duct Epithelium" *Anat Embryol* (2004) 208: 359-366.
Edlund, H., "Factors Controlling Pancreatic Cell Differentiation and Function," *Diabetologia* (2001) 44(9): 1071-1079.
Elms et al., "Overlapping and distinct expression domain of *Zic2* and *Zic3* during mouse gastrulation," *Gene Expression Patterns*, (2004) 4:505-511.
Falasca, et al., "Retinoic Acid Treatment Induces Apoptosis or Expression of a More Differentiated Phenotype on Different Fractions of Cultured Fetal Rat Hepatocytes" *Hepatology* (1998) 28(3): 727-737.
Fehling, et al., "Development and Disease: Tracking Mesoderm Induction and its Specification to the Hemangioblast during Embryonic Stem Cell Differentiation" *Development* (2003) 130: 4217-4227.
Feldman, et al., "Zebrafish Organizer Development and Germ-Layer Formation Require Nodal-Related Signals" *Nature* (1998) 395: 181-185.
Feng, et al., "HIV-1 Entry Cofactor: Functional Cdna Cloning of a Seven-Transmembrane, G Protein-Coupled Receptor" *Science* (1996) 272: 872-877.
Freund, et al., "Insulin Redirect Differentiation from Cardiogenic Mesoderm and Endoderm to Neuroectoderm in Differentiating Human Embryonic Stem Cells" *Stem Cells* (2007), published online Dec. 20, 2007.
Futaki, et al., "Molecular Basis of Constitutive Production of Basement Membrane Components: Gene Expression Profiles of Engelbreth-Holm-Swarm Tumor and F9 Embryonal Carcinoma Cells" *J Biol Chem.* (2003) 278(50): 50691-50701.
Gardner, Robert L., "Stem Cells and Regenerative Medicine: Principles, Prospects and Problems" *C. R. Biologies* (2007) 330: 465-473.
Goumans, et al., "Mouse Embryonic Stem Cells with Aberrant Transforming Growth Factor B signaling Exhibit Impaired Differentiation in Vitro and in Vivo" *Differentiation* (1998) 63: 103-113.
Grapin-Botton, A., and Melton, D. A., "Endoderm Development: From Patterning to Organogenesis" *Trends Genet* (2000) 16: 124-130.
Guo, et al., "Stem Cells to Pancreatic (β-Cells: New Sources for Diabetes Cell Therapy," (2009), Endocrine Review, 30:214-227.
Haegel, et al., "Lack of β-catenin Affects Mouse Development at Gastrulation" *Development* (1995) 121: 3529-3537.
Hallonet, et al., "Maintenance of the Specification of the Anterior Definitive Endoderm and Forebrain Depends on the Axial Mesendoderm: A Study Using *HNF3β/Foxa2* Conditional Mutants" *Dev Biol* (2002) 243: 20-33.
Hamazaki, et al., "Hepatic Maturation in Differentiating Embryonic Stern Cells in Vitro" *FEBS Letter* (2001)497(1): 15-19.
Hansson, et al. "Artifactual Insulin Release from Differentiated Embryonic Stem Cells" *Diabetes* (2004) 53: 2603-2609.
Harris, T. M., and Childs, G., "Global Gene Expression Patterns During Differentiation of F9 Embryonal Carcinoma Cells Into Parietal Endoderm" *Funct Integr Genomics* (2002) 2: 105-119.
Harrison, et al., "Pancreas Doral Lobe Agenesis and Abnormal Islet of Langerhans in *Hlxb9*-deficient Mice" *Nature Genetics* (1999) 23: 71-75.

(56) References Cited

OTHER PUBLICATIONS

Haumaitre, et al. "Functions of HNF1 Family Members in Differentiation of the Visceral Endoderm Cell Lineage" *J. Biol. Chem.* (2003) 278(42): 40933-40942.
Henry, et al., "*Mixer*, a Homeobox Gene Required for Endoderm Development" *Science* (1998) 281: 91-96.
Herrmann, et al., "Cloning of the T Gene Required in Mesoderm Formation in the Mouse" *Nature* (1990) 343: 617-622.
Hogan, B. L., "Bone Morphogenetic Proteins in Development" *Curr Opin Genet Dev* (1996) 6: 432-438.
Holland, et al., "Experimental Control of Pancreatic Development and Maintenance" *Proc Natl Acad Sci USA* (2002) 99(19): 12 236-12 241.
Houard, et al., "HNF-6-Independent Differentiation of Mouse Embryonic Stem Cells into Insulin-Producing Cells" *Diabetologia* (2003) 46: 378-385.
Houde, et al., "Intestinal Epithelial Cell Differentiation Involves Activation of p38 Mitogen-activated Protein Kinase that Regulates the Homeobox Transcription Factor CDX2" *J. Biological Chemistry* (2001) 276(24): 21885-21894.
Howe, et al., "Expression of SPARC/Osteonectin Transcript in Murine Embryos and Gonads" *Differentiation* (1998) 37: 20-25.
Hudson, et al., "Xsox17alpha and -beta Mediate Endoderm Formation in Xenopus" *Cell* (1997) 91: 397-405.
Huelsken, et al., "Requirement for β-Catenin in Anterior-Posterior Axis Formation in Mice" *J Cell Biol* (2000) 148: 567-578.
Humphrey, et al. "Maintenance of Pluripotency in Human Embryonic Stem Cells is STAT3 Independent" *Stem Cells* (2004) 22: 522-530.
Imada, et al., "Fetomodulin: Marker Surface Protein of Fetal Development Which Is Modulatable by Cydic AMP" *Dev Biol* (1987)122: 483-491.
Inami, et al., "Differentiation of induced pluripotent stem cells to thymic epithelial cells by phenotype," Immunology and Cell Biology, (2010), pp. 1-8.
Jacquemin, et al., "The Onecut transcription factor HNF-6 (OC-1) is required for timely specification of the pancreas and acts upstream of Pdx-1 in the specification cascade." 258:105-116 (2003).
Jain, et al., "Glucose Control and Long-Term Survival in Breeding/Worcester Rats After Intraperitoneal Implantation of Hydrophilic Macrobeads containing Porcine Islets without Immunosuppression" *Transplantation* (1999) 68(11): 1693-1700.
Jensen et al., 2000, Diabetes, vol. 49, pp. 163-176.
Jiang et al., Generation of insulin-producing islet-like clusters from human embryonic stem cells, *Stem Cells* (2007) 25(8):1940-53.
Johannesson et al., "FGF4 and retionic acid direct differentiation of hESCs into PDX-1 expressing foregut endoderm in a time and concentration-dependent manner," *PLoS One* (2009) 4(3):e4794.
Jones, et al., "Differences Between Human and Mouse Alpha-Fetoprotein Expression During Early Development" *J. Anat.* (2001) 198: 555-559.
Jonsson, et al., "Insulin-promoter-factor 1 is Required for Pancreas Development in Mice" *Nature* (1994) 371: 606-609.
Kahan, et al., "Pancreatic Precursors and Differentiated Islet Cell Types from Murine Embryonic Stem Cells: An In Vitro Model to Study Islet Differentiation" *Diabetes* (2003) 52(8): 2016-2024.
Kalinichenko, et al., "The Forkhead Box F1 Transcription Factor is Expressed in Brain and Head Mesenchyme During Mouse Embryonic Development" *Gene Expr Patterns* (2003) 3: 153-158.
Kanai-Azuma, et al., "Depletion of Definitive Gut Endoderm in Sox17-Null Mutant Mice" *Development* (2002) 129: 2367-2379.
Katoh, M., "Expression of Human SOX7 in Normal Tissues and Tumors" *Int J Mol Med* (2002) 9: 363-368.
Kawahira, et al., "Hedgehog Signaling Regulates Expansion of Pancreatic Epithelial Cells" *Developmental Biology* (2005) 280: 111-121.
Kawaji, et al., "Exploration of Novel Motifs Derived from Mouse cDNA Sequences" *Genome Research* (2002) 12: 367-378.
Keller, G.M., "In Vitro Differentiation of Embryonic Stem Cells" *Curr Op Cell Biol* (1995) 7: 862-896.
Khoo, et al., "Growth and Differentiation of Embryoid Bodies Derived from Human Embryonic Stem Cells: Effect of Glucose and Basic Fibroblast Growth Factor", Biology of Reproduction (2005) 73: 1147-1156.
Kieffer, T.J., and J.F. Habener, "The Glucagon-Like Peptides" *Endocrinology Reviews* (1999) 20(6): 876-913.
Kikuchi, et al., "Casanova Encodes a Novel Sox-Related Protein Necessary and Sufficient for Early Endoderm Formation in Zebrafish" *Genes Dev* (2001) 15: 1493-1505.
Kilpatrick, et al., "Gene Gun Delivered DNA-Based Immunizations Mediate Rapid Production of Murine Monoclonal Antibodies to the Flt-3 Receptor" *Hybridoma* (1998) 17: 569-576.
Kim, C. H., and Broxmeyer, H. E., "Chemokines: Signal Lamps for Trafficking of T and B Cells for Development and Effector Function" *J Leukoc Biol* (1999) 65: 6-15.
Kim et al., 2001, Genes and Development, vol. 15, pp. 111-127.
Kimelman, D., and Griffin, K. J., "Vertebrate Mesendoderm Induction and Patterning" *Curr Opin Genet Dev* (2000)10: 350-356.
Kinder, et al., The Organizer of the Mouse Gastrula is Composed of a Dynamic Population of Progenitor Cells for the Axial Mesoderm Development (2001) 128: 3623-3634.
Krasemann, et al., "Generation of Monoclonal Antibodies Against Proteins With an Unconventional Nucleic Acid-Based Immunization Strategy" *J. Biotechnol*. (1999) 73: 119-129.
Kroon et al., "Pancreatic endoderm derived from human embryonic stem cells generates glucose-responsive insultin-secreting cells in vivo", *Nat. Biotechnol*. (2008) 26(4):443-52.
Kubo, et al., "Development of definitive endoderm from embryonic stem cells in culture" *Development* (2004)131: 1651-1662.
Kumar, et al., "Nodal Signaling Uses Activin and Transforming Growth Factor-Beta Receptor-Regulated Smads" *J Biol Chem* (2001) 276: 656-661.
Kuo et al., "Roles of histone acetyltransferases and deacetylases in gene regulation", *BioEssays*, (1998) 20:615-626.
Labosky, et al., "Embryonic Germ Cell Lines and Their Derivation From Mouse Primordial Germ Cells" *Ciba Found Symp* (1994) 182: 157-168; discussion: 168-178.
Labosky, et al., "Mouse Embryonic Germ (EG) Cell Lines: Transmission Through the Germline and Differences in the Methylation Imprint of Insulin-Like Growth Factor 2 Receptor (Igf2r) Gene Compared With Embryonic Stem (ES) Cell Lines" *Development* (1994) 120: 3197-3204.
Langley et al., "Expression of the neural cell adhesion molecule NCAM in endocrine cells", *The Journal of Hinochemistry and Cytochemistry*, (1989) 57(6):781-791.
Latif, et al., "A Simple Method of Staining Fresh and Cultured Islets," *Transplantation* (1998) 45(4): 827-830.
Lavial et al., 2010, Develop. Growth Diff., vol. 52, pp. 101-114.
Lawson, et al., "Bmp4 is Required for the Generation of Primordial Germ Cells in the Mouse Embryo" *Genes Dev* (1999) 13: 424-436.
Lee, Young-Hoon and Jean-Pierre Saint-Jeannet, "Sox9, a novel pancreatic marker in Xenopus," Int. J. Dev. Biol. Sep. 2003 47(6):459-62.
Li, et al., "Selective agenesis of the dorsal pancreas in mice lacking homeobox gene HIxb9" *Nature Genetics* (1999) 23: 67-70.
Lickert, et al., "Formation of Multiple Hearts in Mice Following Deletion of Beta-Catenin in the Embryonic Endoderm" *Dev Cell* (2002) 3: 171-181.
Liu, et al., "Requirement for Wnt3 in Vertebrate Axis Formation" Nat Genet (1999) 22: 361-365.
Loebel, et al., "A Gut Feeling" *Nat. Biotechnol*. (2005) 23(12): 1491-1492.
Lowe et al., "Genetic dissection of nodal function in patterning the mouse embryo," *Development*, (2001) 128:1831-1843.
Lu, et al., "From Fertilization to Gastrulation: Axis Formation in the Mouse Embryo" *Curr Opin Genet Dev* (2001) 11: 384-392.
Lumelsky, et al., "Differentiation of Embryonic Stem Cells to Insulin-Secreting Structures Similar to Pancreatic Islets" *Science* (2001) 292: 1389-1394.
Lynn, et al., "Sox9 Coordinates a Transcriptional Network in Pancreatic Progenitor Cells" *PNAS* (2007) 104(25): 10500-10505.

(56) References Cited

OTHER PUBLICATIONS

Ma, et al., "The chemokine receptor CXCR4 is required for the retention of B lineage and granulocytic precursors within the bone marrow microenvironment" *Immunity* (1999)10: 463-471.
Madsen, Ole Dragsbaek, "Stem Cells and Diabetes Treatment" *APMIS* (2005) 113(11-12): 858-875.
Madsen, et al., "Towards Cell Therapy for Diabetes" *Nature Biotechnology* (2006) 24(12): 1481-1483.
Mark et al., "Function of retinoid nuclear receptors: lessons from genetic and pharmacological dissections of the retinoic acid signaling pathway during mouse embryogenesis," *Annu. Rev. Pharmacol. Toxicol.* (2006) 46:451-80.
Martin, et al., "Dorsal Pancreas Agenesis in Retinoic Acid-deficient Raidh2 Mutant Mice" *Developmental Biology* (2005) 284: 399-411.
Maruoka, et al., "Comparison of the Expression of Three Highly Related Genes, Fgf8, Fgf17 and Fgf18, in the Mouse Embryo" Mech Dev (1998) 74: 175-177.
Matsubara, Kousaku, et al. "Acute lymphoblastic leukemia with coexpression of CD56 and CD57: Case reports", Pediatric Hematology and Oncology, vol. 21, No. 7, Oct. 2004 pp. 677-682.
Matsuda, et al., "STAT3 Activation is Sufficient to Maintain an Undifferentiated State of Mouse Embryonic Stem Cells" *EMBO J* (1999) 18(15): 4261-4269.
McGrath, et al., "Expression of Homeobox Genes, Including and Insulin Promoting Factor, in the Murine Yolk Sac at the Time of Hemato poietic Initiation" *Mol Reprod Dev* (1997) 48: 145-153.
McGrath, et al., "Embryonic Expression and Function of the Chemokine SDF-1 and its Receptor, CXCR4" *Dev Biol.* (1999) 213: 442-456.
McLean, et al., "Activin A Efficiently Specifies Definitive Endoderm from Human Embryonic Stem Cells Only When Phosphtidylinositol 3-Kinase Signaling Is Suppressed" *Stem Cells* (2007) 25: 29-38.
Micallef, et al., "Retinoic Acid Induces Pdx1-positive Endoderm in Differentiating Mouse Embryonic Stem Cells" *Diabetes* (2005) 54(2):301-305.
Millonig, et al., "Molecular Analysis of the Distal Enhancer of the Mouse Alpha-Fetoprotein Gene" *Mol. Cell Biol.* (1995) 15: 3848-3856.
Milne, et al. "Generation of Insulin-Expressing Cells from Mouse Embryonic Stem Cells" *Biochemical and Biophysical Research Communications* (2005) 328: 399-403.
Miyazono, et al., "Divergence and Convergence of TGF-beta/BMP Signaling" *J Cell Physiol* (2001)187: 265-276.
Mizusawa, et al., "Differentiation Phenotypes of Pancreatic Islet Beta- and Alpha-Cells are Closely Related with Homeotic Genes and a Group of Defferentially Expressed Genes" *Gene: An Int. Journal on Genes and Genomes* (2004) 331: 53-63.
Molotkov, et al., "Retinoic Acid Generated by Raldh2 in Mesoderm Is Required for Mouse Dorsal Endodermal Pancreas Development" *Development Dynamics* (2005) 232: 950-957.
Moriya, et al., "In Vitro Pancreas Formation from Xenopus Ectoderm Treated with Activin and Retinoic Acid" *Develop. Growth Differ.* (2000) 42: 593-602.
Munoz et al., 2008, Theriogenology, vol. 69, pp. 1159-1164.
Murtaugh, et al., "Notch Signaling Controls Multiple Steps of Pancreatic Differentiation" *PNAS* (2003) 100(25): 14920-14925.
Nagai, et al., "The Expression of the Mouse Zic1, Zic2, and Zic3 Gene Suggests an Essential Role for Zic Genes in Body Pattern Formation" Dev Biol (1997) 182: 299-313.
Nagasawa, et al., "Defects of B-cell Lymphopoiesis and Bone-Marrow Myelopoiesis in Mice Lacking the CXC Chemokine PBSF/SDF-1" *Nature* (1996) 382: 635-638.
Nakagawa, et al., "Recruitment and Activation of Rac1 by the Formation of E-cadherin-mediated Cell-cell Adhesion Sites" J. Cell Science (2001) 114(10): 1829-1838.
Nieto, et al., "Cloning and Developmental Expression of Sna, a Murine Homologue of the *Drosophila snail* Gene" Development (1992) 116: 227-237.

Nieto, M.A., The Snail Superfamily of Zinc-Finger Transcription Factors Nat Rev Mol Cell Biol (2002) 3: 155-166.
Niimi, et al. "SOX7 and SOX17 Regulate the Parietal Endoderm-Specific Enhancer Activity of Mouse Laminin Alpha1 Gene." (2004) J. Biol. Chem. 279 (36): 38055-38061.
Niswander, L. & Martin, G.R., "Fgf-4 Expression During Gastrulation, Myogenesis, Limb and Tooth Development in the Mouse" Development (1992) 114: 755-768.
Niwa, H., "Molecular mechanism to maintain stem cell renewal of ES cells" *Cell Struct Funct* (2001) 26: 137-148.
Offield, et al., "PDX-1 is Required for Pancreatic Outgrowth and Differentiation of the Rostral Duodenum" *Development* (1996) 122: 983-995.
Ogura, et al., "Behavioral abnormalities of Zic1 and Zic2 mutant mice: implications as models for human neurological disorders" *Behav Genet* (2001) 31: 317-324.
O'Hare, et al., "Conditional Immortilization of Freshly Isolated Human Mammary Fibroblast and Endothelial Cells" *Proc. Nat. Acad. Sci.* (2001) 98: 646-651.
Ohlsson et al., "Embryonic stem cells express growth hormone receptors: regulation by retenoic acid," *Endocrinology* (1993) 133(6):2897-2903.
Ormestad, et al., "Differences in the Embryonic Expression Patterns of Mouse Foxf1 and -2 Match Their Distinct Mutant Phenotypes" Developmental Dynamics (2004) 229: 328-333.
Park, et al., "Sox17 Influences the Differentiation of Respiratory Epithelial Cells" *Developmental Biology* (2006) 294: 192-202.
Parker, et al., "Altered Cell Strains in Continuous Culture: A General Survey" *N.Y. Academy of Sciences* (1957) 5: 303-313.
Paris et al., 2010, Theriogenology, vol. 74, pp. 516-524.
Pearce, J.J. & Evans, M.J., "Mml, a Mouse Mix-like Gene Expressed in the Primitive Streak" Mech Dev (1999) 87: 189-192.
Pendeville, et al., "Zebrafish Sox7 and Sox18 Function Together to Control Arterial—Venous Identity" *Developmental Biology* (2008) 317: 405-416.
Pera, et al., "Regulation of Human Embryonic Stem Cell Differentiation by BMP-2 and its Antagonist Noggin" J Cell Sci (2004) 117: 1269-1280.
Perea-Gomez, et al., "Initiation of Gastrulation in the Mouse Embryo is Preceded by an Apparent Shift in the Orientation of the Anterior-Posterior Axis" Curr Biol (2004) 14: 197-207.
Pesce, M. & Scholer, H.R., "Oct-4: Gatekeeper in the Beginnings of Mammalian Development" Stem Cells (2001) 19: 271-278.
Pettite et al., 2004, Mech. of Develop., vol. 121, pp. 1159-1168.
Pevny, et al., "A Role for SOX1 in Neural Determination" Development (1998) 125: 1967-1978.
Phillips, et al., "Differentiation of Embryonic Stem Cells for Pharmacological Studies on Adipose Cells" *Pharmacological Research* (2003) 47:263-268.
Price, Paul J., and Gregory J. Brewer, *Serum-Free Media for Neural Cell Cultures*, Proctocols for Neural Cell Culture, 3$^{rd}$ Ed., Fedoroff and Richardson (Eds.) Humana Press, Totowa, New Jersey, 255-264.
Rajagopal, et al. "Insulin Staining of ES Cell Progeny from Insulin Uptake" (2003) Science 299:363.
Rambhatla, et al., "Generation of Hepatocyte-Like Cells From Human Embryonic Stem Cells" *Cell Transplantation* (2003) 12(1): 1-11.
Ramiya et al., "Reversal of insulin-dependent diabetes using islets generated in vitro from pancreatic stem cells," *Nature Medicine* (2000) 6:278-282.
Reubinoff, et al., "Embryonic Stem Cell Lines From Human Blastocysts: Somatic Differentiation In Vitro" *Nat Biotechnol* (2000) 18: 399-404.
Robb, L. & Tam, P.P., "Gastrula Organiser and Embryonic Patterning in the Mouse" Seminars in Cell & Dev. Biol. (2004) 15: 543-554.
Robertson, "Teratocarcinomas and embryonic stem cells: A practical approach," IRL Press 1987.
Roche, et al. "Ectodermal commitment of insulin-producing cells derived from mouse embryonic stem cells" *Faseb J* (2005) 19: 1341-1343.

(56) References Cited

OTHER PUBLICATIONS

Rodaway, A., and Patient, R., "Mesendoderm: An Ancient Germ Layer?" *Cell* (2001) 105: 169-172.
Rodaway, et al., "Induction of the Mesendoderm in the Zebrafish Germ Ring by Yolk Cell-Derived Tgf-Beta Family Signals and Discrimination of Mesoderm and Endoderm by FGF" *Development* (1999) 126: 3067-3078.
Rohr, et al., "Zebrafish Zic1 Expression in Brain and Somites Is Affected by BMP and Hedgehog Signalling" *Mech Dev* (1999) 85: 147-159.
Rossant, J. & Tam, P.P., "Emerging Asymmetry and Embryonic Patterning in Early Mouse Development" *Dev Cell* (2004) 7: 155-164.
Ruhnke, et al., "Long-Term Culture and Differentiation of Rat Embryonic Stem Cell-Like Cells into Neuronal, Glial, Endothelial, and Hepatic Lineages" *Stem Cells* (2003) 21: 428-436.
Saarma et al., "GDNF—a stranger in the TGF—superfamily?" Eur. J. Biochem. (2000) 267(24):6968-71.
Sander, M. and M.S. German, "The Beta Cell Transcription Factors and Development of the Pancreas" *J. Molecular Medicine* (1997) 75(5): 327-340.
Schier, A. F., "Nodal Signaling in Vertebrate Development" *Annu Rev Cell Dev Biol* (2003) 19: 589-621.
Schmolke, et al., "Identification of Hepatitis G Virus Particles in Human Serum by E2-Specific Monoclonal Antibodies Generated by DNA Immunization" *J. Virol.* (1998) 72: 4541-4545.
Schoenwolf, G. C., and Smith, J. L., "Gastrulation and Early Mesodermal Patterning in Vertebrates" *Methods Mol Biol* (2000) 135: 113-125.
Schuldiner, et al., "Effects of Eight Growth Factors on the Differentiation of Cell Derived from Human Embryonic Stem Cells" *Proc. Natl. Sci.* (2000) 97: 11307-11312.
Schwartz, et al. "Defined Conditions for Development of Functional Hepatic Cells from Human Embryonic Stem Cells" Stem Cells and Development (2005) 14(6): 643-655.
Segev, et al., "Differentiation of human embryonic stem cells into insulin-producing clusters" *Stem Cells* (2004) 22(3): 265-274.
Shalaby, et al., "Failure of Blood-Island Formation and Vasculogenesis in Flk-1-deficient Mice" Nature (1995) 376: 62-66.
Shamblott, et al., "Derivation of Pluripotent Stem Cells From Cultured Human Primordial Germ Cells" *Proc Natl Acad Sci USA* (1998) 95: 13726-13731.
Shamblott et al., "Human embryonic germ cell derivatives express a broad range of developmentally distinct markers and proliferate exensively in vitro," *Proc. Natl. Acad. Sci. USA* (2001) 98(1):113-8.
Shapiro, et al., "Islet Transplantation in Seven Patients With Type 1 Diabetes Mellitus Using a Glucocorticoid-Free Immunosuppressive Regimen" *N Engl J Med* (2000) 343: 230-238.
Shapiro, et al., "Pancreatic Islet Transplantation in the Treatment of Diabetes Mellitus" *Best Pract Res Clin Endocrinol Metab* (2000) 15: 241-264.
Shapiro, et al., "Could Fewer Islet Cells be Transplanted in Type 1 Diabetes?: Insulin Independence Should be Dominant Force in Islet Transplantation" *BMJ* (2001) 322: 861.
Shi, Yan, et al. "Inducing embryonic stem cells to differentiate into pancreatic beta cells by a novel three-step approach with activin A and all-trans retinoic acid." Stem Cells (Dayton, Ohio) May 2005, vol. 23, No. 5, pp. 656-662.
Shiozawa, et al., "Cloning and Characterization of Xenopus laevis xSox7 cDNA" *Biochim Biophys Acta* (1996)1309: 73-76.
Shirahashi, et al., "Differentiation of Human and Mouse Embryonic Stem Cells Along a Hepatocyte Lineage" Cell Transplantation (2004) 13: 197-211.
Shiraki, "TGF-beta signaling potentiates differentiation of embryonic stem cells to PDx-1 expressing endodermal cells," *Genes to Cells* (2005) 21:405-412.
Shook, D. & Keller, R., "Mechanisms, Mechanics and Function of Epithelial-Mesenchymal Transitions in Early Development" Mech Dev (2003) 120: 1351-1383.

Sinner, et al., "Sox17 and β-Catenin Cooperate to Regulate the Transcription of Endodermal Genes" Development (2004) 131: 3069-3080.
Skoudy, et al. "Transforming Growth Factor (TGF) beta, Fibroblast Growth Factor (FGF) and Retinoid Signaling Pathways Promote Pancreatic Exocrine Gene Expression in Mouse Embryonic Stem Cells" *Biochemical J.* (2004) 379(Pt 3): 749-756.
Smith, J "Brachyury and the T-box Genes" *Curr Opin Genet Dev* (1997) 7: 474-480.
Smith, et al., "Upstream and Downstream From Brachyury, A Gene Required for Vertebrate Mesoderm Formation" *Cold Spring Harb Symp Quant Biol* (1997) 62: 337-346.
Soon-Shiong, P., "Treatment of Type I Diabetes using Encapsulated Islets" *Advanced Drug Delivery Reviews* (1999) 35: 259-270.
Soria, et al., "Insulin-Secreting Cells Derived from Embryonic Stem Cells Normalize Glycemia in Streptozotocin-Induced Diabetic Mice" *Diabetes* (2000) 49(2): 157-162.
Soria et al., "In-vitro differentiation of pancreatic beta-cells", *Differentiation*, (2001) 68:205-219.
Stafford, D. and Prince, V., "The Role of Retinoid Signaling in Pancreas Differentiation" Pancreatic Development, Proliferation and Stem Cells, Meeting Abstract, Oct. 18-19, 2001, National Institute of Health.
Stafford, et al., "A Conserved Role for Retoid Signaling in Verterbrate Pancreas Development" Dev Genes Evol. (2004) 214: 432-441.
Stafford, D. and Prince, V., "Retinoic Acid Signaling Is Required for a Critical Early Step in Zebrafish Pancreatic Development" *Current Biology* (2002) 12: 1215-1220.
Stainier, D.Y.R., "A Glimpse into the Molecular Entrails of Endoderm Formation" Genes Dev (2002) 16: 893-907.
Stemmler, et al., "Analysis of Regulatory Elements of E-Cadherin with Reporter Gene Constructs in Transgenic Mouse Embryos" Developmental Dynamics (2003) 227: 238-245.
Stoffers, et al., "Early-onset Type-II Diabetes Mellitus (MODY4) Linked to IPF1" Nature Genetics (1997) 17: 138-139.
Stoffers, et al., "Pancreatic Agenesis Attributable to a Single Nucleotide Deletion in the Human *IPF1* Gene Coding Sequence" *Nature Genetics* (1997) 15: 106-110.
Strooper et al., 1999, Nature, vol. 398, pp. 518-522.
Sun et al., "Conditional inactiviation of Fgf4 reveals complexity of signaling during limb bud development," *Nat. Genet.*, (2000) 25:83-86.
Sun, et al., "Targeted Disruption of Fgf8 Causes Failure of Cell Migration in the Gastrulating Mouse Embryo" Genes Dev (1999) 13: 1834-1846.
Suzuki, et al., "Cloned Cells Develop Renal Cortical Collecting Tubles" *Nephron.* (1994) 68: 118-124.
Tada, et al. "Characterization of Mesendoderm: A Diverging Point of the Definitive Endoderm and Mesoderm in Embryonic Stem Cell Differentiation Culture." (2005) Development 132: 4363-4374.
Takahashi et al., "Induction of pluripotent stem cells from adult human fibroblasts by defined factors," *Cell* (2007) 131(5):861-72.
Takash, et al., "SOX7 Transcription Factor: Sequence, Chromosomal Localisation, Expression, Transactivation and Interference With Wnt Signalling" *Nucleic Acids Res* (2001) 29: 4274-4283.
Tam, et al., "Early endoderm development in vertebrates: lineage differentation and morphogenetic function" *Curr Opin Genet Dev.* 13(4): 393-400, 2003.
Tam, et al., "Gene Function in Mouse Embryogenesis: Get Set for Gastrulation" *Nat. Rev. Genet.* (2007) 8(5): 368-381.
Taniguchi, et al., "Isolation and Characterization of a Mouse SRY-related cDNA, mSox7" *Biochim Biophys Acta* (1999) 1445: 225-231.
Technau, U. "Brachyury, the Blastopore and the Evolution of the Mesoderm" *Bioessays* (2001) 23: 788-794.
Thisse et al., "Antivin, a novel and divergent member of the TGF—superfamily, negatively regulates mesoderm induction," *Development* (1999) 126(2):229-40.
Thomas, et al., "The Murine Gene, Traube, Is Essential for the Growth of Preimplantation Embryos" Dev Biol (2000) 227: 324-342.

(56) References Cited

OTHER PUBLICATIONS

Thomson, et al., "Embryonic Stem Cell Lines Derived from Human Blastocysts" *Science* (1998) 282: 1145-1147.
Tiedemann, et al., "Pluripotent cells (stem cells) and Their Determination and Differentiation in Early Vertebrate Embryogenesis" *Develop. Growth Differ.* (2001) 43: 469-502.
Tomita Tatsuo, "New Markers for Pancreatic Islets and Islet Cell Tumors", Pathology International, vol. 52, No. 7, Jul. 2002, pp. 425-432.
Tremblay, et al., "Formation of the definitive endoderm in mouse is a Smad2-dependent process" *Development* (2000) 127: 3079-3090.
Trueba, et al., "*PAX8, TITF1,* and *FOXE1* Gene Expression Patterns during Human Development: New Insights into Human Thyroid Development and Thyroid Dysgenesis-Associated Malformations" *J. Clinical Endocrinology & Metabolism* (2005) 90(1): 455-462.
Tulachan et al., "All-Trans retionic acid induces differentiation of ducts and endocrine cells by mesenchymal/epithelial interactions in embryonic pancreas", *Diabetes,* (2003) 52:70-84.
Ulivieri, et al., "Generation of a Monoclonal Antibody to a Defined Portion of the Heliobacter Pylori Vacuolating Cytotoxin by DNA Immunization" *J. Biotechnol.* (1996) 51: 191-194.
Urbach, et al., "Modeling Lesch-Nyhan Disease by Gene Targeting in Human Embryonic Stem Cells" *Stem Cells* (2004) 22: 635-641.
Valdirmarsdottir et al., "Functions of the TGFbeta superfamily in human embryonic stem cells", *APMIS* (2005) 113(11-12):773-89.
Vallier, et al. "Activin/Nodal and FGF Pathways Cooperate to Maintain Pluripotency of Human Embryonic Stem Cells" *J Cell Sci.* (2005) 118: 4495-509.
Vallier, et al., "Nodal Inhibits Differentiation of Human Embryonic Stem Cells Along the Neuroectodermal Default Pathway" *Developmental Biology* (2004) 275: 403-421.
Vandesompele, et al., "Accurate Normalization of Real-Time Quantitative RT-PCR Data by Geometric Averaging of Multiple Internal Control Genes" *Genome Biol* (2002) 3(7): 1-12.
Varlet, et al., "Nodal Expression in the Primitive Endoderm Is Required for Specification of the Anterior Axis During Mouse Gastrulation" *Development* (1997) 124: 1033-1044.
Vincent, et al., "Cell Fate Decisions Within the Mouse Organizer Are Governed by Graded Nodal Signals" *Genes Dev* (2003) 17: 1646-1662.
Vogel, G. "Stem Cells are Coaxed to Produce Insulin" *Science* (2001) 292: 615-616.
Wang, et al. "Self-Renewal of Human embryonic Stem Cells Requires Insulin-Like Growth Factor-1 Receptor and ERBB2 Receptor Signaling." Blood (2007), 110; 4110-4119.
Wei, et al., "Transcriptome Profiling of Human and Murine ESCs Identifies Divergent Paths Required to Maintain the Stem Cell State" *Stem Cells* (2005) 23: 166-185.
Weiler-Guettler, et al., "Developmentally Regulated Gene Expression of Thrombomodulin in Postimplantation Mouse Embryos" *Development* (1996) 122: 2271-2281.
Weiler-Guettler, et al., "Thrombomodulin Gene Regulation by cAMP and Retinoic Acid in F9 Embryonal Carcinoma Cells" *PNAS* (1992) 89: 2155-2159.
Weinstein, D.C. et al. The winged-helix transcription factor HNF-3 beta is required for notochord development in the mouse embryo. Cell 78, 575-588 (1994).
Wells, J. M., and Melton, D. A., "Vertebrate Endoderm Development" *Annu Rev Cell Dev Biol* (1999) 15: 393-410.
Wells, J. M., and Melton, D. A. "Early Mouse Endoderm Is Patterned by Soluble Factors From Adjacent Germ Layers" *Development* (2000) 127: 1563-1572.
Wilding, et al., "The Role of *pdxl* and *HNF6* in Proliferation and Differentiation of Endocrine Precursors" *Diabetes/Metabolism Research and Reviews* (2004) 20: 114-123.
Willison, K., "The Mouse Brachyury Gene and Mesoderm Formation" *Trends Genet* (1990) 6: 104-105.
Wilson et al., "Streptozotocin interactions with pancreatic beta cells and the induction of insulin-dependent diabetes," *Current Topics Microbiol. Immunol.* (1990) 158:27-54.
Xu, et al., "Characterization and Enrichment of Cardiomyocytes Derived From Human Embryonic Stem Cells" *Cellular Biology* (2002) 91: 501-508.
Xu, et al., "BMP4 Initiates Human Embryonic Stem Cell Differentiation to Trophoblast" *Nat Biotechnol* (2002) 20: 1261-1264.
Yamaguchi, et al., "flk-1, an flt-related Receptor Tyrosine Kinase is an Early Marker for Endothelial Cell Precursors" Development (1993) 118: 489-498.
Yamaguchi, et al., "T (Brachyury) is a Direct Target of Wnt3a During Paraxial Mesoderm Specification" Genes Dev (1999) 13: 3185-3190.
Yang, et al., "Disabled-2 is Essential for Endodermal Cell Positioning and Structure Formation During Mouse Embryogenesis" Dev Biol (2002) 251: 27-44.
Yantiss, et al. "Prevalence and Prognostic significance of acinar cell differentiation in pancreatic endocrine tumors", American Journal of Surgical Pathology, vol. 26, No. 7, Jul. 2002 pp. 893-901.
Yasunaga, et al. "Induction and Monitoring of Definitive and Visceral Endoderm Differentiation of Mouse ES Cells." Nature Biotechnology (2005) 23: 1542-1550.
Ying, et al. "BMP Induction of Id Proteins Suppresses Differentiation and Sustains Embryonic Stem Cell Self-Renewal in Collaboration with STAT3" *Cell* (2003) 115: 281-292.
Yu, et al., "Transcriptional Regulation of the Thrombomodulin Gene" *J. Biol. Chem.* (1992) 267(32): 23237-23247.
Yu et al., "Human induced pluripotent stem cells free of vector and transgene sequences," *Science* (2007) 324: 797-801.
Yusuf, et al., "Expression of Chemokine Receptor CXCR4 During Chick Embryo Development" *Anat Embryol* (2005) 210(1): 35-41.
Zhang et al., "Highly efficient differentiation of human ES cells and IPS cells into mature pancreatic insulin-producing cells," *Cell Research* (2009): 429-438.
Zhao, G. Q., "Consequences of Knocking Out BMP Signaling in the Mouse" *Genesis* (2003) 35: 43-56.
Zhou, et al., "Nodal is a Novel TGF-beta-like Gene Expressed in the Mouse Node during Gastrulation" *Nature* (1993) 361: 543-547.
Zwaka, et al. "Homologous Recombination in Human Embryonic Stem Cells" *Nature Biotechnology* (2003) 21: 319-321.
International Search Report and Written Opinion dated Jan. 3, 2008, issued in International Application No. PCT/US07/005541.

\* cited by examiner

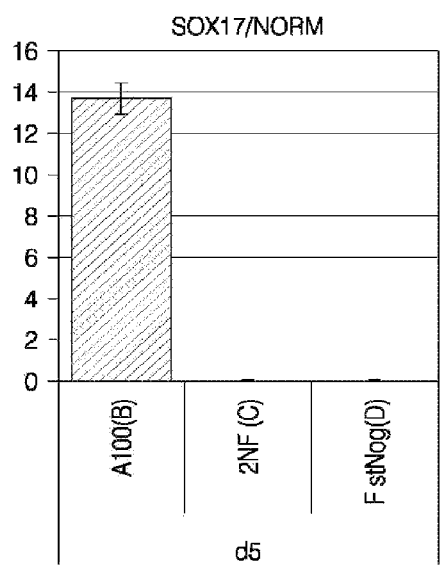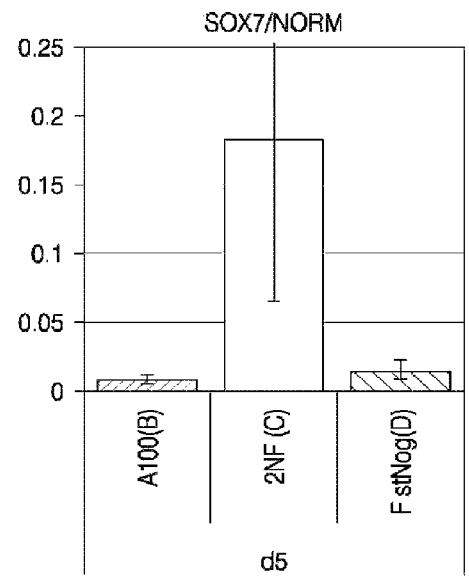
FIG. 2A  FIG. 2C
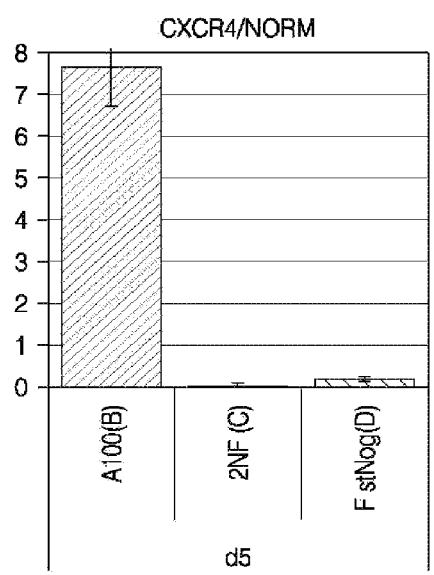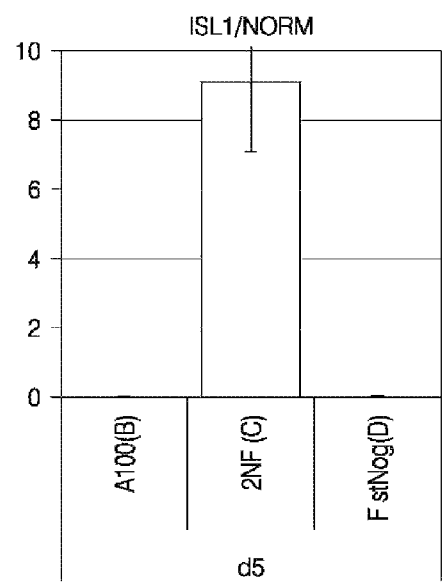
FIG. 2B  FIG. 2D

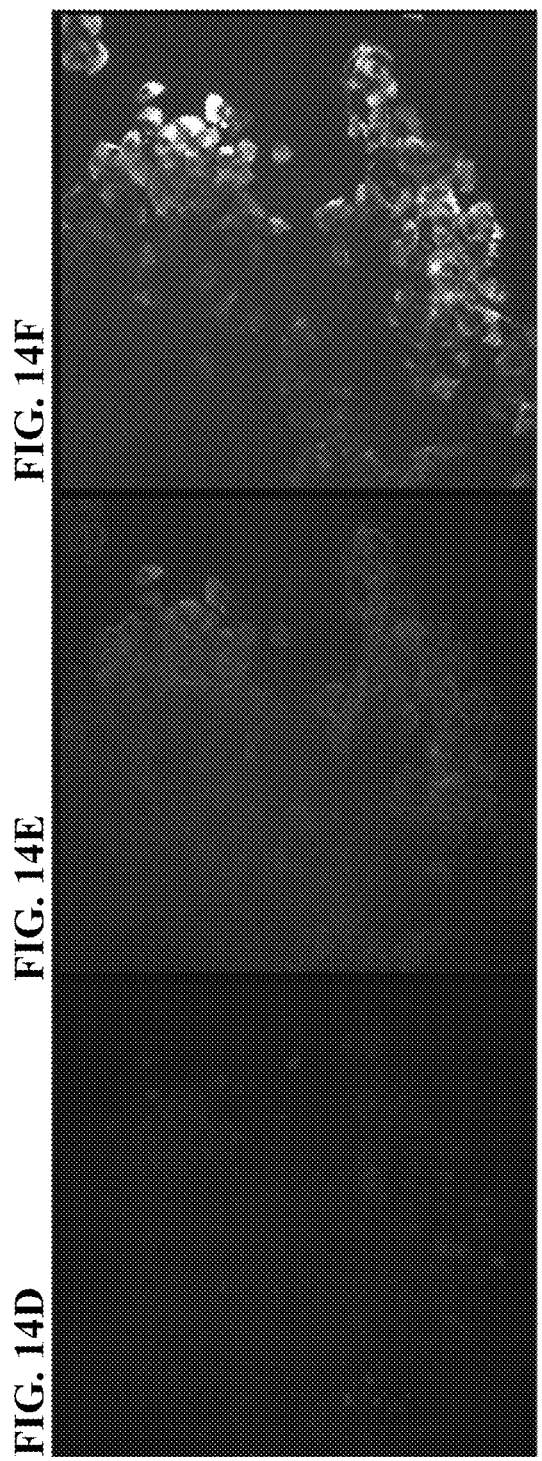

FIG. 20A
FIG. 20B
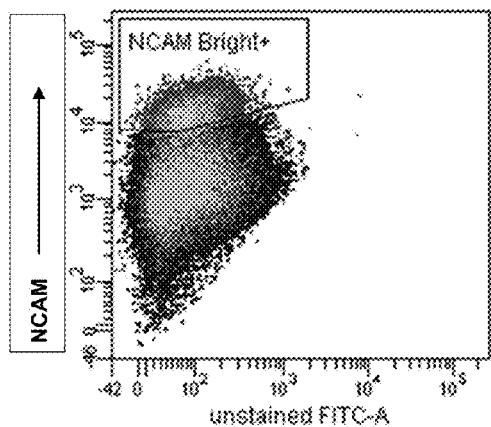
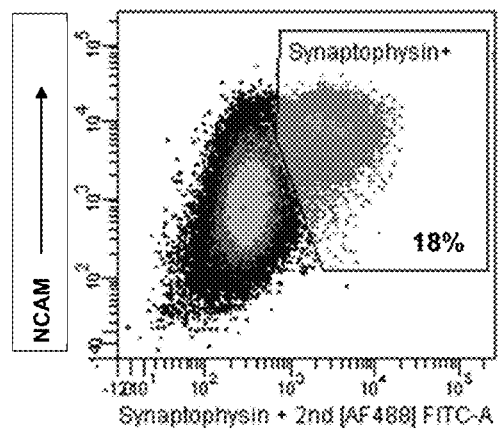
FIG. 20C
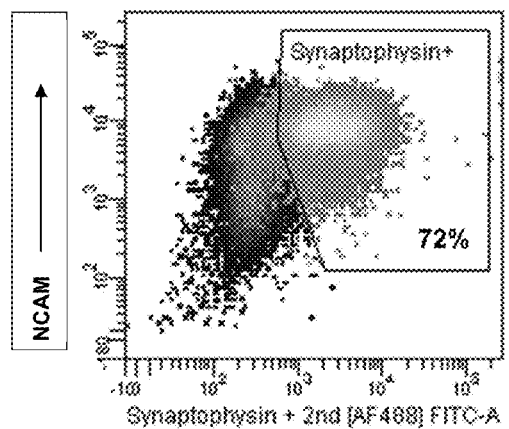

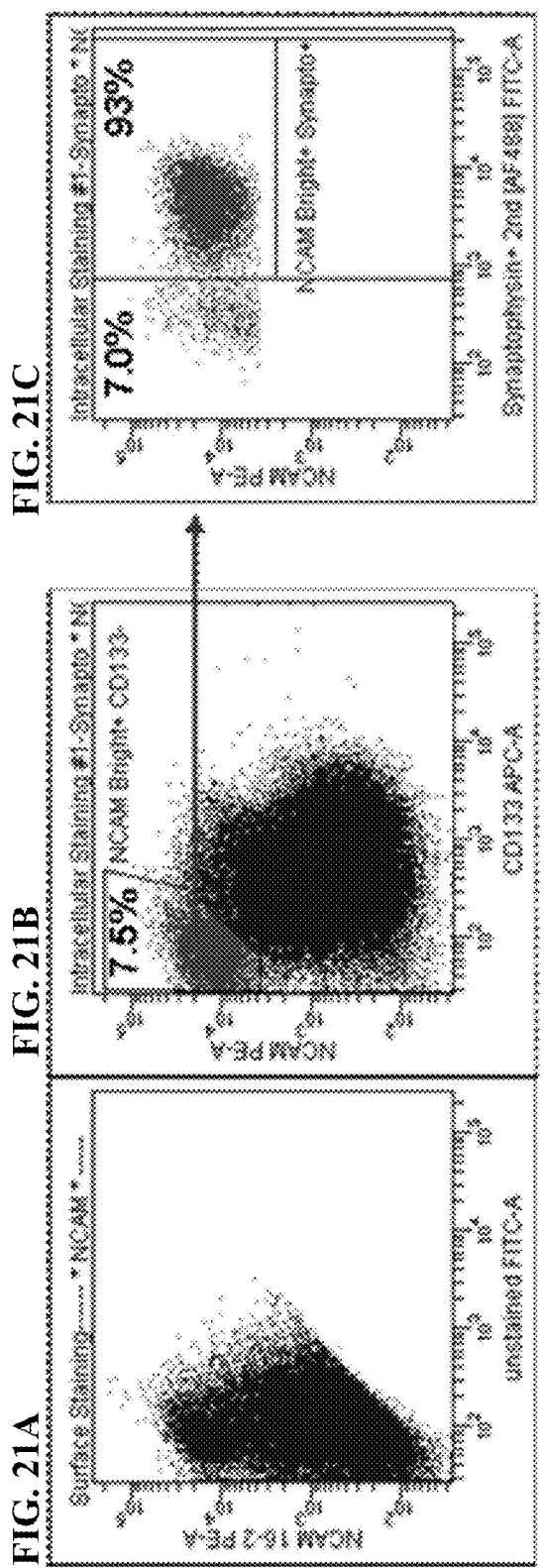

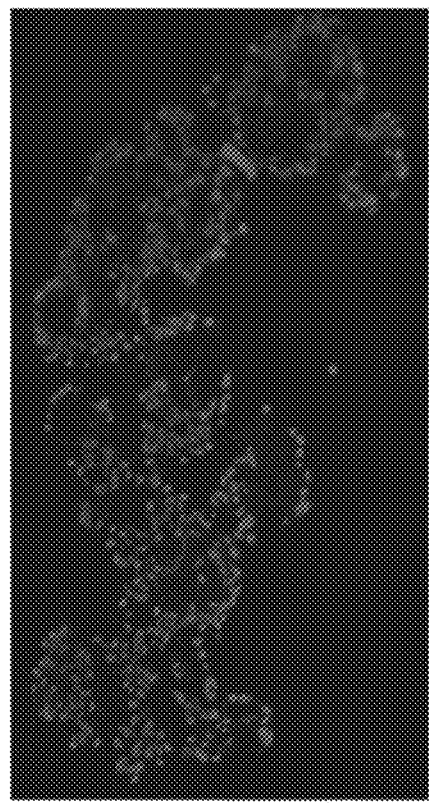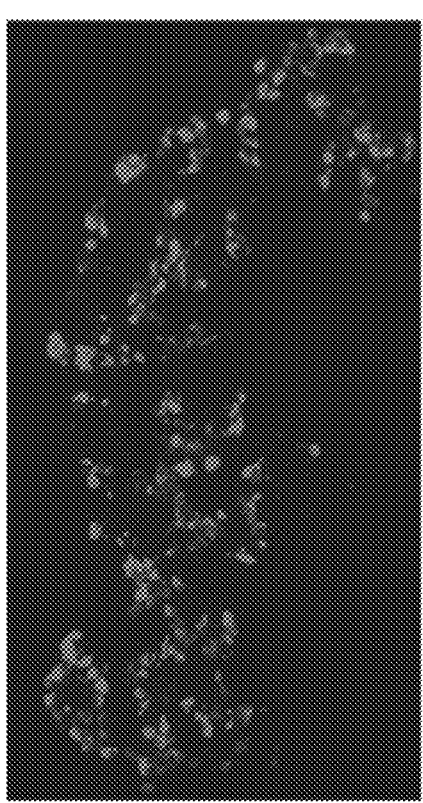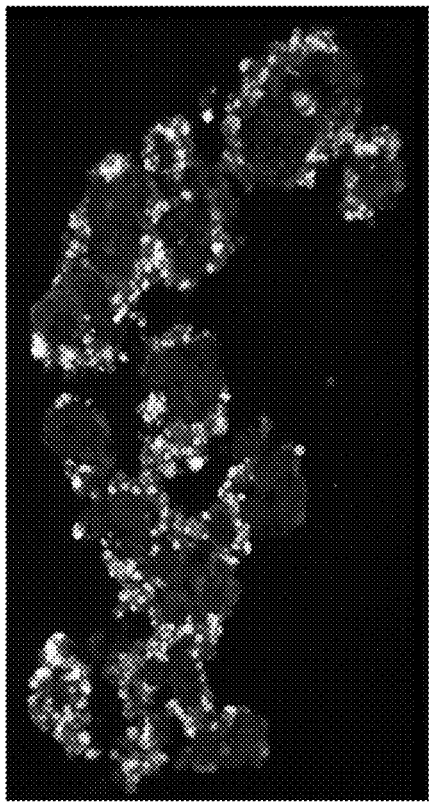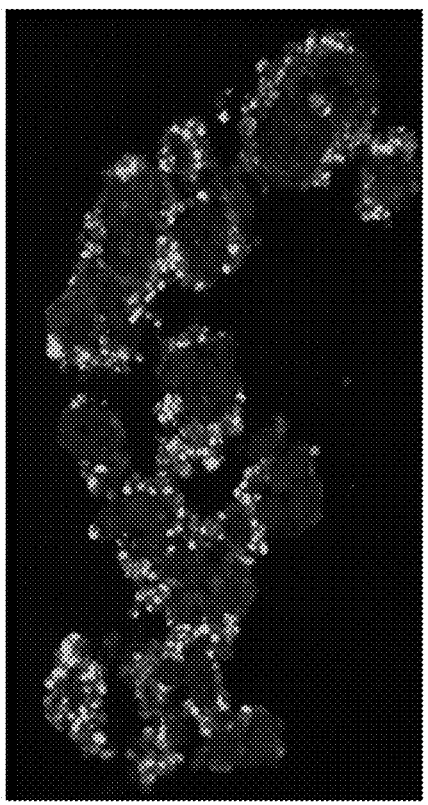

METHODS OF PRODUCING PANCREATIC HORMONES

RELATED APPLICATIONS

This application is a continuation of U.S. application Ser. No. 13/205,511, entitled "METHODS OF PRODUCING PANCREATIC HORMONES," filed Aug. 8, 2011, which is a continuation of U.S. application Ser. No. 12/758,734, entitled "METHODS OF PRODUCING PANCREATIC HORMONES," filed Apr. 12, 2010, now U.S. Pat. No. 7,993,920, which is a continuation of U.S. patent application Ser. No. 11/773,944, entitled METHODS OF PRODUCING PANCREATIC HORMONES, filed Jul. 5, 2007, now U.S. Pat. No. 7,695,965, which is a continuation-in-part of U.S. patent application Ser. No. 11/681,687, entitled ENDOCRINE PRECURSOR CELLS, PANCREATIC HORMONE-EXPRESSING CELLS AND METHODS OF PRODUCTION, filed Mar. 2, 2007, now U.S. Pat. No. 8,129,182, which claims priority under 35 U.S.C. §119(e) to U.S. Provisional Patent Application No. 60/852,878, entitled ENRICHMENT OF ENDOCRINE PRECURSOR CELLS, IMMATURE PANCREATIC ISLET CELLS AND MATURE PANCREATIC ISLET CELLS USING NCAM, filed Oct. 18, 2006, and which claims priority under 35 U.S.C. § 119(e) to U.S. Provisional Patent Application No. 60/833,633, entitled INSULIN-PRODUCING CELLS AND METHOD OF PRODUCTION, filed Jul. 26, 2006, and which claims priority under 35 U.S.C. § 119(e) to U.S. Provisional Patent Application No. 60/778,649, entitled INSULIN-PRODUCING CELLS AND METHOD OF PRODUCTION, filed Mar. 2, 2006. The disclosure of each of the above-listed priority applications is incorporated herein by reference in its entirety.

FIELD OF THE INVENTION

The present invention relates to the fields of medicine and cell biology. In particular, the present invention relates to compositions comprising mammalian endocrine precursor cells and compositions comprising pancreatic hormone-expressing cells in vivo as well as methods of making and using such cells.

BACKGROUND

Human embryonic stem cells (hESCs) have the potential to produce differentiated cell types comprising all human somatic tissues and organs. Of paramount importance for cell therapy treatment of insulin dependent diabetes is the production of unlimited numbers of pancreatic endocrine cells that function similarly to islets with respect to glucose stimulated insulin release. Accordingly, there is need for glucose responsive-insulin producing cells derived from human embryonic stem cells in vitro as well as reliable methods for producing such cells.

SUMMARY OF THE INVENTION

Some embodiments of the present invention relate to compositions, such as cell cultures, comprising human pancreatic islet hormone-expressing cells. In such embodiments, the amount of human pancreatic islet hormone-expressing cells can range from about 2% to about 80% of the human cells present in the cell culture. In some embodiments of the present invention, the pancreatic islet hormone-expressing cells can be either mature pancreatic islet hormone-expressing cells, immature pancreatic islet hormone-expressing cells or combinations of mature and immature pancreatic islet hormone-expressing cells. In certain embodiments, the human pancreatic islet hormone-expressing cells express one or more hormones selected from the group consisting of ghrelin, insulin, somatostatin and glucagon. In some embodiments, the islet hormone-expressing cells express insulin in response to glucose stimulation.

Other embodiments relate to cell cultures comprising both human pancreatic islet hormone-expressing cells and human endocrine precursor cells. In such embodiments, the amount of human endocrine precursor cells can range from about 5% to about 80% of the cells present in the cell culture. In some embodiments, the cell cultures comprise predominately immature pancreatic islet hormone-expressing cells and endocrine precursor cells. In other embodiments, the cell cultures comprise both mature and immature pancreatic islet hormone-expressing cells as well as endocrine precursor cells.

Some embodiments described herein include compositions, such as cell cultures, comprising human endocrine precursor cells but which do not include a substantial amount of human pancreatic islet hormone-expressing cells. In such embodiments, the amount of human endocrine precursor cells can range from about 5% to about 80% of the human cells present in the cell culture. In certain embodiments, the human endocrine precursor cells express a marker selected from the group consisting of neurogenin 3 (NEUROG3 or NGN3) paired box 4 (PAX4) and NKX2 transcription factor related locus 2 (NKX2.2).

Other embodiments relate to cell cultures comprising both human endocrine precursor cells and human PDX1-positive pancreatic endoderm cells (PDX1-positive foregut endoderm cells), wherein the PDX1-positive pancreatic endoderm cells are PDX1-expressing, multipotent cells that can differentiate into cells, tissues or organs derived from the anterior portion of the gut tube. In such embodiments, the human endocrine precursor cells can range from about 5% to about 95% of the cells present in said cell culture. In some embodiments, the amount of human PDX1-positive pancreatic endoderm cells can range from about 5% to about 95% of the cells present in said cell culture.

Still further embodiments of the present invention relate to methods of producing human mature pancreatic islet hormone-expressing cells, human immature pancreatic islet hormone-expressing cells, and human endocrine precursor cells. In some embodiments, human mature pancreatic islet hormone-expressing cells are produced from human immature pancreatic islet hormone-expressing cells. In some embodiments, human immature pancreatic islet hormone-expressing cells are produced from human endocrine precursor cells. In some embodiments, human endocrine precursor cells are produced from human PDX1-positive pancreatic endoderm cells.

Other embodiments of the present invention relate to methods for producing human pancreatic islet hormone-expressing cells from human embryonic stem cells (hESCs) or other human pluripotent cells. In such embodiments, the hESCs or other human pluripotent cells are first differentiated to human definitive endoderm cells. Definitive endoderm cells are multipotent cells that can differentiate into cells of the gut tube or organs derived therefrom. Human definitive endoderm cells and their production have been described in U.S. patent application Ser. No. 11/021,618, filed Dec. 23, 2004, the disclosure of which is incorporated by reference in its entirety. The definitive endoderm cells are then differentiated to foregut endoderm. Human foregut endoderm cells are multipotent cells that can differentiate into cells, tissues or organs derived from the anterior portion of the gut tube. Foregut endoderm cells and their production have been described in U.S. Provisional Patent Application No. 60/730,917, filed Oct. 27, 2005, the disclosure of which is incorporated by reference in its entirety. The foregut endoderm cells are then differentiated to PDX1-positive pancreatic endoderm cells (PDX1-positive foregut endoderm). Human PDX1-positive pancreatic endoderm cells are multipotent cells that can differentiate into cells, tissues or organs derived from the anterior portion of the gut tube. PDX1-positive pancreatic endoderm cells and their production have been described in U.S. patent application Ser. No. 11/115,868, filed Apr. 26, 2005 and U.S. Provisional Patent Application No. 60/730,917, filed Oct. 27, 2005, the disclosures of which are incorporated herein by reference in their entireties. The PDX1-positive pancreatic endoderm cells are differentiated into endocrine precursor cells, which are differentiated into immature, and then finally mature, pancreatic islet hormone-expressing cells as described in U.S. Provisional Patent Application No. 60/833,633, filed Jul. 26, 2006, the disclosure of which is incorporated herein by reference in its entirety, as well as the methods described herein.

Other embodiments described herein relate to methods of producing cell populations enriched in human endocrine precursor cells and methods of producing cell populations enriched in human immature pancreatic islet hormone-expressing cells. In some embodiments, methods of producing cell populations enriched in endocrine precursor cells involves providing a cell population that comprises human endocrine precursor cells with a reagent that binds to neural cell adhesion molecule (NCAM), and separating human endocrine precursor cells bound to the reagent from cells that are not bound to the reagent. Similarly, in some embodiments, methods of producing cell populations enriched in human immature pancreatic islet hormone-expressing cells involves providing a cell population that comprises human immature pancreatic islet hormone-expressing cells with a reagent that binds to NCAM, and separating human immature pancreatic islet hormone-expressing cells bound to the reagent from cells that are not bound to the reagent. In some embodiments, additional enrichment of immature pancreatic islet hormone-expressing cells can be achieved by contacting the NCAM-positive cell population with a second reagent that binds to CD133, and then removing from the cell population cells that are bound to the second reagent.

In some embodiments of the present invention, the cell populations comprising human pancreatic islet hormone-expressing cells produced by the methods described herein can be derived from human endocrine precursor cells. In certain embodiments of the methods of producing cell populations enriched for human endocrine precursor cells, the endocrine precursor cells can be derived from human PDX1-positive pancreatic endoderm cells. In still further embodiments, the human PDX1-positive pancreatic endoderm cells are derived from human foregut endoderm cells. In yet further embodiments, the human foregut endoderm cells are derived from human definitive endoderm cells. In still further embodiments, the human definitive endoderm cells are derived from human embryonic stem cells.

Other embodiments of the present invention relate to cell populations that are enriched for human endocrine precursor cells. In certain embodiments, the cell populations enriched for human endocrine precursor cells comprise from about 5% human endocrine precursor cells that express Neurogenin 3 (NGN3), but that do not substantially express a marker selected from the group consisting of AFP, SOX7, SOX1, ZIC1, NFM, INS, GCG, SST and GHRL. In some embodiments, the cell populations that are enriched for human endocrine precursor cells are obtained using the methods described herein for the production of cell populations enriched for human endocrine precursor cells.

Still other embodiments of the present invention relate to cell populations that are enriched for human immature pancreatic islet hormone-expressing cells. The enriched cell populations can be obtained by the methods described herein, comprising providing cell populations comprising immature pancreatic islet hormone-expressing cells with a reagent that binds NCAM, and separating the cells bound to said reagent from cells that are not bound to the reagent. In certain embodiments, the cell populations comprise at least about 25% to at least about 90% immature pancreatic hormone-expressing cells that express MAFB but do not substantially express MAFA and/or NGN3. In some embodiments, the enriched cell population comprises at least about 50% immature pancreatic islet hormone-expressing cells that express MAFB but do not substantially express MAFA and/or NGN3.

Yet other embodiments of the present invention relate to cell populations that are enriched in human mature pancreatic islet hormone-expressing cells that are derived in vitro from human pluripotent cells. The enriched cell populations can be obtained by the methods described herein, such as by providing cell populations comprising pancreatic islet hormone-expressing cells, which are produced in vitro from human pluripotent cells, with a reagent that binds NCAM and separating the cells bound to said reagent from cells that are not bound to the reagent. In certain embodiments, the cell populations comprise at least about 25% to at least about 90% pancreatic hormone-expressing cells that express at least one marker selected from the group consisting of GHRL, IAPP, INS, GCG, NKX6.1, SST and PP but which do not substantially express at least one marker selected from the group consisting of AFP, SOX7, SOX1, ZIC and NFM. In some embodiments, the enriched cell population comprises at least about 50% immature pancreatic islet hormone-expressing cells that express GHRL, IAPP, INS, GCG, NKX6.1, SST and PP but not substantially express at least one marker selected from the group consisting of AFP, SOX7, SOX1, ZIC and NFM.

Additional embodiments of the present invention relate to ex-vivo reagent-cell complexes comprising an NCAM binding reagent and a human endocrine precursor cell that expresses NCAM, a human immature pancreatic islet hormone-expressing cell that expresses NCAM or a human mature pancreatic islet hormone-expressing cell that expresses NCAM. In certain embodiments, the endocrine precursor cells, the immature pancreatic islet hormone-expressing cells and/or the mature pancreatic islet hormone-expressing cells are derived in vitro from human pluripotent cells. The reagent of the reagent-cell complexes can comprise a molecule such as an anti-NCAM antibody, and anti-NCAM antibody fragment, or an NCAM ligand.

Other aspects of the present invention relate to in vitro cell cultures and in vitro cell populations as set forth herein that have not been differentiated in the presence of sodium butyrate or other histone deacetylase inhibitor during any stage of their development. Other aspects included herein relate to methods of producing endocrine precursor cell cultures or cell populations and/or pancreatic hormone-expressing cell cultures or cell populations in the absence of sodium butyrate or other histone deacetylase inhibitor. In such aspects, hESCs are differentiated to definitive endoderm cells as well as cell types derived from definitive endoderm, such as endocrine precursor cells and pancreatic hormone-expressing cells, in the absence of sodium butyrate or other histone deacetylase inhibitor.

Still other aspects of the present invention relate to cell cultures and cell populations comprising non-recombinant or non-engineered human endocrine precursor cells and/or human pancreatic hormone-expressing cells. In some embodiments, the non-recombinant human endocrine precursor cells and/or human pancreatic hormone-expressing cells of the cell cultures and/or cell populations are differentiated from non-recombinant hESCs. In some embodiments, non-recombinant hESCs are differentiated to definitive endoderm cells as well as cell types derived from definitive endoderm, such as endocrine precursor cells and pancreatic hormone-expressing cells.

Additional aspects of the present invention relate to methods for producing pancreatic hormones. In some embodiments, the hormone production occurs in vivo. In preferred embodiments, the hormone is insulin. In such embodiments, the insulin is synthesized by insulin expressing cells that are capable of secreting insulin in response to glucose stimulation. The insulin expressing cells are obtained by the in vivo differentiation of pancreatic hormone-expressing cell precursors. In preferred embodiments, the pancreatic hormone-expressing cell precursors are human cells. In especially preferred embodiments, the human pancreatic hormone-expressing cell precursors are derived from human pluripotent cells, such as human embryonic stem cells. In such embodiments, the human embryonic stem cells are differentiated in vitro to definitive endoderm cells, or later stage pancreatic precursor cells derived therefrom, prior to transplantation into an animal. In some embodiments, the animal is a human. In a preferred embodiment, human embryonic stem cells are differentiated to definitive endoderm cells in vitro by incubating the stem cells in a medium comprising an agent that activates a member of the family of TGF-β receptors. In a particularly preferred embodiment, the agent that activates the TGF-β family receptor is selected from activin A, activin AB and activin B or combinations thereof. In some embodiments, the agent is Nodal.

Additional aspects of the present invention include an in vitro method of partially differentiating human pluripotent cells in the presence of an agent that activates the TGF-β family receptor followed by transplantation of the partially differentiated cells into a human or other animal to obtain further in vivo differentiation of those cells into cells that are capable of glucose stimulated insulin secretion. Such cells can be used for in vivo insulin production in animals, such as humans, that are in need of insulin production in response to high blood glucose levels. In some embodiments, human embryonic stem cells are incubated in vitro in a first medium comprising an agent that activates the TGF-β family receptor followed by incubation in a second medium that does not comprise such a factor. In other embodiments, the second medium comprises an agent that inhibits the TGF-β family receptor. In a preferred embodiment, the agent that inhibits the TGF-β family receptor is SB-431542. In other embodiments, the second medium lacks nicotinamide.

Certain preferred aspects of the present invention relate to the use on non-recombinant and/or non-engineered human embryonic stem cells as starting material for in vivo methods of producing pancreatic hormones described herein.

Other preferred aspects of the present invention relate to in vitro cell cultures and/or cell populations for transplant in vivo, wherein the cells of the cell cultures and/or cell populations are partially differentiated to glucose stimulated insulin secreting cells. In preferred embodiments, the cell cultures and/or cell populations do not include significant numbers of human embryonic stem cells. In other preferred embodiments, cells of the cell culture and/or cell population do not give rise to teratomas when transplanted in vivo. In especially preferred embodiments, the cells of the cell cultures and/or cell populations terminally differentiate into glucose stimulated insulin secreting cells subsequent to transplantation into a human subject. In some embodiments, the human subject is a human suffering from diabetes or who is otherwise in need of cells that are capable of producing and secreting insulin in response to physiological levels of glucose mediated stimulation.

In certain jurisdictions, there may not be any generally accepted definition of the term "comprising." As used herein, the term "comprising" is intended to represent "open" language which permits the inclusion of any additional elements. With this in mind, additional embodiments of the present inventions are described with reference to the numbered paragraphs below:

1. An in vitro cell culture comprising human cells wherein at least about 2% of said human cells are pancreatic islet hormone-expressing cells that express at least one pancreatic hormone selected from the group consisting of ghrelin, insulin, somatostatin and glucagon, said pancreatic islet hormone-expressing cells being derived in vitro from human pluripotent cells.

2. The in vitro cell culture of paragraph 1, wherein at least about 5% of said human cells are pancreatic islet hormone-expressing cells.

3. The in vitro cell culture of paragraph 1, wherein at least about 10% of said human cells are pancreatic islet hormone-expressing cells.

4. The in vitro cell culture of any of paragraphs 1 to 3, wherein at least about 10% of said human cells are human endocrine precursor cells that express neurogenin 3 (NEUROG3).

5. The in vitro cell culture of paragraph 4, wherein said human endocrine precursor cells express a marker selected from the group consisting of paired box 4 (PAX4) and NKX2 transcription factor related locus 2 (NKX2.2).

6. The in vitro cell culture of any of paragraphs 1 to 3, wherein at least about 50% of said human cells are human endocrine precursor cells that express neurogenin 3 (NEUROG3).

7. The in vitro cell culture of paragraph 6, wherein said human endocrine precursor cells express a marker selected from the group consisting of paired box 4 (PAX4) and NKX2 transcription factor related locus 2 (NKX2.2).

8. The in vitro cell culture of paragraph 1, wherein said pancreatic islet hormone-expressing cells express at least two hormones selected from the group consisting of ghrelin, insulin, somatostatin and glucagon.

9. The in vitro cell culture of paragraph 1, wherein said pancreatic islet hormone-expressing cells express ghrelin, insulin, somatostatin and glucagon.

10. The in vitro cell culture of paragraph 1, wherein at least about 5% of the pancreatic islet hormone-expressing cells express insulin but do not significantly express ghrelin, somatostatin and glucagon.

11. The in vitro cell culture of paragraph 1, wherein at least about 10% of the pancreatic islet hormone-expressing cells express insulin but do not significantly express ghrelin, somatostatin and glucagon..

12. The in vitro cell culture of paragraph 1, wherein at least about 20% of the pancreatic islet hormone-expressing cells express insulin but do not significantly express ghrelin, somatostatin and glucagon.

13. The in vitro cell culture of paragraph 1, wherein at least about 30% of the pancreatic islet hormone-expressing cells express insulin but do not significantly express ghrelin, somatostatin and glucagon.

14. The in vitro cell culture of any one of paragraphs 10 to 13, wherein insulin is secreted in response to glucose stimulation.

15. The in vitro cell culture of any one of paragraphs 10 to 13, wherein C-peptide is secreted in response to glucose stimulation.

16. The in vitro cell culture of paragraph 1, wherein at said least 10% of said pancreatic islet cells are present in islet cell clusters.

17. The in vitro cell culture of paragraph 1, wherein said pancreatic islet hormone-expressing cells further express a marker selected from the group consisting of pancreatic duodenal homeobox 1 (PDX1), islet amyloid polypeptide (IAPP), pancreatic polypeptide (PP), ISL1 transcription factor (ISL1), NKX6 transcription factor related locus 1 (NKX6.1) and paired box 6 (PAX6).

18. The in vitro cell culture of paragraph 17, wherein said pancreatic islet hormone-expressing cells do not substantially express a marker selected from the group consisting of neurogenin 3 (NEUROG3) and paired box gene 4 (PAX4).

19. The in vitro cell culture of paragraph 1, wherein at least about 1 pancreatic islet hormone-expressing cell is present for about every 10 endocrine precursor cells in said cell culture.

20. The in vitro cell culture of paragraph 1, wherein at least about 1 pancreatic islet hormone-expressing cell is present for about every 5 endocrine precursor cells in said cell culture.

21. The in vitro cell culture of paragraph 1, wherein at least about 1 pancreatic islet hormone-expressing cell is present for about every 2 endocrine precursor cells in said cell culture.

22. The in vitro cell culture of paragraph 1, wherein said pancreatic islet hormone-expressing cells are non-recombinant cells.

23. The in vitro cell culture of paragraph 1 further comprising a medium which comprises a factor selected from the group consisting of nicotinamide (MC), exendin 4 (Ex4), hepatocyte growth factor (HGF), insulin-like growth factor (IGF) and combinations thereof.

24. The in vitro cell culture of paragraph 1, further comprising a medium which comprises a factor selected from the group consisting of exendin 4 (Ex4), hepatocyte growth factor (HGF), insulin-like growth factor 1 (IGF1) and combinations thereof.

25. The in vitro cell culture of paragraph 1, further comprising a medium which comprises nicotinamide (MC) at a concentration of about 10 mM.

26. The in vitro cell culture of paragraph 1, further comprising a medium which comprises exendin 4 (Ex4) at a concentration of about 40 ng/ml.

27. The in vitro cell culture of paragraph 1, further comprising a medium which comprises hepatocyte growth factor (HGF) at a concentration of about 25 ng/ml.

28. The in vitro cell culture of paragraph 1, further comprising a medium which comprises insulin-like growth factor 1 (IGF1) at a concentration of about 50 ng/ml.

29. An in vitro cell culture comprising human cells wherein at least about 5% of said human cells are endocrine precursor cells that express neurogenin 3 (NEUROG3), said endocrine precursor cells being multipotent cells that can differentiate into pancreatic islet hormone-expressing cells that express at least one pancreatic hormone selected from the group consisting of insulin, somatostatin and glucagon.

30. The in vitro cell culture of paragraph 29, wherein at least about 10% of said human cells are endocrine precursor cells.

31. The in vitro cell culture of paragraph 29, wherein at least about 25% of said human cells are endocrine precursor cells.

32. The in vitro cell culture of paragraph 29, wherein at least about 50% of said human cells are endocrine precursor cells.

33. The in vitro cell culture of any of paragraphs 29 to 32, wherein at least about 10% of said human cells are human pancreatic duodenal homeobox 1 (PDX1)-positive pancreatic endoderm cells.

34. The in vitro cell culture of any of paragraphs 29 to 32, wherein at least about 25% of said human cells are human pancreatic duodenal homeobox 1 (PDX1)-positive pancreatic endoderm cells.

35. The in vitro cell culture of any of paragraphs 29 to 32, wherein at least about 50% of said human cells are human pancreatic duodenal homeobox 1 (PDX1)-positive pancreatic endoderm cells.

36. The in vitro cell culture of any of paragraphs 29 to 32, wherein said cell culture is substantially devoid of human pancreatic islet hormone-expressing cells.

37. The in vitro cell culture of paragraph 36, wherein at least about 10% of said human cells are human pancreatic duodenal homeobox 1 (PDX1)-positive pancreatic endoderm cells.

38. The in vitro cell culture of paragraph 36, wherein at least about 25% of said human cells are human pancreatic duodenal homeobox 1 (PDX1)-positive pancreatic endoderm cells.

39. The in vitro cell culture of paragraph 36, wherein at least about 50% of said human cells are human pancreatic duodenal homeobox 1 (PDX1)-positive pancreatic endoderm cells.

40. The in vitro cell culture of paragraph 29, wherein said endocrine precursor cells express a marker selected from the group consisting of paired box 4 (PAX4) and NKX2 transcription factor related locus 2 (NKX2.2).

41. The in vitro cell culture of paragraph 29, wherein at least about 1 endocrine precursor cell is present for about every 10 PDX1-positive pancreatic endoderm cells in said cell culture.

42. The in vitro cell culture of paragraph 29, wherein at least about 1 endocrine precursor cell is present for about every 5 PDX1-positive pancreatic endoderm cells in said cell culture.

43. The in vitro cell culture of paragraph 29, wherein at least about 1 endocrine precursor cell is present for about every 2 PDX1-positive pancreatic endoderm cells in said cell culture.

44. The in vitro cell culture of paragraph 29, wherein said endocrine precursor cells are non-recombinant cells.

45. The in vitro cell culture of paragraph 29 further comprising a medium which comprises N—[N-(3,5-difluorophenacetyl)-L-alanyl]-S-phenylglycine t-butyl ester (DAPT).

46. The in vitro cell culture of paragraph 45, wherein said DAPT concentration is at least about 1 µM.

47. The in vitro cell culture of paragraph 45, wherein said DAPT concentration is about 3 µM.

48. The in vitro cell culture of paragraph 45 further comprising a factor selected from retinoic acid (RA) and exendin 4 (Ex4).

49. The in vitro cell culture of paragraph 45, wherein said medium is CMRL.

50. A method of producing human pancreatic islet hormone-expressing cells, said method comprising the steps of obtaining a cell population comprising human endocrine precursor cells, said human endocrine precursor cells being multipotent cells that can differentiate into human pancreatic islet hormone-expressing cells; and incubating said human endocrine precursor cells in a culture medium for a sufficient time to permit human pancreatic islet hormone-expressing cells to form, wherein said sufficient time for human pancreatic islet hormone-expressing cells to form has been determined by detecting the presence of human pancreatic islet hormone-expressing cells in said cell population.

51. The method of paragraph 50, wherein at least about 2% of said human cells in said cell population differentiate into human pancreatic islet hormone-expressing cells.

52. The method of paragraph 50, wherein at least about 5% of said human cells in said cell population differentiate into human pancreatic islet hormone-expressing cells.

53. The method of paragraph 50, wherein at least about 10% of said human cells in said cell population differentiate into human pancreatic islet hormone-expressing cells.

54. The method of paragraph 50 further comprising providing said human pancreatic endocrine cells with a factor selected from the group consisting of nicotinamide (NIC), exendin 4 (Ex4), hepatocyte growth factor (HGF), insulin-like growth factor-1 (IGF1) and combinations thereof in an amount sufficient to further promote differentiation of said human endocrine precursor cells to human pancreatic islet hormone-expressing cells, wherein said human pancreatic islet hormone-expressing cells express at least one pancreatic hormone selected from the group consisting of insulin, somatostatin and glucagon.

55. The method of paragraph 54, wherein said factor is selected from the group consisting of Ex4, HGF and IGF1.

56. The method of paragraph 54, wherein Ex4 is provided to said cell population of endocrine precursor cells at a concentration ranging from about 10 ng/ml to about 100 ng/ml.

57. The method of paragraph 54, wherein Ex4 is provided to said cell population of endocrine precursor cells at a concentration of about 40 ng/ml.

58. The method of paragraph 54, wherein said factor is IGF1.

59. The method of paragraph 58, wherein IGF1 is provided to said cell population of endocrine precursor cells at a concentration ranging from about 10 ng/ml to about 1000 ng/ml.

60. The method of paragraph 58, wherein IGF1 is provided to said cell population of endocrine precursor cells at a concentration ranging from about 10 ng/ml to about 100 ng/ml.

61. The method of paragraph 58, wherein IGF1 is provided to said cell population of endocrine precursor cells at a concentration ranging from about 25 ng/ml to about 75 ng/ml.

62. The method of paragraph 58, wherein IGF1 is provided to said cell population of endocrine precursor cells at a concentration of about 50 ng/ml.

63. The method of paragraph 50, wherein detecting the presence of human pancreatic islet hormone-expressing cells in said cell population comprises detecting the expression of at least one marker selected from the group consisting of pancreatic duodenal homeobox 1 (PDX1), ghrelin (GHRL), islet amyloid polypeptide (IAPP), pancreatic polypeptide (PP), ISL1 transcription factor (ISL1), NKX6 transcription factor related locus 1 (NKX6.1) and paired box 6 (PAX6) in cells of said cell population.

64. The method of paragraph 63, wherein the expression of at least one of said markers is determined by Q-PCR.

65. The method of paragraph 63, wherein the expression of at least one of said markers is determined by immunocytochemistry.

66. The method of paragraph 50, wherein the step of obtaining a cell population comprising human endocrine precursor cells comprises the steps of obtaining a population of human PDX1-positive pancreatic endoderm cells, said human PDX1-positive pancreatic endoderm cells being multipotent cells that can differentiate into cells, tissues or organs derived from the anterior portion of the gut tube; and providing said population of human PDX1-positive pancreatic endoderm cells with a gamma secretase inhibitor, thereby producing a population of human endocrine precursor cells.

67. The method of paragraph 66, wherein said gamma secretase inhibitor comprises N—[N-(3,5-difluorophenacetyl)-L-alanyl]-S-phenylglycine t-butyl ester (DAPT).

68. The method of paragraph 67, wherein DAPT is provided to said population of human PDX1-positive pancreatic endoderm cells at a concentration ranging from about 1 µM to about 10 µM.

69. The method of paragraph 67, wherein DAPT is provided to said population of human PDX1-positive pancreatic endoderm cells at a concentration of about 3 µM.

70. The method of paragraph 66 further comprising providing said population of human PDX1-positive pancreatic endoderm cells with exendin 4 (Ex4).

71. The method of paragraph 70, wherein Ex4 is provided to said population of human PDX1-positive pancreatic endoderm cells at a concentration ranging from about 10 ng/ml to about 100 ng/ml.

72. The method of paragraph 70, wherein Ex4 is provided to said population of human PDX1-positive pancreatic endoderm cells at a concentration of about 40 ng/ml.

73. The method of paragraph 70, wherein the step of obtaining a population of human PDX1-positive pancreatic endoderm cells comprises the steps of obtaining a population of human foregut endoderm cells, said human foregut endoderm cells being PDX1-negative multipotent cells that can differentiate into cells, tissues or organs derived from the anterior portion of the gut tube; and providing said population of human foregut endoderm cells with a retinoid, thereby producing a population of human PDX1-positive pancreatic endoderm cells.

74. The method of paragraph 73, wherein said retinoid is retinoic acid (RA)

75. The method of paragraph 74, wherein RA is provided to said population of human foregut endoderm cells at a concentration ranging from about 1 nM to about 10 µM 76. The method of paragraph 73, wherein the step of obtaining a population of human foregut endoderm cells comprises the steps of obtaining a population of human definitive endoderm cells, said human definitive endoderm cells being multipotent cells that can differentiate into cells of the gut tube or organs derived therefrom; and providing said population of human definitive endoderm cells with fibroblast growth factor 10 (FGF-10) and a hedgehog pathway inhibitor, thereby producing a population of human foregut endoderm cells.

77. The method of paragraph 76 further comprising withdrawing any growth factor of the TGF-β superfamily that may be present in said population of definitive endoderm cells.

78. The method of paragraph 77, wherein said growth factor of the TGF-β superfamily is selected from the group consisting of Nodal, activin A, activin B and combinations thereof.

79. The method of paragraph 77, wherein said growth factor of the TGF-β superfamily is activin A.

80. The method of paragraph 76, wherein said hedgehog inhibitor comprises KAAD-cyclopamine.

81. The method of paragraph 80, wherein KAAD-cyclopamine is provided to said population of human definitive endoderm cells at a concentration ranging from about 0.01 μM to about 1 μM.

82. The method of paragraph 80, wherein KAAD-cyclopamine is provided to said population of human definitive endoderm cells at a concentration of about 0.2 μM.

83. The method of paragraph 76, wherein FGF-10 is provided to said population of human definitive endoderm cells at a concentration ranging from about 1 ng/ml to about 1000 ng/ml.

84. The method of paragraph 76, wherein FGF-10 is provided to said population of human definitive endoderm cells at a concentration ranging from about 10 ng/ml to about 100 ng/ml.

85. The method of paragraph 76, wherein FGF-10 is provided to said population of human definitive endoderm cells at a concentration of about 50 ng/ml.

86. The method of paragraph 76, wherein the step of obtaining a population of human definitive endoderm cells comprises the steps of obtaining a population of pluripotent human embryonic stem cells; and providing said population of pluripotent human embryonic stem cells with at least one growth factor of the TGF-β superfamily.

87. The method of paragraph 86, wherein said at least one growth factor is Nodal.

88. The method of paragraph 86, wherein said at least one growth factor is activin A.

89. The method of paragraph 86, wherein said at least one growth factor is activin B.

90. The method of paragraph 86 further comprising providing said population of pluripotent human embryonic stem cells with wingless-type MMTV integration site family member 3A (Wnt3A).

91. The method of paragraph 86, wherein a plurality of growth factors of the TGFβ superfamily is provided.

92. The method of paragraph 91, wherein Wnt3A is also provided.

93. The method of paragraph 86, wherein said at least one growth factor is provided in a concentration of at least about 10 ng/ml.

94. The method of paragraph 86, wherein said at least one growth factor is provided in a concentration of at least about 100 ng/ml.

95. The method of paragraph 86, wherein said at least one growth factor is provided in a concentration of at least about 500 ng/ml.

96. The method of paragraph 86, wherein said at least one growth factor is provided in a concentration of at least about 1000 ng/ml.

97. The method of paragraph 86, wherein said at least one growth factor is provided in a concentration of at least about 5000 ng/ml.

98. The method of paragraph 86, wherein said pluripotent human embryonic stem cells are differentiated to human definitive endoderm cells in a medium comprising less than about 2% serum.

99. The method of paragraph 86, wherein said pluripotent human embryonic stem cells are derived from a tissue selected from the group consisting of the morula, the ICM of an embryo and the gonadal ridges of an embryo.

100. A human pancreatic islet hormone-expressing cell produced by the method of paragraph 86.

101. A method of producing human pancreatic islet hormone-expressing cells, said method comprising the steps of: (a) obtaining a population of pluripotent human embryonic stem cells; (b) providing said population of pluripotent human embryonic stem cells with at least one growth factor of the TGF-β superfamily, thereby producing a population of human definitive endoderm cells; (c) providing said population of human definitive endoderm cells with at least one fibroblast growth factor, thereby producing a population of human foregut endoderm cells; (d) providing said population of human foregut endoderm cells with a retinoid, thereby producing a population of human PDX1-positive pancreatic endoderm cells; (e) providing said population of human PDX1-positive pancreatic endoderm cells with a gamma secretase inhibitor, thereby producing a population comprising human endocrine precursor cells; and (f) incubating said population of human endocrine precursor cells in a culture medium for a sufficient time to permit human pancreatic islet hormone-expressing cells to form.

102. The method of paragraph 101, wherein step (b) further comprises providing a hedgehog pathway inhibitor.

103. The method of paragraph 101, wherein said fibroblast growth factor is selected from the group consisting of FGF1, FGF2, FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, FGF22 and FGF23.

104. The method of paragraph 101, wherein said fibroblast growth factor comprises FGF10.

105. The method of paragraph 101, wherein step (d) further comprises providing insulin or an insulin-like growth factor.

106. The method of paragraph 101 further comprising substantially withdrawing said at least one growth factor of the TGF-β superfamily.

107. The method of paragraph 101, wherein said retinoid and said gamma secretase are provided at about the same time.

108. The method of paragraph 101, wherein said foregut endoderm cells are competent to further differentiate into pancreatic cells.

109. A method of producing human pancreatic islet hormone-expressing cells, said method comprising the steps of: (a) obtaining a population of pluripotent human embryonic stem cells; (b) providing said population of pluripotent human embryonic stem cells with at least one growth factor of the TGF-β superfamily, thereby producing a population of human definitive endoderm cells; (c) providing said population of human definitive endoderm cells with a retinoid, thereby producing a population of human PDX1-positive pancreatic endoderm cells; and (d) incubating said population of human PDX1-positive pancreatic endoderm cells in the presence of a retinoid for a sufficient time to permit human pancreatic islet hormone-expressing cells to form.

110. The method of paragraph 109 further comprising the step of providing said population of human definitive endoderm cells with a fibroblast family growth factor.

111. The method of paragraph 110, wherein said fibroblast family growth factor comprises FGF10 or FGF7.

112. The method of paragraph 109, further comprising the step of providing said population of human definitive endoderm cells with a hedgehog pathway inhibitor.

113. The method of paragraph 112, wherein said hedgehog pathway inhibitor is KAAD-cyclopamine.

114. The method of paragraph 109, wherein said retinoid is retinoic acid.

115. The method of paragraph 109, further comprising the step of providing said population of human PDX1-positive pancreatic endoderm cells with a gamma secretase inhibitor.

116. The method of paragraph 115, wherein the gamma secretase inhibitor comprises N—[N-(3,5-difluorophenacetyl)-L-alanyl]-S-phenylglycine t-butyl ester (DAPT).

117. A method for producing a cell population enriched in human endocrine precursor cells, said method comprising the steps of providing a cell population comprising human endocrine precursor cells with a reagent that binds to neural cell adhesion molecule (NCAM), and separating human endocrine precursor cells bound to said reagent from cells that are not bound to said reagent, thereby producing a cell population enriched in human endocrine precursor cells.

118. The method of paragraph 117, wherein said human endocrine precursor cells are derived in vitro from human pluripotent cells.

119. The method of paragraph 117, wherein said human endocrine precursor cells express Neurogenin 3 (NGN3) and do not substantially express at least one marker selected from the group consisting of AFP, SOX7, SOX1, ZIC1, NFM, insulin (INS), glucagon (GCG), somatostatin (SST) and ghrelin (GHRL).

120. The method of paragraph 119, wherein said human endocrine precursor cells express paired box gene 4 (PAX4).

121. The method of paragraph 119, wherein said human endocrine precursor cells do not substantially express Paired Box 6 transcription factor (PAX6).

122. The method of paragraph 117, wherein said reagent comprises a molecule selected from the group consisting of an anti-NCAM antibody, an anti-NCAM antibody fragment and an NCAM ligand.

123. The method of paragraph 122, wherein said NCAM ligand is NCAM Binding Protein 10 (NBP10).

124. The method of paragraph 122, wherein said anti-NCAM antibody is labeled.

125. The method of paragraph 124, wherein said anti-NCAM antibody is fluorescently labeled.

126. The method of paragraph 117 further comprising providing said cell population and said reagent with a secondary reagent that binds to said reagent.

127. The method of paragraph 126, wherein said reagent comprises and anti-NCAM antibody and wherein said secondary reagent is fluorescently labeled.

128. The method of paragraph 125 or paragraph 127, wherein said separating step comprises using fluorescence activated cell sorting (FACS) to separate said endocrine precursor cells bound to said anti-NCAM antibodies from said cells that are not bound to said anti-NCAM antibodies.

129. The method of paragraph 117 further comprising the step of disaggregating said cells in said cell population comprising human endocrine precursor cells prior to providing said cell population with said reagent that binds to NCAM.

130. The method of paragraph 117 further comprising the steps of obtaining a cell population comprising a population of human PDX1-positive pancreatic endoderm cells, said human PDX1-positive pancreatic endoderm cells being multipotent cells that can differentiate into cells, tissues or organs derived from the anterior portion of the gut tube and providing said population of human PDX1-positive pancreatic endoderm cells with a gamma secretase inhibitor, thereby producing a population of human endocrine precursor cells.

131. The method of paragraph 130, wherein said gamma secretase inhibitor comprises N—[N-(3,5,-difluorophenacetyl)-L-alanyl]-S-phenylglycine t-butyl ester (DAPT).

132. The method of paragraph 131, wherein said DAPT is provided to said population of human PDX1-positive pancreatic endoderm cells at a concentration ranging from about 1 µM to about 10 µM.

133. The method of paragraph 131, wherein said DAPT is provided to said population of human PDX1-positive pancreatic endoderm cells at a concentration of about 3 µM.

134. The method of paragraph 130, further comprising providing said population of human PDX1-positive pancreatic endoderm cells with exendin 4 (Ex4).

135. The method of paragraph 134, wherein said Ex4 is provided to said population of human PDX1-positive pancreatic endoderm cells at a concentration ranging from about 10 ng/ml to about 100 ng/ml.

136. The method of paragraph 134, wherein said Ex4 is provided to said population of human PDX1-positive pancreatic endoderm cells at a concentration of about 40 ng/ml.

137. The method of paragraph 130, wherein the step of obtaining a population of human PDX1-positive pancreatic endoderm cells comprises the steps of obtaining a population of human foregut endoderm cells, said human foregut endoderm cells being PDX1-negative multipotent cells that can differentiate into cells, tissues or organs derived from the anterior portion of the gut tube and providing said population of human foregut endoderm cells with a retinoid, thereby producing a population of human PDX1-positive pancreatic endoderm cells.

138. The method of paragraph 137, wherein said retinoid is retinoic acid (RA).

139. The method of paragraph 138, wherein RA is provided to said population of human foregut endoderm cells at a concentration ranging from about 1 nM to about 10 µM.

140. The method of paragraph 137, wherein the step of obtaining a population of human foregut endoderm cells comprises the steps of obtaining a population of human definitive endoderm cells, said human definitive endoderm cells being multipotent cells that can differentiate into cells of the gut tube or organs derived therefrom and providing said population of human definitive endoderm cells with fibroblast growth factor 10 (FGF-10) and a hedgehog pathway inhibitor, thereby producing a population of human foregut endoderm cells.

141. The method of paragraph 140, further comprising withdrawing an exogenously added factor of the TGF-β superfamily that may be present in said population of definitive endoderm cells.

142. The method of paragraph 141, wherein said growth factor of the TGF-β superfamily is selected from the group consisting of Nodal, activin A, activin B and combinations thereof.

143. The method of paragraph 142, wherein said growth factor of the TGF-β superfamily is activin A.

144. The method of paragraph 140, wherein said hedgehog inhibitor comprises KAAD-cyclopamine.

145. The method of paragraph 144, wherein KAAD-cyclopamine is provided to said population of human definitive endoderm cells at a concentration ranging from about 0.01 µM to about 1 µM.

146. The method of paragraph 145, wherein KAAD-cyclopamine is provided to said population of human definitive endoderm cells at a concentration of about 0.2 μM.

147. The method of paragraph 140, wherein FGF-10 is provided to said population of human definitive endoderm cells at a concentration ranging from about 10 ng/ml to about 1000 ng/ml.

148. The method of paragraph 140, wherein FGF-10 is provided to said population of human definitive endoderm cells at a concentration ranging from about 1 ng/ml to about 100 ng/ml.

149. The method of paragraph 140, wherein FGF-10 is provided to said population of human definitive endoderm cells at a concentration of about 50 ng/ml.

150. The method of paragraph 140, wherein the step of obtaining a population of human definitive endoderm cells comprises the steps of obtaining a population of human pluripotent cells and providing said population of human pluripotent cells with at least one growth factor of the TGF-β superfamily.

151. The method of paragraph 150, wherein said at least one growth factor is Nodal.

152. The method of paragraph 150, wherein said at least one growth factor is activin A.

153. The method of paragraph 150, wherein said at least one growth factor is activin B.

154. The method of paragraph 150 further comprising providing said population of human pluripotent cells with wingless-type MMTV integration site family member 3A (Wnt3A).

155. The method of paragraph 150, wherein a plurality of growth factors of the TGFβ superfamily is provided.

156. The method of paragraph 155, wherein Wnt3A is also provided.

157. The method of paragraph 150, wherein said at least one growth factor is provided in a concentration of at least about 10 ng/ml.

158. The method of paragraph 150, wherein said at least one growth factor is provided in a concentration of at least about 100 ng/ml.

159. The method of paragraph 150, wherein said at least one growth factor is provided in a concentration of at least about 500 ng/ml.

160. The method of paragraph 150, wherein said at least one growth factor is provided in a concentration of at least about 1000 ng/ml.

161. The method of paragraph 150, wherein said at least one growth factor is provided in a concentration of at least about 5000 ng/ml.

162. The method of paragraph 150, wherein said human pluripotent cells are differentiated to human definitive endoderm cells in a medium comprising less than about 2% serum.

163. The method of paragraph 150, wherein said human pluripotent cells are human embryonic stem cells derived from a tissue selected from the group consisting of the morula, the ICM of an embryo and the gonadal ridges of an embryo.

164. An enriched, in vitro human endocrine precursor cell population, wherein said human endocrine precursor cells express NGN3 and do not substantially express at least one marker selected from the group consisting of AFP, SOX7, SOX1, ZIC1, NFM, INS, GCG, SST and GHRL.

165. The enriched, in vitro human endocrine precursor cell population of paragraph 164, wherein said cell population is derived in vitro from human pluripotent cells.

166. The enriched, in vitro human endocrine precursor cell population of paragraph 164, wherein said enriched human endocrine precursor cell population is produced by the method of paragraph 117.

167. The enriched, in vitro human endocrine precursor cell population of paragraph 164, wherein said enriched human endocrine precursor cell population is produced by the method of paragraph 150.

168. The enriched, in vitro human endocrine precursor cell population of paragraph 164, wherein at least about 5% of said enriched human cell population comprises human endocrine precursor cells that express neurogenin 3 (NGN3) and do not substantially express at least one marker selected from the group consisting of AFP, SOX7, SOX1, ZIC1 NFM, INS, GCG, SST and GHRL.

169. The enriched, in vitro human endocrine precursor cell population of paragraph 168, wherein said human endocrine precursor cells express PAX4.

170. The enriched, in vitro human endocrine precursor cell population of paragraph 164, wherein said endocrine precursor cells are derived in vitro from human PDX1-positive pancreatic endoderm.

171. The enriched, in vitro human endocrine precursor cell population of paragraph 170, wherein said human PDX1-positive pancreatic endoderm cells are derived in vitro from human foregut endoderm cells.

172. The enriched, in vitro human endocrine precursor cell population of paragraph 171, wherein said human foregut endoderm cells are derived in vitro from definitive endoderm cells.

173. The enriched, in vitro human endocrine precursor cell population of paragraph 172, wherein said definitive endoderm cells are derived in vitro from human embryonic stem cells (hESCs).

174. A method for producing a cell population enriched in human immature pancreatic islet hormone-expressing cells, said method comprising the steps of providing a cell population comprising human immature pancreatic islet hormone-expressing cells with a reagent that binds to neural cell adhesion molecule (NCAM) and separating human immature pancreatic islet hormone-expressing cells bound to said reagent from cells that are not bound to said reagent, thereby producing a cell population enriched in human immature pancreatic islet hormone-expressing cells.

175. The method of paragraph 174, wherein said human immature pancreatic islet hormone-expressing cells are derived in vitro from human pluripotent cells.

176. The method of paragraph 174, wherein said human immature pancreatic islet hormone-expressing cells express MAFB and do not substantially express a marker selected from the group consisting of NGN3 and MAFA.

177. The method of paragraph 176, wherein said human immature pancreatic islet hormone-expressing cells do not substantially express at least one marker selected from the group consisting of MOX1, CER, POU5F1, AFP, SOX7, SOX1, ZIC1 and NFM.

178. The method of paragraph 176, wherein said human immature pancreatic islet hormone-expressing cells express at least one marker selected from the group consisting of Synaptophysin (SYP), Chromogranin A (CHGA), NKX2.2, Islet 1 (ISL1), Paired Box Gene 6 (PAX6), and Neurogenic Differentiation 1 (NEUROD), PDX1 and HB9.

179. The method of paragraph 174, wherein said human immature pancreatic islet hormone-expressing cells process less than about 98% of the insulin produced by said immature pancreatic islet hormone-expressing cells.

180. The method of paragraph 174, wherein said human immature pancreatic islet hormone-expressing cells process less than about 70% of the insulin produced by said immature pancreatic islet hormone-expressing cells.

181. The method of paragraph 179 or paragraph 180, wherein said insulin processing is measured by C-peptide release.

182. The method of paragraph 174, wherein said reagent comprises a molecule selected from the group consisting of an anti-NCAM antibody, an anti-NCAM antibody fragment and an NCAM ligand.

183. The method of paragraph 182, wherein said NCAM ligand is NCAM Binding Protein 10 (NBP10).

184. The method of paragraph 182, wherein said anti-NCAM antibody is labeled.

185. The method of paragraph 184, wherein said anti-NCAM antibody is fluorescently labeled.

186. The method of paragraph 174, further comprising providing said cell population with a secondary reagent that binds to said reagent.

187. The method of paragraph 186 wherein said reagent comprises and anti-NCAM antibody and wherein said secondary reagent that binds to said anti-NCAM antibody is fluorescently labeled.

188. The method of paragraph 185 or paragraph 187, wherein said separating step comprises using fluorescence activated cell sorting (FACS) to separate said human immature pancreatic islet hormone-expressing cells bound to said anti-NCAM antibody from said cells that are not bound to said anti-NCAM antibody.

189. The method of paragraph 174 further comprising the step of providing said human immature pancreatic islet hormone-expressing cells with a second reagent that binds to CD133, and separating said human immature pancreatic islet hormone-expressing cells from cells that are bound to said second reagent.

190. The method of paragraph 174 further comprising the step of dissociating said cell population prior to providing said cell population with said reagent that binds NCAM.

191. The method of paragraph 174 further comprising obtaining a cell population comprising human endocrine precursor cells being multipotent cells that can differentiate into human immature pancreatic islet hormone-expressing cells and incubating said human endocrine precursor cells in a culture medium for a sufficient time to permit human immature pancreatic islet hormone-expressing cells to form.

192. The method of paragraph 191 further comprising providing said human endocrine precursor cells with a factor selected from the group consisting of nicotinamide (MC), exendin 4 (Ex4), hepatocyte growth factor (HGF), insulin-like growth factor-1 (IGF1), glucose dependent insulinotropic polypeptide (GIP), nerve growth factor (NGF), vascular endothelial growth factor (VEGF) and combinations thereof in an amount sufficient to further promote differentiation of said human endocrine precursor cells to human immature pancreatic islet hormone-expressing cells.

193. The method of paragraph 192, wherein said factor is selected from the group consisting of Ex4, HGF and IGF1.

194. The method of paragraph 193, wherein said factor is Ex4.

195. The method of paragraph 194, wherein Ex4 is provided to said cell population of endocrine precursor cells at a concentration ranging from about 10 ng/ml to about 100 ng/ml.

196. The method of paragraph 194, wherein Ex4 is provided to said cell population of endocrine precursor cells at a concentration of about 40 ng/ml.

197. The method of paragraph 193, wherein said factor is IGF1.

198. The method of paragraph 197, wherein IGF1 is provided to said cell population of endocrine precursor cells at a concentration ranging from about 10 ng/ml to about 1000 ng/ml.

199. The method of paragraph 197, wherein IGF1 is provided to said cell population of endocrine precursor cells at a concentration ranging from about 10 ng/ml to about 100 ng/ml.

200. The method of paragraph 197, wherein IGF1 is provided to said cell population of endocrine precursor cells at a concentration ranging from about 25 ng/ml to about 75 ng/ml.

201. The method of paragraph 197, wherein IGF1 is provided to said cell population of endocrine precursor cells at a concentration of about 50 ng/ml.

202. The method of paragraph 191 further comprising the steps of obtaining a cell population comprising a population of human PDX1-positive pancreatic endoderm cells, said human PDX1-positive pancreatic endoderm cells being multipotent cells that can differentiate into cells, tissues or organs derived from the anterior portion of the gut tube and providing said population of human PDX1-positive pancreatic endoderm cells with a gamma secretase inhibitor, thereby producing a population of human endocrine precursor cells.

203. The method of paragraph 202, wherein said gamma secretase inhibitor comprises N—[N-(3,5,-difluorophenacetyl)-L-alanyl]-S-phenylglycine t-butyl ester (DAPT).

204. The method of paragraph 203, wherein said DAPT is provided to said population of human PDX1-positive pancreatic endoderm cells at a concentration ranging from about 1 µM to about 10 µM.

205. The method of paragraph 203, wherein said DAPT is provided to said population of human PDX1-positive pancreatic endoderm cells at a concentration of about 3 µM.

206. The method of paragraph 202, further comprising providing said population of human PDX1-positive pancreatic endoderm cells with exendin 4 (Ex4).

207. The method of paragraph 206, wherein said Ex4 is provided to said population of human PDX1-positive pancreatic endoderm cells at a concentration ranging from about 10 ng/ml to about 100 ng/ml.

208. The method of paragraph 206, wherein said Ex4 is provided to said population of human PDX1-positive pancreatic endoderm cells at a concentration of about 40 ng/ml.

209. The method of paragraph 202, wherein the step of obtaining a population of human PDX1-positive pancreatic endoderm cells comprises the steps of obtaining a population of human foregut endoderm cells, said human foregut endoderm cells being PDX1-negative multipotent cells that can differentiate into cells, tissues or organs derived from the anterior portion of the gut tube and providing said population of human foregut endoderm cells with a retinoid, thereby producing a population of human PDX1-positive pancreatic endoderm cells.

210. The method of paragraph 209, wherein said retinoid is retinoic acid (RA).

211. The method of paragraph 210, wherein RA is provided to said population of human foregut endoderm cells at a concentration ranging from about 1 nM to about 10 µM.

212. The method of paragraph 209, wherein the step of obtaining a population of human foregut endoderm cells comprises the steps of obtaining a population of human definitive endoderm cells, said human definitive endoderm cells being multipotent cells that can differentiate into cells of the gut tube or organs derived therefrom and providing said population of human definitive endoderm cells with fibroblast growth factor 10 (FGF-10) and a hedgehog pathway inhibitor, thereby producing a population of human foregut endoderm cells.

213. The method of paragraph 212 further comprising withdrawing an exogenously added factor of the TGF-β superfamily that may be present in said population of definitive endoderm cells.

214. The method of paragraph 213, wherein said growth factor of the TGF-β superfamily is selected from the group consisting of Nodal, activin A, activin B and combinations thereof.

215. The method of paragraph 214, wherein said growth factor of the TGF-β superfamily is activin A.

216. The method of paragraph 212, wherein said hedgehog inhibitor comprises KAAD-cyclopamine.

217. The method of paragraph 216, wherein KAAD-cyclopamine is provided to said population of human definitive endoderm cells at a concentration ranging from about 0.01 µM to about 1 µM.

218. The method of paragraph 216, wherein KAAD-cyclopamine is provided to said population of human definitive endoderm cells at a concentration of about 0.2 µM.

219. The method of paragraph 212, wherein FGF-10 is provided to said population of human definitive endoderm cells at a concentration ranging from about 1 ng/ml to about 1000 ng/ml.

220. The method of paragraph 212, wherein FGF-10 is provided to said population of human definitive endoderm cells at a concentration ranging from about 10 ng/ml to about 100 ng/ml.

221. The method of paragraph 212, wherein FGF-10 is provided to said population of human definitive endoderm cells at a concentration of about 50 ng/ml.

222. The method of paragraph 212, wherein the step of obtaining a population of human definitive endoderm cells comprises the steps of obtaining a population of human pluripotent cells and providing said population of human pluripotent cells with at least one growth factor of the TGF-β superfamily.

223. The method of paragraph 222, wherein said at least one growth factor is Nodal.

224. The method of paragraph 222, wherein said at least one growth factor is activin A.

225. The method of paragraph 222, wherein said at least one growth factor is activin B.

226. The method of paragraph 222 further comprising providing said population of human pluripotent cells with wingless-type MMTV integration site family member 3A (Wnt3A).

227. The method of paragraph 222, wherein a plurality of growth factors of the TGFβ superfamily is provided.

228. The method of paragraph 227, wherein Wnt3A is also provided.

229. The method of paragraph 222, wherein said at least one growth factor is provided in a concentration of at least about 10 ng/ml.

230. The method of paragraph 222, wherein said at least one growth factor is provided in a concentration of at least about 100 ng/ml.

231. The method of paragraph 222, wherein said at least one growth factor is provided in a concentration of at least about 500 ng/ml.

232. The method of paragraph 222, wherein said at least one growth factor is provided in a concentration of at least about 1000 ng/ml.

233. The method of paragraph 222, wherein said at least one growth factor is provided in a concentration of at least about 5000 ng/ml.

234. The method of paragraph 222, wherein said human pluripotent cells are differentiated to human definitive endoderm cells in a medium comprising less than about 2% serum.

235. The method of paragraph 222, wherein said human pluripotent cells are human embryonic stem cells derived from a tissue selected from the group consisting of the morula, the ICM of an embryo and the gonadal ridges of an embryo.

236. An enriched, in vitro human immature pancreatic islet hormone-expressing cell population, wherein said human immature pancreatic islet hormone-expressing cells express MAFB and do not substantially express NGN3 and MAFA 237. The enriched, in vitro human immature pancreatic islet hormone-expressing cell population of paragraph 236, wherein the enriched cell population is derived in vitro from human pluripotent cells.

238. The enriched, in vitro human immature pancreatic islet hormone-expressing cell population of paragraph 236, wherein said enriched cell population is produced by the method of paragraph 174.

239. The enriched, in vitro human immature pancreatic islet hormone-expressing cell population of paragraph 236, wherein said enriched cell population is produced by the method of paragraph 222.

240. The enriched, in vitro human immature pancreatic islet hormone-expressing cell population of paragraph 238 or paragraph 239, wherein at least about 25% of said enriched human cell population comprises human immature pancreatic islet hormone-expressing cells that express MAFB and do not substantially express NGN3 and MAFA.

241. The enriched, in vitro human immature pancreatic islet hormone-expressing cell population of paragraph 238 or paragraph 239, wherein at least about 50% of said enriched human cell population comprises human immature pancreatic islet hormone-expressing cells that express MAFB and do not substantially express NGN3 and MAFA.

242. The enriched, in vitro human immature pancreatic islet hormone-expressing cell population of paragraph 238 or paragraph 239, wherein at least about 70% of said enriched human cell population comprises human immature pancreatic islet hormone-expressing cells that express MAFB and do not substantially express NGN3 and MAFA.

243. The enriched, in vitro human immature pancreatic islet hormone-expressing cell population of paragraph 238 or paragraph 239, wherein at least about 90% of said enriched human cell population comprises human immature pancreatic islet hormone-expressing cells that express MAFB and do not substantially express NGN3 and MAFA.

244. The enriched, in vitro human immature pancreatic islet hormone-expressing cell population of paragraph 236, wherein at least about 25% of said enriched human cell population comprises human immature pancreatic islet hormone-expressing cells that express MAFB and do not substantially express NGN3 and MAFA.

245. The enriched, in vitro human immature pancreatic islet hormone-expressing cell population of paragraph 236, wherein at least about 50% of said enriched human cell population comprises human immature pancreatic islet hormone-expressing cells that express MAFB and do not substantially express NGN3 and MAFA.

246. The enriched, in vitro human immature pancreatic islet hormone-expressing cell population of paragraph 236, wherein at least about 70% of said enriched human cell population comprises human immature pancreatic islet hormone-expressing cells that express MAFB and do not substantially express NGN3 and MAFA.

247. The enriched, in vitro human immature pancreatic islet hormone-expressing cell population of paragraph 236, wherein at least about 90% of said enriched human cell population comprises human immature pancreatic islet hormone-expressing cells that express MAFB and do not substantially express NGN3 and MAFA.

248. The enriched, in vitro human immature pancreatic islet hormone-expressing cell population of paragraph 236, wherein said human immature pancreatic islet hormone-expressing cells do not substantially express at least one marker selected from the group consisting of elected from the group consisting of MOX1, CER, POU5F1, AFP, SOX7, SOX1, ZIC1 and NFM.

249. The enriched, in vitro human immature pancreatic islet hormone-expressing cell population of paragraph 236, wherein said human immature pancreatic islet hormone-expressing cells express at least one marker selected from the group consisting of Synaptophysin (SYP), Chromogranin A (CHGA), NKX2.2, Islet 1 (ISL1), Paired Box Gene 6 (PAX6), Neurogenic Differentiation 1 (NEUROD), PDX1 and HB9.

250. The enriched, in vitro human immature pancreatic islet hormone-expressing cell population of paragraph 236, wherein said human immature pancreatic islet hormone-expressing cells process less than about 98% of the insulin produced by said immature pancreatic islet hormone-expressing cells.

251. The enriched, in vitro human immature pancreatic islet hormone-expressing cell population of paragraph 236, wherein said human immature pancreatic islet hormone-expressing cells process less than about 70% of the insulin produced by said immature pancreatic islet hormone-expressing cells.

252. The enriched, in vitro human immature pancreatic islet hormone-expressing cell population of paragraph 250 or paragraph 251, wherein said insulin processing is measured by C-peptide release.

253. A method for producing a cell population enriched in human pancreatic islet hormone-expressing cells, said pancreatic hormone-expressing cells being derived in vitro from human pluripotent cells, said method comprising the steps of providing a cell population comprising human pancreatic islet hormone-expressing cells with a reagent that binds to neural cell adhesion molecule (NCAM) and separating human endocrine precursor cells bound to said reagent from cells that are not bound to said reagent, thereby producing a cell population enriched in human pancreatic islet hormone-expressing cells.

254. The method of paragraph 253, wherein said reagent comprises a molecule selected from the group consisting of an anti-NCAM antibody, an anti-NCAM antibody fragment and an NCAM ligand.

255. The method of paragraph 254, wherein said NCAM ligand is NCAM Binding Protein 10 (NBP10).

256. The method of paragraph 254, wherein said anti-NCAM antibody is labeled.

257. The method of paragraph 256, wherein said anti-NCAM antibody is fluorescently labeled.

258. The method of paragraph 254 further comprising providing said cell population with a secondary reagent that binds to said reagent.

259. The method of paragraph 258, wherein said reagent comprises and anti-NCAM antibody and wherein said secondary reagent that binds to said anti-NCAM antibody is fluorescently labeled.

260. The method of paragraph 257 or paragraph 259, wherein said separating step comprises using fluorescence activated cell sorting (FACS) to separate said pancreatic islet hormone-expressing cells bound to said anti-NCAM antibody from said cells that are not bound to said anti-NCAM antibody.

261. The method of paragraph 253 further comprising the step of providing said human immature pancreatic islet hormone-expressing cells with a second reagent that binds to CD133, and separating said human immature pancreatic islet hormone-expressing cells from cells that are bound to said second reagent.

262. The method of paragraph 253 further comprising the step of dissociating said cell population prior to providing said cell population with said reagent that binds NCAM.

263. The method of paragraph 253 further comprising obtaining a cell population comprising human endocrine precursor cells being multipotent cells that can differentiate into human pancreatic islet hormone-expressing cells and incubating said human endocrine precursor cells in a culture medium for a sufficient time to permit human pancreatic islet hormone-expressing cells to form.

264. The method of paragraph 263 further comprising providing said human pancreatic endocrine cells with a factor selected from the group consisting of nicotinamide (MC), exendin 4 (Ex4), hepatocyte growth factor (HGF), insulin-like growth factor-1 (IGF1), glucose dependent inslulinotropic polypeptide (GIP), nerve growth factor (NGF), vascular endothelial growth factor (VEGF) and combinations thereof in an amount sufficient to further promote differentiation of said human endocrine precursor cells to human pancreatic islet hormone-expressing cells, wherein said human pancreatic islet hormone-expressing cells express at least one pancreatic hormone selected from the group consisting of insulin, somatostatin and glucagon.

265. The method of paragraph 264, wherein said factor is selected from the group consisting of Ex4, HGF and IGF1.

266. The method of paragraph 265, wherein said factor is Ex4.

267. The method of paragraph 266, wherein Ex4 is provided to said cell population of endocrine precursor cells at a concentration ranging from about 10 ng/ml to about 100 ng/ml.

268. The method of paragraph 266, wherein Ex4 is provided to said cell population of endocrine precursor cells at a concentration of about 40 ng/ml.

269. The method of paragraph 265, wherein said factor is IGF1.

270. The method of paragraph 269 wherein IGF1 is provided to said cell population of endocrine precursor cells at a concentration ranging from about 10 ng/ml to about 1000 ng/ml.

271. The method of paragraph 269, wherein IGF1 is provided to said cell population of endocrine precursor cells at a concentration ranging from about 10 ng/ml to about 100 ng/ml.

272. The method of paragraph 269, wherein IGF1 is provided to said cell population of endocrine precursor cells at a concentration ranging from about 25 ng/ml to about 75 ng/ml.

273. The method of paragraph 269, wherein IGF1 is provided to said cell population of endocrine precursor cells at a concentration of about 50 ng/ml.

274. The method of paragraph 263 further comprising the steps of obtaining a cell population comprising a population of human PDX1-positive pancreatic endoderm cells, said human PDX1-positive pancreatic endoderm cells being multipotent cells that can differentiate into cells, tissues or organs derived from the anterior portion of the gut tube and providing said population of human PDX1-positive pancreatic endoderm cells with a gamma secretase inhibitor, thereby producing a population of human endocrine precursor cells.

275. The method of paragraph 274, wherein said gamma secretase inhibitor comprises N—[N-(3,5,-difluorophenacetyl)-L-alanyl]-S-phenylglycine t-butyl ester (DAPT).

276. The method of paragraph 275, wherein said DAPT is provided to said population of human PDX1-positive pancreatic endoderm cells at a concentration ranging from about 1 μM to about 10 μM.

277. The method of paragraph 275, wherein said DAPT is provided to said population of human PDX1-positive pancreatic endoderm cells at a concentration of about 3 μM.

278. The method of paragraph 274 further comprising providing said population of human PDX1-positive pancreatic endoderm cells with exendin 4 (Ex4).

279. The method of paragraph 278, wherein said Ex4 is provided to said population of human PDX1-positive pancreatic endoderm cells at a concentration ranging from about 10 ng/ml to about 100 ng/ml.

280. The method of paragraph 278, wherein said Ex4 is provided to said population of human PDX1-positive pancreatic endoderm cells at a concentration of about 40 ng/ml.

281. The method of paragraph 274, wherein the step of obtaining a population of human PDX1-positive pancreatic endoderm cells comprises the steps of obtaining a population of human foregut endoderm cells, said human foregut endoderm cells being PDX1-negative multipotent cells that can differentiate into cells, tissues or organs derived from the anterior portion of the gut tube and providing said population of human foregut endoderm cells with a retinoid, thereby producing a population of human PDX1-positive pancreatic endoderm cells.

282. The method of paragraph 281, wherein said retinoid is retinoic acid (RA).

283. The method of paragraph 282, wherein RA is provided to said population of human foregut endoderm cells at a concentration ranging from about 1 nM to about 10 μM.

284. The method of paragraph 281, wherein the step of obtaining a population of human foregut endoderm cells comprises the steps of obtaining a population of human definitive endoderm cells, said human definitive endoderm cells being multipotent cells that can differentiate into cells of the gut tube or organs derived therefrom and providing said population of human definitive endoderm cells with fibroblast growth factor 10 (FGF-10) and a hedgehog pathway inhibitor, thereby producing a population of human foregut endoderm cells.

285 The method of paragraph 284 further comprising withdrawing an exogenously added factor of the TGF-β superfamily that may be present in said population of definitive endoderm cells.

286. The method of paragraph 285, wherein said growth factor of the TGF-β superfamily is selected from the group consisting of Nodal, activin A, activin B and combinations thereof.

287. The method of paragraph 286, wherein said growth factor of the TGF-β superfamily is activin A.

288. The method of paragraph 284, wherein said hedgehog inhibitor comprises KAAD-cyclopamine.

289. The method of paragraph 288, wherein KAAD-cyclopamine is provided to said population of human definitive endoderm cells at a concentration ranging from about 0.01 μM to about 1 μM.

290. The method of paragraph 288, wherein KAAD-cyclopamine is provided to said population of human definitive endoderm cells at a concentration of about 0.2 μM.

291. The method of paragraph 284, wherein FGF-10 is provided to said population of human definitive endoderm cells at a concentration ranging from about 1 ng/ml to about 1000 ng/ml.

292. The method of paragraph 284, wherein FGF-10 is provided to said population of human definitive endoderm cells at a concentration ranging from about 10 ng/ml to about 100 ng/ml.

293. The method of paragraph 284, wherein FGF-10 is provided to said population of human definitive endoderm cells at a concentration of about 50 ng/ml.

294. The method of paragraph 284, wherein the step of obtaining a population of human definitive endoderm cells comprises the steps of obtaining a population of human pluripotent cells and providing said population of human pluripotent cells with at least one growth factor of the TGF-β superfamily.

295. The method of paragraph 294, wherein said at least one growth factor is Nodal.

296. The method of paragraph 294, wherein said at least one growth factor is activin A.

297. The method of paragraph 294, wherein said at least one growth factor is activin B.

298. The method of paragraph 294 further comprising providing said population of human pluripotent cells with wingless-type MMTV integration site family member 3A (Wnt3A).

299. The method of paragraph 294, wherein a plurality of growth factors of the TGFβ superfamily is provided.

300. The method of paragraph 299, wherein Wnt3A is also provided.

301. The method of paragraph 294, wherein said at least one growth factor is provided in a concentration of at least about 10 ng/ml.

302. The method of paragraph 294, wherein said at least one growth factor is provided in a concentration of at least about 100 ng/ml.

303. The method of paragraph 294, wherein said at least one growth factor is provided in a concentration of at least about 500 ng/ml.

304. The method of paragraph 294, wherein said at least one growth factor is provided in a concentration of at least about 1000 ng/ml.

305. The method of paragraph 294, wherein said at least one growth factor is provided in a concentration of at least about 5000 ng/ml.

306. The method of paragraph 294, wherein said human pluripotent cells are differentiated to human definitive endoderm cells in a medium comprising less than about 2% serum.

307. The method of paragraph 294, wherein said human pluripotent cells are human embryonic stem cells derived from a tissue selected from the group consisting of the morula, the ICM of an embryo and the gonadal ridges of an embryo.

308. An enriched, in vitro human pancreatic islet hormone-expressing cell population derived in vitro from human pluripotent cells.

309. The enriched, in vitro human pancreatic islet hormone-expressing cell population of paragraph 308, wherein said enriched cell population is produced by the method of paragraph 253.

310. The enriched, in vitro human pancreatic islet hormone-expressing cell population of paragraph 308, wherein said enriched cell population is produced by the method of paragraph 294.

311. The enriched, in vitro human pancreatic islet hormone-expressing cell population of paragraph 309 or 310, wherein at least about 25% of said enriched human cell population comprises human pancreatic islet hormone-expressing cells that express at least one marker selected from the group consisting of ghrelin, islet amyloid polypeptide (IAPP), insulin (INS), glucagon (GCG), NKX6 transcription factor related, locus 1 (NKX6.1), somatostatin (SOM), and pancreatic polypeptide (PP) and do not substantially express at least one marker selected from the group consisting of AFP, SOX7, SOX1, ZIC1 and NFM.

312. The enriched, in vitro human pancreatic islet hormone-expressing cell population of paragraph 311, wherein at least about 50% of said enriched human cell population comprises human pancreatic islet hormone-expressing cells that express at least one marker selected from the group consisting of ghrelin, islet amyloid polypeptide (IAPP), insulin (INS), glucagon (GCG), NKX6 transcription factor related, locus 1 (NKX6.1), somatostatin (SOM), and pancreatic polypeptide (PP) and do not substantially express at least one marker selected from the group consisting of AFP, SOX7, SOX1, ZIC1 and NFM.

313. The enriched, in vitro human pancreatic islet hormone-expressing cell population of paragraph 311, wherein at least about 90% of said enriched human cell population comprises human pancreatic islet hormone-expressing cells that express at least one marker selected from the group consisting of ghrelin, islet amyloid polypeptide (IAPP), insulin (INS), glucagon (GCG), NKX6 transcription factor related, locus 1 (NKX6.1), somatostatin (SOM) and pancreatic polypeptide (PP) and do not substantially express at least one marker selected from the group consisting of AFP, SOX7, SOX1, ZIC1 and NFM.

314. An ex vivo reagent-cell complex comprising a human endocrine precursor cell expressing NCAM, said endocrine precursor cell being a multipotent cell that can differentiate into human pancreatic islet hormone-expressing cells, and a reagent bound to said NCAM.

315. The ex vivo reagent-cell complex of paragraph 314, wherein said reagent comprises a molecule selected from the group consisting of an anti-NCAM antibody, an anti-NCAM antibody fragment and an NCAM ligand.

316. The ex vivo reagent-cell complex of paragraph 315, wherein said NCAM ligand is NCAM Binding Protein 10 (NBP10).

317. The ex-vivo reagent-cell complex of paragraph 315, wherein said reagent is an anti-NCAM antibody.

318. The ex vivo reagent-cell complex of paragraph 317, wherein said anti-NCAM antibody is labeled.

319. The ex vivo reagent-cell complex of paragraph 318, wherein said anti-NCAM antibody is fluorescently labeled.

320. The ex vivo reagent-cell complex of paragraph 314 further comprising a secondary reagent that binds to said reagent.

321. The ex vivo reagent-cell complex of paragraph 320, wherein said reagent comprises and anti-NCAM antibody and wherein said secondary reagent that binds to said anti-NCAM antibody is fluorescently labeled.

322. An ex vivo reagent-cell complex comprising a human immature islet hormone-expressing cell expressing NCAM, said human immature islet hormone-expressing cell being a multipotent cell that can differentiate into human pancreatic islet hormone-expressing cell, and a reagent bound to said NCAM.

323. The ex vivo reagent-cell complex of paragraph 322, wherein said reagent comprises a molecule selected from the group consisting of an anti-NCAM antibody, an anti-NCAM antibody fragment and an NCAM ligand.

324. The ex vivo reagent-cell complex of paragraph 323, wherein said NCAM ligand is NCAM Binding Protein 10 (NBP10).

325. The ex-vivo reagent-cell complex of paragraph 323, wherein said reagent is an anti-NCAM antibody.

326. The ex vivo reagent-cell complex of paragraph 325, wherein said anti-NCAM antibody is labeled.

327. The ex vivo reagent-cell complex of paragraph 326, wherein said anti-NCAM antibody is fluorescently labeled.

328. The ex vivo reagent-cell complex of paragraph 322 further comprising a secondary reagent that binds to said reagent.

329. The ex vivo reagent-cell complex of paragraph 328, wherein said reagent comprises and anti-NCAM antibody and wherein said secondary reagent that binds to said anti-NCAM antibody is fluorescently labeled.

330. The method of any one of paragraphs 86, 150, 222 or 294, wherein said human pluripotent cells are human embryonic stem cells derived from a preimplantation embryo.

331. A method of producing human pancreatic hormone-expressing cells, said method comprising the steps of: (a) providing a population of pluripotent human embryonic stem cells (hESCs) with at least one growth factor of the TGF-β superfamily, thereby producing a population of human definitive endoderm cells; (b) providing said population of human definitive endoderm cells with at least one fibroblast growth factor, thereby producing a population of human foregut endoderm cells; (c) providing said population of human foregut endoderm cells with noggin, thereby producing a population comprising human endocrine precursor cells; and (d) incubating said population of human endocrine precursor cells in a culture medium for a sufficient time to permit human pancreatic islet hormone-expressing cells to form, wherein said sufficient time for human pancreatic hormone-expressing cells to form has been determined by detecting the presence of human pancreatic hormone-expressing cells in said cell population.

332. The method of paragraph 331, wherein at least about 2% of said human cells in said cell population differentiate into human pancreatic hormone-expressing cells.

333. The method of paragraph 331, wherein at least about 5% of said human cells in said cell population differentiate into human pancreatic hormone-expressing cells.

334. The method of paragraph 331, wherein at least about 10% of said human cells in said cell population differentiate into human pancreatic hormone-expressing cells.

335. The method of paragraph 331, wherein at least about 20% of said human cells in said cell population differentiate into human pancreatic hormone-expressing cells.

336. The method of paragraph 331, wherein at least about 40% of said human cells in said cell population differentiate into human pancreatic hormone-expressing cells.

337. The method of paragraph 331, wherein at least about 50% of said human cells in said cell population differentiate into human pancreatic hormone-expressing cells.

338. The method of paragraph 331, wherein at least about 70% of said human cells in said cell population differentiate into human pancreatic hormone-expressing cells.

339. The method of paragraph 331, wherein at least about 90% of said human cells in said cell population differentiate into human pancreatic hormone-expressing cells.

340. The method of paragraph 331, wherein detecting the presence of human pancreatic islet hormone-expressing cells in said cell population comprises detecting the expression of at least one marker selected from the group consisting of pancreatic duodenal homeobox 1 (PDX1), ghrelin (GHRL), insulin (INS), islet amyloid polypeptide (IAPP), pancreatic polypeptide (PP), ISL1 transcription factor (ISL1), NKX6 transcription factor related locus 1 (NKX6.1) and paired box 6 (PAX6) in cells of said cell population.

341. The method of paragraph 340, wherein the expression of at least one of said markers is determined by Q-PCR.

342. The method of paragraph 340, wherein the expression of at least one of said markers is determined by immunocytochemistry.

343. The method of paragraph 331 further comprising providing the cell population with a gamma secretase inhibitor.

344. The method of paragraph 343, wherein said gamma secretase inhibitor comprises N—[N-(3,5-difluorophenacetyl)-L-alanyl]-S-phenylglycine t-butyl ester (DAPT).

345. The method of paragraph 343, wherein said gamma secretase inhibitor is provided to the cell population at about the same time as providing noggin or after providing noggin.

346. The method of paragraph 344, wherein said gamma secretase inhibitor is provided to the cell population at a concentration ranging from about 0.1 µM to about 10 µM.

347. The method of paragraph 331, wherein said at least one fibroblast growth factor is fibroblast growth factor 7 (FGF-7).

348. The method of paragraph 347, wherein said FGF-7 is provided to the cell culture at a concentration ranging from about 1 ng/ml to about 1000 ng/ml.

349. The method of paragraph 331 further comprising providing the cell population with a hedgehog inhibitor at about the same time as adding the at least one fibroblast growth factor.

350. The method of paragraph 349, wherein said hedgehog inhibitor comprises KAAD-cyclopamine.

351. The method of paragraph 350, wherein said KAAD-cyclopamine is provided to the cell population at a concentration ranging from about 0.01 µM to about 10 µM.

352. The method of paragraph 331 further comprising withdrawing any growth factor of the TGF-β superfamily that may be present in said population of definitive endoderm cells.

353. The method of paragraph 331, wherein said growth factor of the TGF-β superfamily is selected from the group consisting of Nodal, activin A, activin B and combinations thereof.

354. The method of paragraph 353, wherein said growth factor of the TGF-β superfamily comprises activin A.

355. The method of paragraph 354, wherein said activin A is provided to said hESCs at a concentration ranging from about 10 ng/ml to about 1000 ng/ml.

356. The method of paragraph 331 further comprising providing the hESCs with wingless-type MMTV integration site family member 3A (Wnt3A).

357. The method of paragraph 356, wherein said Wnt3A is provided at a concentration ranging from about 1 ng/ml to about 1000 ng/ml.

358. The method of paragraph 331, wherein said hESCs are differentiated to human definitive endoderm cells in a medium comprising less than about 2% serum.

359. The method of paragraph 331, wherein said hESCs are derived from a tissue selected from the group consisting of the morula, the ICM of an embryo and the gonadal ridges of an embryo.

360. The method of paragraph 331 further comprising providing a retinoid to the cell population at about the same time as providing noggin.

361. The method of paragraph 331 further comprising providing a retinoid to the cell population at about the same time or after adding at least one fibroblast growth factor.

362. The method of paragraph 360 or 361, wherein the retinoid is retinol.

363. The method of paragraph 360 or 361, wherein the retinoid is retinoic acid.

364. The method of paragraph 363, wherein the retinoic acid is provided at a concentration ranging from about 0.01 µM to about 10 µM.

365. The cell culture or cell population of any one of paragraphs 1-49, 164-173, 236-252 or 308-313, wherein at least some of the cells are non-recombinant cells.

366. The cell culture or cell population of any one of paragraphs 1-49, 164-173, 236-252 or 308-313, wherein the cells are non-recombinant cells.

367. The cell culture or cell population of any one of paragraphs 1-49, 164-173, 236-252 or 308-313, wherein the cells have not been cultured in the presence of a histone deacetylase inhibitor.

368. The cell culture or cell population of paragraph 367, wherein said histone deacetylase inhibitor comprises sodium butyrate.

369. The method of any one of paragraphs 50-163, 174-235, 253-307 or 331-364, wherein at least some of the cells are non-recombinant cells.

370. The method of any one of paragraphs 50-163, 174-235, 253-307 or 331-364, wherein the cells are non-recombinant cells.

371. The method of any one of paragraphs 50-163, 174-235, 253-307 or 331-364, wherein the cells have not been cultured in the presence of a histone deacetylase inhibitor.

372. The method of paragraph 371, wherein said histone deacetylase inhibitor comprises sodium butyrate.

373. A method for producing insulin, said method comprising the steps of: (a) contacting human embryonic stem (hES) cells in vitro with a first medium comprising an agent that activates a TGF-β receptor family member; (b) culturing in vitro the hES-derived cells of step (a) in a second medium lacking the agent that activates the TGF-β receptor family member; (c) transplanting the hES-derived cells of step (b) and their progeny into a mammalian subject; and (d) maturing the hES-derived cells of step (c) in vivo, thereby obtaining insulin secreting cells.

374. The method of paragraph 373, wherein the agent is an activin selected from the group consisting of activin A, activin AB, activin B, and combinations thereof.

375. The method of paragraph 374, wherein the activin is activin A.

376. The method of paragraph 373, wherein the first and second medium lacks nicotinamide.

377. The method of paragraph 373 further comprising contacting the hES cells with Wnt3A.

378. A method for producing insulin, said method comprising the steps of: (a) contacting human embryonic stem (hES) cells in vitro with a first medium comprising an agent that activates a TGF-β receptor family member; (b) transplanting the hES-derived cells of step (a) and their progeny into a mammalian subject; and (c) maturing the hES-derived cells of step (b) in vivo, thereby obtaining insulin secreting cells.

379. The method of paragraph 378, wherein the agent is an activin selected from the group consisting of activin A, activin AB, activin B, and combinations thereof.

380. The method of paragraph 379, wherein the activin is activin A.

381. The method of paragraph 378, wherein the medium lacks nicotinamide.

382. The method of paragraph 378 further comprising contacting the hES cells with Wnt3A.

383. A method for producing insulin, said method comprising the steps of: (a) contacting human embryonic stem (hES) cells in vitro with a medium comprising a first agent that activates a TGF-β receptor family member; (b) culturing in vitro the hES-derived cells of step (a) in a second medium comprising a second agent that inhibits the TGF-β receptor family member; (c) transplanting the hES-derived cells of step (b) and their progeny into a mammalian subject; and (d) maturing the hES-derived cells of step (c) in vivo, thereby obtaining insulin secreting cells.

384. The method of paragraph 383, wherein the first agent is an activin.

385. The method of paragraph 384, wherein the activin is selected from the group consisting of activin A, activin AB, activin B and combinations thereof.

386. The method of paragraph 385, wherein the activin is activin A.

387. The method of paragraph 383, wherein the TGF-beta family receptor is the activin receptor-like kinase (ALK) receptor.

388. The method of paragraph 383, wherein the second agent is SB-431542.

389. The method of paragraph 383, wherein the first and second medium lack nicotinamide.

390. The method of paragraph 383 further comprising contacting the hES cells with Wnt3A.

391. The method of paragraph 383, wherein the mammalian subject is a human subject.

392. The method of paragraph 391, wherein the human subject has been identified as having a condition which limits the ability of the subject to produce sufficient levels of insulin in response to physiologically high blood glucose concentrations.

393. An in vivo insulin secreting cell derived from an in vitro human embryonic stem cell (hESC) or progeny thereof.

394. The insulin secreting cell of paragraph 393, wherein the in vitro hESC-derived cell or progeny thereof do not form a teratoma in vivo.

It will be appreciated that the methods and compositions described above relate to cells cultured in vitro. However, the above-described in vitro differentiated cell compositions may be used for in vivo applications, such as cell replacement therapies.

Additional embodiments of the present invention may also be found in U.S. Provisional Patent Application No. 60/532,004, entitled DEFINITIVE ENDODERM, filed Dec. 23, 2003; U.S. Provisional Patent Application No. 60/566,293, entitled PDX1 EXPRESSING ENDODERM, filed Apr. 27, 2004; U.S. Provisional Patent Application No. 60/586,566, entitled CHEMOKINE CELL SURFACE RECEPTOR FOR THE ISOLATION OF DEFINITIVE ENDODERM, filed Jul. 9, 2004; U.S. Provisional Patent Application No. 60/587,942, entitled CHEMOKINE CELL SURFACE RECEPTOR FOR THE ISOLATION OF DEFINITIVE ENDODERM, filed Jul. 14, 2004; U.S. patent application Ser. No. 11/021,618, entitled DEFINITIVE ENDODERM, filed Dec. 23, 2004 and U.S. patent application Ser. No. 11/115,868, entitled PDX1 EXPRESSING ENDODERM, filed Apr. 26, 2005; U.S. patent application Ser. No. 11/165,305, entitled METHODS FOR IDENTIFYING FACTORS FOR DIFFERENTIATING DEFINITIVE ENDODERM, filed Jun. 23, 2005; U.S. Provisional Patent Application No. 60/730,917, entitled PDX1-EXPRESSING DORSAL AND VENTRAL FOREGUT ENDODERM, filed Oct. 27, 2005; U.S. Provisional Patent Application No. 60/736,598, entitled MARKERS OF DEFINITIVE ENDODERM, filed Nov. 14, 2005; U.S. Provisional Patent Application No. 60/778,649, entitled INSULIN-PRODUCING CELLS AND METHOD OF PRODUCTION, filed Mar. 2, 2006; U.S. Provisional Patent Application No. 60/833,633, entitled INSULIN-PRODUCING CELLS AND METHOD OF PRODUCTION, filed Jul. 26, 2006; and U.S. Provisional Patent Application No. 60/852,878, entitled ENRICHMENT OF ENDOCRINE PRECURSOR CELLS, IMMATURE PANCREATIC ISLET CELLS AND MATURE PANCREATIC ISLET CELLS USING NCAM, filed Oct. 18, 2006, the disclosures of which are incorporated herein by reference in their entireties.

BRIEF DESCRIPTION OF THE DRAWINGS

FIG. 11C and FIG. 11D show upregulation of NGN3 mRNA for BG01 (FIG. 11C) and BG02 (FIG. 11D); and panels FIG. 11E and FIG. 11F show the upregulation of insulin expression for BG01 (FIG. 11E) and BG02 (FIG. 11F).

FIGS. 14A-14F are photomicrographs showing immunoreactivity of hESC-derived cells treated to differentiate to immature pancreatic islet hormone-expressing cells for NCAM (FIG. 14E), INS (FIG. 14F) and PAX6 (FIG. 14D). Total cell population is stained with DAPI (FIG. 14A). These micrographs indicate that PAX6-positive cells are also NCAM positive (FIG. 14B) and that INS-positive cells are also NCAM positive (FIG. 14C).

FIG. 16A and FIG. 16B show that MAFB and INS are co-expressed in hESC-derived endocrine precursor cells. FIG. 16C and FIG. 16D show the immunoreactivity of 13.5 week old human fetal pancreas for MAFB and INS. MAFB and INS are co-expressed in fetal pancreas.

FIG. 18A is a flow cytometry dot plot showing labeling of hESC-derived cells that have been treated to differentiate into immature pancreatic islet hormone-expressing cells with anti-NCAM antibody. FIG. 18B is a flow cytometry dot plot showing the distribution of hESC-derived cells that are positive or negative for both NCAM and SYP. FIG. 18C is a flow cytometry dot plot showing the distribution of hESC-derived NCAM positive cells of FIG. 18A that have been re-analyzed by FACS for NCAM and SYP. The dot plot shows the distribution of these cells that are positive or negative for both NCAM and SYP. FIG. 18D is a flow cytometry dot plot showing the distribution of hESC-derived NCAM negative cells of FIG. 18A that have been re-analyzed by FACS for NCAM and SYP. The dot plot shows the distribution of these cells that are positive or negative for both NCAM and SYP.

FIG. 19A and FIG. 19B show the distribution of cells that are positive and negative for both NCAM and SYP. FIG. 19C and FIG. 19D show the distribution of cells that are positive and negative for both NCAM and INS.

FIGS. 20A-20C are flow cytometry dot plots of hESC-derived cells that have been treated to differentiate to immature pancreatic islet hormone-expressing cells. FIG. 20A shows a small population of the cells stain brightly for NCAM. FIG. 20B shows a small population of the cells stain brightly for SYP. FIG. 20C shows that a much higher percentage of the hESC-derived cells are SYP positive if the NCAM bright cells of FIG. 20A are collected and analyzed for SYP.

FIGS. 21A-21C are flow cytometry dot plots of hESC-derived cells that have been treated to differentiate to immature pancreatic islet hormone-expressing cells. FIG. 21A shows the distribution of hESC-derived cells stained for NCAM. FIG. 21B shows a small population of hESC cells treated to differentiate to immature pancreatic islet hormone-expressing cells are both NCAM positive and CD133 negative. FIG. 21C shows the distribution of NCAM positive/CD133 negative cells that are SYP positive and SYP negative.

FIGS. 25A, 25C and 25E show the proportion of NCAM positive cells that are SYP, CHGA, and INS positive, respectively, in the cell population prior to sorting the population for NCAM positive cells. FIGS. 25B, 25D, and 25F show the percentage of cells that are SYP, CHGA and INS positive, respectively, following sorting the cells for those that are positive for NCAM expression.

FIG. 26A shows the proportion of NCAM positive cells that are SYP positive. FIG. 26B shows the proportion of NCAM positive cells that are CD133 negative. FIG. 26C shows the proportion of cells that have been sorted for NCAM positive/CD133 negative cells, which are SYP positive.

FIGS. 27A-27D are photomicrographs showing immunoreactivity of immature pancreatic islet hormone-expressing cells for INS (FIG. 27D), PAX6 (FIG. 27C). Total cell population is stained with DAPI (FIG. 27B). The cells are hESC-derived stem cells treated to differentiate to immature pancreatic islet hormone-expressing cells and sorted using Fluorescence Activated Cell Sorting technology. The cells represented in the micrographs also stained brightly for NCAM. A proportion of the NCAM positive hESC-derived cells co-express PAX6 and INS (FIG. 27A).

FIG. 28A shows the overlap of cells that express both INS and GCG.

DETAILED DESCRIPTION

Figure 1:
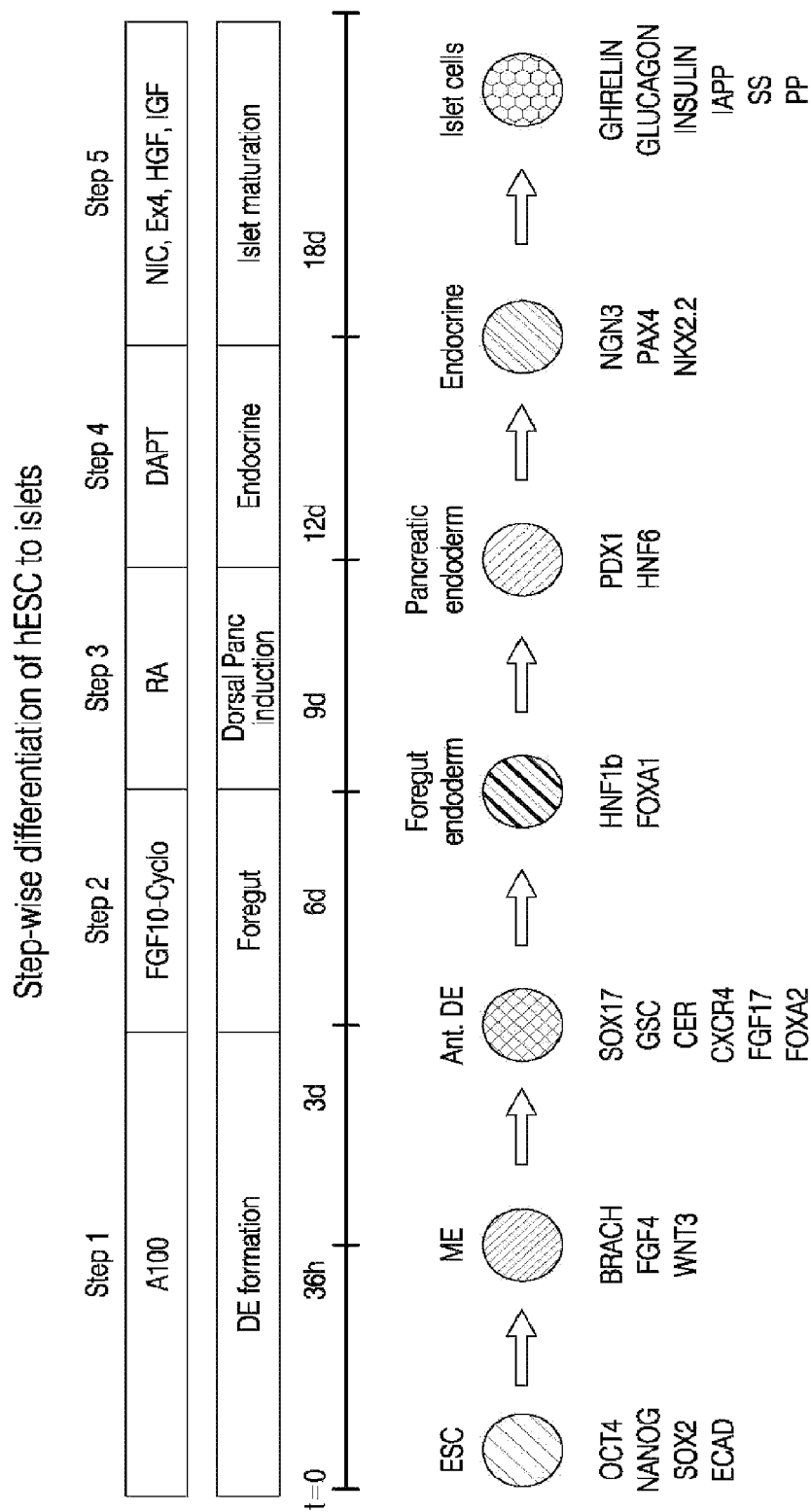
FIG. 1 is a schematic showing the steps in the in vitro differentiation of hESCs to islet cells through the intermediate stages that correspond to those observed during development of the pancreas in vivo. Sequential treatments with various growth factors/media combinations, which are used to elicit this step-wise differentiation of hESCs through each intermediate, are shown. Conditions and cell characteristics are depicted in the boxes. Below the boxes is an exemplary time line showing a typical differentiation from human embryonic stem cells (hESCs) to pancreatic islet hormone-expressing cells with time units indicated in hours (h) or days (d). Below each intermediate is a list of genes for which expression is characteristic of, although not necessarily exclusive for, that intermediate. Monitoring the expression of one or multiple genes for each intermediate along this progression allows for robust demonstration of the occurrence of each transition in vitro. Abbreviations are as follows: ESC—embryonic stem cell; ME—mesendoderm; Ant. DE—anterior definitive endoderm.
Figure 2E:
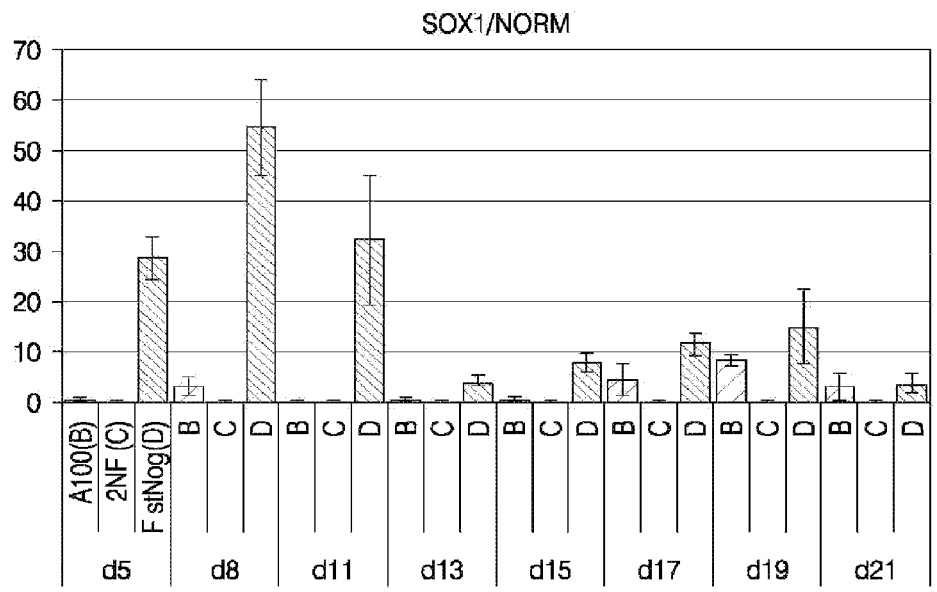
FIGS. 2A-2N are bar charts showing the relative expression of various markers during a 21 day differentiation protocol. Markers that display substantial differences in differentiation generated as a result of the three conditions used in step 1 of differentiation are (FIG. 2A) SOX17, (FIG. 2B) CXCR4, (FIG. 2C) SOX7, (FIG. 2D) ISL1, (FIG. 2E) SOX1 and (FIG. 2F) PAX6. Panels (FIG. 2G) PDX1, (FIG. 2H) NGN3, (FIG. 2I) NKX2.2 and (FIG. 2J) NKX6.1 show the relative expression of markers associated with the differentiation of hESCs to pancreatic endoderm and endocrine precursor cells. Panels (FIG. 2K) insulin, (FIG. 2L) glucagon, (FIG. 2M) ghrelin and (FIG. 2N) SOM show the relative expression of the islet hormones insulin, glucagon, ghrelin, and somatostatin near the end of the differentiation process.
Figure 2F:
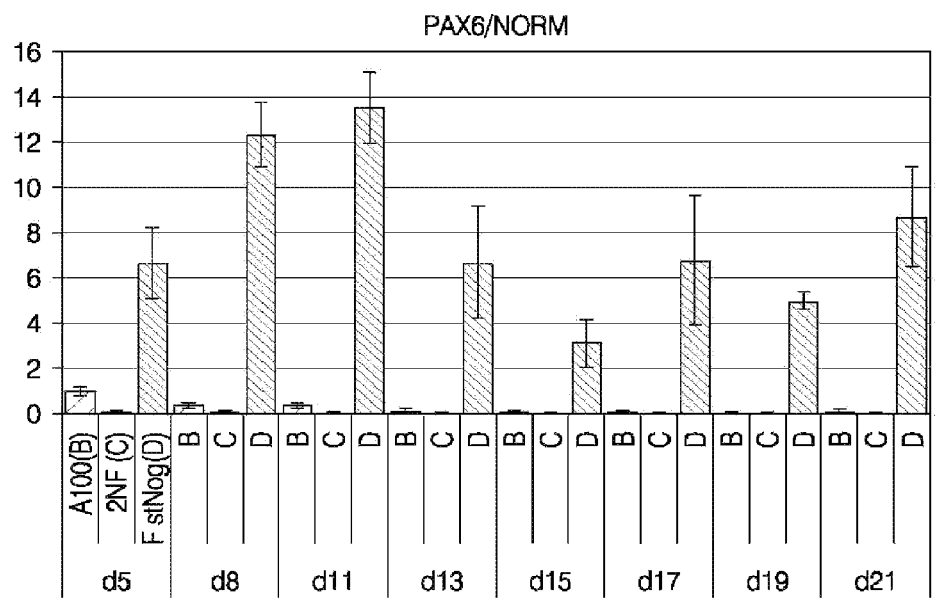
Figure 2G:
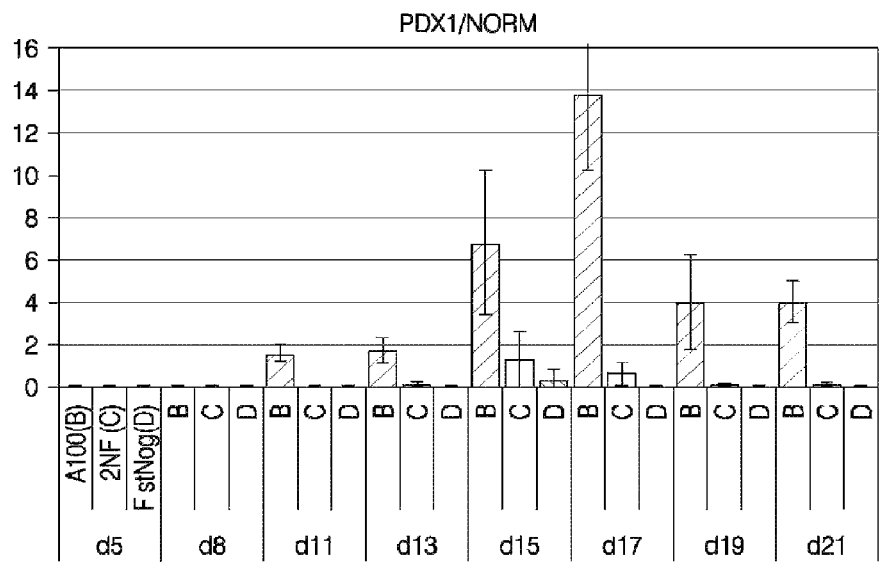
Figure 2H:
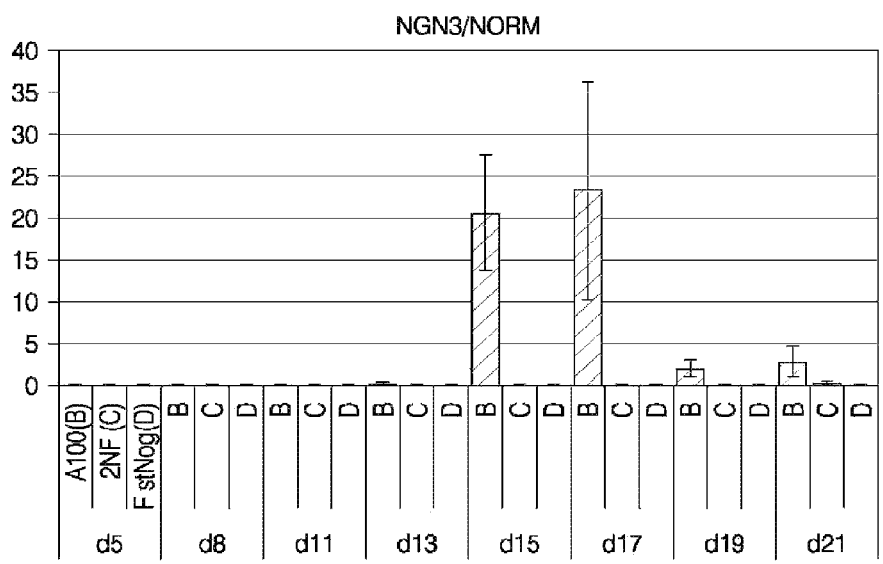
Figure 2I:
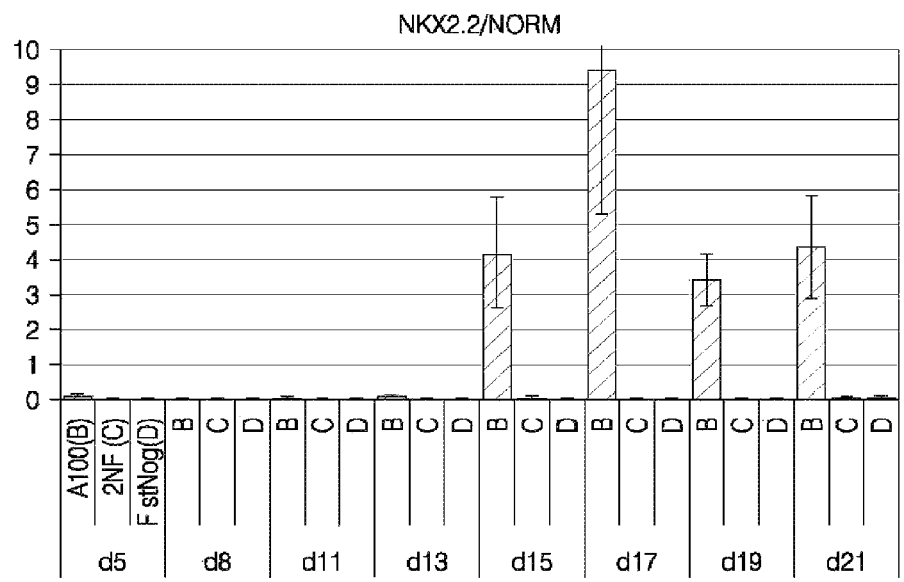
Figure 2J:
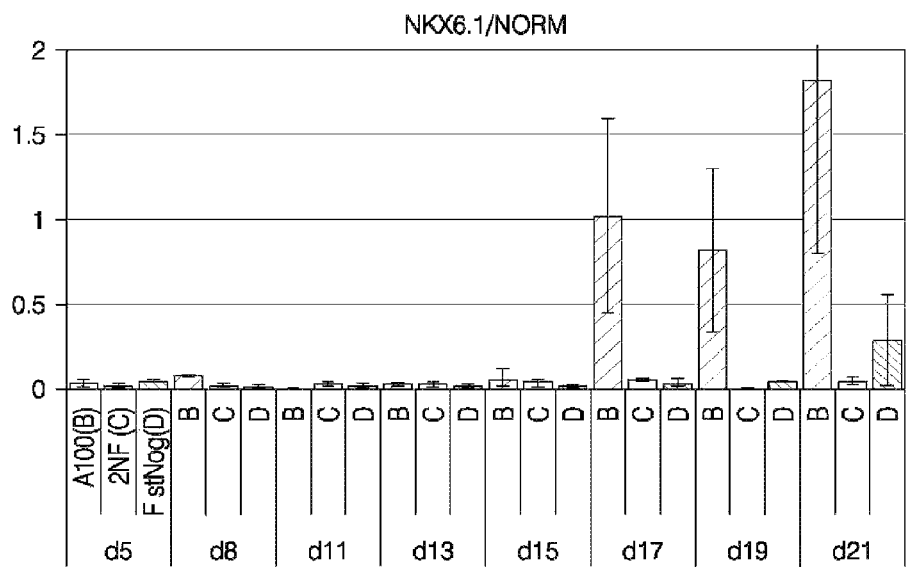
Figure 2K:
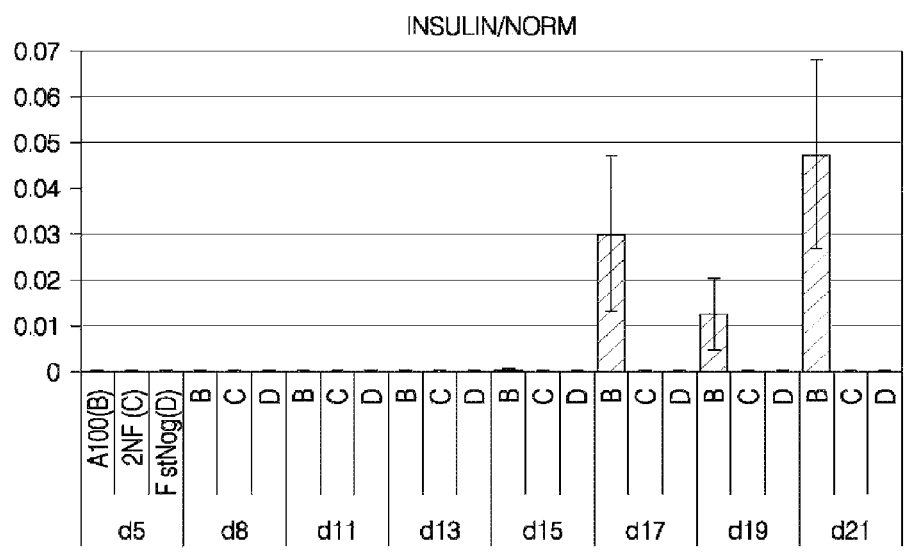
Figure 2L:
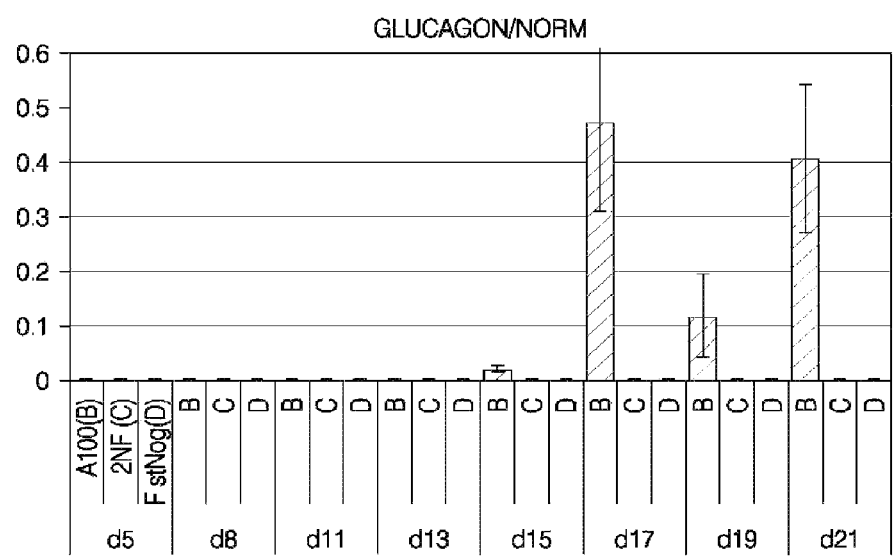
Figure 2M:
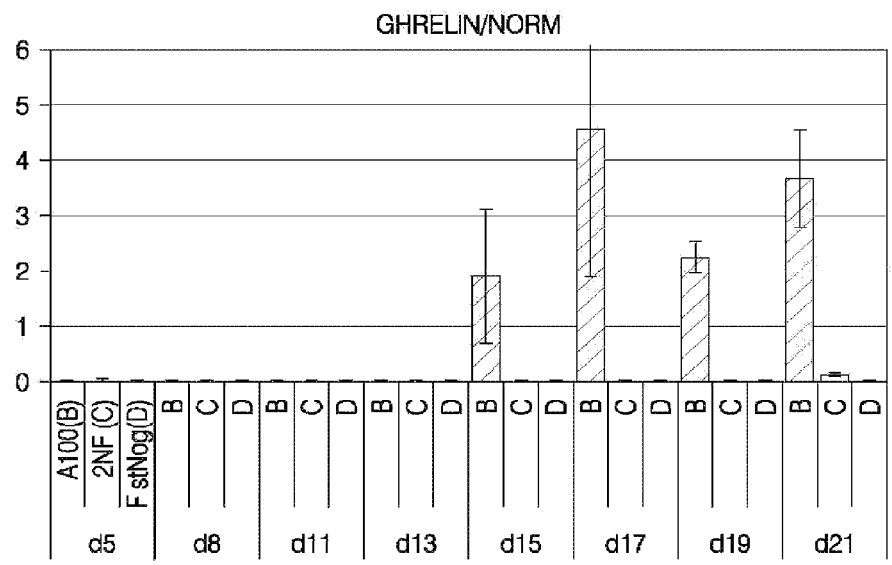
Figure 2N:
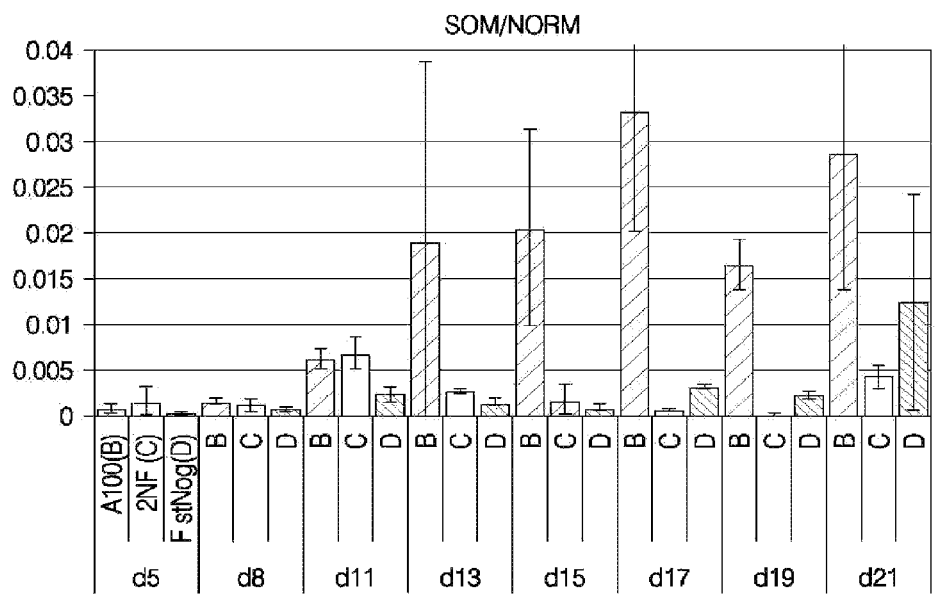

Described herein is a progression of steps for converting undifferentiated hESCs to endocrine precursor cells and immature pancreatic islet hormone-expressing cells, and ultimately to mature pancreatic endocrine cells (mature pancreatic islet hormone-expressing cells) capable of synthesizing insulin, glucagon, somatostatin, pancreatic polypeptide, PPY and ghrelin in vitro. This progression of steps directs the sequential differentiation of hESCs through intermediates that are currently recognized to occur during pancreatic development in vivo. The general method for production of hESC-derived pancreatic endocrine cells begins with the production of definitive endoderm (DE), followed by a DE patterning step in which TGF-beta signaling is modified and a fibroblast growth factor or a ligand that stimulates or otherwise interacts with the fibroblast growth factor 2 receptor IIIb (FGFR2(IIIb) is supplied. The PDX1-positive pre-patterned endoderm is further recruited into the pancreatic endocrine lineage by transient exposure to retinoic acid and gamma secretase inhibition after which pancreatic endocrine hormone producing cells are generated.

As previously demonstrated in U.S. patent application Ser. No. 11/021,618, entitled DEFINITIVE ENDODERM, filed Dec. 23, 2004 and D'Amour et al. *Nat. Biotech.* 23, 1534-1541, (2005), the disclosures of which are incorporated herein by reference in their entireties, we have developed robust methods for the production of the somatic germ layer definitive endoderm (DE). In vivo, the DE lineage is generated during the gastrulation stage of embryonic development arising in an area termed the primitive streak. Generation of DE is a prerequisite for latter specification of tissues and organs such as intestine, stomach, lungs, thymus, pancreatic endocrine, parathyroid, thyroid and pancreas.

In humans as well as most other vertebrates, the pancreas is derived from the foregut endoderm at the foregut-midgut junction as both a ventral and dorsal pancreatic bud. In humans, the dorsal and ventral buds fuse at approximately 41-45 days post conception (p.c.) with the smaller ventral bud forming the posterior portion of the head of the pancreas and a region termed the uncinate process (Bocian-Sobkowska, J., et al. *Histochem. Cell Biol.* 112, 147-153, (1999)). This region in humans is composed primarily of pancreatic polypeptide producing islet cells (Rahier J., et al., *Cell Tissue Res.* 200 (3), 359-366, (1979); Malaisse-Langae F., et al., *Diabetologia* 17(6), 361-365, (1979); Fiocca R., et al., *Histochemistry* 77(4), 511-523, (1983); Stefan Y., et al., *Diabetologica* 23(2), 141-142, (1982)). The dorsal pancreatic bud forms the anterior portion of the head, the body and the tail of the pancreas in humans. It makes all pancreatic hormone producing cells. In frog (*Xenopus*) and fish (zebrafish) only the dorsal bud cells go on to make insulin producing islet cells (Kelly, O. G. and Melton, D. A., *Dev. Dyn.* 218, 615-627, (2000); Chen, Y., et al., *Dev. Biol.* 271(1), 144-160, (2004); Field, H. A., et al., *Dev. Biol.* 263, 197-208 (2003)). Similarly, the ventral bud in human appears to make predominantly pancreatic polypeptide expressing islet cells to the exclusion of insulin (Rahier J., et al., *Cell Tissue Res.* 200 (3), 359-366, (1979); Malaisse-Langae F., et al., *Diabetologia* 17(6), 361-365, (1979); Fiocca R., et al., *Histochemistry* 77(4), 511-523, (1983); Stefan Y., et al., *Diabetologica* 23(2), 141-142, (1982)). In contrast, in the rat and mouse both ventral and dorsal buds make insulin producing islets (Spooner, B. S., et al., *J. Cell Biology,* 47, 235-246, (1970); Li, H., et al., *Nature* 23, 67-70, (1999)).

As depicted in FIG. 1, pancreatic endocrine cells can be efficiently produced from hESCs in a series of developmental steps. The first step is the formation of mesendoderm (ME) characterized by the transitional expression of the T-box gene brachyury. As hESCs differentiate to DE they down regulate E-cadherin and transition from an epithelial epiblast state to a mesenchymal DE cell (D'Amour et al. *Nat. Biotech.* 23, 1534-1541, (2005)). The principal markers defining the early DE cell are FOXA2, GSC, N-cadherin, CXCR4 and SOX17. As explained in our previous U.S. patent application Ser. No. 11/021,618, DE is further characterized by the absence of significant expression of certain other markers, such as SOX1, SOX7, thrombomodulin (TM), SPARC and alpha fetoprotein (AFP). The nascent DE is further patterned from its strong anterior character to a more posterior but still foregut endoderm by removal of activin signaling. Such foregut endoderm is characterized by expression of the HNF1b, and FOXA1 gene markers. This endoderm expands and assumes a more dorsal phenotype by exposure to FGF10, retinoic acid and cyclopamine (Sonic Hedgehog (SHH) inhibitor). The posterior foregut (posterior region of the foregut) patterned cells express PDX1, PTF1a, HNF1b, Onecut1/2 and HB9. These pancreatic endoderm cells are recruited preferentially to the endocrine lineage by modulation of gamma secretase signaling (potentially due to the inhibition of Notch pathway signaling) as indicated by the transient expression of NGN3, indicative of endocrine precursor cells. The hESC-derived endocrine precursor cells also express paired box gene 4 (PAX4), and NKX2.2. Further incubation of endocrine precursor cells gives rise to immature pancreatic islet hormone-expressing cells Immature pancreatic islet hormone-expressing cells express V-maf musculoaponeurotic fibrosarcoma oncogene homolog B (MAFB), as well as NKX2.2 and pancreatic islet hormone-expressing cells express NKX2.2. Finally, further incubation of immature pancreatic islet hormone-expressing cells results in the transition from the immature cells to mature pancreatic islet hormone-expressing cells that can express V-maf musculoaponeurotic fibrosarcoma oncogene homolog A (MAFA) in addition to the endocrine hormones insulin, glucagon, somatostatin, -PPY, ghrelin and the pancreatic transcription factors NKX2.2/6.1, PAX6, NEUROD1, PDX1, ISL1.

DEFINITIONS

It will be appreciated that the numerical ranges expressed herein include the endpoints set forth and describe all integers between the endpoints of the stated numerical range.

As used herein, "pancreatic islet hormone-expressing cell" refers to a cell, which has been derived from a human pluripotent cell in vitro, which expresses one or more pancreatic hormones and which has at least some of the functions of a human pancreatic islet cell. Pancreatic islet hormone-expressing cells can be mature or immature Immature pancreatic islet hormone-expressing cells can be distinguished from mature pancreatic islet hormone-expressing cells based on the differential expression of certain markers.

As used herein, "pancreatic hormone-expressing cell" is used interchangeably with "pancreatic islet hormone-expressing cell."

As used herein, "endocrine precursor cell" refers to a multipotent cell of the definitive endoderm lineage that expresses neurogenin 3 (NEUROG3) and which can further differentiate into cells of the endocrine system including, but not limited to, pancreatic islet hormone-expressing cells. Endocrine precursor cells cannot differentiate into as many different cell, tissue and/or organ types as compared to less specifically differentiated definitive endoderm lineage cells, such as PDX1-positive pancreatic endoderm cell.

As used herein, "PDX1-positive pancreatic endoderm cell" and "PDX1-positive foregut endoderm cell" refer to a multipotent cell of the definitive endoderm lineage that expresses pancreatic and duodenal homeobox gene 1 (PDX1) and which can further differentiate into cells derived from the foregut including, but not limited to, endocrine precursor and pancreatic islet hormone-expressing cells. PDX1-positive pancreatic endoderm cells cannot differentiate into as many different cells, tissue and/or organ types as compared to definitive endoderm cells.

As used herein, "multipotent" or "multipotent cell" refers to a cell type that can give rise to a limited number of other particular cell types. Multipotent cells are committed to one or more embryonic cell fates, and thus, in contrast to pluripotent cells, cannot give rise to each of the three embryonic cell lineages as well as extraembryonic cells.

In some embodiments, "pluripotent cells" are used as the starting material for pancreatic islet hormone-expressing cell differentiation. By "pluripotent" is meant that the cell can give rise to each of the three embryonic cell lineages as well as extraembryonic cells. Pluripotent cells, however, may not be capable of producing an entire organism.

In certain embodiments, the pluripotent cells used as starting material are stem cells, including human embryonic stem cells. As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer.

By "conditioned medium" is meant, a medium that is altered as compared to a base medium. For example, the conditioning of a medium may cause molecules, such as nutrients and/or growth factors, to be added to or depleted from the original levels found in the base medium. In some embodiments, a medium is conditioned by allowing cells of certain types to be grown or maintained in the medium under certain conditions for a certain period of time. For example, a medium can be conditioned by allowing hESCs to be expanded, differentiated or maintained in a medium of defined composition at a defined temperature for a defined number of hours. As will be appreciated by those of skill in the art, numerous combinations of cells, media types, durations and environmental conditions can be used to produce nearly an infinite array of conditioned media.

When used in connection with cell cultures and/or cell populations, the term "portion" means any non-zero amount of the cell culture or cell population, which ranges from a single cell to the entirety of the cell culture or cells population. In preferred embodiments, the term "portion" means at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94% or at least 95% of the cell culture or cell population.

With respect to cells in cell cultures or in cell populations, the term "substantially free of" means that the specified cell type of which the cell culture or cell population is free, is present in an amount of less than about 10%, less than about 9%, less than about 8%, less than about 7%, less than about 6%, less than about 5%, less than about 4%, less than about 3%, less than about 2% or less than about 1% of the total number of cells present in the cell culture or cell population.

As used herein, "exogenously added," compounds such as growth factors, differentiation factors, and the like, in the context of cultures or conditioned media, refers to growth factors that are added to the cultures or media to supplement any compounds or growth factors that may already be present in the culture or media. For example, in some embodiments, of the present invention, cells cultures and or cell populations do not include an exogenously-added retinoid.

As used herein, "produced from hESCs," "derived from hESCs," "differentiated from hESCs" and equivalent expressions refer to the production of a differentiated cell type from hESCs in vitro rather than in vivo.

In some embodiments, hESCs can be derived from a "preimplantation embryo." As used herein, "preimplantation embryo" refers to an embryo between the stages of fertilization and implantation. Thus, a preimplantation embryo typically has not progressed beyond the blastocyst stage. Implantation usually takes place 7-8 days after fertilization. However, implantation may take place about 2, about 3, about 4, about 5, about 6, about 7, about 8, about 9, about 10, about 11, about 12, about 13, about 14 or greater than about 14 days after fertilization.

As used herein, "hedgehog inhibitor" or "hedgehog pathway inhibitor" refers to any molecule that inhibits any member of the hedgehog signaling pathway. Exemplary hedgehog pathway inhibitors include, but are not limited to, KAAD-cyclopamine, cyclopamine analogs, jervine, jervine analogs, hedgehog pathway blocking antibodies and any other inhibitors of hedgehog pathway function known to those of ordinary skill in the art.

As used herein, "gamma secretase inhibitor" refers to any molecule that inhibits gamma secretase or signaling events caused by the activity of gamma secretase. Exemplary gamma secretase inhibitors include, but are not limited to, N—[N-(3,5-Diflurophenacetyl-L-alanyl)]-S-phenylglycine t-Butyl Ester (DAPT), the F-box protein SEL-10, gamma secretase blocking antibodies and any other inhibitors of gamma secretase function known to those of ordinary skill in the art. In some embodiments, the gamma secretase inhibitor inhibits the Notch signaling pathway. In some embodiments, a Notch pathway inhibitor or a Notch-specific inhibitor may be used in place of a gamma secretase inhibitor.

As used herein, "retinoid" refers to retinol, retinal or retinoic acid as well as derivatives of any of these compounds. In a preferred embodiment, the retinoid is retinoic acid.

By "FGF family growth factor," "a fibroblast growth factor" or "member of the fibroblast growth factor family" is meant an FGF selected from the group consisting of FGF1, FGF2, FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, FGF22 and FGF23. In some embodiments, "FGF family growth factor," "a fibroblast growth factor" or "member of the fibroblast growth factor family" means any growth factor having homology and/or function similar to a known member of the fibroblast growth factor family.

As used herein, "expression" refers to the production of a material or substance as well as the level or amount of production of a material or substance. Thus, determining the expression of a specific marker refers to detecting either the relative or absolute amount of the marker that is expressed or simply detecting the presence or absence of the marker.

As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein or a small molecule (for example, molecules having a molecular weight of less than 10,000 amu).

For most markers described herein, the official Human Genome Organisation (HUGO) gene symbol is provided. Such symbols, which are developed by the HUGO Gene Nomenclature Committee, provide unique abbreviations for each of the named human genes and gene products. These gene symbols are readily recognized and can easily be associated with a corresponding unique human gene and/or protein sequence by those of ordinary skill in the art.

In accordance with the HUGO designations, the following gene symbols are defined as follows: GHRL—ghrelin; IAPP—islet amyloid polypeptide; INS—insulin; GCG—glucagon; ISL1—ISL1 transcription factor; PAX6—paired box gene 6; PAX4—paired box gene 4; NEUROG3—neurogenin 3 (NGN3); NKX2-2—NKX2 transcription factor related, locus 2 (NKX2.2); NKX6-1—NKX6 transcription factor related, locus 1 (NKX6.1); IPF1—insulin promoter factor 1 (PDX1); ONECUT1—one cut domain, family member 1 (HNF6); HLXB9—homeobox B9 (HB9); TCF2—transcription factor 2, hepatic (HNF1b); FOXA1—forkhead box A1; HGF—hepatocyte growth factor; IGF1—insulin-like growth factor 1; POU5F1—POU domain, class 5, transcription factor 1 (OCT4); NANOG—Nanog homeobox; SOX2—SRY (sex determining region Y)—box 2; CDH1—cadherin 1, type 1, E-cadherin (ECAD); T—brachyury homolog (BRACH); FGF4—fibroblast growth factor 4; WNT3—wingless-type MMTV integration site family, member 3; SOX17—SRY (sex determining region Y)—box 17; GSC—goosecoid; CER1—(cerberus 1, cysteine knot superfamily, homolog (CER); CXCR4—chemokine (C-X-C motif) receptor 4; FGF17—fibroblast growth factor 17; FOXA2—forkhead box A2; SOX7—SRY (sex determining region Y)—box 7; SOX1—SRY (sex determining region Y)—box 1; AFP—alpha-fetoprotein; SPARC—secreted protein, acidic, cysteine-rich (osteonectin); and THBD—thrombomodulin (TM), NCAM—neural cell adhesion molecule; SYP—synaptophysin; ZIC1—Zic family member 1; NEF3—neurofilament 3 (NFM); SST—somatostatin; MAFA—v-maf musculoaponeurotic fibrosarcoma oncogene homolog A; MAFB—v-maf musculoaponeurotic fibrosarcoma oncogene homolog B; SYP—synaptophysin; CHGA—chromogranin A (parathyroid secretory protein 1).

The following provides the full gene names corresponding to non-HUGO gene symbols as well as other abbreviations that may be used herein: SS—somatostatin (SOM); PP—pancreatic polypeptide; C-peptide—connecting peptide; Ex4—exendin 4; NIC—nicotinamide and DAPT—N—[N-(3,5-difluorophenacetyl)-L-alanyl]-S-phenylglycine t-butyl ester; RA—retinoic acid; RPMI—Roswell Park Memorial Institute medium; CMRL—Connaught Medical Research Labs medium; FBS—fetal bovine serum; NBP10—NCAM binding protein 10; PTF1a—pancreas specific transcription factor 1a.

The terms fibroblast growth factor 7 (FGF7) and keritinocyte growth factor (KGF) are synonymous.

As used herein, the term "label" refers to, for example, radioactive, fluorescent, biological or enzymatic tags or labels of standard use in the art. A label can be conjugated, or otherwise bound, to nucleic acids, polypeptides, such as antibodies, or small molecules. For example, oligonucleotides of the present invention can be labeled subsequent to synthesis, by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. Alternatively, when fluorescently-labeled oligonucleotide probes are used, fluorescein, lissamine, phycoerythirin, rhodamine (Perkin Elmer Cetus), Cy2, Cy3, Cy3.5, Cy5, Cy5.5, Cy7, FluorX (Amersham) and others, can be attached to nucleic acids. Non-limiting examples of detectable labels that may be conjugated to polypeptides such as antibodies include but are not limited to radioactive labels, such as $^{3}H$, $^{11}C$, $^{14}C$, $^{18}F$, $^{32}P$, $^{35}S$, $^{64}Cu$, $^{76}Br$, $^{86}Y$, $^{99}Tc$, $^{111}In$, $^{123}I$, $^{125}I$, or $^{177}L$, enzymes, such as horseradish peroxidase, fluorophores, chromophores, chemiluminescent agents, chelating complexes, dyes, colloidal gold or latex particles.

Human Embryonic Stem Cells

A preferred method for deriving definitive endoderm cells and ultimately endocrine precursor cells and/or pancreatic islet hormone-expressing cells utilizes human embryonic stem cells as the starting material. Such pluripotent cells can be cells that originate from the morula, embryonic inner cell mass or those obtained from embryonic gonadal ridges. Human embryonic stem cells can be maintained in culture in a pluripotent state without substantial differentiation using methods that are known in the art. Such methods are described, for example, in U.S. Pat. Nos. 5,453,357, 5,670, 372, 5,690,926 5,843,780, 6,200,806 and 6,251,671 the disclosures of which are incorporated herein by reference in their entireties.

In some processes, hESCs are maintained on a feeder layer. In such processes, any feeder layer which allows hESCs to be maintained in a pluripotent state can be used. One commonly used feeder layer for the cultivation of human embryonic stem cells is a layer of mouse fibroblasts. More recently, human fibroblast feeder layers have been developed for use in the cultivation of hESCs (see US Patent Application No. 2002/0072117, the disclosure of which is incorporated herein by reference in its entirety). Alternative processes permit the maintenance of pluripotent hESC without the use of a feeder layer. Methods of maintaining pluripotent hESCs under feeder-free conditions have been described in US Patent Application No. 2003/0175956, the disclosure of which is incorporated herein by reference in its entirety.

The human embryonic stem cells used herein can be maintained in culture either with or without serum. In some embryonic stem cell maintenance procedures, serum replacement is used. In others, serum free culture techniques, such as those described in US Patent Application No. 2003/0190748, the disclosure of which is incorporated herein by reference in its entirety, are used.

Stem cells are maintained in culture in a pluripotent state by routine passage until it is desired that they be differentiated into definitive endoderm then ultimately to endocrine precursor cells and/or pancreatic islet hormone-expressing cells.

Production of Definitive Endoderm

In some processes, differentiation to definitive endoderm is achieved by providing to the stem cell culture a growth factor of the TGFβ superfamily in an amount sufficient to promote differentiation to definitive endoderm. Growth factors of the TGFβ superfamily which are useful for the production of definitive endoderm are selected from the Nodal/Activin or BMP subgroups. In some preferred differentiation processes, the growth factor is selected from the group consisting of Nodal, activin A, activin B and BMP4. Additionally, the growth factor Wnt3a and other Wnt family members are useful for the production of definitive endoderm cells. In certain differentiation processes, combinations of any of the above-mentioned growth factors can be used.

With respect to some of the processes for the differentiation of pluripotent stem cells to definitive endoderm cells, the above-mentioned growth factors are provided to the cells so that the growth factors are present in the cultures at concentrations sufficient to promote differentiation of at least a portion of the stem cells to definitive endoderm cells. In some processes, the above-mentioned growth factors are present in the cell culture at a concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, at least about 1000 ng/ml, at least about 2000 ng/ml, at least about 3000 ng/ml, at least about 4000 ng/ml, at least about 5000 ng/ml or more than about 5000 ng/ml.

In certain processes for the differentiation of pluripotent stem cells to definitive endoderm cells, the above-mentioned growth factors are removed from the cell culture subsequent to their addition. For example, the growth factors can be removed within about one day, about two days, about three days, about four days, about five days, about six days, about seven days, about eight days, about nine days or about ten days after their addition. In a preferred process, the growth factors are removed about four days after their addition.

Cultures of definitive endoderm cells can be produced from embryonic stem cells in medium containing reduced serum or no serum. Under certain culture conditions, serum concentrations can range from about 0.05% v/v to about 20% v/v. For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v), less than about 10% (v/v), less than about 15% (v/v) or less than about 20% (v/v). In some processes, definitive endoderm cells are grown without serum or without serum replacement. In still other processes, definitive endoderm cells are grown in the presence of B27. In such processes, the concentration of B27 supplement can range from about 0.1% v/v to about 20% v/v. In other embodiments, the definitive endoderm cells are grown in the absence of B27.

In some processes for differentiating human definitive endoderm cells from hESCs, differentiation is initiated in the absence of serum and in the absence of insulin and/or insulin-like growth factor. During the course of differentiation, the serum concentration may be gradually increased in order to promote adequate cell survival. In preferred embodiments, differentiation of hESCs to definitive endoderm cells is initiated in the absence of serum and in the absence of any supplement comprising insulin or insulin-like growth factors. The absence of serum and absence of supplement comprising insulin or insulin-like growth factors is maintained for about 1 to about 2 days, after which, serum is gradually added to the differentiating cell culture over the course of differentiation. In preferred embodiments, the concentration of serum does not exceed about 2% during the course of differentiation.

Definitive endoderm cell cultures and cell populations as well as detailed processes for the production of definitive endoderm cells from embryonic stem cells are further described in U.S. patent application Ser. No. 11/021,618, entitled DEFINITIVE ENDODERM, filed Dec. 23, 2004, the disclosure of which is incorporated herein by reference in its entirety.

Enrichment, Isolation and/or Purification of Definitive Endoderm

In some embodiments of the processes described herein, definitive endoderm cells are enriched, isolated and/or purified prior to further differentiation. In such embodiments, definitive endoderm cells can be enriched, isolated and/or purified using any known method. In preferred embodiments, the definitive endoderm cells are enriched, isolated and/or purified using one or more of the methods described in U.S. patent application Ser. No. 11/021,618, entitled DEFINITIVE ENDODERM, filed Dec. 23, 2004, and U.S. Provisional Patent Application No. 60/736,598, entitled MARKERS OF DEFINITIVE ENDODERM, filed Nov. 14, 2005, the disclosures of which are incorporated herein by reference in their entireties.

Compositions Comprising Definitive Endoderm Cells

Cell compositions produced by the above-described methods include cell cultures comprising definitive endoderm cells and cell populations enriched in definitive endoderm cells. For example, cell cultures and/or cell populations that comprise definitive endoderm cells can be produced, wherein at least about 50-99% of the cells in the cell culture and/or cell population are definitive endoderm cells. Because the efficiency of the differentiation process can be adjusted by modifying certain parameters, which include but are not limited to, cell growth conditions, growth factor concentrations and the timing of culture steps, the differentiation procedures described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 98%, about 99% or greater than about 99% conversion of pluripotent cells to definitive endoderm. In processes in which isolation of definitive endoderm cells is employed, for example, by using an affinity reagent that binds to the CXCR4 receptor, a substantially pure definitive endoderm cell population can be recovered. In embodiments where the cell cultures or cell populations comprise human feeder cells, the above percentages are calculated without respect to the human feeder cells in the cell cultures or cell populations.

Production of PDX1-Positive Foregut Endoderm

Definitive endoderm cells can be specified toward pancreatic differentiation by further differentiation of these cells to produce PDX1-positive foregut endoderm cells. In some of the differentiation processes described herein, cell cultures as well as enriched or purified cell populations comprising definitive endoderm cells can be used for further differentiation to cell cultures and/or enriched cell populations comprising PDX1-positive foregut endoderm cells.

Typically, definitive endoderm cells are differentiated to PDX1-positive foregut endoderm cells by providing to a cell culture comprising SOX17-positive definitive endoderm cells a retinoid, such as retinoic acid (RA). In some of the differentiation processes, definitive endoderm cells in culture are also provided with a member of the fibroblast growth factor family either prior to or about the same time as the addition of RA. A preferred fibroblast growth factor is FGF-10. In another preferred process, the fibroblast growth factor comprises any fibroblast growth factor or a ligand that stimulates or otherwise interacts with the fibroblast growth factor 2 receptor IIIb (FGFR2(IIIb)). In even more preferred processes, the FGF family growth factor is used in conjunction with a hedgehog pathway inhibitor. A preferred hedgehog pathway inhibitor is KAAD-cyclopamine. In especially preferred differentiation processes, FGF-10 and/or KAAD-cyclopamine is provided to a cell culture comprising PDX1-negative definitive endoderm cells in the presence of RA. In certain processes, BMP4 may be included with FGF-10 and/or KAAD-cyclopamine in the presence of RA. In some processes, the retinoid is used in conjunction with a member of the TGFβ superfamily of growth factors and/or Connaught Medical Research Labs medium (CRML medium) (Invitrogen, Carlsbad, Calif.).

With respect to some of the embodiments of differentiation processes described herein, the retinoid and/or a combination of the above-mentioned differentiation factors are provided to the cells so that these factors are present in the cell culture or cell population at concentrations sufficient to promote differentiation of at least a portion of the definitive endoderm cell culture or cell population to PDX1-positive foregut endoderm cells.

In some processes, the retinoid is provided to the cells of a cell culture such that it is present at a concentration of at least about 1 nM, at least about 0.01 µM, at least about 0.02 µM, at least about 0.04 µM, at least about 0.08 µM, at least about 0.1 µM, at least about 0.2 µM, at least about 0.3 µM, at least about 0.4 µM, at least about 0.5 µM, at least about 0.6 µM, at least about 0.7 µM, at least about 0.8 µM, at least about 0.9 µM, at least about 1 µM, at least about 1.1 µM, at least about 1.2 µM, at least about 1.3 µM, at least about 1.4 µM, at least about 1.5 µM, at least about 1.6 µM, at least about 1.7 µM, at least about 1.8 µM, at least about 1.9 µM, at least about 2 µM, at least about 2.1 µM, at least about 2.2 µM, at least about 2.3 µM, at least about 2.4 µM, at least about 2.5 µM, at least about 2.6 µM, at least about 2.7 µM, at least about 2.8 µM, at least about 2.9 µM, at least about 3 µM, at least about 3.5 µM, at least about 4 µM, at least about 4.5 µM, at least about 5 µM, at least about 10 µM, at least about 20 µM, at least about 30 µM, at least about 40 µM or at least about 50 µM.

In other processes, FGF-10 is provided to the cells of a cell culture such that it is present at a concentration of at least about 1 ng/ml, at least about 2 ng/ml, at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, or at least about 1000 ng/ml. In other embodiments, when used alone or in conjunction with FGF-10, KAAD-cyclopamine can be provided at a concentration of at least about 0.01 µM, at least about 0.02 µM, at least about 0.04 µM, at least about 0.08 µM, at least about 0.1 µM, at least about 0.2 µM, at least about 0.3 µM, at least about 0.4 µM, at least about 0.5 µM, at least about 0.6 µM, at least about 0.7 µM, at least about 0.8 µM, at least about 0.9 µM, at least about 1 µM, at least about 1.1 µM, at least about 1.2 µM, at least about 1.3 µM, at least about 1.4 µM, at least about 1.5 µM, at least about 1.6 µM, at least about 1.7 µM, at least about 1.8 µM, at least about 1.9 µM, at least about 2 µM, at least about 2.1 µM, at least about 2.2 µM, at least about 2.3 µM, at least about 2.4 µM, at least about 2.5 µM, at least about 2.6 µM, at least about 2.7 µM, at least about 2.8 µM, at least about 2.9 µM, at least about 3 µM, at least about 3.5 µM, at least about 4 µM, at least about 4.5 µM, at least about 5 µM, at least about 10 µM, at least about 20 µM, at least about 30 µM, at least about 40 µM or at least about 50 µM. In some embodiments of the present invention, a fibroblast growth factor or a ligand that stimulates or otherwise interacts with the fibroblast growth factor 2 receptor IIIb (FGFR2(IIIb)) is provided either alone or in combination with the hedgehog pathway inhibitor.

In a preferred process for the production of a population of PDX1-positive foregut endoderm cells from definitive endoderm cells, a cell culture or an enriched cell population of definitive endoderm cells is provided with 50 ng/ml of FGF-10 and 0.2 µM KAAD-cyclopamine in CMRL medium in the presence of 2 µM RA.

In some processes described herein, activin A and/or activin B is provided to the cell culture along with the retinoid and/or the fibroblast growth factor and the hedgehog inhibitor. For example, in such processes, activin A and/or activin B is provided to the cell culture at a concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, or at least about 1000 ng/ml.

In some processes, the differentiation factors and/or CRML medium is provided to the definitive endoderm cells at about three days, at about four days, at about five days, at about six days, at about seven days, at about eight days, at about nine days, at about ten days or at about greater than ten days subsequent to the initiation of differentiation from hESCs. In preferred processes, differentiation factors and/or CRML medium is provided to the definitive endoderm cells at about five days subsequent to the initiation of differentiation from hESCs.

In certain processes described herein, the above-mentioned differentiation factors are removed from the cell culture subsequent to their addition. For example, the above-mentioned differentiation factors can be removed within about one day, about two days, about three days, about four days, about five days, about six days, about seven days, about eight days, about nine days or about ten days after their addition.

Cultures of PDX1-positive foregut endoderm cells can be differentiated and further grown in a medium containing reduced or no serum. Serum concentrations can range from about 0.05% (v/v) to about 20% (v/v). In some processes, dorsal PDX1-positive foregut endoderm cells are grown with serum replacement. For example, in certain processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v), less than about 10% (v/v), less than about 15% (v/v) or less than about 20% (v/v). In certain processes described herein, the differentiation medium does not include serum, serum replacement or any supplement comprising insulin or insulin-like growth factors.

In certain processes, PDX1-positive foregut endoderm cells are grown in the presence of B27. In such differentiation processes, B27 can be provided to the culture medium in concentrations ranging from about 0.1% (v/v) to about 20% (v/v) or in concentrations greater than about 20% (v/v). In certain processes, the concentration of B27 in the medium is about 0.1% (v/v), about 0.2% (v/v), about 0.3% (v/v), about 0.4% (v/v), about 0.5% (v/v), about 0.6% (v/v), about 0.7% (v/v), about 0.8% (v/v), about 0.9% (v/v), about 1% (v/v), about 2% (v/v), about 3% (v/v), about 4% (v/v), about 5% (v/v), about 6% (v/v), about 7% (v/v), about 8% (v/v), about 9% (v/v), about 10% (v/v), about 15% (v/v) or about 20% (v/v). Alternatively, the concentration of the added B27 supplement can be measured in terms of multiples of the strength of a commercially available B27 stock solution. For example, B27 is available from Invitrogen (Carlsbad, Calif.) as a 50× stock solution. Addition of a sufficient amount of this stock solution to a sufficient volume of growth medium produces a medium supplemented with the desired amount of B27. For example, the addition of 10 ml of 50× B27 stock solution to 90 ml of growth medium would produce a growth medium supplemented with 5× B27. The concentration of B27 supplement in the medium can be about 0.1×, about 0.2×, about 0.3×, about 0.4×, about 0.5×, about 0.6×, about 0.7×, about 0.8×, about 0.9×, about 1×, about 1.1×, about 1.2×, about 1.3×, about 1.4×, about 1.5×, about 1.6×, about 1.7×, about 1.8×, about 1.9×, about 2×, about 2.5×, about 3×, about 3.5×, about 4×, about 4.5×, about 5×, about 6×, about 7×, about 8×, about 9×, about 10×, about 11×, about 12×, about 13×, about 14×, about 15×, about 16×, about 17×, about 18×, about 19×, about 20× and greater than about 20×.

In some processes for the differentiation of PDX1-positive foregut endoderm cells from definitive endoderm cells, the definitive endoderm cells are differentiated so as to be biased towards further differentiation to either dorsal pancreatic bud or ventral pancreatic bud as described in U.S. Provisional Patent Application No. 60/730,917, entitled PDX1-EXPRESSING DORSAL AND VENTRAL FOREGUT ENDODERM, filed Oct. 27, 2005, the disclosure of which is incorporated herein by reference in its entirety. Additional detailed methods of producing PDX1-positive foregut endoderm cells can be found in U.S. patent application Ser. No. 11/115,868, entitled PDX1 EXPRESSING ENDODERM, filed Apr. 26, 2005, the disclosure of which is incorporated herein by reference in its entirety.

Enrichment, Isolation and/or Purification of PDX1-Positive Foregut Endoderm

In some embodiments of the processes described herein, PDX1-positive foregut endoderm cells are enriched, isolated and/or purified prior to further differentiation. In such embodiments, PDX1-positive foregut endoderm cells can be enriched, isolated and/or purified using any known method. In preferred embodiments, the PDX1-positive foregut endoderm cells are enriched, isolated and/or purified using one or more of the methods described in U.S. patent application Ser. No. 11/115,868, entitled PDX1 EXPRESSING ENDODERM, filed Apr. 26, 2005 and U.S. Provisional Patent Application No. 60/730,917, entitled PDX1-EXPRESSING DORSAL AND VENTRAL FOREGUT ENDODERM, filed Oct. 27, 2005, the disclosures of which are incorporated herein by reference in their entireties.

Compositions Comprising PDX1-Positive Foregut Endoderm Cells

Cell compositions produced by the above-described methods include cell cultures comprising PDX1-positive foregut endoderm cells and cell populations enriched in PDX1-positive foregut endoderm cells. For example, cell cultures and/or cell populations that comprise PDX1-positive foregut endoderm cells can be produced, wherein at least about 50-99% of the cells in the cell culture and/or cell population are PDX1-positive foregut endoderm cells. Because the efficiency of the differentiation process can be adjusted by modifying certain parameters, which include but are not limited to, cell growth conditions, growth factor concentrations and the timing of culture steps, the differentiation procedures described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 98%, about 99% or greater than about 99% conversion of pluripotent cells to PDX1-positive foregut endoderm. In processes in which isolation of PDX1-positive foregut endoderm cells is employed, a substantially pure PDX1-positive foregut endoderm cell population can be recovered. In embodiments where the cell cultures or cell populations comprise human feeder cells, the above percentages are calculated without respect to the human feeder cells in the cell cultures or cell populations.

Production of Endocrine Precursor Cells

Some embodiments of the present invention relate to methods of producing endocrine precursor cells starting from hESCs. As described above, endocrine precursor cells can be produced by first differentiating hESCs to produce definitive endoderm cells then further differentiating the definitive endoderm cells to produce PDX1-positive foregut endoderm cells. In such embodiments, PDX1-positive foregut endoderm cells are further differentiated to multipotent endocrine precursor cells, which are capable of differentiating into human pancreatic islet hormone-expressing cells.

In one embodiment of the present invention, PDX1-positive foregut endoderm cells are differentiated to endocrine precursor cells by continuing the incubation of PDX1-positive foregut endoderm cells in the presence of a retinoid, such as retinoic acid, for an amount of time sufficient to produce endocrine precursor cells. In some embodiment, the amount of time sufficient for the production of endocrine precursor cells ranges from about 1 hour to about 10 days subsequent to the expression of the PDX1 marker in a portion of the cells in the cell culture. In some embodiments, the retinoid is maintained in the cell culture for about 1 hour, about 2 hours, about 4 hours, about 6 hours, about 8 hours, about 10 hours, about 12 hours, about 16 hours, about 1 day, about 2 days, about 3 days, about 4 days, about 5 days, about 6 days, about 7 days, about 8 days, about 9 days, about 10 days or greater than about 10 days subsequent to the expression of the PDX1 marker in a portion of the cells in the cell culture.

In some processes described herein, the concentration of retinoid used to differentiate PDX1-positive foregut endoderm cells in the cell culture or cell population to endocrine precursor cells ranges from about 1 nM to about 100 µM. In some processes, the retinoid is provided to the cells of a cell culture such that it is present at a concentration of at least about 1 nM, at least about 0.01 µM, at least about 0.02 µM, at least about 0.04 µM, at least about 0.08 µM, at least about 0.1 µM, at least about 0.2 µM, at least about 0.3 µM, at least about 0.4 µM, at least about 0.5 µM, at least about 0.6 µM, at least about 0.7 µM, at least about 0.8 µM, at least about 0.9 µM, at least about 1 µM, at least about 1.1 µM, at least about 1.2 µM, at least about 1.3 µM, at least about 1.4 µM, at least about 1.5 µM, at least about 1.6 µM, at least about 1.7 µM, at least about 1.8 µM, at least about 1.9 µM, at least about 2 µM, at least about 2.1 µM, at least about 2.2 µM, at least about 2.3 µM, at least about 2.4 µM, at least about 2.5 µM, at least about 2.6 µM, at least about 2.7 µM, at least about 2.8 µM, at least about 2.9 µM, at least about 3 µM, at least about 3.5 µM, at least about 4 µM, at least about 4.5 µM, at least about 5 µM, at least about 10 µM, at least about 20 µM, at least about 30 µM, at least about 40 µM, at least about 50 µM, at least about 75 µM or at least about 100 µM.

In some preferred embodiments of the present invention, differentiation from PDX1-positive foregut endoderm cells to pancreatic endocrine precursor cells is mediated by providing a cell culture or cell population comprising human PDX1-positive foregut endoderm cells with a gamma secretase inhibitor. In a preferred embodiment, the gamma secretase inhibitor is N—[N-(3,5-Diflurophenacetyl-L-alanyl)]-S-phenylglycine t-Butyl Ester (DAPT).

In other embodiments of the present invention, the gamma secretase inhibitor is provided at the start of the differentiation process, for example, at the hESC stage, and remains in the cell culture throughout the differentiation to pancreatic islet hormone-expressing cells. In still other embodiments, the gamma secretase inhibitor is added to subsequent to the initiation of differentiation but prior to differentiation to the PDX1-positive foregut endoderm stage. In preferred embodiments, the gamma secretase inhibitor is provided to the cell culture or cell population at about the same time as providing the differentiation factors which promote the conversion of definitive endoderm to PDX1-positive endoderm. In other preferred embodiments, the gamma secretase inhibitor is provided to the cell culture or cell population after a substantial portion of the cells in the cell culture or cell population have differentiated to PDX1-positive foregut endoderm cells.

With respect to some embodiments regarding the differentiation of PDX1-positive foregut endoderm cells to endocrine precursor cells, the gamma secretase inhibitor is provided to the cells so that it is present in the cell culture or cell population at concentrations sufficient to promote differentiation of at least a portion of the PDX1-positive cells to endocrine precursor cells. In some embodiments, the gamma secretase inhibitor is present in the cell culture or cell population at a concentration ranging from about 0.01 µM to about 1000 µM. In preferred embodiments, the gamma secretase inhibitor is present in the cell culture or cell population at a concentration ranging from about 0.1 µM to about 100 µM. In more preferred embodiments, the gamma secretase inhibitor is present in the cell culture or cell population at a concentration ranging from about 1 µM to about 10 µM. In other embodiments, the gamma secretase inhibitor is present in the cell culture or cell population at a concentration of at least about 0.01 µM, at least about 0.02 µM, at least about 0.04 µM, at least about 0.08 µM, at least about 0.1 µM, at least about 0.2 µM, at least about 0.3 µM, at least about 0.4 µM, at least about 0.5 µM, at least about 0.6 µM, at least about 0.7 µM, at least about 0.8 µM, at least about 0.9 µM, at least about 1 µM, at least about 1.1 µM, at least about 1.2 µM, at least about 1.3 µM, at least about 1.4 µM, at least about 1.5 µM, at least about 1.6 µM, at least about 1.7 µM, at least about 1.8 µM, at least about 1.9 µM, at least about 2 µM, at least about 2.1 µM, at least about 2.2 µM, at least about 2.3 µM, at least about 2.4 µM, at least about 2.5 µM, at least about 2.6 µM, at least about 2.7 µM, at least about 2.8 µM, at least about 2.9 µM, at least about 3 µM, at least about 3.5 µM, at least about 4 µM, at least about 4.5 µM, at least about 5 µM, at least about 10 µM, at least about 20 µM, at least about 30 µM, at least about 40 µM, at least about 50 µM, at least about 60 µM, at least about 70 µM, at least about 80 µM, at least about 90 µM, at least about 100 µM, at least about 250 µM, at least about 500 µM, at least about 750 µM or at least about 1000 µM.

In certain embodiments of the processes for producing endocrine precursor cells as described herein, the gamma secretase inhibitor is provided after one or more previously provided differentiation factors have been removed from the cell cultures. For example, the one or more previously provided differentiation factors can be removed about 1 day, about 2 days, about 3 days, about 4 days, about 5 days, about 6 days, about 7 days, about 8 days, about 9 days, about 10 days or more than about 10 days prior to the addition of the gamma secretase inhibitor. In other embodiments, the gamma secretase inhibitor is provided to cell cultures or cell populations comprising one or more differentiation factors that were previously provided or provided at about the same time as the gamma secretase inhibitor. In preferred embodiments, differentiation factors that were previously provided or provided at about the same time as the gamma secretase inhibitor include, but are not limited to, FGF-10, KAAD-cyclopamine, activin A, activin B, BMP4 and/or RA.

In some embodiments of the invention described herein, exendin 4 is provided to the differentiating cell culture or cell population at about the same time as the gamma secretase inhibitor. In certain embodiments, exendin 4 is provided so as to be in present in the cell culture or cell population at a concentration of at least about 0.1 ng/ml, at least about 0.2 ng/ml, at least about 0.3 ng/ml, at least about 0.4 ng/ml, at least about 0.5 ng/ml, at least about 0.6 ng/ml, at least about 0.7 ng/ml, at least about 0.8 ng/ml, at least about 0.9 ng/ml, at least about 1 ng/ml, at least about 5 ng/ml, at least about 10 ng/ml, at least about 15 ng/ml, at least about 20 ng/ml, at least about 25 ng/ml, at least about 30 ng/ml, at least about 35 ng/ml, at least about 40 ng/ml, at least about 45 ng/ml, at least about 50 ng/ml, at least about 55 ng/ml, at least about 60 ng/ml, at least about 65 ng/ml, at least about 70 ng/ml, at least about 75 ng/ml, at least about 80 ng/ml, at least about 85 ng/ml, at least about 90 ng/ml, at least about 95 ng/ml, at least about 100 ng/ml, at least about 150 ng/ml, at least about 200 ng/ml, at least about 250 ng/ml, at least about 300 ng/ml, at least about 350 ng/ml, at least about 400 ng/ml, at least about 450 ng/ml, at least about 500 ng/ml, at least about 550 ng/ml, at least about 600 ng/ml, at least about 650 ng/ml, at least about 700 ng/ml, at least about 750 ng/ml, at least about 800 ng/ml, at least about 850 ng/ml, at least about 900 ng/ml, at least about 950 ng/ml or at least about 1000 ng/ml.

In a preferred process for the production of endocrine precursor cells from PDX1-positive foregut endoderm cells, a cell culture or cell population of PDX1-positive foregut endoderm cells is provided with 3 µM DAPT and 40 ng/ml exendin 4. In especially preferred embodiments, the cells are differentiated in CMRL. In another especially preferred process, for the production of a endocrine precursor cells from PDX1-positive foregut endoderm cells, a cell culture or cell population of PDX1-positive foregut endoderm cells is provided with 3 µM DAPT and 40 ng/ml exendin 4 in the presence of 2 µM RA.

In certain processes for producing endocrine precursor cells as described herein, the above-mentioned differentiation factors are removed from the cell culture or cell population subsequent to their addition. For example, the gamma secretase inhibitor and/or exendin 4 can be removed within about one day, about two days, about three days, about four days, about five days, about six days, about seven days, about eight days, about nine days or about ten days after their addition. In some embodiments, the differentiation factors are not removed from the cell culture.

Cultures of endocrine precursor cells can be produced in medium containing reduced serum or no serum. Under certain culture conditions, serum concentrations can range from about 0.05% v/v to about 20% v/v. For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v), less than about 10% (v/v), less than about 15% (v/v) or less than about 20% (v/v). In some processes, endocrine precursor cells are grown without serum, without serum replacement and/or without any supplement containing insulin or insulin-like growth factor. In still other processes, endocrine precursor cells are grown in the presence of B27. In such processes, the concentration of B27 supplement can range from about 0.1% v/v to about 20% v/v. In other embodiments, the endocrine precursor cells are grown in the absence of B27.

Monitoring the Differentiation of PDX1-Positive Cells to Endocrine Precursor Cells The progression of PDX1-positive endoderm cells to endocrine precursor cells can be monitored by determining the expression of markers characteristic of endocrine precursor cells. In some processes, the expression of certain markers is determined by detecting the presence or absence of the marker. Alternatively, the expression of certain markers can be determined by measuring the level at which the marker is present in the cells of the cell culture or cell population. In such processes, the measurement of marker expression can be qualitative or quantitative. One method of quantitating the expression of markers that are produced by marker genes is through the use of quantitative PCR (Q-PCR). Methods of performing Q-PCR are well known in the art. Other methods which are known in the art can also be used to quantitate marker gene expression. For example, the expression of a marker gene product can be detected by using antibodies specific for the marker gene product of interest. In certain processes, the expression of marker genes characteristic of endocrine precursor cells as well as the lack of significant expression of marker genes characteristic of hESCs, definitive endoderm, PDX1-positive foregut endoderm, extraembryonic endoderm, mesoderm, ectoderm, immature pancreatic islet hormone-expressing cells or mature pancreatic islet hormone-expressing cells and/or other cell types is determined.

As described further in the Examples below, a reliable marker of endocrine precursor cells is the NGN3 gene. As such, the endocrine precursor cells produced by the processes described herein express the NGN3 marker gene, thereby producing the NGN3 gene product. Other markers of endocrine precursor cells are NKX2.2 and PAX4.

In some processes, the expression of genes indicative of hESCs, definitive endoderm cells and/or PDX1-positive foregut endoderm cells is also monitored. For example, in some processes, the expression of AFP, SOX7, SOX1, ZIC1, and NFM are monitored. In some processes, the expression of genes indicative of immature pancreatic islet hormone-expressing cells and/or mature pancreatic islet hormone-expressing cells is also monitored. For example, in some embodiments, the expression of MAFB, SYP, CHGA, INS, GCG, SST, GHRL and PAX6 is monitored.

It will be appreciated that NGN3, NKX2.2 and/or PAX4 marker expression is induced over a range of different levels in endocrine precursor cells depending on the differentiation conditions. As such, in some embodiments described herein, the expression of the NGN3, NKX2.2 and/or PAX4 marker in endocrine precursor cells or cell populations is at least about 2-fold higher to at least about 10,000-fold higher than the expression of the NGN3, NKX2.2 and/or PAX4 marker in non-endocrine precursor cells or cell populations, for example pluripotent stem cells, definitive endoderm cells, PDX1-positive foregut endoderm cells, immature pancreatic islet hormone-expressing cells, mature pancreatic islet hormone-expressing cells, extraembryonic endoderm cells, mesoderm cells and/or ectoderm cells. In other embodiments, the expression of the NGN3, NKX2.2 and/or PAX4 marker in endocrine precursor cells or cell populations is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher than the expression of the NGN3, NKX2.2 and/or PAX4 marker in non-endocrine precursor cells or cell populations, for example pluripotent stem cells, definitive endoderm cells, PDX1-positive foregut endoderm cells, immature pancreatic islet hormone-expressing cells, mature pancreatic islet hormone-expressing cells, extraembryonic endoderm cells, mesoderm cells and/or ectoderm cells. In some embodiments, the expression of the NGN3, NKX2.2 and/or PAX4 marker in endocrine precursor cells or cell populations is infinitely higher than the expression of the NGN3, NKX2.2 and/or PAX4 marker in non-endocrine precursor cells or cell populations, for example pluripotent stem cells, definitive endoderm cells, PDX1-positive foregut endoderm cells, immature pancreatic islet hormone-expressing cells, mature pancreatic islet hormone-expressing cells, extraembryonic endoderm cells, mesoderm cells and/or ectoderm cells.

Enrichment, Isolation and/or Purification of Endocrine Precursor Cells

With respect to additional aspects of the present invention, endocrine precursor cells can be enriched, isolated and/or purified. In some embodiments of the present invention, cell populations enriched, isolated and/or purified for endocrine precursor cells are produced by isolating such cells from cell cultures.

Endocrine precursor cells produced by any of the processes described herein can be enriched, isolated and/or purified by using an affinity tag that is specific for such cells. Examples of affinity tags specific for endocrine precursor cells are antibodies, antibody fragments, ligands or other binding agents that are specific to a marker molecule, such as a polypeptide, that is present on the cell surface of endocrine precursor cells but which is not substantially present on other cell types that would be found in a cell culture produced by the methods described herein. In some processes, an antibody which binds to NCAM is used as an affinity tag for the enrichment, isolation or purification of endocrine precursor cells. In other processes, the NCAM ligand NBP10, or any other NCAM ligand now known or discovered in the future can also be used as affinity tags, for example, see Ronn, L. (2002) *Eur J Neurosci.*, 16:1720-30, the disclosure of which is incorporated herein by reference in its entirety. Such molecules include, but are not limited to, NBP10 fusions and NBP10 mimetics.

Methods for making antibodies and using them for cell isolation are known in the art and such methods can be implemented for use with the antibodies and endocrine precursor cells described herein. In one process, an antibody which binds to NCAM is attached to a magnetic bead and then allowed to bind to endocrine precursor cells in a cell culture which has been enzymatically treated to reduce intercellular and substrate adhesion. The cell/antibody/bead complexes are then exposed to a movable magnetic field which is used to separate bead-bound endocrine precursor cells from unbound cells. Once the endocrine precursor cells are physically separated from other cells in culture, the antibody binding is disrupted and the cells are replated in appropriate tissue culture medium. If desired, the isolated cell compositions can be further purified by using an alternate affinity-based method or by additional rounds of enrichment using the same or different markers that are specific for endocrine precursor cells.

Additional methods for obtaining enriched, isolated or purified endocrine precursor cell cultures or populations can also be used. For example, in some embodiments, the NCAM antibody is incubated with an endocrine precursor-containing cell culture that has been treated to reduce intercellular and substrate adhesion. (WE DON'T USE SECONDARY ANTIBODIES. THE NCAM ANTIBODY IS DIRECTLY CONJUGATED TO EITHER PE, APC, OR FITC) The cells are then washed, centrifuged and resuspended. The cell suspension is then incubated with a secondary antibody, such as an FITC-conjugated antibody that is capable of binding to the primary antibody. The cells are then washed, centrifuged and resuspended in buffer. The cell suspension is then analyzed and sorted using a fluorescence activated cell sorter (FACS). NCAM-positive cells are collected separately from NCAM-negative cells, thereby resulting in the isolation of such cell types. If desired, the isolated cell compositions can be further purified by using an alternate affinity-based method or by additional rounds of sorting using the same or different markers that are specific for endocrine precursor cells. Alternatively, isolated cell compositions can be further purified by negatively sorting for a marker that is present on most cells in the cell population other than endocrine precursor cells.

In still other processes, endocrine precursor cells are enriched, isolated and/or purified using a ligand or other molecule that binds to NCAM. In some processes, the molecule is NBP10 or a fragment, fusion or mimetic thereof.

In some embodiments of the processes described herein, a nucleic acid encoding green fluorescent protein (GFP) or another nucleic acid encoding an expressible fluorescent marker gene (e.g., yellow fluorescent protein (YFP), luciferase or the like) is used to label NCAM-positive cells. For example, in some embodiments, at least one copy of a nucleic acid encoding GFP or a biologically active fragment thereof is introduced into a pluripotent cell, preferably a human embryonic stem cell, downstream of the NCAM promoter, the NGN3 promoter, the PAX4 promoter, or the promoter of any endocrine precursor cell-specific gene such that the expression of the GFP gene product or biologically active fragment thereof is under control of the NCAM, NGN3, or PAX4 promoter. In some embodiments, the entire coding region of the nucleic acid, which encodes NCAM, NGN3, or PAX4, is replaced by a nucleic acid encoding GFP or a biologically active fragment thereof. In other embodiments, the nucleic acid encoding GFP or a biologically active fragment thereof is fused in frame with at least a portion of the nucleic acid encoding NCAM, NGN3, or PAX4, thereby generating a fusion protein. In such embodiments, the fusion protein retains a fluorescent activity similar to GFP.

Fluorescently marked cells, such as the above-described pluripotent cells, are differentiated to endocrine precursor cells as described herein. Because endocrine precursor cells express the fluorescent marker gene, whereas other cell types do not, endocrine precursor cells can be separated from the other cell types. In some embodiments, cell suspensions comprising a mixture of fluorescently-labeled endocrine precursor cells and unlabeled non-endocrine precursor cells are sorted using a FACS. Endocrine precursor cells are collected separately from non-fluorescing cells, thereby resulting in the isolation of endocrine precursors. If desired, the isolated cell compositions can be further purified by additional rounds of sorting using the same or different markers that are specific for endocrine precursor cells.

In preferred processes, endocrine precursor cells are enriched, isolated and/or purified from other non-endocrine precursor cells after endodermal cell cultures are induced to differentiate towards the endocrine precursor lineage. It will be appreciated that the above-described enrichment, isolation and purification procedures can be used with such cultures at any stage of differentiation.

In addition to the procedures just described, endocrine precursor cells may also be isolated by other techniques for cell isolation. Additionally, endocrine precursor cells may also be enriched or isolated by methods of serial subculture in growth conditions which promote the selective survival or selective expansion of the endocrine precursor cells.

Using the methods described herein, enriched, isolated and/or purified populations of endocrine precursor cells and or tissues can be produced in vitro from pluripotent cell cultures or cell populations, such as stem cell cultures or populations, which have undergone at least some differentiation. In some methods, the cells undergo random differentiation. In a preferred method, however, the cells are directed to differentiate primarily into endocrine precursor cells. Some preferred enrichment, isolation and/or purification methods relate to the in vitro production of endocrine precursor cells from human embryonic stem cells.

Using the methods described herein, cell populations or cell cultures can be enriched in endocrine precursor cell content by at least about 2- to about 1000-fold as compared to untreated cell populations or cell cultures. In some embodiments, endocrine precursor cells can be enriched by at least about 5- to about 500-fold as compared to untreated cell populations or cell cultures. In other embodiments, endocrine precursor cells can be enriched from at least about 10- to about 200-fold as compared to untreated cell populations or cell cultures. In still other embodiments, endocrine precursor cells can be enriched from at least about 20- to about 100-fold as compared to untreated cell populations or cell cultures. In yet other embodiments, endocrine precursor cells can be enriched from at least about 40- to about 80-fold as compared to untreated cell populations or cell cultures. In certain embodiments, endocrine precursor cells can be enriched from at least about 2- to about 20-fold as compared to untreated cell populations or cell cultures.

Compositions Comprising Endocrine Precursor Cells

Some embodiments of the present invention relate to cell compositions, such as cell cultures or cell populations, comprising endocrine precursor cells, wherein the endocrine precursor cells are multipotent cells that can differentiate into cells of the endocrine system, such as pancreatic islet hormone-expressing cells. In accordance with certain embodiments, the endocrine precursor cells are mammalian cells, and in a preferred embodiment, such cells are human cells.

Other embodiments of the present invention relate to compositions, such as cell cultures or cell populations, comprising endocrine precursor cells and cells that are less specifically differentiated than endocrine precursor cells. In such embodiments, cells that are less specifically differentiated than endocrine precursor cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture.

Other embodiments relate to compositions, such as cell cultures or cell populations, comprising endocrine precursor cells and cells that are more specifically differentiated than endocrine precursor cells, such as immature pancreatic islet hormone-expressing cells and/or mature pancreatic islet hormone-expressing cells. In such embodiments, cells that are more specifically differentiated than endocrine precursor cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture.

Certain other embodiments of the present invention relate to compositions, such as cell cultures or cell populations, comprising endocrine precursor cells and cells of one or more cell types selected from the group consisting of hESCs, pre-primitive streak cells, mesendoderm cells, definitive endoderm cells, PDX1-negative foregut endoderm cells, PDX1-positive foregut endoderm cells (PDX1-positive pancreatic endoderm cells) and mesoderm cells. In some embodiments, hESCs comprise less than about 25%, less than about 20%, less than about 15%, less than about 10%, less than about 5%, less than about 4%, less than about 3%, less than about 2% or less than about 1% of the total cells in the culture. In certain embodiments, pre-primitive streak cells comprise less than about 25%, less than about 20%, less than about 15%, less than about 10%, less than about 5%, less than about 4%, less than about 3%, less than about 2% or less than about 1% of the total cells in the culture. In other embodiments, mesendoderm cells comprise less than about 25%, less than about 20%, less than about 15%, less than about 10%, less than about 5%, less than about 4%, less than about 3%, less than about 2% or less than about 1% of the total cells in the culture. In still other embodiments, definitive endoderm cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture. In yet other embodiments, PDX1-negative foregut endoderm cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture. In certain embodiments, PDX1-positive foregut endoderm cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture. In still other embodiments, mesoderm cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture.

Certain other embodiments of the present invention relate to compositions, such as cell cultures or cell populations, comprising endocrine precursor cells and cells of one or more cell types selected from the group consisting of immature pancreatic islet hormone-expressing cells and/or mature pancreatic hormone-expressing cells. In some embodiments, immature pancreatic islet hormone-expressing cells comprise less than about 25%, less than about 20%, less than about 15%, less than about 10%, less than about 5%, less than about 4%, less than about 3%, less than about 2% or less than about 1% of the total cells in the culture. In certain embodiments, mature pancreatic islet hormone-expressing cells comprise less than about 25%, less than about 20%, less than about 15%, less than about 10%, less than about 5%, less than about 4%, less than about 3%, less than about 2% or less than about 1% of the total cells in the culture.

Additional embodiments of the present invention relate to compositions, such as cell cultures or cell populations, produced by the processes described herein and which comprise endocrine precursor cells as the majority cell type. In some embodiments, the processes described herein produce cell cultures and/or cell populations comprising at least about 99%, at least about 98%, at least about 97%, at least about 96%, at least about 95%, at least about 94%, at least about 93%, at least about 92%, at least about 91%, at least about 90%, at least about 89%, at least about 88%, at least about 87%, at least about 86%, at least about 85%, at least about 84%, at least about 83%, at least about 82%, at least about 81%, at least about 80%, at least about 79%, at least about 78%, at least about 77%, at least about 76%, at least about 75%, at least about 74%, at least about 73%, at least about 72%, at least about 71%, at least about 70%, at least about 69%, at least about 68%, at least about 67%, at least about 66%, at least about 65%, at least about 64%, at least about 63%, at least about 62%, at least about 61%, at least about 60%, at least about 59%, at least about 58%, at least about 57%, at least about 56%, at least about 55%, at least about 54%, at least about 53%, at least about 52%, at least about 51% or at least about 50% endocrine precursor cells. In preferred embodiments, the cells of the cell cultures or cell populations comprise human cells. In other embodiments, the processes described herein produce cell cultures or cell populations comprising at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about 11%, at least about 10%, at least about 9%, at least about 8%, at least about 7%, at least about 6%, at least about 5%, at least about 4%, at least about 3%, at least about 2% or at least about 1% endocrine precursor cells. In preferred embodiments, the cells of the cell cultures or cell populations comprise human cells. In some embodiments, the percentage of endocrine precursor cells in the cell cultures or populations is calculated without regard to the feeder cells remaining in the culture.

Still other embodiments of the present invention relate to compositions, such as cell cultures or cell populations, comprising mixtures of endocrine precursor cells and PDX1-positive foregut endoderm cells. For example, cell cultures or cell populations comprising at least about 5 endocrine precursor cells for about every 95 PDX1-positive foregut endoderm cells can be produced. In other embodiments, cell cultures or cell populations comprising at least about 95 endocrine precursor cells for about every 5 PDX1-positive foregut endoderm cells can be produced. Additionally, cell cultures or cell populations comprising other ratios of endocrine precursor cells to PDX1-positive foregut endoderm cells are contemplated. For example, compositions comprising at least about 1 endocrine precursor cell for about every 1,000,000 PDX1-positive foregut endoderm cells, at least about 1 endocrine precursor cell for about every 100,000 PDX1-positive foregut endoderm cells, at least about 1 endocrine precursor cell for about every 10,000 PDX1-positive foregut endoderm cells, at least about 1 endocrine precursor cell for about every 1000 PDX1-positive foregut endoderm cells, at least about 1 endocrine precursor cell for about every 500 PDX1-positive foregut endoderm cells, at least about 1 endocrine precursor cell for about every 100 PDX1-positive foregut endoderm cells, at least about 1 endocrine precursor cell for about every 10 PDX1-positive foregut endoderm cells, at least about 1 endocrine precursor cell for about every 5 PDX1-positive foregut endoderm cells, at least about 1 endocrine precursor cell for about every 4 PDX1-positive foregut endoderm cells, at least about 1 endocrine precursor cell for about every 2 PDX1-positive foregut endoderm cells, at least about 1 endocrine precursor cell for about every 1 PDX1-positive foregut endoderm cell, at least about 2 endocrine precursor cells for about every 1 PDX1-positive foregut endoderm cell, at least about 4 endocrine precursor cells for about every 1 PDX1-positive foregut endoderm cell, at least about 5 endocrine precursor cells for about every 1 PDX1-positive foregut endoderm cell, at least about 10 endocrine precursor cells for about every 1 PDX1-positive foregut endoderm cell, at least about 20 endocrine precursor cells for about every 1 PDX1-positive foregut endoderm cell, at least about 50 endocrine precursor cells for about every 1 PDX1-positive foregut endoderm cell, at least about 100 endocrine precursor cells for about every 1 PDX1-positive foregut endoderm cell, at least about 1000 endocrine precursor cells for about every 1 PDX1-positive foregut endoderm cell, at least about 10,000 endocrine precursor cells for about every 1 PDX1-positive foregut endoderm cell, at least about 100,000 endocrine precursor cells for about every 1 PDX1-positive foregut endoderm cell and at least about 1,000,000 endocrine precursor cells for about every 1 PDX1-positive foregut endoderm cell are contemplated.

Still other embodiments of the present invention relate to compositions, such as cell cultures or cell populations, comprising mixtures of endocrine precursor cells and immature pancreatic islet hormone-expressing and/or mature pancreatic islet hormone-expressing cells. For example, cell cultures or cell populations comprising at least about 5 endocrine precursor cells for about every 95 immature pancreatic islet hormone-expressing and/or mature pancreatic islet hormone-expressing cells can be produced. In other embodiments, cell cultures or cell populations comprising at least about 95 endocrine precursor cells for about every 5 immature pancreatic islet hormone-expressing and/or mature pancreatic islet hormone-expressing cells can be produced. Additionally, cell cultures or cell populations comprising other ratios of endocrine precursor cells to immature pancreatic islet hormone-expressing and/or mature pancreatic islet hormone-expressing cells are contemplated. For example, compositions comprising at least about 1 endocrine precursor cell for about every 1,000,000 immature pancreatic islet hormone-expressing and/or mature pancreatic islet hormone-expressing cells, at least about 1 endocrine precursor cell for about every 100,000 immature pancreatic islet hormone-expressing and/or mature pancreatic islet hormone-expressing cells, at least about 1 endocrine precursor cell for about every 10,000 immature pancreatic islet hormone-expressing and/or mature pancreatic islet hormone-expressing cells, at least about 1 endocrine precursor cell for about every 1000 immature pancreatic islet hormone-expressing and/or mature pancreatic islet hormone-expressing cells, at least about 1 endocrine precursor cell for about every immature pancreatic islet hormone-expressing and/or mature pancreatic islet hormone-expressing cells, at least about 1 endocrine precursor cell for about every 100 immature pancreatic islet hormone-expressing and/or mature pancreatic islet hormone-expressing cells, at least about 1 endocrine precursor cell for about every 10 immature pancreatic islet hormone-expressing and/or mature pancreatic islet hormone-expressing cells, at least about 1 endocrine precursor cell for about every 5 immature pancreatic islet hormone-expressing and/or mature pancreatic islet hormone-expressing cells, at least about 1 endocrine precursor cell for about every 4 immature pancreatic islet hormone-expressing and/or mature pancreatic islet hormone-expressing cells, at least about 1 endocrine precursor cell for about every 2 immature pancreatic islet hormone-expressing and/or mature pancreatic islet hormone-expressing cells, at least about 1 endocrine precursor cell for about every 1 immature pancreatic islet hormone-expressing cell and/or mature pancreatic islet hormone-expressing cell, at least about 2 endocrine precursor cells for about every 1 immature pancreatic islet hormone-expressing cell and/or mature pancreatic islet hormone-expressing cell, at least about 4 endocrine precursor cells for about every 1 immature pancreatic islet hormone-expressing cell and/or mature pancreatic islet hormone-expressing cell, at least about 5 endocrine precursor cells for about every 1 immature pancreatic islet hormone-expressing cell and/or mature pancreatic islet hormone-expressing cell, at least about 10 endocrine precursor cells for about every immature pancreatic islet hormone-expressing cell and/or mature pancreatic islet hormone-expressing cell, at least about 20 endocrine precursor cells for about every 1 immature pancreatic islet hormone-expressing cell and/or mature pancreatic islet hormone-expressing cell, at least about 50 endocrine precursor cells for about every 1 immature pancreatic islet hormone-expressing cell and/or mature pancreatic islet hormone-expressing cell, at least about 100 endocrine precursor cells for about every 1 immature pancreatic islet hormone-expressing cell and/or mature pancreatic islet hormone-expressing cell, at least about 1000 endocrine precursor cells for about every 1 immature pancreatic islet hormone-expressing cell and/or mature pancreatic islet hormone-expressing cell, at least about 10,000 endocrine precursor cells for about every 1 immature pancreatic islet hormone-expressing cell and/or mature pancreatic islet hormone-expressing cell, at least about 100,000 endocrine precursor cells for about every 1 immature pancreatic islet hormone-expressing cell and/or mature pancreatic islet hormone-expressing cell and at least about 1,000,000 endocrine precursor cells for about every 1 immature pancreatic islet hormone-expressing cell and/or mature pancreatic islet pancreatic hormone-expressing cell are contemplated.

In some embodiments of the present invention, the PDX1-positive foregut endoderm cells from which endocrine precursor cells are produced are derived from human pluripotent cells, such as human pluripotent stem cells. In certain embodiments, the human pluripotent cells are derived from a morula, the inner cell mass of an embryo or the gonadal ridges of an embryo. In certain other embodiments, the human pluripotent cells are derived from the gonadal or germ tissues of a multicellular structure that has developed past the embryonic stage.

Further embodiments of the present invention relate to compositions, such as cell cultures or cell populations, comprising human cells, including human endocrine precursor cells, wherein the expression of the NGN3 marker is greater than the expression of the AFP, SOX7, SOX1, ZIC1, NFM, MAFA, SYP, CHGA, INS, GCG, SST, GHRL, and/or PAX6 marker in at least about 2% of the human cells. In other embodiments, the expression of the NGN3 marker is greater than the expression of the AFP, SOX7, SOX1, ZIC1, NFM, MAFA, SYP, CHGA, INS, GCG, SST, GHRL, and/or PAX6 marker in at least about 5% of the human cells, in at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells or in at least about 98% of the human cells. In some embodiments, the percentage of human cells in the cell cultures or populations, wherein the expression of NGN3 is greater than the expression of the AFP, SOX7, SOX1, ZIC1, NFM, MAFA, SYP, CHGA, INS, GCG, SST, GHRL, and/or PAX6 marker, is calculated without regard to feeder cells.

It will be appreciated that some embodiments of the present invention relate to compositions, such as cell cultures or cell populations, comprising human endocrine precursor cells, wherein the expression of NKX2.2 and/or PAX4 is greater than the expression of the AFP, SOX7, SOX1, ZIC1, NFM, MAFA, SYP, CHGA, INS, GCG, SST, GHRL, and/or PAX6 marker in from at least about 2% to greater than at least about 98% of the human cells. In some embodiments, the expression of NKX2.2 and/or PAX4 is greater than the expression of the AFP, SOX7, SOX1, ZIC1, NFM, MAFA, SYP, CHGA, INS, GCG, SST, GHRL, and/or PAX6 marker in at least about 5% of the human cells, in at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells or in at least about 98% of the human cells. In some embodiments, the percentage of human cells in the cell cultures or populations, wherein the expression of NKX2.2 and/or PAX4 is greater than the expression of the AFP, SOX7, SOX1, ZIC1, NFM, MAFA, SYP, CHGA, INS, GCG, SST, GHRL, and/or PAX6 marker, is calculated without regard to feeder cells.

Additional embodiments of the present invention relate to compositions, such as cell cultures or cell populations, comprising mammalian cells differentiated from definitive endoderm in vitro, such as human cells differentiated from definitive endoderm in vitro, wherein the expression of the NGN3, NKX2.2 and/or PAX4 marker is greater than the expression of the AFP, SOX7, SOX1, ZIC1, NFM, MAFA, SYP, CHGA, INS, GCG, SST, GHRL, and/or PAX6 marker in at least about 2% of the cells differentiated from definitive endoderm in vitro. In other embodiments, the expression of the NGN3, NKX2.2 and/or PAX4 marker is greater than the expression of the AFP, SOX7, SOX1, ZIC1, NFM, MAFA, SYP, CHGA, INS, GCG, SST, GHRL, and/or PAX6 marker in at least about 5% of the cells differentiated from definitive endoderm in vitro, in at least about 10% of the cells differentiated from definitive endoderm in vitro, in at least about 15% of the cells differentiated from definitive endoderm in vitro, in at least about 20% of the cells differentiated from definitive endoderm in vitro, in at least about 25% of the cells differentiated from definitive endoderm in vitro, in at least about 30% of the cells differentiated from definitive endoderm in vitro, in at least about 35% of the cells differentiated from definitive endoderm in vitro, in at least about 40% of the cells differentiated from definitive endoderm in vitro, in at least about 45% of the cells differentiated from definitive endoderm in vitro, in at least about 50% of the cells differentiated from definitive endoderm in vitro, in at least about 55% of the cells differentiated from definitive endoderm in vitro, in at least about 60% of the cells differentiated from definitive endoderm in vitro, in at least about 65% of the cells differentiated from definitive endoderm in vitro, in at least about 70% of the cells differentiated from definitive endoderm in vitro, in at least about 75% of the cells differentiated from definitive endoderm in vitro, in at least about 80% of the cells differentiated from definitive endoderm in vitro, in at least about 85% of the cells differentiated from definitive endoderm in vitro, in at least about 90% of the cells differentiated from definitive endoderm in vitro, in at least about 95% of the cells differentiated from definitive endoderm in vitro or in at least about 98% of the cells differentiated from definitive endoderm in vitro.

In preferred embodiments of the present invention, cell cultures and/or cell populations of endocrine precursor cells comprise human endocrine precursor cells that are non-recombinant cells. In such embodiments, the cell cultures and/or cell populations are devoid of or substantially free of recombinant human endocrine precursor cells.

In some embodiments of the present invention, cell cultures and/or cell populations comprising endocrine precursor cells also include a medium which comprises a gamma secretase inhibitor. In a preferred embodiment, the gamma secretase inhibitor is N—[N-(3,5-difluorophenacetyl)-L-alanyl]-S-phenylglycine t-butyl ester (DAPT). In some preferred embodiments, the DAPT concentration is at least about 1 µM. In more preferred embodiments, the DAPT concentration is at least about 3 µM. In some embodiments, the medium also comprises a factor selected from retinoic acid (RA) and exendin 4 (Ex4). In some embodiments, the medium is CMRL.

Using the processes described herein, compositions comprising endocrine precursor cells substantially free of other cell types can be produced. In some embodiments of the present invention, the endocrine precursor cell populations or cell cultures produced by the methods described herein are substantially free of cells that significantly express the AFP, SOX7, SOX1, ZIC1 and/or NFM markers. In some embodiments, the endocrine precursor cell populations of cell cultures produced by the methods described herein are substantially free of cells that significantly express the AFP, SOX7, SOX1, ZIC1, NFM, MAFA, SYP, CHGA, INS, GCG, SST, GHRL, and/or PAX6 markers.

In one embodiment of the present invention, a description of a endocrine precursor cell based on the expression of markers is, NGN3 high, NKX2.2 high, PAX4 high, AFP low, SOX7 low, SOX1 low, ZIC1 low NFM low, MAFA low; SYP low; CHGA low; INS low, GCG low, SST low, GHRL low and/or PAX6 low.

Screening Pancreatic Endocrine Precursor Cells

Certain screening methods described herein relate to methods for identifying at least one differentiation factor that is capable of promoting the differentiation of endocrine precursor cells.

In some embodiments of these differentiation screening methods, cell populations comprising endocrine precursor cells, such as human endocrine precursor cells, are obtained. The cell population is then provided with a candidate differentiation factor. At a first time point, which is prior to or at approximately the same time as providing the candidate differentiation factor, expression of a marker is determined. Alternatively, expression of the marker can be determined after providing the candidate differentiation factor. At a second time point, which is subsequent to the first time point and subsequent to the step of providing the candidate differentiation factor to the cell population, expression of the same marker is again determined Whether the candidate differentiation factor is capable of promoting the differentiation of the endocrine precursor cells is determined by comparing expression of the marker at the first time point with the expression of the marker at the second time point. If expression of the marker at the second time point is increased or decreased as compared to expression of the marker at the first time point, then the candidate differentiation factor is capable of promoting the differentiation of endocrine precursor cells.

Some embodiments of the screening methods described herein utilize cell populations or cell cultures which comprise human endocrine precursor cells. For example, the cell population can be a substantially purified population of endocrine precursor cells. Alternatively, the cell population can be an enriched population of human endocrine precursor cells, wherein at least about 90%, at least about 91%, at least about 92%, at least about 93%, at least about 94%, at least about 95%, at least about 96%, at least about 97% or greater than at least about 97% of the human cells in the cell population are human endocrine precursor cells. In other embodiments described herein, the cell population comprises human cells wherein at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85% or greater than at least about 85% of the human cells are human endocrine precursor cells. In some embodiments, the cell population includes non-human cells such as non-human feeder cells. In other embodiments, the cell population includes human feeder cells. In such embodiments, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or greater than at least about 95% of the human cells, other than said feeder cells, are human endocrine precursor cells.

In embodiments of the screening methods described herein, the cell population is contacted or otherwise provided with a candidate (test) differentiation factor. The candidate differentiation factor can comprise any molecule that may have the potential to promote the differentiation of human endocrine precursor cells. In some embodiments described herein, the candidate differentiation factor comprises a molecule that is known to be a differentiation factor for one or more types of cells. In alternate embodiments, the candidate differentiation factor comprises a molecule that in not known to promote cell differentiation. In preferred embodiments, the candidate differentiation factor comprises a molecule that is not known to promote the differentiation of human endocrine precursor cells.

In some embodiments of the screening methods described herein, the candidate differentiation factor comprises a small molecule. In preferred embodiments, a small molecule is a molecule having a molecular mass of about 10,000 amu or less.

In other embodiments described herein, the candidate differentiation factor comprises a polypeptide. The polypeptide can be any polypeptide including, but not limited to, a glycoprotein, a lipoprotein, an extracellular matrix protein, a cytokine, a chemokine, a peptide hormone, an interleukin or a growth factor. Preferred polypeptides include growth factors.

In some embodiments of the screening methods described herein, the candidate differentiation factors comprise one or more growth factors selected from the group consisting of Amphiregulin, B-lymphocyte stimulator, IL-16, Thymopoietin, TRAIL/Apo-2, Pre B cell colony enhancing factor, Endothelial differentiation-related factor 1 (EDF1), Endothelial monocyte activating polypeptide II, Macrophage migration inhibitory factor (MIF), Natural killer cell enhancing factor (NKEFA), Bone morphogenetic protein 2, Bone morphogenetic protein 8 (osteogeneic protein 2), Bone morphogenic protein 6, Bone morphogenic protein 7, Connective tissue growth factor (CTGF), CGI-149 protein (neuroendocrine differentiation factor), Cytokine A3 (macrophage inflammatory protein 1-alpha), Gliablastoma cell differentiation-related protein (GBDR1), Hepatoma-derived growth factor, Neuromedin U-25 precursor, Vascular endothelial growth factor (VEGF), Vascular endothelial growth factor B (VEGF-B), T-cell specific RANTES precursor, thymic dendritic cell-derived factor 1, Transferrin, Interleukin-1 (IL 1), Interleukin-2 (IL 2), Interleukin-3 (IL 3), Interleukin-4 (IL 4), Interleukin-5 (IL 5), Interleukin-6 (IL 6), Interleukin-7 (IL 7), Interleukin-8 (IL 8), Interleukin-9 (IL 9), Interleukin-10 (IL 10), Interleukin-11 (IL 11), Interleukin-12 (IL 12), Interleukin-13 (IL 13), Granulocyte-colony stimulating factor (G-CSF), Granulocyte macrophage colony stimulating factor (GM-CSF), Macrophage colony stimulating factor (M-CSF), Erythropoietin, Thrombopoietin, Vitamin $D_3$, Epidermal growth factor (EGF), Brain-derived neurotrophic factor, Leukemia inhibitory factor, Thyroid hormone, Basic fibroblast growth factor (bFGF), aFGF, FGF-4, FGF-6, FGF-7/Keratinocyte growth factor (KGF), Platelet-derived growth factor (PDGF), Platelet-derived growth factor-BB, beta nerve growth factor, activin A, Transforming growth factor beta 1 (TGF-β1), Interferon-α, Interferon-β, Interferon-γ, Tumor necrosis factor-α, Tumor necrosis factor-β, Burst promoting activity (BPA), Erythroid promoting activity (EPA), $PGE_2$, insulin growth factor-1 (IGF-1), IGF-II, Neutrophin growth factor (NGF), Neutrophin-3, Neutrophin 4/5, Ciliary neurotrophic factor, Glial-derived nexin, Dexamethasone, β-mercaptoethanol, Retinoic acid, Butylated hydroxyanisole, 5-azacytidine, Amphotericin B, Ascorbic acid, Ascrorbate, isobutylxanthine, indomethacin, β-glycerolphosphate, nicotinamide, DMSO, Thiazolidinediones, TWS119, oxytocin, vasopressin, melanocyte-stimulating hormone, corticortropin, lipotropin, thyrotropin, growth hormone, prolactin, luteinizing hormone, human chorionic gonadotropin, follicle stimulating hormone, corticotropin-releasing factor, gonadotropin-releasing factor, prolactin-releasing factor, prolactin-inhibiting factor, growth-hormone releasing factor, somatostatin, thyrotropin-releasing factor, calcitonin gene-related peptide, parathyroid hormone, glucagon-like peptide 1, glucose-dependent insulinotropic polypeptide, gastrin, secretin, cholecystokinin, motilin, vasoactive intestinal peptide, substance P, pancreatic polypeptide, peptide tyrosine tyrosine, neuropeptide tyrosine, insulin, glucagon, placental lactogen, relaxin, angiotensin II, calctriol, atrial natriuretic peptide, and melatonin. thyroxine, triiodothyronine, calcitonin, estradiol, estrone, progesterone, testosterone, cortisol, corticosterone, aldosterone, epinephrine, norepinepherine, androstiene, calcitriol, collagen, Dexamethasone, β-mercaptoethanol, Retinoic acid, Butylated hydroxyanisole, 5-azacytidine, Amphotericin B, Ascorbic acid, Ascrorbate, isobutylxanthine, indomethacin, β-glycerolphosphate, nicotinamide, DMSO, Thiazolidinediones, and TWS119.

In some embodiments of the screening methods described herein, the candidate differentiation factor is provided to the cell population in one or more concentrations. In some embodiments, the candidate differentiation factor is provided to the cell population so that the concentration of the candidate differentiation factor in the medium surrounding the cells ranges from about 0.1 ng/ml to about 10 mg/ml. In some embodiments, the concentration of the candidate differentiation factor in the medium surrounding the cells ranges from about 1 ng/ml to about 1 mg/ml. In other embodiments, the concentration of the candidate differentiation factor in the medium surrounding the cells ranges from about 10 ng/ml to about 100 μg/ml. In still other embodiments, the concentration of the candidate differentiation factor in the medium surrounding the cells ranges from about 100 ng/ml to about 10 μg/ml. In preferred embodiments, the concentration of the candidate differentiation factor in the medium surrounding the cells is about 5 ng/ml, about 25 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml, about 400 ng/ml, about 425 ng/ml, about 450 ng/ml, about 475 ng/ml, about 500 ng/ml, about 525 ng/ml, about 550 ng/ml, about 575 ng/ml, about 600 ng/ml, about 625 ng/ml, about 650 ng/ml, about 675 ng/ml, about 700 ng/ml, about 725 ng/ml, about 750 ng/ml, about 775 ng/ml, about 800 ng/ml, about 825 ng/ml, about 850 ng/ml, about 875 ng/ml, about 900 ng/ml, about 925 ng/ml, about 950 ng/ml, about 975 ng/ml, about 1 μg/ml, about 2 μg/ml, about 3 μg/ml, about 4 μg/ml, about 5 μg/ml, about 6 μg/ml, about 7 μg/ml, about 8 μg/ml, about 9 μg/ml, about 10 μg/ml, about 11 μg/ml, about 12 μg/ml, about 13 μg/ml, about 14 μg/ml, about 15 μg/ml, about 16 μg/ml, about 17 μg/ml, about 18 μg/ml, about 19 μg/ml, about 20 μg/ml, about 25 μg/ml, about 50 μg/ml, about 75 μg/ml, about 100 μg/ml, about 125 μg/ml, about 150 μg/ml, about 175 μg/ml, about 200 μg/ml, about 250 μg/ml, about 300 μg/ml, about 350 μg/ml, about 400 μg/ml, about 450 μg/ml, about 500 μg/ml, about 550 μg/ml, about 600 μg/ml, about 650 μg/ml, about 700 μg/ml, about 750 μg/ml, about 800 μg/ml, about 850 μg/ml, about 900 μg/ml, about 950 μg/ml, about 1000 μg/ml or greater than about 1000 μg/ml.

In some embodiments, steps of the screening methods described herein comprise determining expression of at least one marker at a first time point and a second time point. In some of these embodiments, the first time point can be prior to or at approximately the same time as providing the cell population with the candidate differentiation factor. Alternatively, in some embodiments, the first time point is subsequent to providing the cell population with the candidate differentiation factor. In some embodiments, expression of a plurality of markers is determined at a first time point.

Some preferred markers for use in the above embodiments include one or more markers selected from the group consisting of NGN3, NKX2.2 and PAX4.

In addition to determining expression of at least one marker at a first time point, some embodiments of the screening methods described herein contemplate determining expression of at least one marker at a second time point, which is subsequent to the first time point and which is subsequent to providing the cell population with the candidate differentiation factor. In such embodiments, expression of the same marker is determined at both the first and second time points. In some embodiments, expression of a plurality of markers is determined at both the first and second time points. In such embodiments, expression of the same plurality of markers is determined at both the first and second time points. In some embodiments, marker expression is determined at a plurality of time points, each of which is subsequent to the first time point, and each of which is subsequent to providing the cell population with the candidate differentiation factor. In certain embodiments, marker expression is determined by Q-PCR. In other embodiments, marker expression is determined by immunocytochemistry.

In certain embodiments of the screening methods described herein, the marker having its expression determined at the first and second time points is a marker that is associated with the differentiation of endocrine precursor cells to cells which are the precursors of terminally differentiated cells which make up pancreatic islet tissues. Such cells can include immature pancreatic islet hormone-expressing cells. In some embodiments, the marker is indicative of endocrine precursor cells. In preferred embodiments, the marker is NGN3, NKX2.2, NKX6.1, PAX4, PDX1, insulin, ghrelin and/or glucagon.

In some embodiments of the screening methods described herein, sufficient time is allowed to pass between providing the cell population with the candidate differentiation factor and determining marker expression at the second time point. Sufficient time between providing the cell population with the candidate differentiation factor and determining expression of the marker at the second time point can be as little as from about 1 hour to as much as about 10 days. In some embodiments, the expression of at least one marker is determined multiple times subsequent to providing the cell population with the candidate differentiation factor. In some embodiments, sufficient time is at least about 1 hour, at least about 6 hours, at least about 12 hours, at least about 18 hours, at least about 24 hours, at least about 30 hours, at least about 36 hours, at least about 42 hours, at least about 48 hours, at least about 54 hours, at least about 60 hours, at least about 66 hours, at least about 72 hours, at least about 78 hours, at least about 84 hours, at least about 90 hours, at least about 96 hours, at least about 102 hours, at least about 108 hours, at least about 114 hours, at least about 120 hours, at least about 126 hours, at least about 132 hours, at least about 138 hours, at least about 144 hours, at least about 150 hours, at least about 156 hours, at least about 162 hours, at least about 168 hours, at least about 174 hours, at least about 180 hours, at least about 186 hours, at least about 192 hours, at least about 198 hours, at least about 204 hours, at least about 210 hours, at least about 216 hours, at least about 222 hours, at least about 228 hours, at least about 234 hours, at least about 240 hours, at least about 246 hours, at least about 252 hours, at least about 258 hours, at least about 264 hours, or at least about 270 hours.

In some embodiments of the methods described herein, it is further determined whether the expression of the marker at the second time point has increased or decreased as compared to the expression of this marker at the first time point. An increase or decrease in the expression of the at least one marker indicates that the candidate differentiation factor is capable of promoting the differentiation of the endocrine precursor cells. Similarly, if expression of a plurality of markers is determined, it is further determined whether the expression of the plurality of markers at the second time point has increased or decreased as compared to the expression of this plurality of markers at the first time point. An increase or decrease in marker expression can be determined by measuring or otherwise evaluating the amount, level or activity of the marker in the cell population at the first and second time points. Such determination can be relative to other markers, for example housekeeping gene expression, or absolute. In certain embodiments, wherein marker expression is increased at the second time point as compared with the first time point, the amount of increase is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of increase is less than 2-fold. In embodiments where marker expression is decreased at the second time point as compared with the first time point, the amount of decrease is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of decrease is less than 2-fold.

Production of Immature Pancreatic Islet Hormone-Expressing Cells

Embodiments of the present invention relate to methods of producing immature pancreatic islet hormone-expressing cells starting from hESCs. As described above, immature pancreatic islet hormone-expressing cells can be produced by first differentiating hESCs to produce definitive endoderm cells, differentiating the definitive endoderm cells to produce foregut endoderm cells, differentiating foregut endoderm to produce PDX1-positive foregut endoderm cells and then further differentiating the PDX1-positive foregut endoderm cells to produce endocrine precursor cells. In some embodiments, the process is continued by allowing the endocrine precursor cells to further differentiate to immature pancreatic islet hormone-expressing cells.

In some embodiments of the present invention, differentiation from endocrine precursor cells to immature pancreatic islet hormone-expressing cells proceeds by continuing the incubation of a culture of endocrine precursor cells with a gamma secretase inhibitor for a sufficient time that the cells stop substantially expressing NGN3, and start expressing PAX6, and to permit the cells to become competent to express at least one pancreatic islet cell hormone. In some embodiments, the gamma secretase inhibitor is removed about 1 day, about 2 days, about 3 days, about 4 days, about 5 days, about 6 days, about 7 days, about 8 days, about 9 days, about 10 days or more than about 10 days after the induction of endocrine precursor cells. In a preferred embodiment, the gamma secretase inhibitor is N—[N-(3,5-Diflurophenacetyl-L-alanyl)]-S-phenylglycine t-Butyl Ester (DAPT).

Certain processes for the production of immature pancreatic islet hormone-expressing cells disclosed herein are mediated by providing a cell culture or cell population comprising human endocrine precursor cells with one or more factors selected from the group consisting of nicotinamide, exendin 4, hepatocyte growth factor (HGF), insulin-like growth factor-1 (IGF1). In some embodiments, all four of the above-described factors are provided together. In some embodiments, one or more of the above-described factors are provided to the cell culture prior to the differentiation of endocrine precursor cells and remain present in the cell culture during the differentiation of at least a portion of the cells in the cell culture to endocrine precursor cells. In other embodiments, one or more of the above-described factors are provided to the cell culture at or about the time of differentiation of a substantial portion of the cells to endocrine precursor cells and remain present in the cell culture until at least a substantial portion of the cells have differentiated into immature pancreatic islet hormone-expressing cells. In some embodiments of the present invention, one or more of the above-described factors are provided at the start of the differentiation process, for example, at the hESC stage, and remain in the cell culture throughout the differentiation to immature pancreatic islet hormone-expressing cells.

In some processes for the production of immature pancreatic islet hormone-expressing cells disclosed herein, nicotinamide, nicotinamide-adenine dinucleotide (NAD), or nicotinic acid is provided to the cells so that it is present in the cell culture or cell population at concentrations sufficient to promote differentiation of at least a portion of the endocrine precursor cells to immature pancreatic islet hormone-expressing cells. In some embodiments, nicotinamide is present in the cell culture or cell population at a concentration of at least about 0.1 mM, at least about 0.5 mM, at least about 1 mM, at least about 2 mM, at least about 3 mM, at least about 4 mM, at least about 5 mM, at least about 6 mM, at least about 7 mM, at least about 8 mM, at least about 9 mM, at least about 10 mM, at least about 11 mM, at least about 12 mM, at least about 13 mM, at least about 14 mM, at least about 15 mM, at least about 16 mM, at least about 17 mM, at least about 18 mM, at least about 19 mM, at least about 20 mM, at least about 25 mM, at least about 30 mM, at least about 35 mM, at least about 40 mM, at least about 45 mM, at least about 50 mM, at least about 55 mM, at least about 60 mM, at least about 65 mM, at least about 70 mM, at least about 75 mM, at least about 80 mM, at least about 85 mM, at least about 90 mM, at least about 95 mM, at least about 100 mM, at least about 250 mM, at least about 500 mM or at least about 1000 mM.

In other processes for the production of immature pancreatic islet hormone-expressing cells disclosed herein, exendin 4 is provided to the cells so that it is present in the cell culture or cell population at concentrations sufficient to promote differentiation of at least a portion of the endocrine precursor cells to immature pancreatic islet hormone-expressing cells. In some embodiments, exendin 4 is present in the cell culture or cell population at a concentration of at least about 1 ng/ml at least about 5 ng/ml, at least about 10 ng/ml, at least about 15 ng/ml, at least about 20 ng/ml, at least about 25 ng/ml, at least about 30 ng/ml, at least about 35 ng/ml, at least about 40 ng/ml, at least about 45 ng/ml, at least about 50 ng/ml, at least about 55 ng/ml, at least about 60 ng/ml, at least about 65 ng/ml, at least about 70 ng/ml, at least about 75 ng/ml, at least about 80 ng/ml, at least about 85 ng/ml, at least about 90 ng/ml, at least about 95 ng/ml, at least about 100 ng/ml, at least about 110 ng/ml, at least about 120 ng/ml, at least about 130 ng/ml, at least about 140 ng/ml, at least about 150 ng/ml, at least about 160 ng/ml, at least about 170 ng/ml, at least about 180 ng/ml, at least about 190 ng/ml, at least about 200 ng/ml, at least about 250 ng/ml, at least about 300 ng/ml, at least about 350 ng/ml, at least about 400 ng/ml, at least about 450 ng/ml, at least about 500 ng/ml, at least about 750 ng/ml, or at least about 1000 ng/ml.

In still other processes for the production of immature pancreatic islet hormone-expressing cells disclosed herein, HGF is provided to the cells so that it is present in the cell culture or cell population at concentrations sufficient to promote differentiation of at least a portion of the endocrine precursor cells to immature pancreatic islet hormone-expressing cells. In some embodiments, HGF is present in the cell culture or cell population at a concentration of at least about 1 ng/ml at least about 5 ng/ml, at least about 10 ng/ml, at least about 15 ng/ml, at least about 20 ng/ml, at least about 25 ng/ml, at least about 30 ng/ml, at least about 35 ng/ml, at least about 40 ng/ml, at least about 45 ng/ml, at least about 50 ng/ml, at least about 55 ng/ml, at least about 60 ng/ml, at least about 65 ng/ml, at least about 70 ng/ml, at least about 75 ng/ml, at least about 80 ng/ml, at least about 85 ng/ml, at least about 90 ng/ml, at least about 95 ng/ml, at least about 100 ng/ml, at least about 110 ng/ml, at least about 120 ng/ml, at least about 130 ng/ml, at least about 140 ng/ml, at least about 150 ng/ml, at least about 160 ng/ml, at least about 170 ng/ml, at least about 180 ng/ml, at least about 190 ng/ml, at least about 200 ng/ml, at least about 250 ng/ml, at least about 300 ng/ml, at least about 350 ng/ml, at least about 400 ng/ml, at least about 450 ng/ml, at least about 500 ng/ml, at least about 750 ng/ml, or at least about 1000 ng/ml.

In yet other processes for the production of immature pancreatic islet hormone-expressing cells disclosed herein, IGF1 is provided to the cells so that it is present in the cell culture or cell population at concentrations sufficient to promote differentiation of at least a portion of the endocrine precursor cells to immature pancreatic islet hormone-expressing cells. In some embodiments, IGF1 is present in the cell culture or cell population at a concentration of at least about 1 ng/ml at least about 5 ng/ml, at least about 10 ng/ml, at least about 15 ng/ml, at least about 20 ng/ml, at least about 25 ng/ml, at least about 30 ng/ml, at least about 35 ng/ml, at least about 40 ng/ml, at least about 45 ng/ml, at least about 50 ng/ml, at least about 55 ng/ml, at least about 60 ng/ml, at least about 65 ng/ml, at least about 70 ng/ml, at least about 75 ng/ml, at least about 80 ng/ml, at least about 85 ng/ml, at least about 90 ng/ml, at least about 95 ng/ml, at least about 100 ng/ml, at least about 110 ng/ml, at least about 120 ng/ml, at least about 130 ng/ml, at least about 140 ng/ml, at least about 150 ng/ml, at least about 160 ng/ml, at least about 170 ng/ml, at least about 180 ng/ml, at least about 190 ng/ml, at least about 200 ng/ml, at least about 250 ng/ml, at least about 300 ng/ml, at least about 350 ng/ml, at least about 400 ng/ml, at least about 450 ng/ml, at least about 500 ng/ml, at least about 750 ng/ml, or at least about 1000 ng/ml.

In certain embodiments of the processes for producing immature pancreatic islet hormone-expressing cells as described herein, one or more of nicotinamide, exendin 4, HGF and IGF1 are provided after one or more previously provided differentiation factors have been removed from the cell cultures. In other embodiments, one or more of nicotinamide, exendin 4, HGF and IGF1 are provided to cell culture or cell population comprising one or more differentiation factors that were previously provided or provided at about the same time as one or more of nicotinamide, exendin 4, HGF and IGF1. In preferred embodiments, differentiation factors that were previously provided or provided at about the same time as one or more of nicotinamide, exendin 4, HGF and IGF1 include, but are not limited to, DAPT, FGF-10, KAAD-cyclopamine, activin A, activin B, BMP4 and/or RA.

In one process for the production of immature pancreatic islet hormone-expressing cells from endocrine precursor cells, a cell culture or a cell population of endocrine precursor cells is provided with 10 mM nicotinamide, 40 ng/ml exendin 4, 25 ng/ml HGF and 50 ng/ml IGF1. In a preferred process, the cells are differentiated in Dulbecco's Modified Eagle's Medium (DMEM).

In certain processes for producing immature pancreatic islet hormone-expressing cells as described herein, one or more of the above-mentioned differentiation factors are removed from the cell culture or cell population subsequent to their addition. For example, nicotinamide can be removed within about one day, about two days, about three days, about four days, about five days, about six days, about seven days, about eight days, about nine days or about ten days after the addition. In some embodiments, the differentiation factors are not removed from the cell culture.

Cultures of immature pancreatic islet hormone-expressing cells can be produced in medium containing reduced serum or no serum. Under certain culture conditions, serum concentrations can range from about 0.05% v/v to about 20% v/v. For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v), less than about 10% (v/v), less than about 15% (v/v) or less than about 20% (v/v). In some processes, immature pancreatic islet hormone-expressing cells are grown without serum, without serum replacement and/or without any supplement containing insulin or insulin-like growth factor.

In still other processes, immature pancreatic islet hormone-expressing cells are grown in the presence of B27. In such processes, the concentration of B27 supplement can range from about 0.1% (v/v) to about 20% (v/v) or in concentrations greater than about 20% (v/v). In certain processes, the concentration of B27 in the medium is about 0.1% (v/v), about 0.2% (v/v), about 0.3% (v/v), about 0.4% (v/v), about 0.5% (v/v), about 0.6% (v/v), about 0.7% (v/v), about 0.8% (v/v), about 0.9% (v/v), about 1% (v/v), about 2% (v/v), about 3% (v/v), about 4% (v/v), about 5% (v/v), about 6% (v/v), about 7% (v/v), about 8% (v/v), about 9% (v/v), about 10% (v/v), about 15% (v/v) or about 20% (v/v). Alternatively, the concentration of the added B27 supplement can be measured in terms of multiples of the strength of a commercially available B27 stock solution. For example, B27 is available from Invitrogen (Carlsbad, Calif.) as a 50× stock solution. Addition of a sufficient amount of this stock solution to a sufficient volume of growth medium produces a medium supplemented with the desired amount of B27. For example, the addition of 10 ml of 50× B27 stock solution to 90 ml of growth medium would produce a growth medium supplemented with 5× B27. The concentration of B27 supplement in the medium can be about 0.1×, about 0.2×, about 0.3×, about 0.4×, about 0.5×, about 0.6×, about 0.7×, about 0.8×, about 0.9×, about 1×, about 1.1×, about 1.2×, about 1.3×, about 1.4×, about 1.5×, about 1.6×, about 1.7×, about 1.8×, about 1.9×, about 2×, about 2.5×, about 3×, about 3.5×, about 4×, about 4.5×, about 5×, about 6×, about 7×, about 8×, about 9×, about 10×, about 11×, about 12×, about 13×, about 14×, about 15×, about 16×, about 17×, about 18×, about 19×, about 20× and greater than about 20×.

Monitoring the Production of Immature Pancreatic Islet Hormone-Expressing Cells

The progression of endocrine precursor cells to immature pancreatic islet hormone-expressing cells can be monitored by determining the expression of markers characteristic of immature islet hormone-expressing cells, including genetic markers and phenotypic markers such as, the expression of islet hormones and the processing of proinsulin into insulin and C peptide. In some processes, the expression of certain markers is determined by detecting the presence or absence of the marker. Alternatively, the expression of certain markers can be determined by measuring the level at which the marker is present in the cells of the cell culture or cell population. In certain processes, the expression of markers characteristic of immature pancreatic islet hormone-expressing cells as well as the lack of significant expression of markers characteristic of hESCs, definitive endoderm, foregut endoderm, PDX1-positive foregut endoderm, endocrine precursor, extraembryonic endoderm, mesoderm, ectoderm, mature pancreatic islet hormone-expressing cells and/or other cell types is determined.

As described in connection with monitoring the production of other less differentiated cell types of the definitive endoderm lineage, qualitative or semi-quantitative techniques, such as blot transfer methods and immunocytochemistry, can be used to measure marker expression. Alternatively, marker expression can be accurately quantitated through the use of technique such as Q-PCR. Additionally, it will be appreciated that at the polypeptide level, many of the markers of pancreatic islet hormone-expressing cells are secreted proteins. As such, techniques for measuring extracellular marker content, such as ELISA, may be utilized.

As set forth in the Examples below, markers of immature pancreatic islet hormone-expressing cells include, but are not limited to, MAFB, SYP, CHGA, NKX2.2, ISL1, PAX6, NEUROD, PDX1, HB9, GHRL, IAPP, INS, GCG, SST, PP, and/or connecting peptide (C-peptide). The immature pancreatic islet hormone-expressing cells produced by the processes described herein express one or more of the above-listed markers, thereby producing the corresponding gene products. However, it will be appreciated that immature pancreatic islet hormone-expressing cells need not express all of the above-described markers. For example, pancreatic islet hormone-expressing cells differentiated from hESCs do not co-express INS and GHRL.

Because pancreatic islet hormone-expressing cells do not substantially express the endocrine precursor cell markers NGN3 and PAX4, transition of endocrine precursor cells to immature pancreatic islet hormone-expressing cells can be validated by monitoring the decrease in expression of NGN3 and PAX4 while monitoring the increase in expression of one or more of MAFB, PAX6, GHRL, IAPP, INS, GCG, NKX6.1, SST, PP, CHGA, SYP and/or C-peptide. In addition to monitoring the increase and/or decrease in expression of one or more the above-described markers, in some processes, the expression of genes indicative hESCs, definitive endoderm cells, foregut endoderm cells, PDX1-positive foregut endoderm cells and/or endocrine precursor cells is also monitored.

It will be appreciated that MAFB, PAX6, GHRL, IAPP, INS, GCG, NKX6.1, SST, PP, CHGA, SYP and/or C-peptide marker expression is induced over a range of different levels in immature pancreatic islet hormone-expressing cells depending on the differentiation conditions. As such, in some embodiments described herein, the expression of MAFB, PAX6, GHRL, IAPP, INS, GCG, NKX6.1, SST, PP, CHGA, SYP, and/or C-peptide markers in pancreatic islet hormone-expressing cells or cell populations is at least about 2-fold higher to at least about 10,000-fold higher than the expression of MAFB, PAX6, GHRL, IAPP, INS, GCG, NKX6.1, SST, PP, CHGA, SYP and/or C-peptide markers in non-immature pancreatic islet hormone-expressing cells or cell populations, for example pluripotent stem cells, definitive endoderm cells, foregut endoderm, PDX1-positive foregut endoderm cells, endocrine precursor cells, extraembryonic endoderm cells, mesoderm cells, and/or ectoderm cells. In other embodiments, the expression of the MAFB, PAX6, GHRL, IAPP, INS, GCG, NKX6.1, SST, PP, CHGA, SYP and/or C-peptide markers in immature pancreatic islet hormone-expressing cells or cell populations is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher than the expression of the MAFB, PAX6, GHRL, IAPP, INS, GCG, NKX2.2, SST, PP, CHGA, SYP and/or C-peptide markers in non-immature pancreatic islet hormone-expressing cells or cell populations, for example pluripotent stem cells, definitive endoderm cells, foregut endoderm cells, PDX1-positive foregut endoderm cells, endocrine precursor cells, extraembryonic endoderm cells, mesoderm cells and/or ectoderm cells. In some embodiments, the expression of the MAFB, PAX6, GHRL, IAPP, INS, GCG, NKX2.2, SST, PP, CHGA, SYP and/or C-peptide markers in immature pancreatic islet hormone-expressing cells or cell populations is infinitely higher than the expression of the MAFB, PAX6, GHRL, IAPP, INS, GCG, NKX2.2, SST, PP, CHGA, SYP and/or C-peptide markers in non-immature pancreatic islet hormone-expressing cells or cell populations, for example pluripotent stem cells, definitive endoderm cells, foregut endoderm cells PDX1-positive foregut endoderm cells, endocrine precursor cells, extraembryonic endoderm cells, mesoderm cells and/or ectoderm cells.

It will also be appreciated that NGN3 and/or PAX4 marker expression decreases over a range of different levels in immature pancreatic islet hormone-expressing cells depending on the differentiation conditions. As such, in some embodiments described herein, the expression of NGN3 and/or PAX4 markers in immature pancreatic islet hormone-expressing cells or cell populations is at least about 2-fold lower to at least about 10,000-fold lower than the expression of NGN3 and/or PAX4 markers in endocrine precursor cells. In other embodiments, the expression of the NGN3 and/or PAX4 markers in immature pancreatic islet hormone-expressing cells or cell populations is at least about 4-fold lower, at least about 6-fold lower, at least about 8-fold lower, at least about 10-fold lower, at least about 15-fold lower, at least about 20-fold lower, at least about 40-fold lower, at least about 80-fold lower, at least about 100-fold lower, at least about 150-fold lower, at least about 200-fold lower, at least about 500-fold lower, at least about 750-fold lower, at least about 1000-fold lower, at least about 2500-fold lower, at least about 5000-fold lower, at least about 7500-fold lower or at least about 10,000-fold lower than the expression of the NGN3 and/or PAX4 markers in endocrine precursor cells. In some embodiments, the NGN3 and/or PAX4 markers are not substantially expressed in immature pancreatic islet hormone-expressing cells or cell populations.

In some embodiments of the processes described herein, the amount of hormone release from cells and/or cell populations can be determined. For example, the amount of insulin release, glucagon release, somatostatin release and/or ghrelin release can be monitored. In a preferred embodiment, the amount of insulin secreted in response to glucose (GSIS) is measured. In still other embodiments, secreted breakdown or by-products produced by the immature pancreatic islet hormone-expressing cells, such as c-peptide and islet amyloid protein, can be monitored.

It will be appreciated that methods of measuring the expression of secreted proteins are well known in the art. For example, an antibody against one or more hormones produced by islet cells can be used in ELISA assays.

In some embodiments of the present invention, insulin release by immature pancreatic islet hormone-expressing cells is measured by measuring C-peptide release. C-peptide is a cleavage product that is produced in equal molar amounts to insulin during the maturation of pro-insulin. Measuring C-peptide is advantageous because its half life is longer than that of insulin. Methods of measuring C-peptide release are well known in the art, for example, ELISA using anti-C-peptide monoclonal antibody (Linco Research, St. Louis, Mo.). In some embodiments of the present invention, immature pancreatic islet hormone-expressing cells produced from hESCs secrete at least about 50 pmol of C-peptide (insulin)/µg of cellular DNA, at least about 100 pmol of C-peptide (insulin)/µg of cellular DNA, at least about 150 pmol of C-peptide (insulin)/µg of cellular DNA, at least about 200 pmol of C-peptide (insulin)/µg of cellular DNA, at least about 250 pmol of C-peptide (insulin)/µg of cellular DNA, at least about 300 pmol of C-peptide (insulin)/µg of cellular DNA, at least about 350 pmol of C-peptide (insulin)/µg of cellular DNA, at least about 400 pmol of C-peptide (insulin)/µg of cellular DNA, at least about 450 pmol of C-peptide (insulin)/µg of cellular DNA, at least about 500 pmol of C-peptide (insulin)/µg of cellular DNA, at least about 550 pmol of C-peptide (insulin)/µg of cellular DNA, at least about 600 pmol of C-peptide (insulin)/µg of cellular DNA, at least about 650 pmol of C-peptide (insulin)/µg of cellular DNA, at least about 700 pmol of C-peptide (insulin)/µg of cellular DNA, at least about 750 pmol of C-peptide (insulin)/µg of cellular DNA, at least about 800 pmol of C-peptide (insulin)/µg of cellular DNA, at least about 850 pmol of C-peptide (insulin)/µg of cellular DNA, at least about 900 pmol of C-peptide (insulin)/µg of cellular DNA, at least about 950 pmol of C-peptide (insulin)/µg of cellular DNA or at least about 1000 pmol of C-peptide (insulin)/µg of cellular DNA. In preferred embodiments, the immature pancreatic islet hormone-expressing cells are cells that secrete a single type of islet cell hormone (for example, the cells secrete only insulin). In certain preferred embodiments, the insulin is secreted in response to glucose. In other embodiments, the immature pancreatic islet hormone-expressing cells are cells that secrete insulin in addition to one or more islet cell hormones, for example, somatostatin, glucagon and/or ghrelin.

In some embodiments of the present invention, immature pancreatic islet hormone-expressing cells process less than about 98% of the insulin produced by said immature pancreatic islet hormone-expressing cells. In other embodiments, the immature pancreatic islet hormone-expressing cells process less than about 97%, less than about 96%, less than about 95%, less than about 94%, less than about 93%, less than about 92%, less than about 91%, less than about 90%, less than about 85%, less than about 80%, less than about 75%, less than about 70%, less than about 65%, less than about 60%, less than about 55%, less than about 50%, less than about 45%, less than about 40%, less than about 35%, or less than about 30% of the insulin produced by said immature pancreatic islet hormone-expressing cells.

In other embodiments of the present invention, immature pancreatic islet hormone-expressing cells produced from hESCs secrete at least about 50 pmol of glucagon/μg of cellular DNA, at least about 100 pmol of glucagon/μg of cellular DNA, at least about 150 pmol of glucagon/μg of cellular DNA, at least about 200 pmol of glucagon/μg of cellular DNA, at least about 250 pmol of glucagon/μg of cellular DNA, at least about 300 pmol of glucagon/μg of cellular DNA, at least about 350 pmol of glucagon/μg of cellular DNA, at least about 400 pmol of glucagon/μg of cellular DNA, at least about 450 pmol of glucagon/μg of cellular DNA, at least about 500 pmol of glucagon/μg of cellular DNA, at least about 550 pmol of glucagon/μg of cellular DNA, at least about 600 pmol of glucagon/μg of cellular DNA, at least about 650 pmol of glucagon/μg of cellular DNA, at least about 700 pmol of glucagon/μg of cellular DNA, at least about 750 pmol of glucagon/μg of cellular DNA, at least about 800 pmol of glucagon/μg of cellular DNA, at least about 850 pmol of glucagon/μg of cellular DNA, at least about 900 pmol of glucagon/μg of cellular DNA, at least about 950 pmol of glucagon/μg of cellular DNA or at least about 1000 pmol of glucagon/μg of cellular DNA. In preferred embodiments, the immature pancreatic islet hormone-expressing cells are cells that secrete a single type of islet cell hormone (for example, the cells secrete only glucagon). In other embodiments, the immature pancreatic islet hormone-expressing cells are cells that secrete glucagon in addition to one or more islet cell hormones, for example, ghrelin, somatostatin and insulin.

In still other embodiments of the present invention, immature pancreatic islet hormone-expressing cells produced from hESCs secrete at least about 50 pmol of somatostatin/μg of cellular DNA, at least about 100 pmol of somatostatin/μg of cellular DNA, at least about 150 pmol of somatostatin/μg of cellular DNA, at least about 200 pmol of somatostatin/μg of cellular DNA, at least about 250 pmol of somatostatin/μg of cellular DNA, at least about 300 pmol of somatostatin/μg of cellular DNA, at least about 350 pmol of somatostatin/μg of cellular DNA, at least about 400 pmol of somatostatin/μg of cellular DNA, at least about 450 pmol of somatostatin/μg of cellular DNA, at least about 500 pmol of somatostatin/μg of cellular DNA, at least about 550 pmol of somatostatin/μg of cellular DNA, at least about 600 pmol of somatostatin/μg of cellular DNA, at least about 650 pmol of somatostatin/μg of cellular DNA, at least about 700 pmol of somatostatin/μg of cellular DNA, at least about 750 pmol of somatostatin/μg of cellular DNA, at least about 800 pmol of somatostatin/μg of cellular DNA, at least about 850 pmol of somatostatin/μg of cellular DNA, at least about 900 pmol of somatostatin/μg of cellular DNA, at least about 950 pmol of somatostatin/μg of cellular DNA or at least about 1000 pmol of somatostatin/μg of cellular DNA. In preferred embodiments, the immature pancreatic islet hormone-expressing cells are cells that secrete a single type of islet cell hormone (for example, the cells secrete only somatostatin). In other embodiments, the immature pancreatic islet hormone-expressing cells are cells that secrete somatostatin in addition to one or more islet cell hormones, for example, ghrelin, glucagon and insulin.

In other embodiments of the present invention, immature pancreatic islet hormone-expressing cells produced from hESCs secrete at least about 50 pmol of ghrelin/μg of cellular DNA, at least about 100 pmol of ghrelin/μg of cellular DNA, at least about 150 pmol of ghrelin/μg of cellular DNA, at least about 200 pmol of ghrelin/μg of cellular DNA, at least about 250 pmol of ghrelin/μg of cellular DNA, at least about 300 pmol of ghrelin/μg of cellular DNA, at least about 350 pmol of ghrelin/μg of cellular DNA, at least about 400 pmol of ghrelin/μg of cellular DNA, at least about 450 pmol of ghrelin/μg of cellular DNA, at least about 500 pmol of ghrelin/μg of cellular DNA, at least about 550 pmol of ghrelin/μg of cellular DNA, at least about 600 pmol of ghrelin/μg of cellular DNA, at least about 650 pmol of ghrelin/μg of cellular DNA, at least about 700 pmol of ghrelin/μg of cellular DNA, at least about 750 pmol of ghrelin/μg of cellular DNA, at least about 800 pmol of ghrelin/μg of cellular DNA, at least about 850 pmol of ghrelin/μg of cellular DNA, at least about 900 pmol of ghrelin/μg of cellular DNA, at least about 950 pmol of ghrelin/μg of cellular DNA or at least about 1000 pmol of ghrelin/μg of cellular DNA. In preferred embodiments, the immature pancreatic islet hormone-expressing cells are cells that secrete a single type of islet cell hormone (for example, the cells secrete only ghrelin). In other embodiments, the immature pancreatic islet hormone-expressing cells are cells that secrete ghrelin in addition to one or more islet cell hormones.

Enrichment, Isolation and/or Purification of Immature Pancreatic Islet Hormone-Expressing Cells Immature pancreatic islet hormone-expressing cells produced by any of the above-described processes can be enriched, isolated and/or purified by using an affinity tag that is specific for such cells using the methods described in connection with the enrichment, isolation and/or purification of endocrine precursor cells. Examples of affinity tags specific for immature pancreatic islet hormone-expressing cells are antibodies, ligands or other binding agents that are specific to a marker molecule, such as a polypeptide, that is present on the cell surface of immature pancreatic islet hormone-expressing cells but which is not substantially present on other cell types that would be found in a cell culture produced by the methods described herein. A preferred example of an affinity tag for the enrichment, isolation and/or purification of immature pancreatic islet hormone-expressing cells is an antibody against NCAM. Anti-NCAM antibodies are commercially available, for example from Abcam (Cambridge, Mass.). Another example of an affinity tag for the enrichment, isolation and/or purification of immature pancreatic islet hormone-expressing is an antibody against synaptophysin (SYP). Anti-synaptophysin antibodies are commercially available from Dako (Glostrup, Denmark). In other processes, the NCAM ligand NBP10, or any other NCAM ligand now known or discovered in the future can also be used to bind affinity tags. (Ronn, L., 2002). Such molecules include, but are not limited to, NBP10 fusions and NBP10 mimetics.

Additional methods for obtaining enriched, isolated or purified immature pancreatic islet hormone-expressing cell cultures or populations can also be used. For example, in some embodiments, the reagent, such as an NCAM antibody, is incubated with a cell culture containing immature pancreatic islet hormone-expressing cells, wherein the cell culture has been treated to reduce intercellular and substrate adhesion. The cells are then washed, centrifuged and resuspended. The cell suspension is then incubated with a secondary antibody, such as an FITC-conjugated antibody that is capable of binding to the primary antibody. The cells are then washed, centrifuged and resuspended in buffer. The cell suspension is then analyzed and sorted using a fluorescence activated cell sorter (FACS). Antibody-bound, fluorescent cells are collected separately from non-bound, non-fluorescent, thereby resulting in the isolation of such cell types.

In preferred embodiments of the processes described herein, the isolated cell compositions can be further purified by using an alternate affinity-based method or by additional rounds of sorting using the same or different markers that are specific for immature pancreatic islet hormone-expressing cells. For example, in some embodiments, FACS sorting is used to first isolate NCAM-positive immature pancreatic hormone-expressing cells from NCAM negative cells from cell populations comprising immature pancreatic hormone-expressing cells. Those skilled in the art will appreciate that other conventional marker-based cell sorting methods can be used in the methods described herein, including but not limited to differential magnetic bead sorting, or panning Sorting the NCAM positive cells again using FACS to isolate cells that are NCAM positive enriches the cell population for immature pancreatic hormone expressing cells that express markers characteristic of this cell type, including SYP, CHGA, NKX2.2, ISL1, PAX6, NEUROD, PDX1, or HB9. In other embodiments, FACS sorting is used to separate cells by negatively sorting for a marker that is present on most cells in the cell population other than the immature pancreatic islet hormone-expressing cells. An example of such a negative sort is the use of CD133, which is a marker that is not substantially expressed on the surface of immature pancreatic islet hormone-expressing cells in the NCAM positive cell population after the first round of enrichment but which is expressed on many other NCAM positive cells in this cell population.

In some embodiments of the processes described herein, immature pancreatic islet hormone-expressing cells are fluorescently labeled without the use of an antibody then isolated from non-labeled cells by using a fluorescence activated cell sorter (FACS) methods similar to those described for the enrichment, isolation and/or purification of endocrine precursor cells. For example, in some embodiments, nucleic acids encoding GFP, YFP, luciferase biologically active fragments thereof can be introduced into a pluripotent cell downstream of the promoter of a marker useful in the identification of immature pancreatic islet hormone-expressing cells such as those described above, for example, SYP, CHGA, NKX2.2, ISL1, PAX6, NEUROD, PDX1, or HB9. Thereby, the expression GFP gene product or biologically active fragment thereof is under control of the immature pancreatic islet hormone-expressing cell marker. As described in connection with the enrichment, isolation and/ or purification of endocrine precursor cells, fluorescently marked cells can be differentiated to immature pancreatic islet hormone-expressing cells and separated from other cell types, thereby producing an enriched or purified population of immature pancreatic islet hormone-expressing cells.

It will be appreciated that in addition to the procedures just described, immature pancreatic islet hormone-expressing cells may also be isolated by other techniques for cell isolation. Additionally, immature pancreatic islet hormone-expressing cells may also be enriched or isolated by methods of serial subculture in growth conditions which promote the selective survival or selective expansion of the immature pancreatic islet hormone-expressing cells.

Using the methods described herein, enriched, isolated and/or purified populations of immature pancreatic islet hormone-expressing cells and or tissues can be produced in vitro from pluripotent cell cultures or cell populations, such as stem cell cultures or populations, which have undergone sufficient differentiation to produce at least some immature pancreatic islet hormone-expressing cells. In a preferred method, the cells are directed to differentiate primarily into immature pancreatic islet hormone-expressing cells. Some preferred enrichment, isolation and/or purification methods relate to the in vitro production of immature pancreatic islet hormone-expressing cells from human embryonic stem cells.

Using the methods described herein, cell populations or cell cultures can be enriched in immature pancreatic islet hormone-expressing cell content by at least about 2- to about 1000-fold as compared to untreated or less specifically differentiated cell populations or cell cultures. In some embodiments, immature pancreatic islet hormone-expressing cells can be enriched by at least about 5- to about 500-fold as compared to untreated or less specifically differentiated cell populations or cell cultures. In other embodiments, immature pancreatic islet hormone-expressing cells can be enriched from at least about 10- to about 200-fold as compared to untreated or less specifically differentiated cell populations or cell cultures. In still other embodiments, immature pancreatic islet hormone-expressing cells can be enriched from at least about 20- to about 100-fold as compared to untreated or less specifically differentiated cell populations or cell cultures. In yet other embodiments, immature pancreatic islet hormone-expressing cells can be enriched from at least about 40- to about 80-fold as compared to untreated or less specifically differentiated cell populations or cell cultures. In certain embodiments, immature pancreatic islet hormone-expressing cells can be enriched from at least about 2- to about 20-fold as compared to untreated or less specifically differentiated cell populations or cell cultures.

Compositions Comprising Immature Pancreatic Islet Hormone-Expressing Cells

Some embodiments of the present invention relate to cell compositions, such as cell cultures or cell populations, comprising immature pancreatic islet hormone-expressing cells, wherein the immature pancreatic islet hormone-expressing cells are cells, which have been derived from human pluripotent cells in vitro, which express one or more pancreatic hormones and which have at least some of the functions of human pancreatic islet cells. In accordance with certain embodiments, the immature pancreatic islet hormone-expressing cells are mammalian cells, and in a preferred embodiment, such cells are human cells.

Other embodiments of the present invention relate to compositions, such as cell cultures or cell populations, comprising immature pancreatic islet hormone-expressing cells and cells that are less specifically differentiated than immature pancreatic islet hormone-expressing cells. In such embodiments, cells that are less specifically differentiated than immature pancreatic islet hormone-expressing cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture.

Certain other embodiments of the present invention relate to compositions, such as cell cultures or cell populations, comprising immature pancreatic islet hormone-expressing cells and cells of one or more cell types selected from the group consisting of hESCs, pre-primitive streak cells, mesendoderm cells, definitive endoderm cells, PDX1-negative foregut endoderm cells, PDX1-positive foregut endoderm cells (PDX1-positive pancreatic endoderm cells), endocrine precursor cells and mesoderm cells. In some embodiments, hESCs comprise less than about 25%, less than about 20%, less than about 15%, less than about 10%, less than about 5%, less than about 4%, less than about 3%, less than about 2% or less than about 1% of the total cells in the culture. In certain embodiments, pre-primitive streak cells comprise less than about 25%, less than about 20%, less than about 15%, less than about 10%, less than about 5%, less than about 4%, less than about 3%, less than about 2% or less than about 1% of the total cells in the culture. In other embodiments, mesendoderm cells comprise less than about 25%, less than about 20%, less than about 15%, less than about 10%, less than about 5%, less than about 4%, less than about 3%, less than about 2% or less than about 1% of the total cells in the culture. In still other embodiments, definitive endoderm cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture. In yet other embodiments, PDX1-negative foregut endoderm cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture. In certain embodiments, PDX1-positive foregut endoderm cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture. In other embodiments, endocrine precursor cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture. In still other embodiments, mesoderm cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture.

Additional embodiments of the present invention relate to compositions, such as cell cultures or cell populations, produced by the processes described herein and which comprise immature pancreatic islet hormone-expressing cells as the majority cell type. In some embodiments, the processes described herein produce cell cultures and/or cell populations comprising at least about 99%, at least about 98%, at least about 97%, at least about 96%, at least about 95%, at least about 94%, at least about 93%, at least about 92%, at least about 91%, at least about 90%, at least about 89%, at least about 88%, at least about 87%, at least about 86%, at least about 85%, at least about 84%, at least about 83%, at least about 82%, at least about 81%, at least about 80%, at least about 79%, at least about 78%, at least about 77%, at least about 76%, at least about 75%, at least about 74%, at least about 73%, at least about 72%, at least about 71%, at least about 70%, at least about 69%, at least about 68%, at least about 67%, at least about 66%, at least about 65%, at least about 64%, at least about 63%, at least about 62%, at least about 61%, at least about 60%, at least about 59%, at least about 58%, at least about 57%, at least about 56%, at least about 55%, at least about 54%, at least about 53%, at least about 52%, at least about 51% or at least about 50% immature pancreatic islet hormone-expressing cells. In preferred embodiments, the cells of the cell cultures or cell populations comprise human cells. In other embodiments, the processes described herein produce cell cultures or cell populations comprising at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about 11%, at least about 10%, at least about 9%, at least about 8%, at least about 7%, at least about 6%, at least about 5%, at least about 4%, at least about 3%, at least about 2% or at least about 1% immature pancreatic islet hormone-expressing cells. In preferred embodiments, the cells of the cell cultures or cell populations comprise human cells. In some embodiments, the percentage of immature pancreatic islet hormone-expressing cells in the cell cultures or populations is calculated without regard to the feeder cells remaining in the culture.

Still other embodiments of the present invention relate to compositions, such as cell cultures or cell populations, comprising mixtures of immature pancreatic islet hormone-expressing cells and endocrine precursor cells. For example, cell cultures or cell populations comprising at least about 5 immature pancreatic islet hormone-expressing cells for about every 95 endocrine precursor cells can be produced. In other embodiments, cell cultures or cell populations comprising at least about 95 immature pancreatic islet hormone-expressing cells for about every 5 endocrine precursor cells can be produced. Additionally, cell cultures or cell populations comprising other ratios of immature pancreatic islet hormone-expressing cells to endocrine precursor cells are contemplated. For example, compositions comprising at least about 1 immature pancreatic islet hormone-expressing cell for about every 1,000,000 endocrine precursor cells, at least about 1 immature pancreatic islet hormone-expressing cell for about every 100,000 endocrine precursor cells, at least about 1 immature pancreatic islet hormone-expressing cell for about every 10,000 endocrine precursor cells, at least about 1 immature pancreatic islet hormone-expressing cell for about every 1000 endocrine precursor cells, at least about 1 immature pancreatic islet hormone-expressing cell for about every 500 endocrine precursor cells, at least about 1 immature pancreatic islet hormone-expressing cell for about every 100 endocrine precursor cells, at least about 1 immature pancreatic islet hormone-expressing cell for about every 10 endocrine precursor cells, at least about 1 immature pancreatic islet hormone-expressing cell for about every 5 endocrine precursor cells, at least about 1 immature pancreatic islet hormone-expressing cell for about every 4 endocrine precursor cells, at least about 1 immature pancreatic islet hormone-expressing cell for about every 2 endocrine precursor cells, at least about 1 immature pancreatic islet hormone-expressing cell for about every 1 endocrine precursor cell, at least about 2 immature pancreatic islet hormone-expressing cells for about every 1 endocrine precursor cell, at least about 4 immature pancreatic islet hormone-expressing cells for about every 1 endocrine precursor cell, at least about 5 immature pancreatic islet hormone-expressing cells for about every 1 endocrine precursor cell, at least about 10 immature pancreatic islet hormone-expressing cells for about every 1 endocrine precursor cell, at least about 20 immature pancreatic islet hormone-expressing cells for about every 1 endocrine precursor cell, at least about 50 immature pancreatic islet hormone-expressing cells for about every 1 endocrine precursor cell, at least about 100 immature pancreatic islet hormone-expressing cells for about every 1 endocrine precursor cell, at least about 1000 immature pancreatic islet hormone-expressing cells for about every 1 endocrine precursor cell, at least about 10,000 immature pancreatic islet hormone-expressing cells for about every 1 endocrine precursor cell, at least about 100,000 immature pancreatic islet hormone-expressing cells for about every 1 endocrine precursor cell and at least about 1,000,000 immature pancreatic islet hormone-expressing cells for about every 1 endocrine precursor cell are contemplated.

In some embodiments of the present invention, immature pancreatic islet hormone-expressing cells that are produced are derived from human pluripotent cells, such as human pluripotent stem cells. In certain embodiments, the human pluripotent cells are derived from a morula, the inner cell mass of an embryo or the gonadal ridges of an embryo. In certain other embodiments, the human pluripotent cells are derived from the gonadal or germ tissues of a multicellular structure that has developed past the embryonic stage.

Further embodiments of the present invention relate to compositions, such as cell cultures or cell populations, comprising human cells, including human immature pancreatic islet hormone-expressing cells, wherein the expression of the MAFB, SYP, CHGA, NKX2.2, ISL1, PAX6, NEUROD, PDX1, HB9, GHRL, IAPP, INS GCG, SST, PP, and/or C-peptide marker is greater than the expression of the NGN3, MAFA, MOX1, CER, POU5F1, AFP, SOX7, SOX1, ZIC1 and/or NFM marker in at least about 2% of the human cells. In other embodiments, the expression of the MAFB, SYP, CHGA, NKX2.2, ISL1, PAX6, NEUROD, PDX1, HB9, GHRL, IAPP INS GCG, SST, PP, and/or C-peptide marker is greater than the expression of the NGN3, MAFA, MOX1, CER, POU5F1, AFP, SOX7, SOX1, ZIC1 and/or NFM marker in at least about 5% of the human cells, in at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells or in at least about 98% of the human cells. In some embodiments, the percentage of human cells in the cell cultures or populations, wherein the expression of MAFB, SYP, CHGA, NKX2.2, ISL1, PAX6, NEUROD, PDX1, HB9, GHRL, IAPP, INS GCG, SST, PP, and/or C-peptide is greater than the expression of the NGN3, MAFA, MOX1, CER, POU5F1, AFP, SOX7, SOX1, ZIC1 and/or NFM marker, is calculated without regard to feeder cells.

Additional embodiments of the present invention relate to compositions, such as cell cultures or cell populations, comprising mammalian cells differentiated from definitive endoderm in vitro, such as human cells differentiated from definitive endoderm in vitro, wherein the expression of the MAFB, SYP, CHGA, NKX2.2, ISL1, PAX6, NEUROD, PDX1, HB9, GHRL, IAPP, INS GCG, SST, PP, and/or C-peptide is greater than the expression of the NGN3, MAFA, MOX1, CER, POU5F1, AFP, SOX7, SOX1, ZIC1 and/or NFM marker in at least about 2% of the cells differentiated from definitive endoderm in vitro. In other embodiments, the expression of the MAFB, PAX6, GHRL, IAPP, INS, GCG, NKX2.2, SST, PP, CHGA, and/or C-peptide is greater than the expression of the NGN3, MAFA, MOX1, CER, POU5F1, AFP, SOX7, SOX1, ZIC1 and/or NFM marker in at least about 5% of the cells differentiated from definitive endoderm in vitro, in at least about 10% of the cells differentiated from definitive endoderm in vitro, in at least about 15% of the cells differentiated from definitive endoderm in vitro, in at least about 20% of the cells differentiated from definitive endoderm in vitro, in at least about 25% of the cells differentiated from definitive endoderm in vitro, in at least about 30% of the cells differentiated from definitive endoderm in vitro, in at least about 35% of the cells differentiated from definitive endoderm in vitro, in at least about 40% of the cells differentiated from definitive endoderm in vitro, in at least about 45% of the cells differentiated from definitive endoderm in vitro, in at least about 50% of the cells differentiated from definitive endoderm in vitro, in at least about 55% of the cells differentiated from definitive endoderm in vitro, in at least about 60% of the cells differentiated from definitive endoderm in vitro, in at least about 65% of the cells differentiated from definitive endoderm in vitro, in at least about 70% of the cells differentiated from definitive endoderm in vitro, in at least about 75% of the cells differentiated from definitive endoderm in vitro, in at least about 80% of the cells differentiated from definitive endoderm in vitro, in at least about 85% of the cells differentiated from definitive endoderm in vitro, in at least about 90% of the cells differentiated from definitive endoderm in vitro, in at least about 95% of the cells differentiated from definitive endoderm in vitro or in at least about 98% of the cells differentiated from definitive endoderm in vitro.

In preferred embodiments of the present invention, cell cultures and/or cell populations of immature pancreatic islet hormone-expressing cells comprise human immature pancreatic islet hormone-expressing cells, that are non-recombinant cells. In such embodiments, the cell cultures and/or cell populations are devoid of or substantially free of recombinant human immature pancreatic islet hormone-expressing cells.

In some embodiments of the present invention, cell cultures and/or cell populations comprising immature pancreatic islet hormone-expressing cells also include a medium which comprises one or more factors selected from nicotinamide, exendin 4, HGF and/or IGF1. In some preferred embodiments, the nicotinamide concentration is at least about 10 mM, the exendin 4 concentration is at least about 40 ng/ml, the HGF concentration is at least about 25 ng/ml and the IGF1 concentration is at least about 50 ng/ml. In some embodiments, the medium is DMEM.

In certain embodiments of the present invention, cell cultures and/or cell populations comprising immature pancreatic islet hormone-expressing cells also include a medium which comprises one or more secreted hormones selected from ghrelin, insulin, somatostatin and/or glucagon. In other embodiments, the medium comprises C-peptide. In a preferred embodiment, the concentration of one or more secreted hormones or C-peptide in the medium ranges from at least about 1 pmol of ghrelin, insulin, somatostatin, glucagon or C-peptide/μg of cellular DNA to at least about 1000 pmol of ghrelin, insulin, somatostatin, glucagon or C-peptide/μg of cellular DNA. In even more preferred embodiments, the concentration of one or more secreted hormones or C-peptide in the medium is at least about 1 pmol of ghrelin, insulin, somatostatin, glucagon or C-peptide/μg of cellular DNA, at least about 10 pmol of ghrelin, insulin, somatostatin, glucagon or C-peptide/μg of cellular DNA, at least about 25 pmol of ghrelin, insulin, somatostatin, glucagon or C-peptide/μg of cellular DNA, at least about 50 pmol of ghrelin, insulin, somatostatin, glucagon or C-peptide/μg of cellular DNA, at least about 75 pmol of ghrelin, insulin, somatostatin, glucagon or C-peptide/μg of cellular DNA, at least about 100 pmol of ghrelin, insulin, somatostatin, glucagon or C-peptide/μg of cellular DNA, at least about 150 pmol of ghrelin, insulin, somatostatin, glucagon or C-peptide/μg of cellular DNA, at least about 200 pmol of ghrelin, insulin, somatostatin, glucagon or C-peptide/μg of cellular DNA, 250 pmol of ghrelin, insulin, somatostatin, glucagon or C-peptide/μg of cellular DNA, at least about 300 pmol of ghrelin, insulin, somatostatin, glucagon or C-peptide/μg of cellular DNA, at least about 350 pmol of ghrelin, insulin, somatostatin, glucagon or C-peptide/μg of cellular DNA, at least about 400 pmol of ghrelin, insulin, somatostatin, glucagon or C-peptide/μg of cellular DNA, at least about 450 pmol of ghrelin, insulin, somatostatin, glucagon or C-peptide/μg of cellular DNA, at least about 500 pmol of ghrelin, insulin, somatostatin, glucagon or C-peptide/μg of cellular DNA, at least about 550 pmol of ghrelin, insulin, somatostatin, glucagon or C-peptide/μg of cellular DNA, at least about 600 pmol of ghrelin, insulin, somatostatin, glucagon or C-peptide/μg of cellular DNA, 650 pmol of ghrelin, insulin, somatostatin, glucagon or C-peptide/μg of cellular DNA, at least about 700 pmol of ghrelin, insulin, somatostatin, glucagon or C-peptide/μg of cellular DNA, at least about 750 pmol of ghrelin, insulin, somatostatin, glucagon or C-peptide/μg of cellular DNA, at least about 800 pmol of ghrelin, insulin, somatostatin, glucagon or C-peptide/μg of cellular DNA, at least about 850 pmol of ghrelin, insulin, somatostatin, glucagon or C-peptide/μg of cellular DNA, at least about 900 pmol of ghrelin, insulin, somatostatin, glucagon or C-peptide/μg of cellular DNA, at least about 950 pmol of ghrelin, insulin, somatostatin, glucagon or C-peptide/μg of cellular DNA or at least about 1000 pmol of ghrelin, insulin, somatostatin, glucagon or C-peptide/μg of cellular DNA.

In some embodiments of the cell cultures and/or cell populations described herein, the immature pancreatic islet hormone-expressing cells secrete more than one pancreatic hormone. In other embodiments of the cell cultures and/or cell populations described herein, the immature pancreatic islet hormone-expressing cells secrete a single pancreatic hormone. In preferred embodiments, the hormone is insulin. In even more preferred embodiments, the pancreatic islet insulin-expressing cells are responsive to glucose. In other embodiments, human pancreatic islet insulin-expressing cells differentiated in vitro secrete insulin in an amount similar to or greater than the amount of insulin secreted by pancreatic beta cells of the human pancreas in vivo.

Using the processes described herein, compositions comprising immature pancreatic islet hormone-expressing cells substantially free of other cell types can be produced. In some embodiments of the present invention, the immature pancreatic islet hormone-expressing cell populations or cell cultures produced by the methods described herein are substantially free of cells that significantly express the NGN3, MAFA, MOX1, CER, POU5F1, AFP, SOX7, SOX1, ZIC1 and/or NFM markers. In some embodiments of immature pancreatic islet hormone-expressing cell populations or cell cultures produced by the methods described herein, the expression of one or more markers selected from the group consisting of MAFB, SYP, CHGA, NKX2.2, ISL1, PAX6, NEUROD, PDX1, HB9, GHRL, IAPP, INS GCG, SST, PP, and/or C-peptide is greater than the expression of one or more markers selected from the group consisting of NGN3, MAFA, MOX1, CER, POU5F1, AFP, SOX7, SOX1, ZIC1 and/or NFM marker In one embodiment of the present invention, a description of an immature pancreatic islet hormone-expressing cell based on the expression of markers is MAFB high; PAX6 high; NKX2.2 high; SYP high; PP high; CHGA high; NGN3 low; PAX4 low and MAFA low.

Production of Mature Pancreatic Islet Hormone-Expressing Cells

Embodiments of the present invention relate to methods of producing mature pancreatic islet hormone-expressing cells starting from hESCs. As described above, pancreatic islet hormone-expressing cells can be produced by first differentiating hESCs to produce definitive endoderm cells, differentiating the definitive endoderm cells to produce PDX1-positive foregut endoderm cells, differentiating the PDX1-positive foregut endoderm cells to produce endocrine precursor cells and then further differentiating the endocrine precursor cells to produce immature pancreatic islet hormone-expressing cells. In some embodiments, the process is finished by allowing the immature pancreatic islet hormone-expressing cells to further differentiate to mature pancreatic islet hormone-expressing cells.

In some embodiments of the present invention, differentiation from immature pancreatic islet hormone-expressing cells to mature pancreatic islet hormone-expressing cells proceeds by continuing the incubation of a culture of immature pancreatic islet hormone-expressing cells with a gamma secretase inhibitor for a sufficient time to permit the cells to become competent to express at least one mature pancreatic islet cell hormone. In some embodiments, the gamma secretase inhibitor is removed about 1 day, about 2 days, about 3 days, about 4 days, about 5 days, about 6 days, about 7 days, about 8 days, about 9 days, about 10 days or more than about 10 days after the induction of endocrine precursor cells. In a preferred embodiment, the gamma secretase inhibitor is N—[N-(3,5-Diflurophenacetyl-L-alanyl)]-S-phenylglycine t-Butyl Ester (DAPT).

Certain processes for the production of mature pancreatic islet hormone-expressing cells disclosed herein are mediated by providing a cell culture or cell population comprising human endocrine precursor cells and/or immature pancreatic islet hormone-expressing cells with one or more factors selected from the group consisting of nicotinamide, exendin 4, hepatocyte growth factor (HGF), insulin-like growth factor-1 (IGF1). In some embodiments, all four of the above-described factors are provided together. In some embodiments, one or more of the above-described factors are provided to the cell culture prior to the differentiation of endocrine precursor cells and/or immature pancreatic islet hormone-expressing cells and remain present in the cell culture during the differentiation of at least a portion of the cells in the cell culture to mature pancreatic islet hormone-expressing cells. In other embodiments, one or more of the above-described factors are provided to the cell culture at or about the time of differentiation of a substantial portion of the cells to endocrine precursor cells and/or immature pancreatic islet hormone-expressing cells and remain present in the cell culture until at least a substantial portion of the cells have differentiated into mature pancreatic islet hormone-expressing cells. In some embodiments of the present invention, one or more of the above-described factors are provided at the start of the differentiation process, for example, at the hESC stage, and remain in the cell culture throughout the differentiation to mature pancreatic islet hormone-expressing cells.

In some processes for the production of mature pancreatic islet hormone-expressing cells disclosed herein, nicotinamide is provided to the cells so that it is present in the cell culture or cell population at concentrations sufficient to promote differentiation of at least a portion of the endocrine precursor cells and/or immature pancreatic islet hormone-expressing cells to mature pancreatic islet hormone-expressing cells. In some embodiments, nicotinamide is present in the cell culture or cell population at a concentration of at least about 0.1 mM, at least about 0.5 mM, at least about 1 mM, at least about 2 mM, at least about 3 mM, at least about 4 mM, at least about 5 mM, at least about 6 mM, at least about 7 mM, at least about 8 mM, at least about 9 mM, at least about 10 mM, at least about 11 mM, at least about 12 mM, at least about 13 mM, at least about 14 mM, at least about 15 mM, at least about 16 mM, at least about 17 mM, at least about 18 mM, at least about 19 mM, at least about 20 mM, at least about 25 mM, at least about 30 mM, at least about 35 mM, at least about 40 mM, at least about 45 mM, at least about 50 mM, at least about 55 mM, at least about 60 mM, at least about 65 mM, at least about 70 mM, at least about 75 mM, at least about 80 mM, at least about 85 mM, at least about 90 mM, at least about 95 mM, at least about 100 mM, at least about 250 mM, at least about 500 mM or at least about 1000 mM.

In other processes for the production of mature pancreatic islet hormone-expressing cells disclosed herein, exendin 4 is provided to the cells so that it is present in the cell culture or cell population at concentrations sufficient to promote differentiation of at least a portion of the endocrine precursor cells and/or immature pancreatic islet hormone-expressing cells to pancreatic islet hormone-expressing cells. In some embodiments, exendin 4 is present in the cell culture or cell population at a concentration of at least about 1 ng/ml at least about 5 ng/ml, at least about 10 ng/ml, at least about 15 ng/ml, at least about 20 ng/ml, at least about 25 ng/ml, at least about 30 ng/ml, at least about 35 ng/ml, at least about 40 ng/ml, at least about 45 ng/ml, at least about 50 ng/ml, at least about 55 ng/ml, at least about 60 ng/ml, at least about 65 ng/ml, at least about 70 ng/ml, at least about 75 ng/ml, at least about 80 ng/ml, at least about 85 ng/ml, at least about 90 ng/ml, at least about 95 ng/ml, at least about 100 ng/ml, at least about 110 ng/ml, at least about 120 ng/ml, at least about 130 ng/ml, at least about 140 ng/ml, at least about 150 ng/ml, at least about 160 ng/ml, at least about 170 ng/ml, at least about 180 ng/ml, at least about 190 ng/ml, at least about 200 ng/ml, at least about 250 ng/ml, at least about 300 ng/ml, at least about 350 ng/ml, at least about 400 ng/ml, at least about 450 ng/ml, at least about 500 ng/ml, at least about 750 ng/ml, or at least about 1000 ng/ml.

In still other processes for the production of mature pancreatic islet hormone-expressing cells disclosed herein, HGF is provided to the cells so that it is present in the cell culture or cell population at concentrations sufficient to promote differentiation of at least a portion of the endocrine precursor cells and/or immature pancreatic islet hormone-expressing cells to pancreatic islet hormone-expressing cells. In some embodiments, HGF is present in the cell culture or cell population at a concentration of at least about 1 ng/ml at least about 5 ng/ml, at least about 10 ng/ml, at least about 15 ng/ml, at least about 20 ng/ml, at least about 25 ng/ml, at least about 30 ng/ml, at least about 35 ng/ml, at least about 40 ng/ml, at least about 45 ng/ml, at least about 50 ng/ml, at least about 55 ng/ml, at least about 60 ng/ml, at least about 65 ng/ml, at least about 70 ng/ml, at least about 75 ng/ml, at least about 80 ng/ml, at least about 85 ng/ml, at least about 90 ng/ml, at least about 95 ng/ml, at least about 100 ng/ml, at least about 110 ng/ml, at least about 120 ng/ml, at least about 130 ng/ml, at least about 140 ng/ml, at least about 150 ng/ml, at least about 160 ng/ml, at least about 170 ng/ml, at least about 180 ng/ml, at least about 190 ng/ml, at least about 200 ng/ml, at least about 250 ng/ml, at least about 300 ng/ml, at least about 350 ng/ml, at least about 400 ng/ml, at least about 450 ng/ml, at least about 500 ng/ml, at least about 750 ng/ml, or at least about 1000 ng/ml.

In yet other processes for the production of mature pancreatic islet hormone-expressing cells disclosed herein, IGF1 is provided to the cells so that it is present in the cell culture or cell population at concentrations sufficient to promote differentiation of at least a portion of the endocrine precursor cells and/or immature pancreatic islet hormone-expressing cells to pancreatic islet hormone-expressing cells. In some embodiments, IGF1 is present in the cell culture or cell population at a concentration of at least about 1 ng/ml at least about 5 ng/ml, at least about 10 ng/ml, at least about 15 ng/ml, at least about 20 ng/ml, at least about 25 ng/ml, at least about 30 ng/ml, at least about 35 ng/ml, at least about 40 ng/ml, at least about 45 ng/ml, at least about 50 ng/ml, at least about 55 ng/ml, at least about 60 ng/ml, at least about 65 ng/ml, at least about 70 ng/ml, at least about 75 ng/ml, at least about 80 ng/ml, at least about 85 ng/ml, at least about 90 ng/ml, at least about 95 ng/ml, at least about 100 ng/ml, at least about 110 ng/ml, at least about 120 ng/ml, at least about 130 ng/ml, at least about 140 ng/ml, at least about 150 ng/ml, at least about 160 ng/ml, at least about 170 ng/ml, at least about 180 ng/ml, at least about 190 ng/ml, at least about 200 ng/ml, at least about 250 ng/ml, at least about 300 ng/ml, at least about 350 ng/ml, at least about 400 ng/ml, at least about 450 ng/ml, at least about 500 ng/ml, at least about 750 ng/ml, or at least about 1000 ng/ml.

In certain embodiments of the processes for producing mature pancreatic islet hormone-expressing cells as described herein, one or more of nicotinamide, exendin 4, HGF and IGF1 are provided after one or more previously provided differentiation factors have been removed from the cell cultures. In other embodiments, one or more of nicotinamide, exendin 4, HGF and IGF1 are provided to cell culture or cell population comprising one or more differentiation factors that were previously provided or provided at about the same time as one or more of nicotinamide, exendin 4, HGF and IGF1. In preferred embodiments, differentiation factors that were previously provided or provided at about the same time as one or more of nicotinamide, exendin 4, HGF and IGF1 include, but are not limited to, DAPT, FGF-10, KAAD-cyclopamine activin A, activin B, BMP4 and/or RA.

In one process for the production of mature pancreatic islet hormone-expressing cells from endocrine precursor cells and/or immature pancreatic islet hormone-expressing cells, a cell culture or a cell population of endocrine precursor cells and/or immature pancreatic islet hormone-expressing cells is provided with 10 mM nicotinamide, 40 ng/ml exendin 4, 25 ng/ml HGF and 50 ng/ml IGF1. In a preferred process, the cells are differentiated in Dulbecco's Modified Eagle's Medium (DMEM).

In certain processes for producing mature pancreatic islet hormone-expressing cells as described herein, one or more of the above-mentioned differentiation factors are removed from the cell culture or cell population subsequent to their addition. For example, nicotinamide can be removed within about one day, about two days, about three days, about four days, about five days, about six days, about seven days, about eight days, about nine days or about ten days after the addition. In some embodiments, the differentiation factors are not removed from the cell culture.

Cultures of mature pancreatic islet hormone-expressing cells can be produced in medium containing reduced serum or no serum. Under certain culture conditions, serum concentrations can range from about 0.05% v/v to about 20% v/v. For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v), less than about 10% (v/v), less than about 15% (v/v) or less than about 20% (v/v). In some processes, mature pancreatic islet hormone-expressing cells are grown without serum, without serum replacement and/or without any supplement containing insulin or insulin-like growth factor.

In still other processes, mature pancreatic islet hormone-expressing cells are grown in the presence of B27. In such processes, the concentration of B27 supplement can range from about 0.1% (v/v) to about 20% (v/v) or in concentrations greater than about 20% (v/v). In certain processes, the concentration of B27 in the medium is about 0.1% (v/v), about 0.2% (v/v), about 0.3% (v/v), about 0.4% (v/v), about 0.5% (v/v), about 0.6% (v/v), about 0.7% (v/v), about 0.8% (v/v), about 0.9% (v/v), about 1% (v/v), about 2% (v/v), about 3% (v/v), about 4% (v/v), about 5% (v/v), about 6% (v/v), about 7% (v/v), about 8% (v/v), about 9% (v/v), about 10% (v/v), about 15% (v/v) or about 20% (v/v). Alternatively, the concentration of the added B27 supplement can be measured in terms of multiples of the strength of a commercially available B27 stock solution. For example, B27 is available from Invitrogen (Carlsbad, Calif.) as a 50× stock solution. Addition of a sufficient amount of this stock solution to a sufficient volume of growth medium produces a medium supplemented with the desired amount of B27. For example, the addition of 10 ml of 50× B27 stock solution to 90 ml of growth medium would produce a growth medium supplemented with 5× B27. The concentration of B27 supplement in the medium can be about 0.1×, about 0.2×, about 0.3×, about 0.4×, about 0.5×, about 0.6×, about 0.7×, about 0.8×, about 0.9×, about 1×, about 1.1×, about 1.2×, about 1.3×, about 1.4×, about 1.5×, about 1.6×, about 1.7×, about 1.8×, about 1.9×, about 2×, about 2.5×, about 3×, about 3.5×, about 4×, about 4.5×, about 5×, about 6×, about 7×, about 8×, about 9×, about 10×, about 11×, about 12×, about 13×, about 14×, about 15×, about 16×, about 17×, about 18×, about 19×, about 20× and greater than about 20×.

Monitoring the Production of Mature Pancreatic Islet Hormone-Expressing Cells

The progression of endocrine precursor cells and immature pancreatic islet hormone-expressing cells to mature pancreatic islet hormone-expressing cells can be monitored by determining the expression of markers characteristic of islet hormone-expressing cells. In some processes, the expression of certain markers is determined by detecting the presence or absence of the marker. Alternatively, the expression of certain markers can be determined by measuring the level at which the marker is present in the cells of the cell culture or cell population. In certain processes, the expression of markers characteristic of mature pancreatic islet hormone-expressing cells as well as the lack of significant expression of markers characteristic of hESCs, definitive endoderm, PDX1-positive foregut endoderm, endocrine precursor, immature pancreatic islet hormone-expressing, extraembryonic endoderm, mesoderm, ectoderm and/or other cell types is determined.

As described in connection with monitoring the production of other less differentiated cell types of the definitive endoderm lineage, qualitative or semi-quantitative techniques, such as blot transfer methods and immunocytochemistry, can be used to measure marker expression. Alternatively, marker expression can be accurately quantitated through the use of technique such as Q-PCR. Additionally, it will be appreciated that at the polypeptide level, many of the markers of pancreatic islet hormone-expressing cells are secreted proteins. As such, techniques for measuring extracellular marker content, such as ELISA, may be utilized.

As set forth in the Examples below, markers of mature pancreatic islet hormone-expressing cells include, but are not limited to, ghrelin (GHRL), islet amyloid polypeptide (TAPP), insulin (INS), glucagon (GCG), NKX6 transcription factor related, locus 1 (NKX6.1), somatostatin (SOM; SST), pancreatic polypeptide (PP); synaptophysin (SYP), glucokinase, (GCK), Chromogranin A (CHGA) and/or connecting peptide (C-peptide). The mature pancreatic islet hormone-expressing cells produced by the processes described herein express one or more of the above-listed markers, thereby producing the corresponding gene products. However, it will be appreciated that mature pancreatic islet hormone-expressing cells need not express all of the above-described markers. For example, pancreatic islet hormone-expressing cells differentiated from hESCs do not co-express INS and GHRL. This pattern of gene expression is consistent with the expression of these genes in human fetal pancreas.

Because mature pancreatic islet hormone-expressing cells do not substantially express the endocrine precursor cell markers NGN3 and PAX4, transition of endocrine precursor cells to mature pancreatic islet hormone-expressing cells can be validated by monitoring the decrease in expression of NGN3 and PAX4 while monitoring the increase in expression of one or more of GHRL, IAPP, INS, GCG, NKX6.1, SST, PP, SYP, GCK, CHGA and/or C-peptide. In addition to monitoring the increase and/or decrease in expression of one or more the above-described markers, in some processes, the expression of genes indicative hESCs, definitive endoderm cells, PDX1-positive foregut endoderm cells endocrine precursor cells and/or immature pancreatic islet hormone-expressing cells is also monitored.

It will be appreciated that GHRL, IAPP, INS, GCG, NKX6.1, SST, PP, SYP, GCK, CHGA and C-peptide marker expression is induced over a range of different levels in mature pancreatic islet hormone-expressing cells depending on the differentiation conditions. As such, in some embodiments described herein, the expression of GHRL, IAPP, INS, GCG, NKX6.1, SST, PP, SYP, GCK, CHGA and/or C-peptide markers in mature pancreatic islet hormone-expressing cells or cell populations is at least about 2-fold higher to at least about 10,000-fold higher than the expression of GHRL, IAPP, INS, GCG, NKX6.1, SST, PP, SYP, GCK, CHGA and/or C-peptide markers in non-pancreatic islet hormone-expressing cells or cell populations, for example pluripotent stem cells, definitive endoderm cells, PDX1-positive foregut endoderm cells, endocrine precursor cells, extraembryonic endoderm cells, mesoderm cells and/or ectoderm cells. In other embodiments, the expression of the GHRL, IAPP, INS, GCG, NKX6.1, SST, PP, SYP, GCK, CHGA and/or C-peptide markers in mature pancreatic islet hormone-expressing cells or cell populations is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher than the expression of the GHRL, IAPP, INS, GCG, NKX6.1, SST, PP, SYP, GCK, CHGA and/or C-peptide markers in non-pancreatic islet hormone-expressing cells or cell populations, for example pluripotent stem cells, definitive endoderm cells, PDX1-positive foregut endoderm cells, endocrine precursor cells, extraembryonic endoderm cells, mesoderm cells and/or ectoderm cells. In some embodiments, the expression of the GHRL, IAPP, INS, GCG, NKX6.1, SST, PP, SYP, GCK, CHGA and/or C-peptide markers in mature pancreatic islet hormone-expressing cells or cell populations is infinitely higher than the expression of the GHRL, IAPP, INS, GCG, NKX6.1, SST, PP, SYP, GCK, CHGA and/or C-peptide markers in non-pancreatic islet hormone-expressing cells or cell populations, for example pluripotent stem cells, definitive endoderm cells, PDX1-positive foregut endoderm cells, endocrine precursor cells, extraembryonic endoderm cells, mesoderm cells and/or ectoderm cells.

It will also be appreciated that the MAFA marker expression increases, for example, in cells that co-express INS, over a range of different levels in mature pancreatic islet hormone-expressing cells. Depending on the differentiation conditions, MAFA marker expression is induced over a range of different levels in mature pancreatic islet hormone-expressing cells. As such, in some embodiments described herein, the expression of the MAFA marker in mature pancreatic islet hormone-expressing cells or cell populations is at least about 2-fold higher to at least about 10,000-fold higher than the expression of MAFA marker expression in immature pancreatic islet hormone-expressing cells or in non-pancreatic islet hormone-expressing cell populations, for example pluripotent stem cells, definitive endoderm cells, PDX1-positive foregut endoderm cells, endocrine precursor cells, extraembryonic endoderm cells, mesoderm cells and/or ectoderm cells. In other embodiments, the expression of the MAFA marker in mature pancreatic islet hormone-expressing cells or cell populations is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher than the expression of the MAFA markers in immature pancreatic islet hormone-expressing cells or non-pancreatic islet hormone-expressing cells, for example pluripotent stem cells, definitive endoderm cells, PDX1-positive foregut endoderm cells, endocrine precursor cells, extraembryonic endoderm cells, mesoderm cells and/or ectoderm cells. In some embodiments, the expression of the MAFA marker in mature pancreatic islet hormone-expressing cells or cell populations is infinitely higher than the expression of the MAFA marker in immature pancreatic islet hormone-expressing cells or in other non-pancreatic islet hormone-expressing cells, for example pluripotent stem cells, definitive endoderm cells, PDX1-positive foregut endoderm cells, endocrine precursor cells, extraembryonic endoderm cells, mesoderm cells and/or ectoderm cells.

It will also be appreciated that NGN3 and/or PAX4 marker expression decreases over a range of different levels in mature pancreatic islet hormone-expressing cells depending on the differentiation conditions. As such, in some embodiments described herein, the expression of NGN3 and/or PAX4 markers in mature pancreatic islet hormone-expressing cells or cell populations is at least about 2-fold lower to at least about 10,000-fold lower than the expression of NGN3 and/or PAX4 markers in endocrine precursor cells. In other embodiments, the expression of the NGN3 and/or PAX4 markers in mature pancreatic islet hormone-expressing cells or cell populations is at least about 4-fold lower, at least about 6-fold lower, at least about 8-fold lower, at least about 10-fold lower, at least about 15-fold lower, at least about 20-fold lower, at least about 40-fold lower, at least about 80-fold lower, at least about 100-fold lower, at least about 150-fold lower, at least about 200-fold lower, at least about 500-fold lower, at least about 750-fold lower, at least about 1000-fold lower, at least about 2500-fold lower, at least about 5000-fold lower, at least about 7500-fold lower or at least about 10,000-fold lower than the expression of the NGN3 and/or PAX4 markers in endocrine precursor cells. In some embodiments, the NGN3 and/or PAX4 markers are not substantially expressed in mature pancreatic islet hormone-expressing cells or cell populations.

In some embodiments of the processes described herein, the amount of hormone release from cells and/or cell populations can be determined. For example, the amount of insulin release, glucagon release, somatostatin release and/or ghrelin release can be monitored. In a preferred embodiment, the amount of insulin secreted in response to glucose (GSIS) is measured. In still other embodiments, secreted breakdown or by-products produced by the mature pancreatic islet hormone-expressing cells, such as c-peptide and islet amyloid protein, can be monitored.

It will be appreciated that methods of measuring the expression of secreted proteins are well known in the art. For example, an antibody against one or more hormones produced by islet cells can be used in ELISA assays.

In some embodiments of the present invention, insulin release by mature pancreatic islet hormone-expressing cells is measured by measuring C-peptide release. C-peptide is a cleavage product that is produced in equal molar amounts to insulin during the maturation of pro-insulin. Measuring C-peptide is advantageous because its half life is longer than that of insulin. Methods of measuring C-peptide release are well known in the art, for example, ELISA using anti-C-peptide monoclonal antibody (Linco Research, St. Louis, Mo.). In some embodiments of the present invention, mature pancreatic islet hormone-expressing cells produced from hESCs secrete at least about 50 pmol of C-peptide (insulin)/μg of cellular DNA, at least about 100 pmol of C-peptide (insulin)/μg of cellular DNA, at least about 150 pmol of C-peptide (insulin)/μg of cellular DNA, at least about 200 pmol of C-peptide (insulin)/μg of cellular DNA, at least about 250 pmol of C-peptide (insulin)/μg of cellular DNA, at least about 300 pmol of C-peptide (insulin)/μg of cellular DNA, at least about 350 pmol of C-peptide (insulin)/μg of cellular DNA, at least about 400 pmol of C-peptide (insulin)/μg of cellular DNA, at least about 450 pmol of C-peptide (insulin)/μg of cellular DNA, at least about 500 pmol of C-peptide (insulin)/μg of cellular DNA, at least about 550 pmol of C-peptide (insulin)/μg of cellular DNA, at least about 600 pmol of C-peptide (insulin)/μg of cellular DNA, at least about 650 pmol of C-peptide (insulin)/μg of cellular DNA, at least about 700 pmol of C-peptide (insulin)/μg of cellular DNA, at least about 750 pmol of C-peptide (insulin)/μg of cellular DNA, at least about 800 pmol of C-peptide (insulin)/μg of cellular DNA, at least about 850 pmol of C-peptide (insulin)/μg of cellular DNA, at least about 900 pmol of C-peptide (insulin)/μg of cellular DNA, at least about 950 pmol of C-peptide (insulin)/μg of cellular DNA or at least about 1000 pmol of C-peptide (insulin)/μg of cellular DNA. In preferred embodiments, the mature pancreatic islet hormone-expressing cells are cells that secrete a single type of islet cell hormone (for example, the cells secrete only insulin). In certain preferred embodiments, the insulin is secreted in response to glucose. In other embodiments, the mature pancreatic islet hormone-expressing cells are cells that secrete insulin in addition to one or more islet cell hormones, for example, somatostatin, glucagon and/or ghrelin.

In some embodiments, mature pancreatic islet hormone-expressing cells process greater than about 80% of the insulin produced by said mature pancreatic islet hormone-expressing cells. In some embodiments, mature pancreatic islet hormone-expressing cells process greater than about 85%, greater than about 90%, greater than about 91%, greater than about 92%, greater than about 93%, greater than about 94%, greater than about 95%, greater than about 96%, greater than about 97%, greater than about 98% or greater than about 99% of the insulin produced by said mature pancreatic islet hormone-expressing cells.

In other embodiments of the present invention, mature pancreatic islet hormone-expressing cells produced from hESCs secrete at least about 50 pmol of glucagon/μg of cellular DNA, at least about 100 pmol of glucagon/μg of cellular DNA, at least about 150 pmol of glucagon/μg of cellular DNA, at least about 200 pmol of glucagon/μg of cellular DNA, at least about 250 pmol of glucagon/μg of cellular DNA, at least about 300 pmol of glucagon/μg of cellular DNA, at least about 350 pmol of glucagon/μg of cellular DNA, at least about 400 pmol of glucagon/μg of cellular DNA, at least about 450 pmol of glucagon/μg of cellular DNA, at least about 500 pmol of glucagon/μg of cellular DNA, at least about 550 pmol of glucagon/μg of cellular DNA, at least about 600 pmol of glucagon/μg of cellular DNA, at least about 650 pmol of glucagon/μg of cellular DNA, at least about 700 pmol of glucagon/μg of cellular DNA, at least about 750 pmol of glucagon/μg of cellular DNA, at least about 800 pmol of glucagon/μg of cellular DNA, at least about 850 pmol of glucagon/μg of cellular DNA, at least about 900 pmol of glucagon/μg of cellular DNA, at least about 950 pmol of glucagon/μg of cellular DNA or at least about 1000 pmol of glucagon/μg of cellular DNA. In preferred embodiments, the mature pancreatic islet hormone-expressing cells are cells that secrete a single type of islet cell hormone (for example, the cells secrete only glucagon). In other embodiments, the mature pancreatic islet hormone-expressing cells are cells that secrete glucagon in addition to one or more islet cell hormones, for example, ghrelin, somatostatin and insulin.

In still other embodiments of the present invention, mature pancreatic islet hormone-expressing cells produced from hESCs secrete at least about 50 pmol of somatostatin/μg of cellular DNA, at least about 100 pmol of somatostatin/μg of cellular DNA, at least about 150 pmol of somatostatin/μg of cellular DNA, at least about 200 pmol of somatostatin/μg of cellular DNA, at least about 250 pmol of somatostatin/μg of cellular DNA, at least about 300 pmol of somatostatin/μg of cellular DNA, at least about 350 pmol of somatostatin/μg of cellular DNA, at least about 400 pmol of somatostatin/μg of cellular DNA, at least about 450 pmol of somatostatin/μg of cellular DNA, at least about 500 pmol of somatostatin/μg of cellular DNA, at least about 550 pmol of somatostatin/μg of cellular DNA, at least about 600 pmol of somatostatin/μg of cellular DNA, at least about 650 pmol of somatostatin/μg of cellular DNA, at least about 700 pmol of somatostatin/μg of cellular DNA, at least about 750 pmol of somatostatin/μg of cellular DNA, at least about 800 pmol of somatostatin/μg of cellular DNA, at least about 850 pmol of somatostatin/μg of cellular DNA, at least about 900 pmol of somatostatin/μg of cellular DNA, at least about 950 pmol of somatostatin/μg of cellular DNA or at least about 1000 pmol of somatostatin/μg of cellular DNA. In preferred embodiments, the mature pancreatic islet hormone-expressing cells are cells that secrete a single type of islet cell hormone (for example, the cells secrete only somatostatin). In other embodiments, the mature pancreatic islet hormone-expressing cells are cells that secrete somatostatin in addition to one or more islet cell hormones, for example, ghrelin, glucagon and insulin.

In other embodiments of the present invention, mature pancreatic islet hormone-expressing cells produced from hESCs secrete at least about 50 pmol of ghrelin/μg of cellular DNA, at least about 100 pmol of ghrelin/μg of cellular DNA, at least about 150 pmol of ghrelin/μg of cellular DNA, at least about 200 pmol of ghrelin/μg of cellular DNA, at least about 250 pmol of ghrelin/μg of cellular DNA, at least about 300 pmol of ghrelin/μg of cellular DNA, at least about 350 pmol of ghrelin/μg of cellular DNA, at least about 400 pmol of ghrelin/μg of cellular DNA, at least about 450 pmol of ghrelin/μg of cellular DNA, at least about 500 pmol of ghrelin/μg of cellular DNA, at least about 550 pmol of ghrelin/μg of cellular DNA, at least about 600 pmol of ghrelin/μg of cellular DNA, at least about 650 pmol of ghrelin/μg of cellular DNA, at least about 700 pmol of ghrelin/μg of cellular DNA, at least about 750 pmol of ghrelin/μg of cellular DNA, at least about 800 pmol of ghrelin/μg of cellular DNA, at least about 850 pmol of ghrelin/μg of cellular DNA, at least about 900 pmol of ghrelin/μg of cellular DNA, at least about 950 pmol of ghrelin/μg of cellular DNA or at least about 1000 pmol of ghrelin/μg of cellular DNA. In preferred embodiments, the mature pancreatic islet hormone-expressing cells are cells that secrete a single type of islet cell hormone (for example, the cells secrete only ghrelin). In other embodiments, the mature pancreatic islet hormone-expressing cells are cells that secrete ghrelin in addition to one or more islet cell hormones.

Enrichment, Isolation and/or Purification of Mature Pancreatic Islet Hormone-Expressing Cells Mature pancreatic islet hormone-expressing cells produced by any of the above-described processes can be enriched, isolated and/or purified by using an affinity tag that is specific for such cells. Examples of affinity tags specific for mature pancreatic islet hormone-expressing cells are antibodies, ligands or other binding agents that are specific to a marker molecule, such as a polypeptide, that is present on the cell surface of mature pancreatic islet hormone-expressing cells but which is not substantially present on other cell types that would be found in a cell culture produced by the methods described herein. In some processes, an antibody which binds to a cell surface antigen on human pancreatic islet cells is used as an affinity tag for the enrichment, isolation or purification of mature pancreatic islet hormone-expressing cells produced by in vitro methods, such as the methods described herein. Such antibodies are known and commercially available. For example, a monoclonal antibody that is highly specific for a cell surface marker on human islet cells is available from USBiological, Swampscott, Mass. (Catalog Number P2999-40). Other examples include the highly specific monoclonal antibodies to glycoproteins located on the pancreatic islet cell surface, which have been described by Srikanta, et al., (1987) Endocrinology, 120:2240-2244, the disclosure of which is incorporated herein by reference in its entirety. A preferred example of an affinity tag for mature pancreatic islet hormone-expressing cells, such as those derived in vitro from human pluripotent cells, is NCAM. Antibodies against NCAM are commercially available, for example from Abcam (Cambridge, Mass.).

The skilled artisan will readily appreciate that the processes for making and using antibodies for the enrichment, isolation and/or purification of immature pancreatic islet hormone-expressing are also readily adaptable for the enrichment, isolation and/or purification of pancreatic islet hormone-expressing cells. For example, in some embodiments, the reagent, such as an NCAM antibody, is incubated with a cell culture containing mature pancreatic islet hormone-expressing cells, wherein the cell culture has been treated to reduce intercellular and substrate adhesion. The cells are then washed, centrifuged and resuspended. (WE DO NOT USE A SECONDARY ANTIBODY. WE USE A DIRECT FLUORESCENT CONJUGATED NCAM ANTIBODY. The cell suspension is then incubated with a secondary antibody, such as an FITC-conjugated antibody that is capable of binding to the primary antibody. The cells are then washed, centrifuged and resuspended in buffer. The cell suspension is then analyzed and sorted using a fluorescence activated cell sorter (FACS). Antibody-bound, fluorescent cells are collected separately from non-bound, non-fluorescent, thereby resulting in the isolation of such cell types.

In preferred embodiments of the processes described herein, the isolated cell compositions can be further purified by using an alternate affinity-based method or by additional rounds of sorting using the same or different markers that are specific for mature pancreatic islet hormone-expressing cells. For example, in some embodiments, FACS sorting is used to first isolate NCAM-positive mature pancreatic hormone-expressing cells from NCAM negative cells from cell populations comprising mature pancreatic hormone-expressing cells. Sorting the NCAM positive cells again using FACS to isolate cells that are NCAM positive enriches the cell population for mature pancreatic hormone expressing cells that express markers characteristic of this cell type, including NKX6.1, MAFA, ISL1 or PAX6. In other embodiments, FACS sorting is used to separate cells by negatively sorting for a marker that is present on most cells in the cell population other than the mature pancreatic islet hormone-expressing cells. An example of such a negative sort is the use of CD133, which is a marker that is not substantially expressed on the surface of mature pancreatic islet hormone-expressing cells in the NCAM positive cell population after the first round of enrichment but which is expressed on many other NCAM positive cells in this cell population.

In some embodiments of the processes described herein, mature pancreatic islet hormone-expressing cells are fluorescently labeled without the use of an antibody then isolated from non-labeled cells by using a fluorescence activated cell sorter (FACS). In such embodiments, a nucleic acid encoding GFP, YFP or another nucleic acid encoding an expressible fluorescent marker gene, such as the gene encoding luciferase, is used to label mature pancreatic islet hormone-expressing cells using the methods described above. For example, in some embodiments, at least one copy of a nucleic acid encoding GFP or a biologically active fragment thereof is introduced into a pluripotent cell, preferably a human embryonic stem cell, downstream of the NKX6.1 promoter such that the expression of the GFP gene product or biologically active fragment thereof is under control of the NKX6.1 promoter. In some embodiments, the entire coding region of the nucleic acid, which encodes NKX6.1, is replaced by a nucleic acid encoding GFP or a biologically active fragment thereof. In other embodiments, the nucleic acid encoding GFP or a biologically active fragment thereof is fused in frame with at least a portion of the nucleic acid encoding NKX6.1, thereby generating a fusion protein. In such embodiments, the fusion protein retains a fluorescent activity similar to GFP.

It will be appreciated that promoters other than the NKX6.1 promoter can be used provided that the promoter corresponds to a marker that is expressed in pancreatic islet hormone-expressing cells. One exemplary marker is NKX2.2.

Fluorescently marked cells, such as the above-described pluripotent cells, are differentiated to mature pancreatic islet hormone-expressing cells as described previously above. Because mature pancreatic islet hormone-expressing cells express the fluorescent marker gene, whereas other cell types do not, pancreatic islet hormone-expressing cells can be separated from the other cell types. In some embodiments, cell suspensions comprising a mixture of fluorescently-labeled mature pancreatic islet hormone-expressing cells and unlabeled non-pancreatic islet hormone-expressing cells are sorted using a FACS. Mature pancreatic islet hormone-expressing cells are collected separately from non-fluorescing cells, thereby resulting in the isolation of mature pancreatic islet hormone-expressing cells. If desired, the isolated cell compositions can be further purified by additional rounds of sorting using the same or different markers that are specific for mature pancreatic islet hormone-expressing cells.

In preferred processes, mature pancreatic islet hormone-expressing cells are enriched, isolated and/or purified from other non-pancreatic islet hormone-expressing cells after the cultures are induced to differentiate towards mature pancreatic islet hormone-expressing cells.

In addition to the procedures just described, mature pancreatic islet hormone-expressing cells may also be isolated by other techniques for cell isolation. Additionally, mature pancreatic islet hormone-expressing cells may also be enriched or isolated by methods of serial subculture in growth conditions which promote the selective survival or selective expansion of the pancreatic islet hormone-expressing cells.

Using the methods described herein, enriched, isolated and/or purified populations of mature pancreatic islet hormone-expressing cells and or tissues can be produced in vitro from pluripotent cell cultures or cell populations, such as stem cell cultures or populations, which have undergone sufficient differentiation to produce at least some mature pancreatic islet hormone-expressing cells. In a preferred method, the cells are directed to differentiate primarily into mature pancreatic islet hormone-expressing cells. Some preferred enrichment, isolation and/or purification methods relate to the in vitro production of mature pancreatic islet hormone-expressing cells from human embryonic stem cells.

Using the methods described herein, cell populations or cell cultures can be enriched in mature pancreatic islet hormone-expressing cell content by at least about 2- to about 1000-fold as compared to untreated or less specifically differentiated cell populations or cell cultures. In some embodiments, mature pancreatic islet hormone-expressing cells can be enriched by at least about 5- to about 500-fold as compared to untreated or less specifically differentiated cell populations or cell cultures. In other embodiments, mature pancreatic islet hormone-expressing cells can be enriched from at least about 10- to about 200-fold as compared to untreated or less specifically differentiated cell populations or cell cultures. In still other embodiments, mature pancreatic islet hormone-expressing cells can be enriched from at least about 20- to about 100-fold as compared to untreated or less specifically differentiated cell populations or cell cultures. In yet other embodiments, mature pancreatic islet hormone-expressing cells can be enriched from at least about 40- to about 80-fold as compared to untreated or less specifically differentiated cell populations or cell cultures. In certain embodiments, mature pancreatic islet hormone-expressing cells can be enriched from at least about 2- to about 20-fold as compared to untreated or less specifically differentiated cell populations or cell cultures.

Compositions Comprising Pancreatic Islet Hormone-Expressing Cells

Some embodiments of the present invention relate to cell compositions, such as cell cultures or cell populations, comprising mature pancreatic islet hormone-expressing cells, wherein the mature pancreatic islet hormone-expressing cells are cells, which have been derived from human pluripotent cells in vitro, which express one or more pancreatic hormones and which have at least some of the functions of human pancreatic islet cells. In accordance with certain embodiments, the pancreatic islet hormone-expressing cells are mammalian cells, and in a preferred embodiment, such cells are human cells.

Other embodiments of the present invention relate to compositions, such as cell cultures or cell populations, comprising mature pancreatic islet hormone-expressing cells and cells that are less specifically differentiated than mature pancreatic islet hormone-expressing cells. In such embodiments, cells that are less specifically differentiated than mature pancreatic islet hormone-expressing cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture.

Certain other embodiments of the present invention relate to compositions, such as cell cultures or cell populations, comprising mature pancreatic islet hormone-expressing cells and cells of one or more cell types selected from the group consisting of hESCs, pre-primitive streak cells, mesendoderm cells, definitive endoderm cells, PDX1-negative foregut endoderm cells, PDX1-positive foregut endoderm cells (PDX1-positive pancreatic endoderm cells), endocrine precursor cells and mesoderm cells. In some embodiments, hESCs comprise less than about 25%, less than about 20%, less than about 15%, less than about 10%, less than about 5%, less than about 4%, less than about 3%, less than about 2% or less than about 1% of the total cells in the culture. In certain embodiments, pre-primitive streak cells comprise less than about 25%, less than about 20%, less than about 15%, less than about 10%, less than about 5%, less than about 4%, less than about 3%, less than about 2% or less than about 1% of the total cells in the culture. In other embodiments, mesendoderm cells comprise less than about 25%, less than about 20%, less than about 15%, less than about 10%, less than about 5%, less than about 4%, less than about 3%, less than about 2% or less than about 1% of the total cells in the culture. In still other embodiments, definitive endoderm cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture. In yet other embodiments, PDX1-negative foregut endoderm cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture. In certain embodiments, PDX1-positive foregut endoderm cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture. In other embodiments, endocrine precursor cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture. In still other embodiments, mesoderm cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture.

Other embodiments of the present invention relate to compositions, such as cell cultures or cell populations, comprising mature pancreatic islet hormone-expressing cells and immature pancreatic islet hormone-expressing cells. In such embodiments, immature pancreatic islet hormone-expressing cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the culture.

Additional embodiments of the present invention relate to compositions, such as cell cultures or cell populations, produced by the processes described herein and which comprise mature pancreatic islet hormone-expressing cells as the majority cell type. In some embodiments, the processes described herein produce cell cultures and/or cell populations comprising at least about 99%, at least about 98%, at least about 97%, at least about 96%, at least about 95%, at least about 94%, at least about 93%, at least about 92%, at least about 91%, at least about 90%, at least about 89%, at least about 88%, at least about 87%, at least about 86%, at least about 85%, at least about 84%, at least about 83%, at least about 82%, at least about 81%, at least about 80%, at least about 79%, at least about 78%, at least about 77%, at least about 76%, at least about 75%, at least about 74%, at least about 73%, at least about 72%, at least about 71%, at least about 70%, at least about 69%, at least about 68%, at least about 67%, at least about 66%, at least about 65%, at least about 64%, at least about 63%, at least about 62%, at least about 61%, at least about 60%, at least about 59%, at least about 58%, at least about 57%, at least about 56%, at least about 55%, at least about 54%, at least about 53%, at least about 52%, at least about 51% or at least about 50% mature pancreatic islet hormone-expressing cells. In preferred embodiments, the cells of the cell cultures or cell populations comprise human cells. In other embodiments, the processes described herein produce cell cultures or cell populations comprising at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about 11%, at least about 10%, at least about 9%, at least about 8%, at least about 7%, at least about 6%, at least about 5%, at least about 4%, at least about 3%, at least about 2% or at least about 1% mature pancreatic islet hormone-expressing cells. In preferred embodiments, the cells of the cell cultures or cell populations comprise human cells. In some embodiments, the percentage of mature pancreatic islet hormone-expressing cells in the cell cultures or populations is calculated without regard to the feeder cells remaining in the culture.

Still other embodiments of the present invention relate to compositions, such as cell cultures or cell populations, comprising mixtures of mature pancreatic islet hormone-expressing cells and endocrine precursor cells and/or immature pancreatic islet hormone-expressing cells. For example, cell cultures or cell populations comprising at least about 5 mature pancreatic islet hormone-expressing cells for about every 95 endocrine precursor and/or immature pancreatic islet hormone-expressing cells can be produced. In other embodiments, cell cultures or cell populations comprising at least about 95 mature pancreatic islet hormone-expressing cells for about every 5 endocrine precursor cells and/or immature pancreatic islet hormone-expressing cells can be produced. Additionally, cell cultures or cell populations comprising other ratios of mature pancreatic islet hormone-expressing cells to endocrine precursor and/or immature pancreatic islet hormone-expressing cells are contemplated. For example, compositions comprising at least about 1 mature pancreatic islet hormone-expressing cell for about every 1,000,000 endocrine precursor cells and/or immature pancreatic islet hormone-expressing cells, at least about 1 mature pancreatic islet hormone-expressing cell for about every 100,000 endocrine precursor cells and/or immature pancreatic islet hormone-expressing cells, at least about 1 mature pancreatic islet hormone-expressing cell for about every 10,000 endocrine precursor cells and/or immature pancreatic islet hormone-expressing cells, at least about 1 mature pancreatic islet hormone-expressing cell for about every 1000 endocrine precursor cells and/or immature pancreatic islet hormone-expressing cells, at least about 1 mature pancreatic islet hormone-expressing cell for about every 500 endocrine precursor cells and/or immature pancreatic islet hormone-expressing cells, at least about 1 mature pancreatic islet hormone-expressing cell for about every 100 endocrine precursor cells and/or immature pancreatic islet hormone-expressing cells, at least about 1 mature pancreatic islet hormone-expressing cell for about every 10 endocrine precursor cells and/or immature pancreatic islet hormone-expressing cells, at least about 1 mature pancreatic islet hormone-expressing cell for about every 5 endocrine precursor cells and/or immature pancreatic islet hormone-expressing cells, at least about 1 mature pancreatic islet hormone-expressing cell for about every 4 endocrine precursor cells and/or immature pancreatic islet hormone-expressing cells, at least about 1 mature pancreatic islet hormone-expressing cell for about every 2 endocrine precursor cells and/or immature pancreatic islet hormone-expressing cells, at least about 1 mature pancreatic islet hormone-expressing cell for about every 1 endocrine precursor cell and/or immature pancreatic islet hormone-expressing cell, at least about 2 mature pancreatic islet hormone-expressing cells for about every 1 endocrine precursor cell and/or immature pancreatic islet hormone-expressing cell, at least about 4 mature pancreatic islet hormone-expressing cells for about every 1 endocrine precursor cell and/or immature pancreatic islet hormone-expressing cell, at least about 5 mature pancreatic islet hormone-expressing cells for about every 1 endocrine precursor cell and/or immature pancreatic islet hormone-expressing cell, at least about 10 mature pancreatic islet hormone-expressing cells for about every 1 endocrine precursor cell and/or immature pancreatic islet hormone-expressing cell, at least about 20 mature pancreatic islet hormone-expressing cells for about every 1 endocrine precursor cell and/or immature pancreatic islet hormone-expressing cell, at least about 50 mature pancreatic islet hormone-expressing cells for about every 1 endocrine precursor cell and/or immature pancreatic islet hormone-expressing cell, at least about 100 mature pancreatic islet hormone-expressing cells for about every 1 endocrine precursor cell and/or immature pancreatic islet hormone-expressing cell, at least about 1000 mature pancreatic islet hormone-expressing cells for about every 1 endocrine precursor cell and/or immature pancreatic islet hormone-expressing cell, at least about 10,000 mature pancreatic islet hormone-expressing cells for about every 1 endocrine precursor cell and/or immature pancreatic islet hormone-expressing cell, at least about 100,000 mature pancreatic islet hormone-expressing cells for about every 1 endocrine precursor cell and/or immature pancreatic islet hormone-expressing cell and at least about 1,000,000 mature pancreatic islet hormone-expressing cells for about every 1 endocrine precursor cell and/or immature pancreatic islet hormone-expressing cell are contemplated.

In some embodiments of the present invention, the mature pancreatic islet hormone-expressing cells produced are derived from human pluripotent cells, such as human pluripotent stem cells. In certain embodiments, the human pluripotent cells are derived from a morula, the inner cell mass of an embryo or the gonadal ridges of an embryo. In certain other embodiments, the human pluripotent cells are derived from the gonadal or germ tissues of a multicellular structure that has developed past the embryonic stage.

Further embodiments of the present invention relate to compositions, such as cell cultures or cell populations, comprising human cells, including human mature pancreatic islet hormone-expressing cells, wherein the expression of the GHRL, IAPP, INS, GCG, NKX6.1, SS, PP, SYP, GCK, CHGA and/or C-peptide marker is greater than the expression of the AFP, SOX7, SOX1, ZIC1 and/or NFM marker in at least about 2% of the human cells. In other embodiments, the expression of the GHRL, IAPP, INS, GCG, NKX6.1, SS, PP, SYP, GCK, CHGA and/or C-peptide marker is greater than the expression of the AFP, SOX7, SOX1, ZIC1, NFM, NGN3 and/or PAX4 marker in at least about 5% of the human cells, in at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells, in at least about 70% of the human cells, in at least about 75% of the human cells, in at least about 80% of the human cells, in at least about 85% of the human cells, in at least about 90% of the human cells, in at least about 95% of the human cells or in at least about 98% of the human cells. In some embodiments, the percentage of human cells in the cell cultures or populations, wherein the expression of GHRL, IAPP, INS, GCG, NKX6.1, SS, PP, SYP, GCK, CHGA and/or C-peptide is greater than the expression of the AFP, SOX7, SOX1, ZIC1, NFM, NGN3 and/or PAX4 marker, is calculated without regard to feeder cells.

Additional embodiments of the present invention relate to compositions, such as cell cultures or cell populations, comprising mammalian cells differentiated from definitive endoderm in vitro, such as human cells differentiated from definitive endoderm in vitro, wherein the expression of the GHRL, IAPP, INS, GCG, NKX6.1, SS, PP, SYP, GCK, CHGA and/or C-peptide marker is greater than the expression of the AFP, SOX7, SOX1, ZIC1, NFM, NGN3 and/or PAX4 marker in at least about 2% of the cells differentiated from definitive endoderm in vitro. In other embodiments, the expression of the GHRL, IAPP, INS, GCG, NKX6.1, SS, PP, SYP, GCK, CHGA and/or C-peptide marker is greater than the expression of the AFP, SOX7, SOX1, ZIC1, NFM, NGN3 and/or PAX4 marker in at least about 5% of the cells differentiated from definitive endoderm in vitro, in at least about 10% of the cells differentiated from definitive endoderm in vitro, in at least about 15% of the cells differentiated from definitive endoderm in vitro, in at least about 20% of the cells differentiated from definitive endoderm in vitro, in at least about 25% of the cells differentiated from definitive endoderm in vitro, in at least about 30% of the cells differentiated from definitive endoderm in vitro, in at least about 35% of the cells differentiated from definitive endoderm in vitro, in at least about 40% of the cells differentiated from definitive endoderm in vitro, in at least about 45% of the cells differentiated from definitive endoderm in vitro, in at least about 50% of the cells differentiated from definitive endoderm in vitro, in at least about 55% of the cells differentiated from definitive endoderm in vitro, in at least about 60% of the cells differentiated from definitive endoderm in vitro, in at least about 65% of the cells differentiated from definitive endoderm in vitro, in at least about 70% of the cells differentiated from definitive endoderm in vitro, in at least about 75% of the cells differentiated from definitive endoderm in vitro, in at least about 80% of the cells differentiated from definitive endoderm in vitro, in at least about 85% of the cells differentiated from definitive endoderm in vitro, in at least about 90% of the cells differentiated from definitive endoderm in vitro, in at least about 95% of the cells differentiated from definitive endoderm in vitro or in at least about 98% of the cells differentiated from definitive endoderm in vitro.

In preferred embodiments of the present invention, cell cultures and/or cell populations of mature pancreatic islet hormone-expressing cells comprise human mature pancreatic islet hormone-expressing cells, that are non-recombinant cells. In such embodiments, the cell cultures and/or cell populations are devoid of or substantially free of recombinant human mature pancreatic islet hormone-expressing cells.

In some embodiments of the present invention, cell cultures and/or cell populations comprising mature pancreatic islet hormone-expressing cells also include a medium which comprises one or more factors selected from nicotinamide, exendin 4, HGF and/or IGF1. In some preferred embodiments, the nicotinamide concentration is at least about 10 mM, the exendin 4 concentration is at least about 40 ng/ml, the HGF concentration is at least about 25 ng/ml and the IGF1 concentration is at least about 50 ng/ml. In some embodiments, the medium is DMEM.

In certain embodiments of the present invention, cell cultures and/or cell populations comprising mature pancreatic islet hormone-expressing cells also include a medium which comprises one or more secreted hormones selected from ghrelin, insulin, somatostatin and/or glucagon. In other embodiments, the medium comprises C-peptide. In a preferred embodiment, the concentration of one or more secreted hormones or C-peptide in the medium ranges from at least about 1 pmol of ghrelin, insulin, somatostatin, glucagon or C-peptide/μg of cellular DNA to at least about 1000 pmol of ghrelin, insulin, somatostatin, glucagon or C-peptide/μg of cellular DNA. In even more preferred embodiments, the concentration of one or more secreted hormones or C-peptide in the medium is at least about 1 pmol of ghrelin, insulin, somatostatin, glucagon or C-peptide/μg of cellular DNA, at least about 10 pmol of ghrelin, insulin, somatostatin, glucagon or C-peptide/μg of cellular DNA, at least about 25 pmol of ghrelin, insulin, somatostatin, glucagon or C-peptide/μg of cellular DNA, at least about 50 pmol of ghrelin, insulin, somatostatin, glucagon or C-peptide/μg of cellular DNA, at least about 75 pmol of ghrelin, insulin, somatostatin, glucagon or C-peptide/μg of cellular DNA, at least about 100 pmol of ghrelin, insulin, somatostatin, glucagon or C-peptide/μg of cellular DNA, at least about 150 pmol of ghrelin, insulin, somatostatin, glucagon or C-peptide/μg of cellular DNA, at least about 200 pmol of ghrelin, insulin, somatostatin, glucagon or C-peptide/μg of cellular DNA, 250 pmol of ghrelin, insulin, somatostatin, glucagon or C-peptide/μg of cellular DNA, at least about 300 pmol of ghrelin, insulin, somatostatin, glucagon or C-peptide/μg of cellular DNA, at least about 350 pmol of ghrelin, insulin, somatostatin, glucagon or C-peptide/μg of cellular DNA, at least about 400 pmol of ghrelin, insulin, somatostatin, glucagon or C-peptide/μg of cellular DNA, at least about 450 pmol of ghrelin, insulin, somatostatin, glucagon or C-peptide/μg of cellular DNA, at least about 500 pmol of ghrelin, insulin, somatostatin, glucagon or C-peptide/μg of cellular DNA, at least about 550 pmol of ghrelin, insulin, somatostatin, glucagon or C-peptide/μg of cellular DNA, at least about 600 pmol of ghrelin, insulin, somatostatin, glucagon or C-peptide/μg of cellular DNA, 650 pmol of ghrelin, insulin, somatostatin, glucagon or C-peptide/μg of cellular DNA, at least about 700 pmol of ghrelin, insulin, somatostatin, glucagon or C-peptide/μg of cellular DNA, at least about 750 pmol of ghrelin, insulin, somatostatin, glucagon or C-peptide/μg of cellular DNA, at least about 800 pmol of ghrelin, insulin, somatostatin, glucagon or C-peptide/μg of cellular DNA, at least about 850 pmol of ghrelin, insulin, somatostatin, glucagon or C-peptide/μg of cellular DNA, at least about 900 pmol of ghrelin, insulin, somatostatin, glucagon or C-peptide/μg of cellular DNA, at least about 950 pmol of ghrelin, insulin, somatostatin, glucagon or C-peptide/μg of cellular DNA or at least about 1000 pmol of ghrelin, insulin, somatostatin, glucagon or C-peptide/μg of cellular DNA.

In some embodiments of the cell cultures and/or cell populations described herein, the mature pancreatic islet hormone-expressing cells secrete more than one pancreatic hormone. In other embodiments of the cell cultures and/or cell populations described herein, the mature pancreatic islet hormone-expressing cells secrete a single pancreatic hormone. In preferred embodiments, the hormone is insulin. In even more preferred embodiments, the mature pancreatic islet insulin-expressing cells are responsive to glucose. In other embodiments, human mature pancreatic islet insulin-expressing cells differentiated in vitro secrete insulin in an amount similar to or greater than the amount of insulin secreted by pancreatic beta cells of the human pancreas in vivo.

Using the processes described herein, compositions comprising mature pancreatic islet hormone-expressing cells substantially free of other cell types can be produced. In some embodiments of the present invention, the mature pancreatic islet hormone-expressing cell populations or cell cultures produced by the methods described herein are substantially free of cells that significantly express the AFP, SOX7, SOX1, ZIC1 and/or NFM markers.

In one embodiment of the present invention, a description of a mature pancreatic islet insulin-expressing cell based on the expression of markers is NKX6.1 high; NKX2.2 high; INS high; IAPP high; SYP high; GCK high; CHGA high; NGN3 low; PAX4 low and MAFB low. For a mature pancreatic islet glucogon-expressing cell, the description based on marker expression is NKX6.1 high; NKX2.2 high; GLC high; SYP high; GCK high; CHGA high; NGN3 low; PAX4 low and MAFB high.

Screening Pancreatic Islet Hormone-Expressing Cells

Certain screening methods described herein relate to methods for identifying at least one compound that is capable of affecting at least one pancreatic function of immature and/or mature pancreatic islet hormone-expressing cells (together referred to as pancreatic islet hormone-expressing cells).

In some embodiments of these screening methods, cell populations comprising pancreatic islet hormone-expressing cells that have been differentiated from pluripotent cells in vitro, such as human pancreatic islet hormone-expressing cells, are obtained. The cell population is then provided with a candidate compound. At a first time point, which is prior to or at approximately the same time as providing the candidate compound, the activity of a desired pancreatic function is determined. Alternatively, activity of the desired pancreatic function can be determined after providing the candidate compound. At a second time point, which is subsequent to the first time point and subsequent to the step of providing the candidate compound to the cell population, activity of the desired pancreatic function is again determined Whether the candidate compound is capable of affecting at least one pancreatic function of the pancreatic islet hormone-expressing cells is determined by comparing the activity of the desired pancreatic function at the first time point with the activity of the desired pancreatic function at the second time point. If activity of the desired pancreatic function at the second time point is increased or decreased as compared to activity of the desired pancreatic function at the first time point, then the candidate compound is capable of affecting the activity of a pancreatic function of pancreatic islet hormone-expressing cells.

Some embodiments of the screening methods described herein utilize cell populations or cell cultures which comprise human pancreatic islet hormone-expressing cells. For example, the cell population can be a substantially purified population of pancreatic islet hormone-expressing cells. Alternatively, the cell population can be an enriched population of human pancreatic islet hormone-expressing cells, wherein at least about 90%, at least about 91%, at least about 92%, at least about 93%, at least about 94%, at least about 95%, at least about 96%, at least about 97% or greater than at least about 97% of the human cells in the cell population are human pancreatic islet hormone-expressing cells. In other embodiments described herein, the cell population comprises human cells wherein at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85% or greater than at least about 85% of the human cells are human pancreatic islet hormone-expressing cells. In some embodiments, the cell population includes non-human cells such as non-human feeder cells. In other embodiments, the cell population includes human feeder cells. In such embodiments, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or greater than at least about 95% of the human cells, other than said feeder cells, are human pancreatic islet hormone-expressing cells.

In embodiments of the screening methods described herein, the cell population is contacted or otherwise provided with a candidate (test) compound. The candidate compound can comprise any molecule that may have the potential to affect the activity of one or more pancreatic functions of human pancreatic islet hormone-expressing cells. In some embodiments described herein, the candidate compound comprises a molecule that is known to be a compound that affects a one or more cellular functions. In alternate embodiments, the candidate compound comprises a molecule that is not known to affect any cellular function. In preferred embodiments, the candidate compound comprises a molecule that is not known to affect the activity of a pancreatic function of human pancreatic islet hormone-expressing cells.

In some embodiments of the screening methods described herein, the candidate compound comprises a small molecule. In preferred embodiments, a small molecule is a molecule having a molecular mass of about 10,000 amu or less.

In other embodiments described herein, the candidate compound comprises a polypeptide. The polypeptide can be any polypeptide including, but not limited to, a glycoprotein, a lipoprotein, an extracellular matrix protein, a cytokine, a chemokine, a peptide hormone, an interleukin or a growth factor.

In some embodiments of the screening methods described herein, the candidate compound is provided to the cell population in one or more concentrations. In some embodiments, the candidate compound is provided to the cell population so that the concentration of the candidate compound in the medium surrounding the cells ranges from about 0.1 ng/ml to about 10 mg/ml. In some embodiments, the concentration of the candidate compound in the medium surrounding the cells ranges from about 1 ng/ml to about 1 mg/ml. In other embodiments, the concentration of the candidate compound in the medium surrounding the cells ranges from about 10 ng/ml to about 100 μg/ml. In still other embodiments, the concentration of the candidate compound in the medium surrounding the cells ranges from about 100 ng/ml to about 10 μg/ml. In preferred embodiments, the concentration of the candidate compound in the medium surrounding the cells is about 5 ng/ml, about 25 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml, about 400 ng/ml, about 425 ng/ml, about 450 ng/ml, about 475 ng/ml, about 500 ng/ml, about 525 ng/ml, about 550 ng/ml, about 575 ng/ml, about 600 ng/ml, about 625 ng/ml, about 650 ng/ml, about 675 ng/ml, about 700 ng/ml, about 725 ng/ml, about 750 ng/ml, about 775 ng/ml, about 800 ng/ml, about 825 ng/ml, about 850 ng/ml, about 875 ng/ml, about 900 ng/ml, about 925 ng/ml, about 950 ng/ml, about 975 ng/ml, about 1 μg/ml, about 2 μg/ml, about 3 μg/ml, about 4 μg/ml, about 5 μg/ml, about 6 μg/ml, about 7 μg/ml, about 8 μg/ml, about 9 μg/ml, about 10 μg/ml, about 11 μg/ml, about 12 μg/ml, about 13 μg/ml, about 14 μg/ml, about 15 μg/ml, about 16 μg/ml, about 17 μg/ml, about 18 μg/ml, about 19 μg/ml, about 20 μg/ml, about 25 μg/ml, about 50 μg/ml, about 75 μg/ml, about 100 μg/ml, about 125 μg/ml, about 150 μg/ml, about 175 μg/ml, about 200 μg/ml, about 250 μg/ml, about 300 μg/ml, about 350 μg/ml, about 400 μg/ml, about 450 μg/ml, about 500 μg/ml, about 550 μg/ml, about 600 μg/ml, about 650 μg/ml, about 700 μg/ml, about 750 μg/ml, about 800 μg/ml, about 850 μg/ml, about 900 μg/ml, about 950 μg/ml, about 1000 μg/ml or greater than about 1000 μg/ml.

In some embodiments, steps of the screening methods described herein comprise determining the activity of a desired pancreatic function at a first time point and a second time point. In some of these embodiments, the first time point can be prior to or at approximately the same time as providing the cell population with the candidate compound. Alternatively, in some embodiments, the first time point is subsequent to providing the cell population with the candidate compound. In some embodiments, the activities of several pancreatic functions are determined at a first time point.

Some preferred pancreatic functions determined in the above embodiments include one or more pancreatic functions selected from the group consisting of ghrelin secretion, insulin secretion, glucagon secretion and somatostatin secretion.

In addition to determining the activity of a desired pancreatic function at a first time point, some embodiments of the screening methods described herein contemplate determining the activity of the desired pancreatic function at least one marker at a second time point, which is subsequent to the first time point and which is subsequent to providing the cell population with the candidate compound. In such embodiments, the activity of the same desired pancreatic function is determined at both the first and second time points. In some embodiments, the activities of a plurality of desired pancreatic functions are determined at both the first and second time points. In such embodiments, activities of the same plurality of pancreatic functions are determined at both the first and second time points. In some embodiments, activities of a plurality of desired pancreatic functions are determined at a plurality of time points, each of which is subsequent to the first time point, and each of which is subsequent to providing the cell population with the candidate compound. In certain embodiments, the activity of the desired pancreatic function is determined by Q-PCR. In other embodiments, the activity of the desired pancreatic function is determined by immunocytochemistry.

In certain embodiments of the screening methods described herein, the activity of the desired pancreatic function determined at the first and second time points is an activity of a pancreatic function, such as hormone secretion. In some embodiments, the hormone is insulin, ghrelin, somatostatin or glucagon.

In some embodiments of the screening methods described herein, sufficient time is allowed to pass between providing the cell population with the candidate compound and determining the activity of the desired pancreatic function at the second time point. Sufficient time between providing the cell population with the candidate compound and determining the activity of the desired pancreatic function at the second time point can be as little as from about 1 hour to as much as about 10 days. In some embodiments, the activity of the desired pancreatic function is determined multiple times subsequent to providing the cell population with the candidate compound. In some embodiments, sufficient time is at least about 1 hour, at least about 6 hours, at least about 12 hours, at least about 18 hours, at least about 24 hours, at least about 30 hours, at least about 36 hours, at least about 42 hours, at least about 48 hours, at least about 54 hours, at least about 60 hours, at least about 66 hours, at least about 72 hours, at least about 78 hours, at least about 84 hours, at least about 90 hours, at least about 96 hours, at least about 102 hours, at least about 108 hours, at least about 114 hours, at least about 120 hours, at least about 126 hours, at least about 132 hours, at least about 138 hours, at least about 144 hours, at least about 150 hours, at least about 156 hours, at least about 162 hours, at least about 168 hours, at least about 174 hours, at least about 180 hours, at least about 186 hours, at least about 192 hours, at least about 198 hours, at least about 204 hours, at least about 210 hours, at least about 216 hours, at least about 222 hours, at least about 228 hours, at least about 234 hours, at least about 240 hours, at least about 246 hours, at least about 252 hours, at least about 258 hours, at least about 264 hours, or at least about 270 hours.

In some embodiments of the methods described herein, it is further determined whether the activity of the desired pancreatic function at the second time point has increased or decreased as compared to the activity of the desired pancreatic function at the first time point. An increase or decrease in the activity of the desired pancreatic function indicates that the candidate compound is capable of affecting the activity of the desired pancreatic function in the pancreatic islet hormone-expressing cells. Similarly, if the activities of a plurality of pancreatic functions are determined, it is further determined whether the activities of the plurality of pancreatic functions at the second time point have increased or decreased as compared to the activities of the plurality of pancreatic functions at the first time point. In certain embodiments, wherein the activity of the desired pancreatic function is increased at the second time point as compared with the first time point, the amount of increase is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of increase is less than 2-fold. In embodiments where the activity of the desired pancreatic function is decreased at the second time point as compared with the first time point, the amount of decrease is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of decrease is less than 2-fold.

Exemplary Factors for Differentiation of hESCs to Pancreatic Islet Hormone-Expressing Cells Table 1 sets out 8 exemplary combinations of factors that can be used to produce at least some pancreatic islet hormone-expressing cells from hESC cultures. It will be appreciated that, among other things, the concentration of each factor used in the differentiation process, the timing of addition and/or removal of each factor during the differentiation process, the concentration of components in the differentiation medium, such as serum, during the differentiation process will significantly affect the proportion of hESCs that will differentiate through the definitive cell lineage and ultimately to pancreatic islet hormone-expressing cells.

The leftmost column of Table 1 provides the example number. The next six columns list the factor that may be used to produce or potentially enhance the production of the cell type described in the column heading. For example, Table 1 shows that incubating hESCs (stage 0) with a growth factor of the TGFβ superfamily results in the differentiation of the hESCs to definitive endoderm to definitive endoderm (stage 1). From Table 1 it can be seen that application of a TGFβ superfamily growth factor and retinoid at the appropriate times is sufficient to permit the production of at least a detectable amount of pancreatic islet hormone producing cells from hESCs.

TABLE 1

| Number | hESCs Stage 0 | Definitive Endoderm Stage 1 | Foregut Endoderm Stage 2 | Pancreatic Endoderm Stage 3 | Endocrine Precursor Stage 4 | Hormone Expression Stage 5 |
|---|---|---|---|---|---|---|
| 1 | NF | TGFβ | NF | Ret | NF | NF |
| 2 | NF | TGFβ | FGF | Ret | NF | NF |
| 3 | NF | TGFβ | NF | Ret + HI | NF | NF |
| 4 | NF | TGFβ + Wnt3a | NF | Ret | NF | NF |
| 5 | NF | TGFβ + Wnt3a | FGF + HI | Ret + HI + FGF | NF | NF |
| 6 | NF | TGFβ + Wnt3a | FGF + HI | Ret + HI + FGF | GSI | NF |
| 7 | NF | TGFβ + Wnt3a | FGF + HI | Ret + HI + FGF | GSI + Ex4 | Ex4 |
| 8 | NF | TGFβ | FGF + HI | Ret + HI + FGF | GSI + Ex4 | Ex4 + HGF + IGF |

NF—No factor
TGFβ—Growth factor of the TGFβ family, preferably activin A
FGF—FGF family member, preferably FGF10 and/or FGF7
HI—Hedgehog pathway inhibitor, preferably KAAD-cyclopamine
Ret—Retinoid, preferably retinoic acid (RA)
GSI—Gamma secretase inhibitor, preferably DAPT
Ex4—Exendin 4
HGF—Hepatocyte growth factor
IGF—Insulin-like growth factor, preferably IGF1

Reagent-Cell Complexes

Aspects of the present invention relate to compositions, such as cell cultures and/or cell populations, that comprise complexes of one or more endocrine precursor cells or immature pancreatic islet hormone-expressing cells bound to one or more reagents (reagent-cell complexes). For example, cell cultures and/or cell populations comprising reagent-cell complexes, wherein at least about 5% to at least about 100% of the endocrine precursor cells in culture are in the form of reagent-cell complexes, can be produced. In other embodiments, cell cultures and/or cell populations can be produced which comprise at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99% or at least about 100% reagent-cell complexes. In some embodiments, the reagent cell complexes comprise one or more endocrine precursor cells bound to one or more antibodies that bind to NCAM. In still other embodiments, the reagent cell complexes comprise one or more endocrine precursor cells bound to one or more ligands that bind to NCAM, such as NBP10.

Other embodiments provide cell cultures and/or cell populations comprising reagent-cell complexes, wherein at least about 5% to at least about 100% of the immature pancreatic islet hormone-expressing cells in culture are in the form of reagent-cell complexes. In other embodiments, cell cultures and/or cell populations can be produced which comprise at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99% or at least about 100% reagent-cell complexes. In some embodiments, the reagent cell complexes comprise one or more immature pancreatic islet hormone-expressing cells bound to one or more antibodies that bind to NCAM. In still other embodiments, the reagent cell complexes comprise one or more immature pancreatic islet hormone-expressing cells bound to one or more ligands that bind to NCAM, such as NBP10.

Some embodiments described herein relate to cell cultures and/or cell populations comprising from at least about 5% reagent cell complexes to at least about 95% reagent-cell complexes. In some embodiments the cell cultures or cell populations comprise mammalian cells. In preferred embodiments, the cell cultures or cell populations comprise human cells. For example, certain specific embodiments relate to cell cultures comprising human cells, wherein from at least about 5% to at least about 95% of the human cells are endocrine precursor cells in the form of reagent cell complexes. Other embodiments relate to cell cultures comprising human cells, wherein from at least about 5% to at least about 95% of the human cells are immature pancreatic islet hormone-expressing cells in the form of reagent cell complexes. Other embodiments relate to cell cultures comprising human cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or greater than 90% of the human cells are reagent cell complexes. In embodiments where the cell cultures or cell populations comprise human feeder cells, the above percentages are calculated without respect to the human feeder cells in the cell cultures or cell populations. In some embodiments, the reagent cell complexes comprise one or more endocrine precursor cells or immature pancreatic islet hormone-expressing cells bound to NCAM or SYP.

In some embodiments, the expression of NGN3, PAX4, and/or NKX2.2 is enhanced in the endocrine precursor cells present in the reagent-cell complexes that have been described above compared to the expression of AFP, SOX7, SOX1, ZIC1, NFM, SYP, SST, GHRL, PAX6, MAFA, INS, GCG, and/or CHGA. In preferred embodiments, the endocrine precursor cells expressing NGN3, NKX2.2 and/or PAX4 do not express significant levels or amounts of AFP, SOX7, SOX1, ZIC1, NFM, SYP, SST, GHRL, PAX6, MAFA, INS, GCG and/or CHGA.

In some embodiments, the expression of MAFB is enhanced in the immature pancreatic islet hormone-expressing cells present in the reagent-cell complexes that have been described above compared to the expression of AFP, SOX7, SOX1, ZIC1, NFM, NGN3 and/or MAFA. In preferred embodiments, the immature pancreatic islet hormone-expressing cells expressing MAFB do not express significant levels or amounts of AFP, SOX7, SOX1, ZIC1, NFM, NGN3 and/or MAFA.

Additional embodiments described herein relate to compositions, such as cell cultures and/or cell populations that comprise both pluripotent cells, such as stem cells, and reagent-cell complexes. In some embodiments, the compositions also comprise multipotent cells, such as definitive endoderm cells, foregut endoderm cells, PDX1-positive pancreatic endoderm cells. For example, using the methods described herein, compositions comprising mixtures of hESCs and/or definitive endoderm cells and reagent-cell complexes of endocrine precursor cells can be produced. Further, using the methods described herein, compositions comprising mixtures of hESCs, definitive endoderm cells, foregut endoderm cells, and/or PDX1-positive pancreatic endoderm cells, and reagent-cell complexes of endocrine precursor cells and/or reagent-cell complexes of immature pancreatic islet hormone-expressing cells can be produced. In some embodiments, compositions comprising at least about 5 reagent-cell complexes for about every 95 pluripotent, definitive endoderm cells, foregut endoderm cells, and/or PDX1-positive pancreatic endoderm cells, are provided. In other embodiments, compositions comprising at least about 95 reagent-cell complexes for about every 5 pluripotent cells, definitive endoderm cells, foregut endoderm cells, and/or PDX1-positive pancreatic endoderm cells are provided. Additionally, compositions comprising other ratios of reagent-cell complexes cells to pluripotent, definitive endoderm cells, foregut endoderm cells, and/or PDX1-positive pancreatic endoderm cells are contemplated. For example, compositions comprising at least about 1 reagent-cell complex for about every 1,000,000 pluripotent, definitive endoderm cells, foregut endoderm cells, and/or PDX1-positive pancreatic endoderm cells, at least about 1 reagent-cell complex for about every 100,000 pluripotent, definitive endoderm cells, foregut endoderm cells, and/or PDX1-positive pancreatic endoderm cells, at least about 1 reagent-cell complex cell for about every 10,000 pluripotent, definitive endoderm cells, foregut endoderm cells, and/or PDX1-positive pancreatic endoderm cells, at least about 1 reagent-cell complex for about every 1000 pluripotent, definitive endoderm cells, foregut endoderm cells, and/or PDX1-positive pancreatic endoderm cells, at least about 1 reagent-cell complex for about every 500 pluripotent, definitive endoderm cells, foregut endoderm cells, and/or PDX1-positive pancreatic endoderm cells, at least about 1 reagent-cell complex for about every 100 pluripotent, definitive endoderm cells, foregut endoderm cells, and/or PDX1-positive pancreatic endoderm cells, at least about 1 reagent-cell complex for about every 10 pluripotent, definitive endoderm cells, foregut endoderm cells, and/or PDX1-positive pancreatic endoderm cells, at least about 1 reagent-cell complex for about every 5 pluripotent, definitive endoderm cells, foregut endoderm cells, and/or PDX1-positive pancreatic endoderm cells, at least about 1 reagent-cell complex for about every 2 pluripotent, definitive endoderm cells, foregut endoderm cells, and/or PDX1-positive pancreatic endoderm cells, at least about reagent-cell complexes for about every 1 pluripotent, definitive endoderm cell, foregut endoderm cell, and/or PDX1-positive pancreatic endoderm cell, at least about 5 reagent-cell complexes for about every 1 pluripotent, definitive endoderm cell, foregut endoderm cell, and/or PDX1-positive pancreatic endoderm cell, at least about 10 definitive endoderm cells for about every 1 pluripotent, definitive endoderm cell, foregut endoderm cell, and/or PDX1-positive pancreatic endoderm cell, at least about 20 reagent-cell complexes for about every 1 pluripotent, definitive endoderm cell, foregut endoderm cell, and/or PDX1-positive pancreatic endoderm cell, at least about 50 reagent-cell complexes for about every 1 pluripotent, definitive endoderm cell, foregut endoderm cell, and/or PDX1-positive pancreatic endoderm cell, at least about reagent-cell complexes for about every 1 pluripotent, definitive endoderm cell, foregut endoderm cell, and/or PDX1-positive pancreatic endoderm cell, at least about 1000 reagent-cell complexes for about every 1 pluripotent, definitive endoderm cell, foregut endoderm cell, and/or PDX1-positive pancreatic endoderm cell, at least about 10,000 reagent-cell complexes for about every 1 pluripotent, definitive endoderm cell, foregut endoderm cell, and/or PDX1-positive pancreatic endoderm cell, at least about 100,000 reagent-cell complexes for about every 1 pluripotent, definitive endoderm cell, foregut endoderm cell, and/or PDX1-positive pancreatic endoderm cell; and at least about 1,000,000 reagent-cell complexes for about every 1 pluripotent, definitive endoderm cell, foregut endoderm cell, and/or PDX1-positive pancreatic endoderm cell are contemplated. In some embodiments of the present invention, the pluripotent cells are human pluripotent stem cells. In certain embodiments the stem cells are derived from a morula, the inner cell mass of an embryo or the gonadal ridges of an embryo. In certain other embodiments, the pluripotent cells are derived from the gonadal or germ tissues of a multicellular structure that has developed past the embryonic stage.

Method of Producing Pancreatic Hormone-Expressing Cells Using Noggin

Methods for differentiating pancreatic hormone-expressing cells from less differentiated cell types have been described above. These methods can be enhanced by the addition of noggin to the differentiation medium at the appropriate stage of differentiation. In some embodiments, noggin can facilitate differentiation of foregut endoderm cells without the addition of supplemental retinoid. However, when noggin is used in combination with a retinoid, the production of pancreatic hormone-expressing cells is generally increased. Specific protocols which describe the use of noggin in the differentiation of hESC cells to pancreatic hormone-expressing cells are described in Examples 18 and 19 below. The following paragraphs provide a general description of how noggin can be used in the differentiation process. It should be appreciated that the disclosure below incorporates methods already fully described above and in the US patent applications that have been incorporated into this document by reference. As such, the disclosure of method steps already previously described apply to the paragraphs that follow.

Some embodiments of the present invention include a method of producing human pancreatic hormone-expressing cells comprising the steps of providing a population of pluripotent human embryonic stem cells (hESCs) with at least one growth factor of the TGF-β superfamily to obtain human definitive endoderm cells, providing the population of human definitive endoderm cells with at least one fibroblast growth factor to obtain human foregut endoderm cells and then providing the population of human foregut endoderm cells with noggin to obtain human endocrine precursor cells, which are then incubated for a sufficient time to permit human pancreatic islet hormone-expressing cells to form. In some embodiment, a sufficient time for human pancreatic hormone-expressing cells to form has been determined by detecting the presence of human pancreatic hormone-expressing cells in the cell population. As described above, human pancreatic hormone-expressing cells can be characterized by certain marker expression. Accordingly, methods of detecting such marker expression, such as Q-PCR or immunocytochemistry can be used to determine the about of time that is sufficient to permit pancreatic hormone-expressing cell formation. In some embodiments, one or more markers selected from the group consisting of pancreatic duodenal homeobox 1 (PDX1), ghrelin (GHRL), islet amyloid polypeptide (IAPP), insulin (INS), pancreatic polypeptide (PP), ISL1 transcription factor (ISL1), NKX6 transcription factor related locus 1 (NKX6.1), paired box 6 (PAX6), and pancreas specific transcription factor 1a (PTF1a) are detected.

In some embodiments of the above-described method, from at least about 2% to at least about 95% of the human cells in the cell population differentiate into human pancreatic hormone-expressing cells. In some embodiments, at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or greater than about 95% of the human cells in the cell population differentiate into human pancreatic hormone-expressing cells.

In some embodiments of the above-described methods, the differentiating cell population with a gamma secretase inhibitor, such as DAPT. In certain embodiments, the gamma secretase inhibitor is provided to the cell population at about the same time as providing noggin or after providing noggin. In some embodiments, the gamma secretase inhibitor is provided just prior to providing noggin. For example, the gamma secretase inhibitor can be provided from about 3 days prior to about 7 days subsequent to the addition of noggin. In a preferred embodiment, the gamma secretase inhibitor is provided about 1 day to about 4 days subsequent to providing noggin to the cell culture or cell population. In a more preferred embodiment, the gamma secretase inhibitor is provided about 3 days subsequent to providing noggin to the cell culture or cell population. In some embodiments of the present invention, the gamma secretase inhibitor is provided to the cell population at a concentration ranging from about 0.1 µM to about 10 µM. In a preferred embodiment, the gamma secretase inhibitor is provided to the cell population at a concentration of about 1 µM.

In other embodiments of the above-described method, the at least one fibroblast growth factor is selected from FGF-10, FGF-22 or FGF-7 (KGF). In a preferred embodiment, the fibroblast growth factor that is provided is KGF. In such embodiments, KGF is provided to the cell culture at a concentration ranging from about 1 ng/ml to about 1000 ng/ml. In some embodiments, KGF can be provided to the differentiating cell culture at a concentration of at least about 1 ng/ml, at least about 2 ng/ml, at least about 5 ng/ml, at least about 10 ng/ml, at least about 15 ng/ml, at least about 20 ng/ml, at least about 25 ng/ml, at least about 30 ng/ml, at least about 35 ng/ml, at least about 40 ng/ml, at least about 45 ng/ml, at least about 50 ng/ml, at least about 55 ng/ml, at least about 60 ng/ml, at least about 65 ng/ml, at least about 70 ng/ml, at least about 75 ng/ml, at least about 80 ng/ml, at least about 85 ng/ml, at least about 90 ng/ml, at least about 95 ng/ml, at least about 100 ng/ml, at least about 110 ng/ml, at least about 120 ng/ml, at least about 130 ng/ml, at least about 140 ng/ml, at least about 150 ng/ml, at least about 160 ng/ml, at least about 170 ng/ml, at least about 180 ng/ml, at least about 190 ng/ml, at least about 200 ng/ml, at least about 250 ng/ml, at least about 300 ng/ml, at least about 350 ng/ml, at least about 400 ng/ml, at least about 450 ng/ml, at least about 500 ng/ml, at least about 750 ng/ml, or at least about 1000 ng/ml. In some embodiments of the above-described method, the at least one fibroblast growth factor comprises any fibroblast growth factor or a ligand that stimulates or otherwise interacts with the fibroblast growth factor 2 receptor IIIb (FGFR2(IIIb).

In still other embodiments of the above-described method, a hedgehog inhibitor is provided to the differentiating cell population at about the same time as adding the at least one fibroblast growth factor. In some embodiments, the hedgehog inhibitor is provided just prior to providing the fibroblast growth factor. For example, the hedgehog inhibitor can be provided from about 2 days prior to about 3 days subsequent to the addition of the fibroblast growth factor. In a preferred embodiment, the hedgehog inhibitor is provided at about the same time as providing the fibroblast growth factor to the cell culture or cell population. In a preferred embodiment, the hedgehog inhibitor is KAAD-cyclopamine.

In a preferred embodiment, the hedgehog inhibitor is provided to the cell culture at a concentration ranging from about 0.01 µM to about 10 µM. In some embodiments, the hedgehog inhibitor can be provided at a concentration of at least about 0.01 µM, at least about 0.02 µM, at least about 0.04 µM, at least about 0.08 µM, at least about 0.1 µM, at least about 0.2 µM, at least about 0.3 µM, at least about 0.4 µM, at least about 0.5 µM, at least about 0.6 µM, at least about 0.7 µM, at least about 0.8 µM, at least about 0.9 µM, at least about 1 µM, at least about 1.1 µM, at least about 1.2 µM, at least about 1.3 µM, at least about 1.4 µM, at least about 1.5 µM, at least about 1.6 µM, at least about 1.7 µM, at least about 1.8 µM, at least about 1.9 µM, at least about 2 µM, at least about 2.1 µM, at least about 2.2 µM, at least about 2.3 µM, at least about 2.4 µM, at least about 2.5 µM, at least about 2.6 µM, at least about 2.7 µM, at least about 2.8 µM, at least about 2.9 µM, at least about 3 µM, at least about 3.5 µM, at least about 4 µM, at least about 4.5 µM, at least about 5 µM, at least about 10 µM, at least about 20 µM, at least about 30 µM, at least about 40 µM or at least about 50 µM.

In the step of differentiating hESCs to definitive endoderm cells, a growth factor of the TGF-β superfamily is provided to the cell population. In some embodiments, the TGF-β superfamily is selected from the group consisting of Nodal, activin A, activin B and combinations thereof. In a preferred embodiment, the TGF-β superfamily comprises activin A. In some embodiments, the activin A is provided to said hESCs at a concentration ranging from about 10 ng/ml to about 1000 ng/ml. In some embodiments, activin A is provided to the cell population at a concentration of at least about 1 ng/ml, at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, or at least about 1000 ng/ml.

In some embodiments, of the above-described methods the hESCs are also provided with wingless-type MMTV integration site family member 3A (Wnt3A). In a preferred embodiment, Wnt3A is provided at a concentration ranging from about 1 ng/ml to about 1000 ng/ml. In some embodiments, Wnt3A is provided to the cell population at a concentration of at least about 1 ng/ml, at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, or at least about 1000 ng/ml.

Some embodiments of the above-described methods comprise withdrawing any growth factor of the TGF-β superfamily that may be present in said population of definitive endoderm cells. In such embodiments, the TGF-β superfamily growth factor is TGF-β superfamily growth factor that has been exogenously provided to the cell culture. That is, the TGF-β superfamily growth factor that is withdrawn is not TGF-β superfamily growth factor that is present as a basal component of the medium as formulated by those of ordinary skill in the art.

Additional embodiments of the above-described methods further comprise providing a retinoid to the cell population at about the same time or after providing at least one fibroblast growth factor. In certain embodiments, the retinoid is provided to the cell population at about the same time as providing at least one fibroblast growth factor or after providing at least one fibroblast growth factor. In some embodiments, the retinoid is provided just prior to providing at least one fibroblast growth factor. In other embodiments, the retinoid is provided to the cell population at about the same time as providing noggin. For example, the retinoid can be provided from about 3 days prior to about 7 days subsequent to the addition of at least one fibroblast growth factor. In a preferred embodiment, the retinoid is provided about 1 day to about 4 days subsequent to providing at least one fibroblast growth factor to the cell culture or cell population. In a more preferred embodiment, the retinoid is provided about 3 days subsequent to providing at least one fibroblast growth factor to the cell culture or cell population.

In some embodiments, of the above-described methods the retinoid is provided to the differentiating cell population at a concentration ranging from about 0.01 µM to about 100 µM. In some embodiments, the retinoid is provided at a concentration at a concentration of at least about 1 nM, at least about 0.01 µM, at least about 0.02 µM, at least about 0.04 µM, at least about 0.08 µM, at least about 0.1 µM, at least about 0.2 µM, at least about 0.3 µM, at least about 0.4 µM, at least about 0.5 µM, at least about 0.6 µM, at least about 0.7 µM, at least about 0.8 µM, at least about 0.9 µM, at least about 1 µM, at least about 1.1 µM, at least about 1.2 µM, at least about 1.3 µM, at least about 1.4 µM, at least about 1.5 µM, at least about 1.6 µM, at least about 1.7 µM, at least about 1.8 µM, at least about 1.9 µM, at least about 2 µM, at least about 2.1 µM, at least about 2.2 µM, at least about 2.3 µM, at least about 2.4 µM, at least about 2.5 µM, at least about 2.6 µM, at least about 2.7 µM, at least about 2.8 µM, at least about 2.9 µM, at least about 3 µM, at least about 3.5 µM, at least about 4 µM, at least about 4.5 µM, at least about 5 µM, at least about 10 µM, at least about 20 µM, at least about 30 µM, at least about 40 µM, at least about 50 µM, at least about 75 µM or at least about 100 µM. I a preferred embodiment, the retinoid is retinol. In such embodiment, the retinol can be that included in B27 supplement. In more preferred embodiments, the retinoid is retinoic acid.

In some embodiments of the methods described above, the hESCs are differentiated to human definitive endoderm cells in a medium comprising less than about 2% serum. For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v) or less than about 2% (v/v). In some embodiments, differentiation is initiated in the absence of serum and in the absence of insulin and/or insulin-like growth factor. During the course of differentiation, the serum concentration may be gradually increased in order to promote adequate cell survival. In preferred embodiments, differentiation of hESCs to definitive endoderm cells is initiated in the absence of serum and in the absence of any supplement comprising insulin or insulin-like growth factors. The absence of serum and absence of supplement comprising insulin or insulin-like growth factors is maintained for about 1 to about 2 days, after which, serum is gradually added to the differentiating cell culture over the course of differentiation. In preferred embodiments, the concentration of serum does not exceed about 2% during the course of differentiation.

With respect to the above-described method, the hESCs can be derived from a tissue selected from the group consisting of the morula, the ICM of an embryo and the gonadal ridges of an embryo. In preferred embodiments, the hESCs are derived from a preimplantation embryo.

Differentiation of hESCs to Endocrine Precursor Cells and Pancreatic Hormone-Expressing Cells without the Use of Histone Deacetylase Inhibitors Some embodiments of the invention included herein relate to in vitro cell cultures and in vitro cell populations as set forth herein that have not been cultured and/or differentiated in the presence of a substantial amount of sodium butyrate or other histone deacetylase inhibitor for a substantial length of time during any stage of their development. With respect to culturing and/or differentiating cells in the presence of sodium butyrate or other histone deacetylase inhibitor, "substantial amount" means any amount sufficient to allow the sodium butyrate or other histone deacetylase inhibitor to mediate inhibitory effects on histone deacetylase in approximately half of the human cells in the cell culture or cell population. With respect to culturing and/or differentiating cells in the presence of sodium butyrate or other histone deacetylase inhibitor, "substantial length of time" means any length of time sufficient to allow the sodium butyrate or other histone deacetylase inhibitor to mediate inhibitory effects on histone deacetylase in approximately half of the human cells in the cell culture or cell population. Accordingly, both the concentration of sodium butyrate or other histone deacetylase inhibitor and the time that it is present in the cell culture will influence the extent of the inhibitory effect. For example, a substantial amount can range from about 1 nM to about 100 mM. In some embodiments, a substantial amount is about 1 nM, about 2 nM, about 5 nM, about 10 nM, about 20 nM, about 30 nM, about 40 nM, about 50 nM, about 75 nM, about 100 nM, about 250 nM, about 500 nM, about 750 nM, about 1 µM, about 10 µM, about 25 µM, about 50 µM, about 75 µM, about 100 µM, about 250 µM, about 500 µM, about 750 µM, about 1 mM, about 10 mM, about 25 mM, about 50 mM, about 75 mM, about 100 mM or greater than about 100 mM. In some embodiments, a substantial length of time can be about 10 minutes, about 30 minutes, about 1 hour, about 2 hours, about 4 hours, about 8 hours, about 12 hours, about 16 hours, about 1 day, about 2 days, about 3 days, about 4 day, about 5 days or greater than about 5 days. For example, cell types that have not been cultured and/or differentiated in the presence of sodium butyrate or another histone deacetylase inhibitor include hESCs, human definitive endoderm cells, human foregut endoderm cells, human PDX1-positive foregut endoderm cells, human endocrine precursor cells, human immature pancreatic hormone-expressing cells and mature pancreatic hormone-expressing cells. In some embodiments of the present invention, in vitro cell cultures and in vitro cell populations as set forth herein are cultured and/or differentiated in the complete absence of sodium butyrate or other histone deacetylase inhibitor at one or more times during the stages of their development.

Additional embodiments described herein include methods of producing one or more of the above-described cell cultures or cell populations in the absence of a substantial amount of sodium butyrate or other histone deacetylase inhibitor. In such embodiments, no substantial amount of exogenous sodium butyrate or other histone deacetylase inhibitor is supplied to the cells of the cell culture or cell population for any substantial length of time during any stage of the differentiation process. As indicated above, "substantial amount" means any amount of sodium butyrate or other histone deacetylase inhibitor sufficient to mediate inhibitory effects on histone deacetylase in approximately half of the human cells in the cell culture or cell population. Also as indicated above, "substantial length of time" means any length of time sufficient to allow the sodium butyrate or other histone deacetylase inhibitor to mediate inhibitory effects on histone deacetylase in approximately half of the human cells in the cell culture or cell population. In certain embodiments, differentiation methods described herein include differentiating hESCs, human definitive endoderm cells, human foregut endoderm cells, human PDX1-positive foregut endoderm cells, human endocrine precursor cells, human immature pancreatic hormone-expressing cells and mature pancreatic hormone-expressing cells in the absence of a substantial amount of sodium butyrate or other histone deacetylase inhibitor. In some embodiments of the present invention, hESCs, human definitive endoderm cells, human foregut endoderm cells, human PDX1-positive foregut endoderm cells, human endocrine precursor cells, human immature pancreatic hormone-expressing cells and mature pancreatic hormone-expressing cells are cultured and/or differentiated in the complete absence of sodium butyrate or other histone deacetylase inhibitor.

Differentiation of Non-Recombinant hESCs to Endocrine Precursor Cells and Pancreatic Hormone-Expressing Cells Additional embodiments of the present invention relate non-recombinant cell cultures and non-recombinant cell populations comprising one or more cell types selected from hESCs, human definitive endoderm cells, human foregut endoderm cells, human PDX1-positive foregut endoderm cells, human endocrine precursor cells, human immature pancreatic hormone-expressing cells and mature pancreatic hormone-expressing cells. In some embodiments of the non-recombinant cell cultures and non-recombinant cell populations at least one of the cell types is a non-recombinant cell type. In preferred embodiments, all the cell types in the cell culture or cell population are non-recombinant cell types. By "non-recombinant" is meant that the cell are not engineered to express the product of one or more exogenous genes or the product of a functional portion of one or more exogenous genes, especially an exogenous marker gene, which includes, but is not limited to, exogenous marker genes that can be used for selection and/or screening. Specific examples of exogenous marker genes include, but are not limited to, genes encoding green fluorescent protein (GFP), enhanced green fluorescent protein (EGFP), luciferase and any other marker useful for cell sorting. Other exemplary exogenous marker genes include antibiotic resistance genes. In some embodiments, non-recombinant cells include cells that have not been engineered to contain an exogenous or foreign gene. In some embodiments, the cells cultures and cell populations described herein are karyotypically normal.

Further embodiments of the present invention relate to methods of producing non-recombinant cell cultures and non-recombinant cell populations comprising one or more cell types selected from hESCs, human definitive endoderm cells, human foregut endoderm cells, human PDX1-positive foregut endoderm cells, human endocrine precursor cells, human immature pancreatic hormone-expressing cells and mature pancreatic hormone-expressing cells. In such embodiments, one or more cell types in the cell culture or cell population are non-recombinant cell types. In a preferred embodiment, all of the cell types in the cell culture or cell population are non-recombinant cell types. In especially preferred embodiments of the methods described herein, non-recombinant hESCs are differentiated to definitive endoderm cells and further into hormone-expressing cells, thereby producing non-recombinant hormone-expressing cells. In certain embodiments, the methods described herein do not include a step of sorting cells based on the expression or nonexpression of an exogenous or foreign marker gene product. Examples of products of marker genes are green fluorescent protein (GFP), enhanced green fluorescent protein (EGFP), luciferase and any other marker useful for cell sorting. In some embodiments, non-recombinant cells in the cell cultures or cell populations, which have not been engineered to contain a gene encoding an exogenous or foreign marker protein, are differentiated to definitive endoderm cells and further into hormone-expressing cells. In some embodiments, non-recombinant cells include cells that have not been engineered to contain an exogenous or foreign gene. In some embodiments, karyotypically normal cells are differentiated to definitive endoderm cells and further into hormone-expressing cells, thereby producing non-recombinant hormone-expressing cells.

Methods of Producing Pancreatic Hormones

Certain embodiments of the present invention relate to the production of pancreatic hormones, such as insulin. In preferred embodiments, the hormone production occurs in vivo by pancreatic hormone-expressing cells that have been previously differentiated in vitro to pancreatic hormone-expressing cell precursors. The pancreatic hormone-expressing cell precursors are then transplanted into a mammalian subject where they undergo further differentiation in vivo to produce functional pancreatic hormone-expressing cells. In some preferred embodiments, the pancreatic hormone-expressing cells and the pancreatic hormone-expressing cell precursors are human cells. In especially preferred embodiments, the pancreatic hormone-expressing cells and the pancreatic hormone-expressing cell precursors are derived from human pluripotent cells, such as human embryonic stem cells. In such embodiments, the human embryonic stem cells are differentiated in vitro to definitive endoderm cells, or later stage pancreatic precursor cells derived therefrom, prior to transplantation into a mammalian subject. In preferred embodiments, the mammalian subject is a human.

The pancreatic hormone-expressing cells produced by the above-described in vivo method are capable of producing one, or more than one, pancreatic hormone. In a preferred embodiment, the in vivo-produced pancreatic hormone-expressing cells express only insulin. In especially preferred embodiments, the insulin is secreted in response to glucose stimulation. Glucose stimulated insulin secretion is a natural process in which certain cells, such as pancreatic β-cells, secrete insulin in response to blood glucose levels that exceed the normal range of physiological blood glucose concentration. The normal physiological blood glucose concentration range for various mammalian species, including humans, can readily be determined by those of ordinary skill in the art.

Certain preferred embodiments of the present invention, which relate to methods of producing human insulin in vivo, include differentiating human embryonic stem cells in vitro to produce definitive endoderm cells, and/or cells further derived from definitive endoderm cells, by incubating the human stem cells in a medium comprising one or more agents that activate a member of the family of TGF-β receptors. The in vitro-produced cells are then transplanted into a mammalian subject, such as a human, where the cells are permitted to mature into insulin secreting cells. In preferred embodiments, the insulin secreting cells that are produced secrete insulin in response to glucose stimulation.

Other preferred embodiments of the present invention relate to methods for producing insulin by contacting human embryonic stem cells in vitro with a first medium that comprises one or more agents that activate a TGF-β receptor family member and then culturing these cells in a second medium lacking the one or more agents that activate the TGF-β receptor family member. In some embodiments, the second medium comprises one or more agents that inhibit the TGF-β receptor family member. In other embodiments, the second medium both lacks the one or more agents that activate the TGF-β receptor family member and comprises one or more agents that inhibit the TGF-β receptor family member. The cells that are produced by the in vitro cell culture methods are then transplanted into a mammalian subject, such as a human, where the cells are permitted to mature into insulin secreting cells. In preferred embodiments, the insulin secreting cells that are produced secrete insulin in response to glucose stimulation.

In the above-described methods for producing pancreatic hormones, such as insulin, one or more agents that activate the TGF-β family receptor are used. In preferred embodiments these agents include, but are not limited to, activin A, activin AB, activin B, Nodal or combinations of any of these agents. In some embodiments, the one or more agents that activate the TGF-β family receptor are supplied at a final concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, at least about 1000 ng/ml, at least about 2000 ng/ml, at least about 3000 ng/ml, at least about 4000 ng/ml, at least about 5000 ng/ml or more than about 5000 ng/ml. In a preferred embodiment, the one or more agents that activate the TGF-β family receptor activate the activin receptor—like kinase (ALK) receptor.

In some embodiments of the above-described methods for producing pancreatic hormones, such as insulin, one or more media that are used lack the one or more agents that activate the TGF-β family receptor. As used with respect to such embodiments, "to lack," or variations thereof, means to have any of the following concentrations of one or more agents that activate the TGF-β family receptor: (a) a concentration that is 0, (b) a concentration that is not detectable by conventional methods of measuring the concentration of such agents, or (c) a concentration that is measurable but insufficient to produce any significant effect on the cells in the cell culture with respect to cell differentiation. In some embodiments, the term "to lack," or variations thereof, is used only to refer to exogenously added agents that activate the TGF-β family receptor but not basal components of the growth medium that may activate the TGF-β family receptor.

In some embodiments of the above-described methods for producing pancreatic hormones, such as insulin, one or more media that are used lack nicotinamide. As used with respect to such embodiments, "to lack," or variations thereof, means to have any of the following concentrations of nicotinamide: (a) a concentration that is 0, (b) a concentration that is not detectable by conventional methods of measuring the concentration of nicotinamide, or (c) a concentration that is measurable but insufficient to produce any significant effect on the cells in the cell culture with respect to cell differentiation. In some embodiments, the term "to lack," or variations thereof, is used only to refer to exogenously added nicotinamide but not basal nicotinamide contained in the growth medium.

Certain embodiments of the above-described methods for producing pancreatic hormones, such as insulin, include a step of contacting the human embryonic stem cells in culture with Wnt3A. In some embodiments, the Wnt3A is provided at the time of contacting the cells with the agent that activates the TGF-β receptor family member. In other embodiments, the Wnt3A is provided shortly before or shortly after contacting the cell with the agent that activates the TGF-β receptor family member. In some embodiments of the present invention, the Wnt3A is supplied at a final concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, at least about 1000 ng/ml, at least about 2000 ng/ml, at least about 3000 ng/ml, at least about 4000 ng/ml, at least about 5000 ng/ml or more than about 5000 ng/ml.

In some embodiments of the above-described methods for producing pancreatic hormones, such as insulin, where one or more agents that inhibit the TGF-β family receptor are provided to the in vitro cell culture, an agent such as SB-431542 is provided. In some embodiments, SB-431542 at a final concentration of at least about 0.1 µM, at least about 0.2 µM, at least about 0.3 µM, at least about 0.4 µM, at least about 0.5 µM, at least about 0.6 µM, at least about 0.7 µM, at least about 0.8 µM, at least about 0.9 µM, at least about 1.0 µM, at least about 1.5 µM, at least about 2.0 µM, at least about 2.5 µM, at least about 3.0 µM, at least about 3.5 µM, at least about 4.0 µM, at least about 4.5 µM, at least about 5.0 µM, at least about 5.5 µM, at least about 6.0 µM, at least about 6.5 µM, at least about 7.0 µM, at least about 7.5 µM, at least about 8.0 µM, at least about 8.5 µM, at least about 9.0 µM, at least about 9.5 µM, at least about 10 µM, at least about 20 µM, at least about 30 µM, at least about 40 µM, at least about 50 µM, at least about 60 µM, at least about 70 µM, at least about 80 µM, at least about 90 µM, at least about 100 µM, at least about 200 µM, at least about 300 µM, at least about 400 µM, at least about 500 µM, at least about 600 µM, at least about 700 µM, at least about 800 µM, at least about 900 µM, at least about 1000 µM, at least about greater than 1000 µM.

In some embodiments of the present invention, in vitro-derived pancreatic hormone-expressing cell precursor cells that are described-above are transplanted into a mammalian subject. In a preferred embodiment, the mammalian subject is a human subject. Particularly preferred subjects are those that have been identified as having a condition which limits the ability of the subject to produce sufficient levels of insulin in response to physiologically high blood glucose concentrations. A range of blood glucose levels that constitutes a physiologically high blood glucose level for any particular mammalian species can be readily determined by those of ordinary skill in the art. Any persistent blood glucose level that results in a recognized disease or condition is considered to be a physiologically high blood glucose level.

Additional embodiments of the present invention relate to an in vivo insulin secreting cell that is derived from an in vitro human embryonic stem cell or progeny thereof. In preferred embodiments the cell does not form a teratoma in vivo. In especially preferred embodiments, the cell does not contain any karyotypic abnormality nor is it an engineered or genetically recombinant cell.

Having generally described this invention, a further understanding can be obtained by reference to certain specific examples which are provided herein for purposes of illustration only, and are not intended to be limiting.

EXAMPLES

Many of the examples below describe the use of pluripotent human cells. Methods of producing pluripotent human cells are well known in the art and have been described numerous scientific publications, including U.S. Pat. Nos. 5,453,357, 5,670,372, 5,690,926, 6,090,622, 6,200,806 and 6,251,671 as well as U.S. Patent Application Publication No. 2004/0229350, the disclosures of which are incorporated herein by reference in their entireties.

Example 1

Human ES Cells

For our studies of pancreatic islet hormone-expressing cell development, we employed human embryonic stem cells, which are pluripotent and can divide seemingly indefinitely in culture while maintaining a normal karyotype. ES cells were derived from the 5-day-old embryo inner cell mass using either immunological or mechanical methods for isolation. In particular, the human embryonic stem cell line hESCyt-25 was derived from a supernumerary frozen embryo from an in vitro fertilization cycle following informed consent by the patient. Upon thawing the hatched blastocyst was plated on mouse embryonic fibroblasts (MEF), in ES medium ((DMEM, 20% FBS, non essential amino acids, beta-mercaptoethanol, and FGF2). The embryo adhered to the culture dish and after approximately two weeks, regions of undifferentiated hESCs were transferred to new dishes with MEFs. Transfer was accomplished with mechanical cutting and a brief digestion with dispase, followed by mechanical removal of the cell clusters, washing and re-plating. Since derivation, hESCyt-25 has been serially passaged over 100 times. We employed the hESCyt-25 human embryonic stem cell line as our starting material for the production of endocrine precursor cells, and subsequently, pancreatic islet hormone-expressing cells. Additionally, we have used other hESC lines developed both by us and by others including, but not limited to, Cyt-49, Cyt-203, BG01, BGO2 and BG03.

It will be appreciated by those of skill in the art that stem cells or other pluripotent cells can also be used as starting material for the differentiation procedures described herein. For example, cells obtained from embryonic gonadal ridges, which can be isolated by methods known in the art, can be used as pluripotent cellular starting material.

Example 2 hESCyt-25 Characterization

The human embryonic stem cell line, hESCyt-25 has maintained a normal morphology, karyotype, growth and self-renewal properties over 18 months in culture. This cell line displays strong immunoreactivity for the OCT4, SSEA-4 and TRA-1-60 antigens, all of which are characteristic of undifferentiated hESCs and displays alkaline phosphatase activity as well as a morphology identical to other established hESC lines. Furthermore, the human stem cell line, hESCyt-25, also readily forms embryoid bodies (EBs) when cultured in suspension. As a demonstration of its pluripotent nature, hESCyT-25 differentiates into various cell types that represent the three principal germ layers. Ectoderm production was demonstrated by Q-PCR for ZIC1 as well as immunocytochemistry (ICC) for nestin and more mature neuronal markers. Immunocytochemical staining for β-III tubulin was observed in clusters of elongated cells, characteristic of early neurons. Previously, we treated EBs in suspension with retinoic acid, to induce differentiation of pluripotent stem cells to visceral endoderm (VE), an extraembryonic lineage. Treated cells expressed high levels of α-fetoprotein (AFP) and SOX7, two markers of VE, by 54 hours of treatment. Cells differentiated in monolayer expressed AFP in sporadic patches as demonstrated by immunocytochemical staining. As will be described below, the hESCyT-25 cell line was also capable of forming definitive endoderm, as validated by real-time quantitative polymerase chain reaction (Q-PCR) and immunocytochemistry for SOX17, in the absence of AFP expression. To demonstrate differentiation to mesoderm, differentiating EBs were analyzed for Brachyury gene expression at several time points. Brachyury expression increased progressively over the course of the experiment. In view of the foregoing, the hESCyT-25 line is pluripotent as shown by the ability to form cells representing the three germ layers.

Example 3

Definitive Endoderm Cells as Intermediates in the Production of Cells Expressing Pancreatic Hormones Human embryonic stem cells were differentiated for 21 days via a 4-step protocol to achieve islet hormone-expressing cells. Three different conditions were used for the first step after which all plates received the identical treatment. The first step comprised 5 days differentiation under one of the following conditions: i) activin A (100 ng/ml) to robustly produce DE (D'Amour, K., et al., *Nature Biotechnology* 23, 1534-1541, (2005)), ii) 2% FBS with no exogenous growth factors, thereby producing mesoderm and extraembryonic endoderm, or iii) follistatin (50 ng/ml) and noggin (100 ng/ml), thereby producing neural ectoderm. Step 2 comprised 3 days differentiation in RPMI with 2% FBS containing FGF10 (50 ng/mL) and KAAD-cyclopamine (1 μM). Step 3 comprised 5 days differentiation in CMRL with B27 supplement (1:100) containing FGF10 (50 ng/mL), KAAD-cyclopamine (1 μM), retinoic acid (2 μM), and DAPT (1 μM). The fourth step consisted of 8 days differentiation in DMEM with B27 supplement (1:100) containing nicotinamide (10 mM), exendin 4 (40 ng/mL), hepatocyte growth factor (HGF-25 ng/mL), and insulin-like growth factor (IGF)-1 (50 ng/mL). Duplicate samples were taken from each plate at multiple time points and gene expression was analyzed by real-time quantitative PCR.

As shown in FIGS. 2A-2F, at 5 days of differentiation, the activin A treatment yielded robust production of definitive endoderm (DE) as indicated by elevated expression of SOX17 and CXCR4. The relative absence of expression for SOX17 and CXCR4 in the no factor (2NF) and the follistatin/noggin treatments indicated that little or no DE was produced under these conditions. Conversely, the no factor treatment induced robust expression of SOX7, a marker of extraembryonic endoderm, and ISL1, which is expressed in various mesoderm populations. Treatment with follistatin and noggin induced robust expression of SOX1 and PAX6, which indicated robust differentiation to neural ectoderm. As shown in FIGS. 2G-2N, we found that the expression of the pancreatic endoderm marker PDX1 as well as the pancreatic endocrine transcription factors (NGN3, NKX2.2, NKX6.1) and endocrine hormones occur subsequent to the production of DE. Efficient production of these cells correlates with the efficient production of DE. When extraembryonic endoderm/mesoderm or early neural ectoderm lineages are induced instead of DE, the pancreatic endoderm or pancreatic endocrine markers are not appreciably expressed in those cells after treatment with the identical culture conditions that produce islet hormone gene expression when applied to cultures enriched in DE. However, pre-specification of hESCs to DE is sufficient to achieve the mature pancreatic phenotypes characterized by the expression of PDX1, NGN3, insulin, and glucagon.

Example 4

Insulin/IGF Signaling Promotes Translation of PDX1 Protein

Human embryonic stem cells were differentiated in RPMI medium containing activin A (100 ng/ml) for 5 days. The FBS concentrations changed from 0% for the first 24 hours followed by 0.2% for the next 24 hrs and then to 2% for the remaining 3 days. During the next 4 days, the plates were subjected to different media conditions. They were either incubated in i) RPMI with 2% FBS and activin A (100 ng/ml), ii) RPMI with 2% FBS, activin A (25 ng/ml) and retinoic acid, iii) CMRL with 0.2% FBS and B27 supplement (1:100), activin A (25 ng/ml) and retinoic acid, and iv) CMRL with 0.2% FBS and B27 supplement (1:100), activin A (25 ng/ml), retinoic acid and exendin (40 ng/ml). The concentration of retinoic acid changed from 2 μM for 48 hours followed by 1 μM for 24 hours to 0.2 μM for the last 24 hours. The cells were harvested for protein and mRNA analyses on days 7, 8 and 9.

Figure 4A:
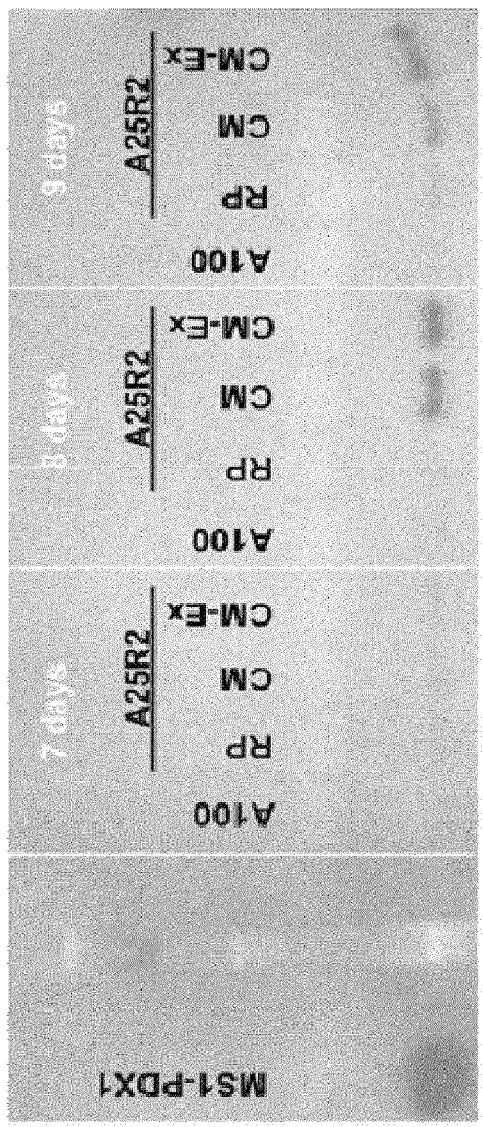
FIG. 4A depicts a Western blot analysis of PDX1 protein expression in cells subjected to different media conditions. Abbreviations: MS1-PDX1—Protein lysate from MS1 cells transfected with PDX1 (positive control), A100—100 ng/ml activin A; A25R2—25 ng/ml activin A and 2 µM RA; RP—RPMI medium; CM—CMRL medium; Ex—40 ng/ml exendin 4.
Figure 4B:
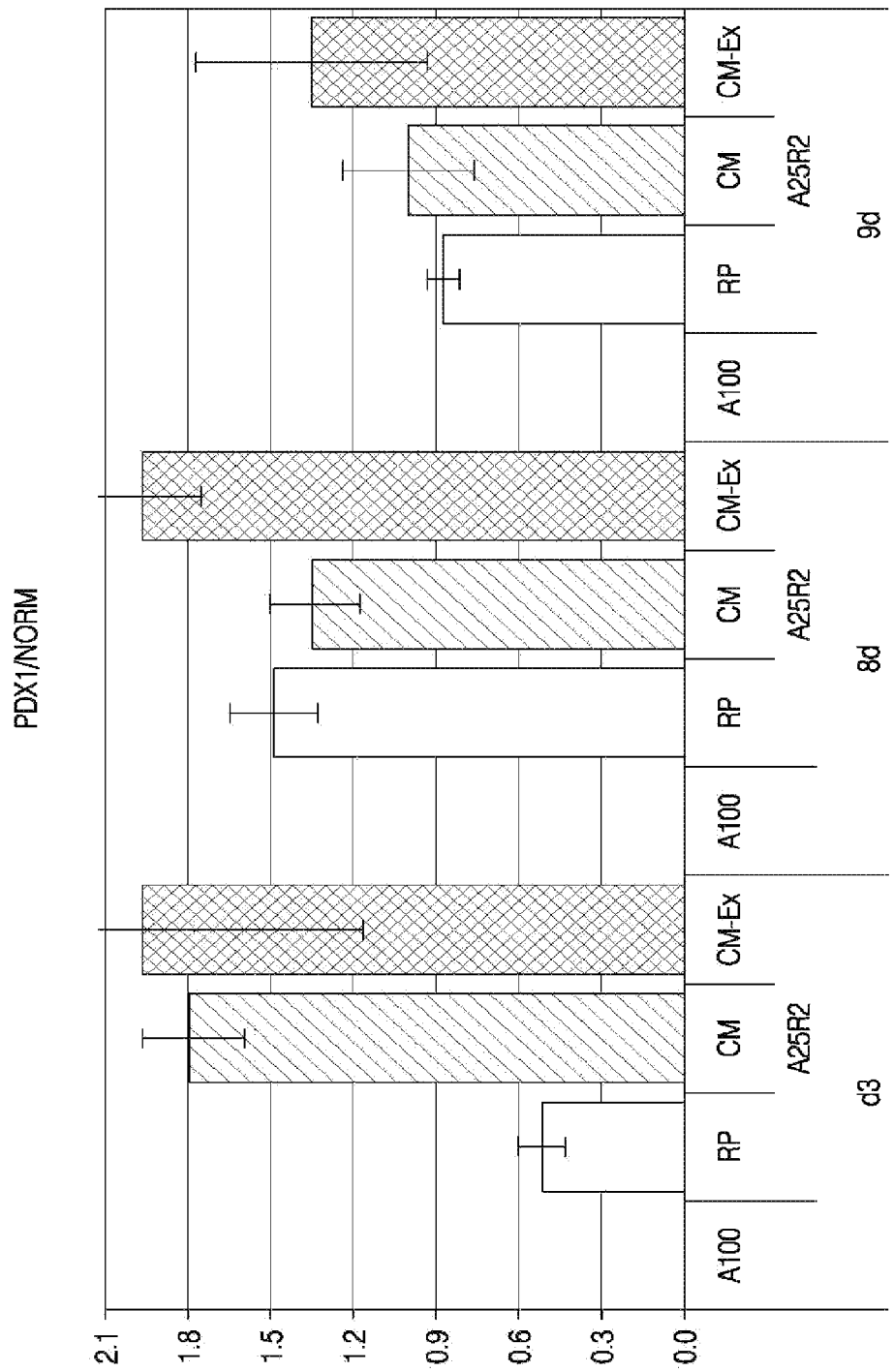
FIG. 4B is a bar chart showing the relative expression of PDX1 mRNA in the 7 day, 8 day and 9 day cultures set forth in FIG. 4A.
Figure 5A:
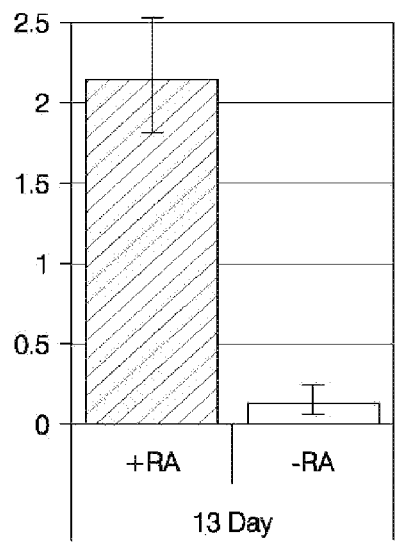
FIGS. 5A-5H are bar charts showing the relative expression of (FIG. 5A) HB9, (FIG. 5B) PDX1, (FIG. 5C) NGN3, and (FIG. 5D) NKX2.2 after 13 days of differentiation and (FIG. 5E) PDX1, (FIG. 5F) NKX2.2, (FIG. 5G) insulin and (FIG. 5H) glucagon after 17 days of differentiation in the presence or absence of retinoic acid.
Figure 5B:
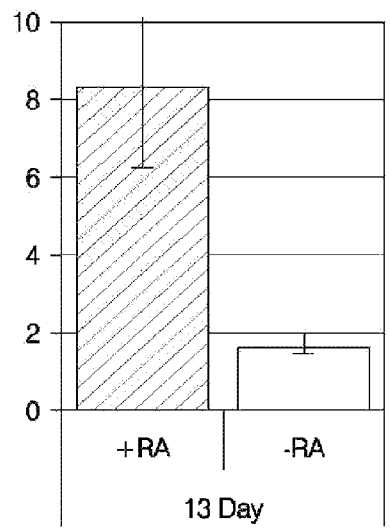
Figure 5C:
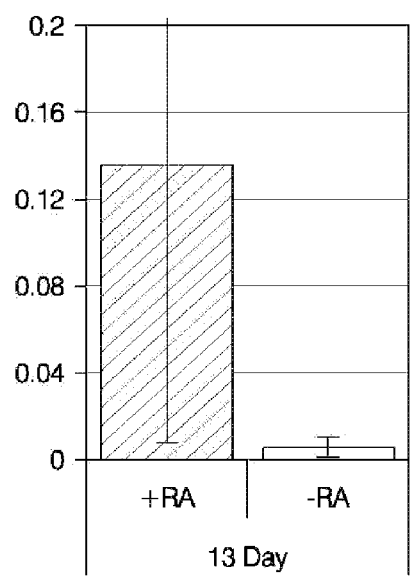
Figure 5D:
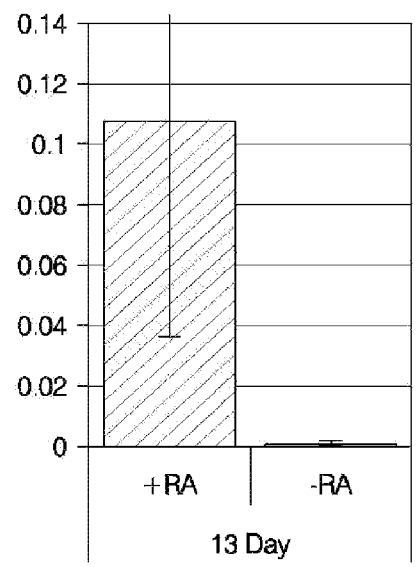
Figure 5E:
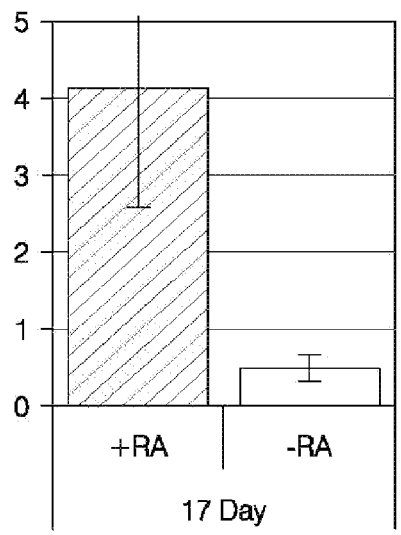
Figure 5F:
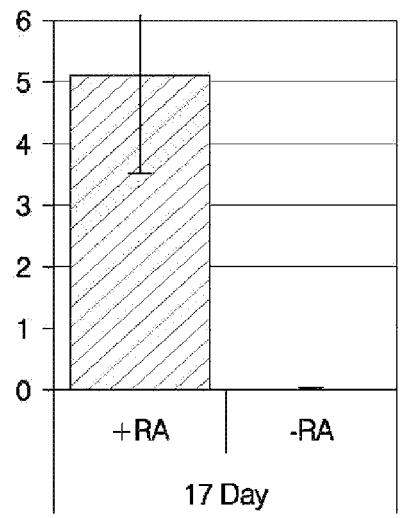
Figure 5G:
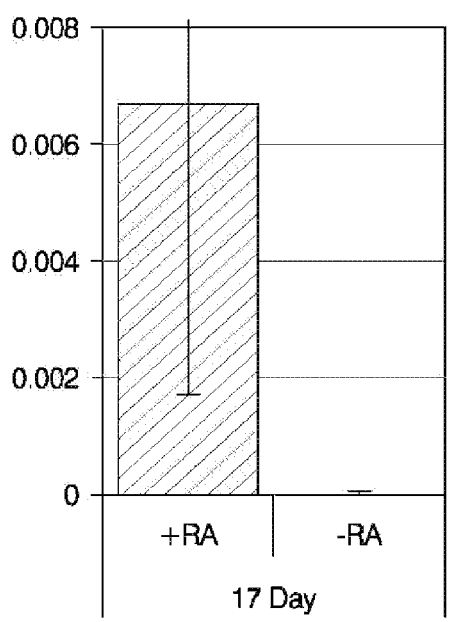
Figure 5H:
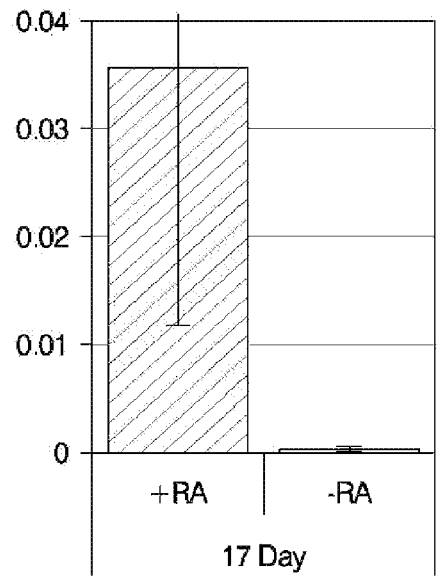
Figure 6A:
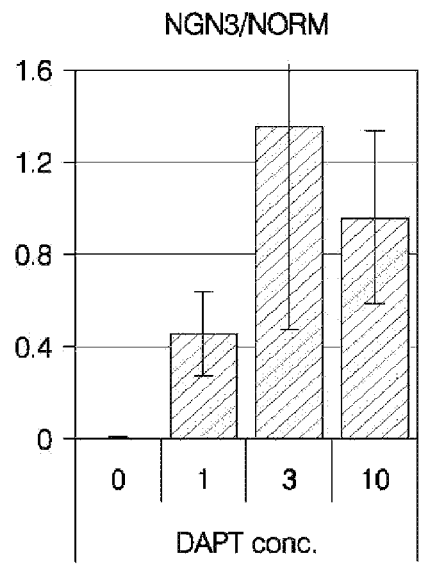
FIGS. 6A-6F are bar charts showing the relative expression of (FIG. 6A) NGN3, (FIG. 6B) NKX2.2, (FIG. 6C) insulin, (FIG. 6D) glucagon, (FIG. 6E) ghrelin, and (FIG. 6F) somatostatin (SOM) after 19 days of differentiation and exposure to three different concentrations of the gamma secretase inhibitor DAPT or no DAPT at all.
Figure 6C:
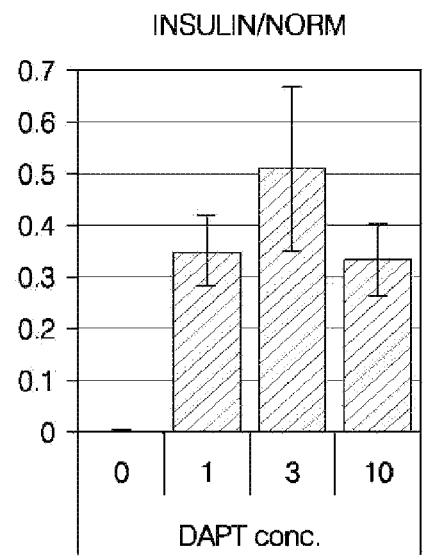
Figure 6B:
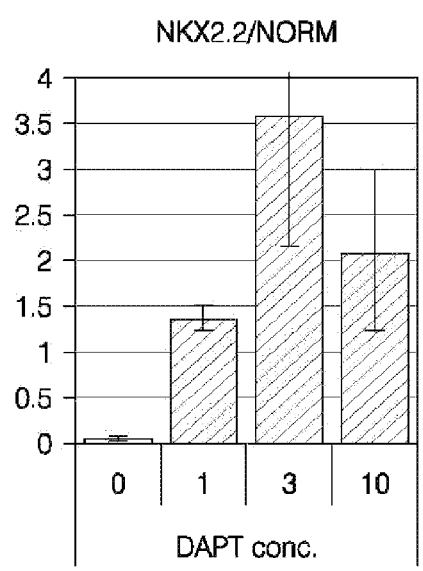
Figure 6D:
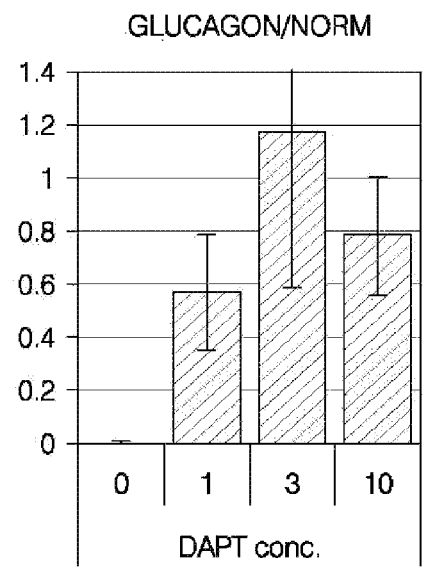
Figure 6E:
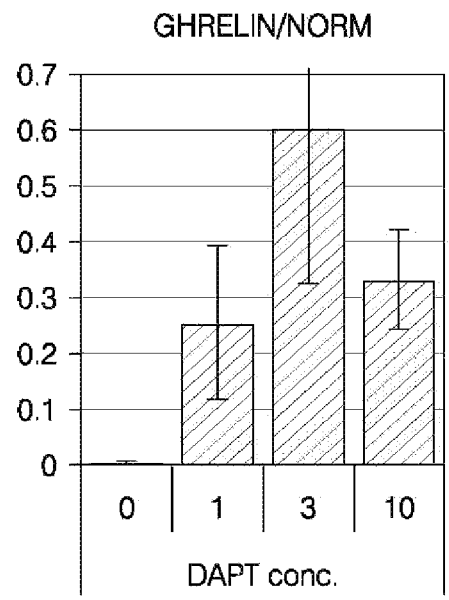
Figure 6F:
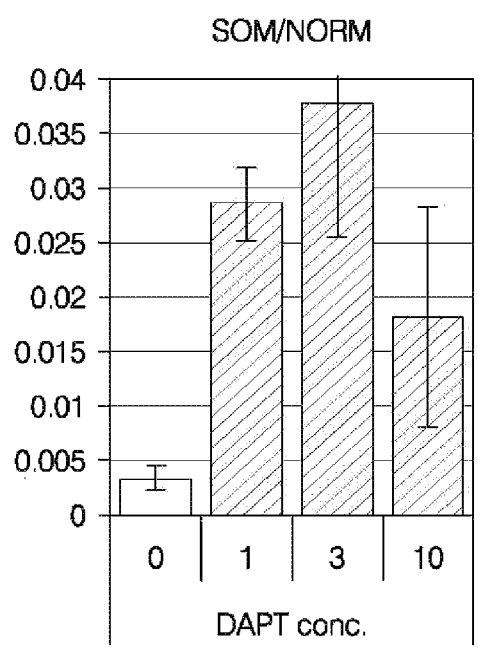
Figure 7A:
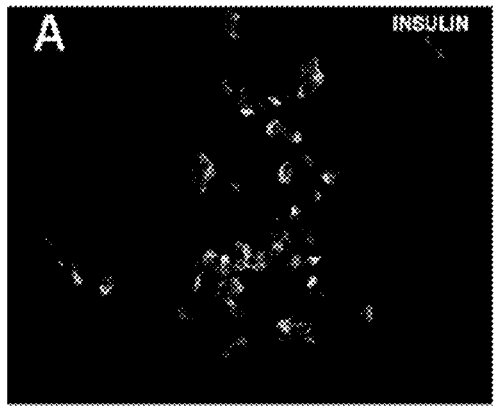
FIGS. 7A-7D are photomicrographs of (FIG. 7A) insulin, (FIG. 7B) glucagon and (FIG. 7C) somatostatin (SOM) immunoreactive cells. The merge of these three images is shown (FIG. 7D) and triple labeled cells are identified by the arrowheads.
Figure 7B:
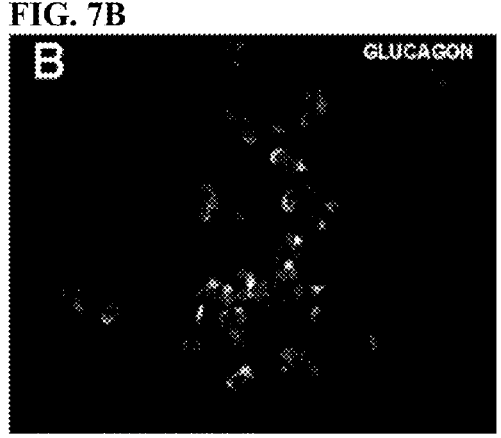
Figure 7C:
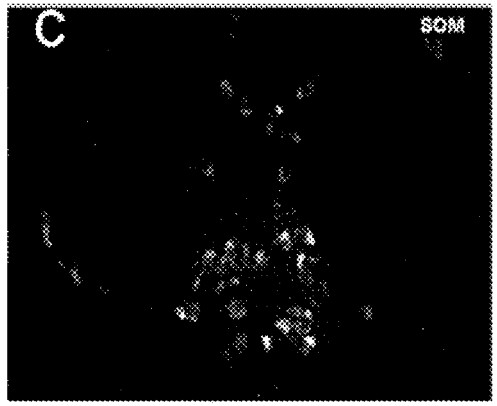
Figure 7D:
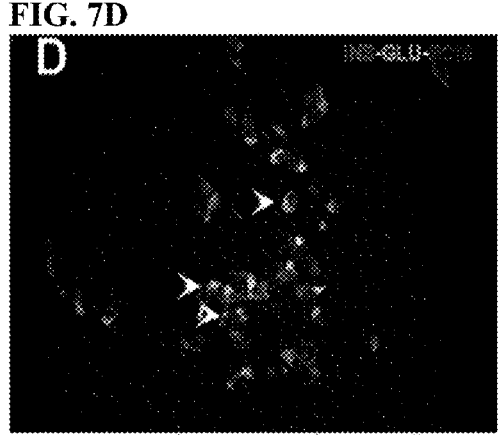
Figure 8A:
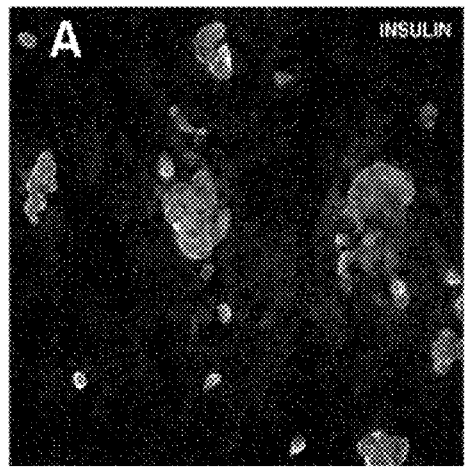
FIGS. 8A-8D are photomicrographs showing immunoreactivity for (FIG. 8A) insulin and (FIG. 8B) PAX6. These micrographs indicate that insulin positive cells are also PAX6 positive. Photomicrographs showing immunoreactivity for (FIG. 8C) insulin and (FIG. 8D) ISL1 indicate that insulin positive cells are also ISL1 positive. There are also many ISL1 cells that are negative for insulin immunoreactivity (compare FIG. 8C and FIG. 8D).
Figure 8B:
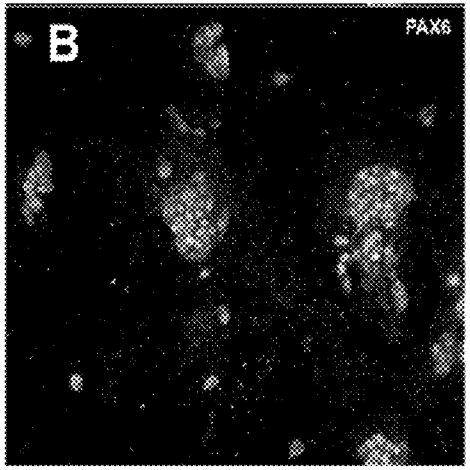
Figure 8C:
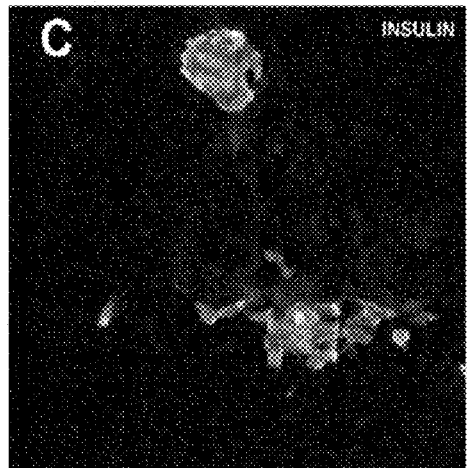
Figure 8D:
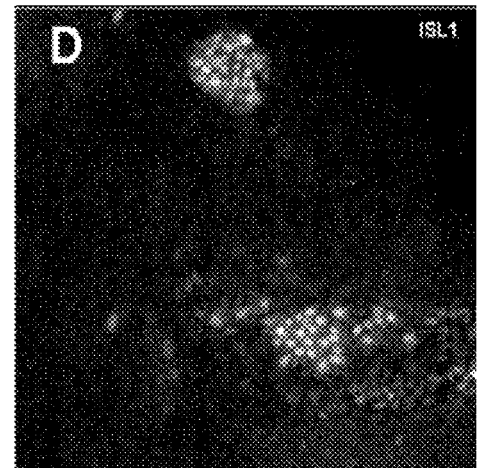

Another factor that promotes the expression of PDX1 protein is insulin (e.g., concentrations from about 0.2-20 μg/ml) or insulin-like growth factor (e.g., concentrations from about 10-500 ng/ml). Without sufficient insulin signaling, PDX1 mRNA was expressed without significant translation into PDX1 protein (FIGS. 4A-4B). The base medium can be RPMI, CMRL, OptiMEM or DMEM with or without 2% FBS. If the base medium is supplemented with sufficient insulin/IGF and FGF10, PDX1 protein will be expressed.

Example 5

Retinoic Acid Promotes the Differentiation of hESCs to the Pancreatic Insulin Expressing Phenotype Human embryonic stem cells were differentiated for 17 days via a 4-step protocol to achieve islet hormone-expressing cells. The first step comprised 5 days differentiation in activin A (100 ng/mL) to robustly produce DE (D'Amour, K., et al., *Nature Biotechnology* 23, 1534-1541, (2005)). Step 2 comprised 2 days differentiation in RPMI with 2% FBS containing FGF10 (50 ng/mL) and KAAD-cyclopamine (1 μM) followed by 2 more days that also contained DAPT (1 μM). Step 3 comprised 5 days differentiation in CMRL with B27 supplement (1:100) containing FGF10 (50 ng/mL), KAAD-cyclopamine (1 μM), DAPT (1 μM) and either with or without the addition of retinoic acid (1 μM). The fourth step comprised 4 days differentiation in CMRL with B27 supplement (1:100) containing nicotinamide (10 mM), exendin 4 (50 ng/mL), hepatocyte growth factor (HGF 25 ng/mL), and insulin-like growth factor (IGF)-1 (50 ng/mL). Duplicate samples were taken from each plate at multiple time points and gene expression was analyzed by real-time quantitative PCR.

This early foregut endoderm became further specified by application of retinoic acid which promoted the production of the pancreatic hormone producing cells. Importantly, the pancreatic endocrine hormone insulin was not expressed unless retinoic acid was applied (at a concentration of about 0.1-5 μM) for at least about 1 day (see FIGS. 5A-5H). This strongly suggests that the dorsal pancreatic bud is dominant with respect to production of insulin producing beta cells. This result is in direct contrast to the rat and mouse in which insulin and glucagon are expressed in both the ventral and dorsal buds. This pancreatic endoderm stage is marked by expression of PDX1, HB9 and HNF6/onecut 2 markers.

Example 6

Gamma Secretase Inhibition Promotes Efficient Induction of Endocrine Progenitors and Hormone-Expressing Cells Human embryonic stem cells were differentiated for 19 days via a 5-step protocol to achieve islet hormone-expressing cells. The first step comprised 5 days differentiation in activin A (100 ng/mL) to robustly produce DE (D'Amour, K., et al., *Nature Biotechnology* 23, 1534-1541, (2005)). Step 2 comprised 2 days differentiation in RPMI with 2% FBS containing FGF10 (50 ng/mL) and KAAD-cyclopamine (0.5 μM). Step 3 comprised 4 days differentiation in CMRL with B27 supplement (1:100) containing FGF10 (50 ng/mL), KAAD-cyclopamine (0.2 μM), and retinoic acid (1 μM). The fourth step comprised 2 days treatment with CMRL with B27 supplement (1:100) containing exendin 4 (40 ng/mL) and with varying concentrations of the gamma secretase inhibitor DAPT (0 μM, 1 μM, 3 μM, or 10 μM). The last step comprised 6 days differentiation in DMEM with B27 supplement (1:100) containing nicotinamide (10 mM), exendin 4 (40 ng/mL), and insulin-like growth factor (IGF)-1 (50 ng/mL). Duplicate samples were taken from each plate and gene expression was analyzed by real-time quantitative PCR.

Following production of high levels of PDX1 protein in accordance with the temporal application of factors and medium conditions described above, a final step to endocrine hormone production was addition of a gamma secretase inhibitor. The gamma secretase inhibitor promoted the transient induction of the transcription factor NGN3. It is known that the gamma secretase inhibitor efficiently blocks enzymatic release of the Notch intracellular domain, and thus, also functions as an inhibitor of Notch pathway activity (Notch inbitior). Application of any of the standard gamma secretase inhibitors in the range of their KD's results in Notch inhibition as measured by inhibition of expression of the Notch target genes such as HES1. As shown in FIGS. 6A-6F, very little to no insulin, glucagon, somatostatin or principal pancreatic transcription factors were produced in the absence of DAPT. It is beneficial to provide gamma secretase inhibition or Notch inhibition for a short interval after or during the retinoic acid differentiation step.

Example 7

Definitive Endoderm can be Differentiated Through a Sequential Series of Steps in Order to Achieve Endocrine Hormone Expression Human embryonic stem cells were differentiated for 16 days via either a 4-step or 5-step protocol to achieve islet hormone-expressing cells. The first step comprised 3 days differentiation in activin A (100 ng/mL) to robustly produce DE (D'Amour, K., et al., *Nature Biotechnology* 23, 1534-1541, (2005)). Step 2 comprised 3 days differentiation in RPMI with 2% FBS containing FGF10 (50 ng/mL) and KAAD-cyclopamine (0.2 μM). In the 4-step protocol, step 3 comprised 4 days differentiation in CMRL with B27 supplement (1:100) containing FGF10 (50 ng/mL), KAAD-cyclopamine (0.2 μM), retinoic acid (2 μM), and DAPT (1 μM). In the 5-step protocol, this 4 day period was broken into two separate treatments in the same base media. For 2 days the media contained FGF10 (50 ng/mL), KAAD-cyclopamine (0.2 μM), and retinoic acid (2 μM). During the subsequent 2 days, the FGF10 was removed and the gamma-secretase inhibitor DAPT (1 μM) was added. The last step of both protocols comprised 6 days differentiation in DMEM with B27 supplement (1:100) containing nicotinamide (10 mM), exendin 4 (40 ng/mL), hepatocyte growth factor (HGF 25 ng/mL), and insulin-like growth factor (IGF)-1 (50 ng/mL). Duplicate samples were taken from each plate at multiple time points and gene expression was analyzed by real-time quantitative PCR.

Figure 3A:
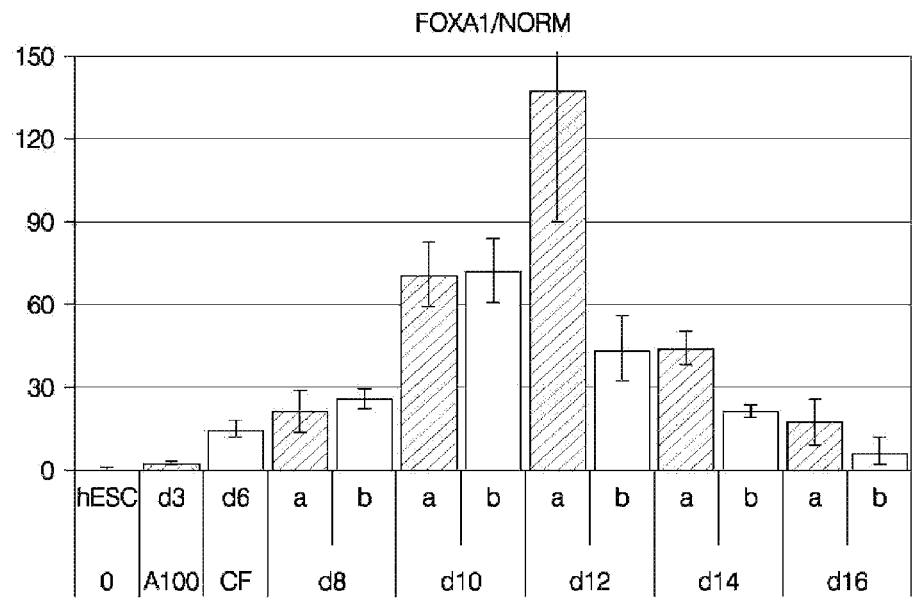
FIGS. 3A-3L are bar charts showing the relative expression of (FIG. 3A) FOXA1, (FIG. 3B) HNF1b, (FIG. 3C) HNF6, (FIG. 3D) PDX1, (FIG. 3E) NGN3, (FIG. 3F) PAX4, (FIG. 3G) NKX2.2, (FIG. 3H) NKX6.1, (FIG. 3I) ghrelin, (FIG. 3J) glucagon, (FIG. 3K) insulin and (FIG. 3L) IAPP from day 0 to day 16 of a differentiation protocol.
Figure 3B:
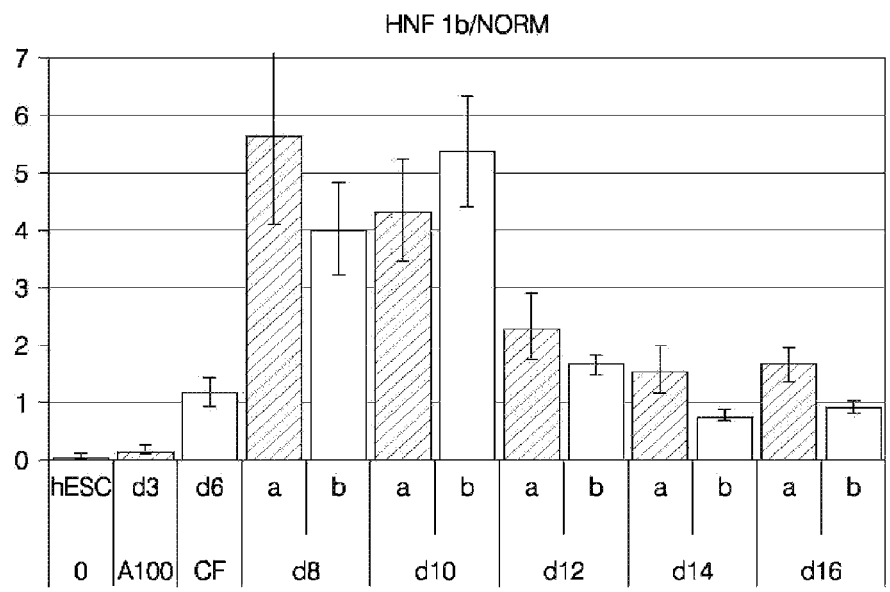
Figure 3C:
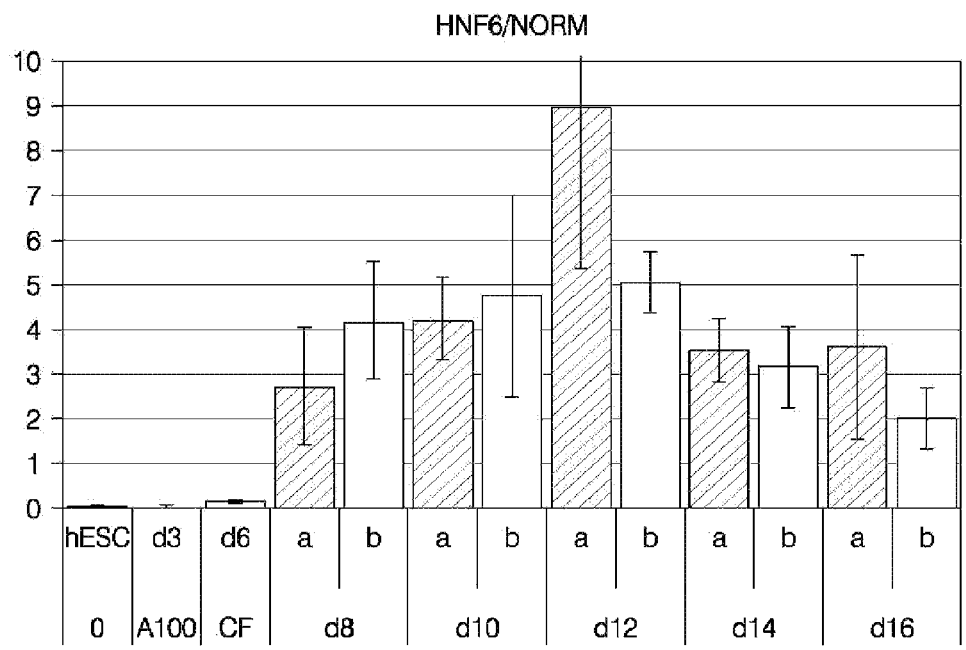
Figure 3D:
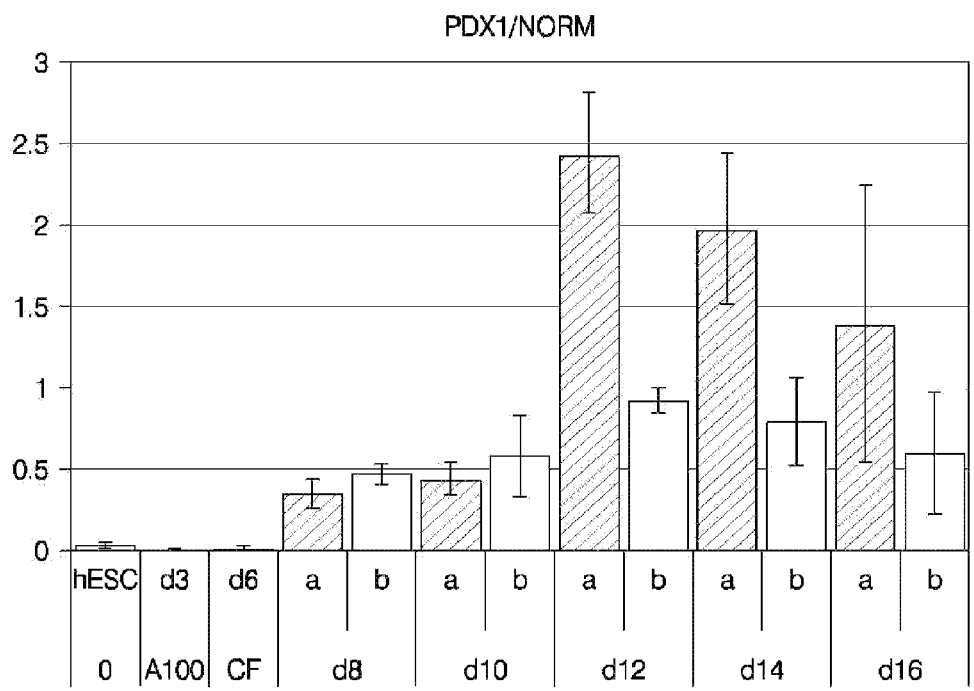
Figure 3E:
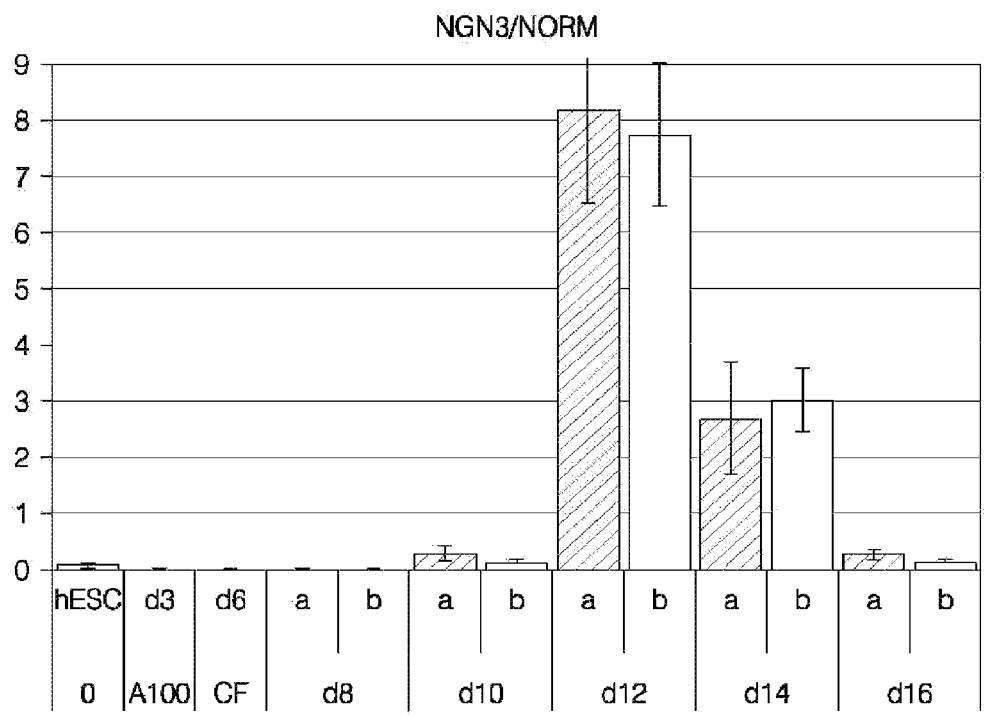
Figure 3F:
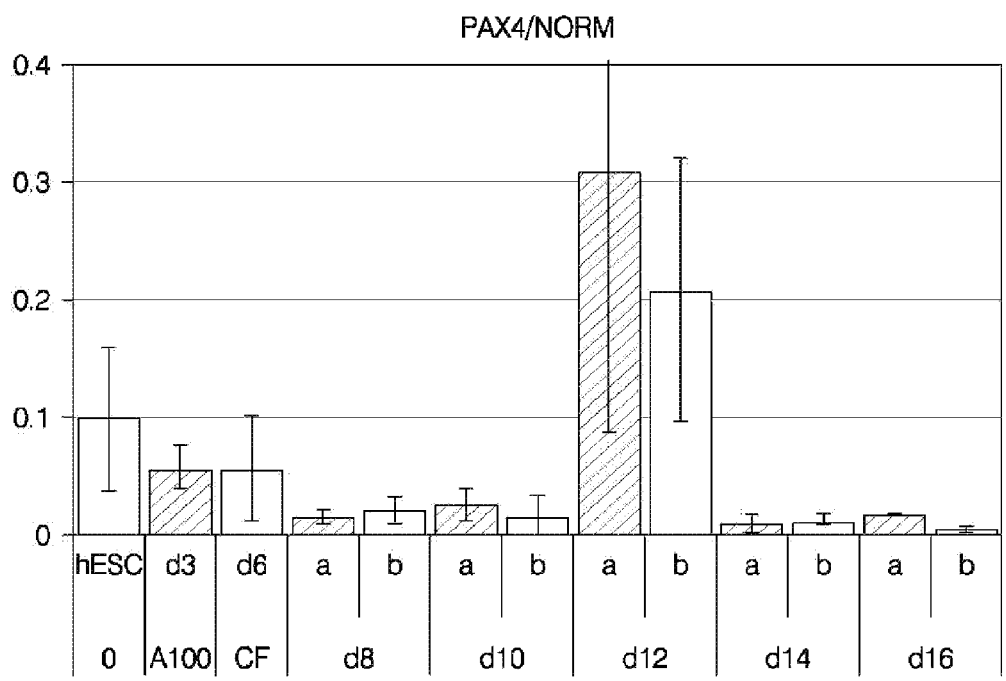
Figure 3G:
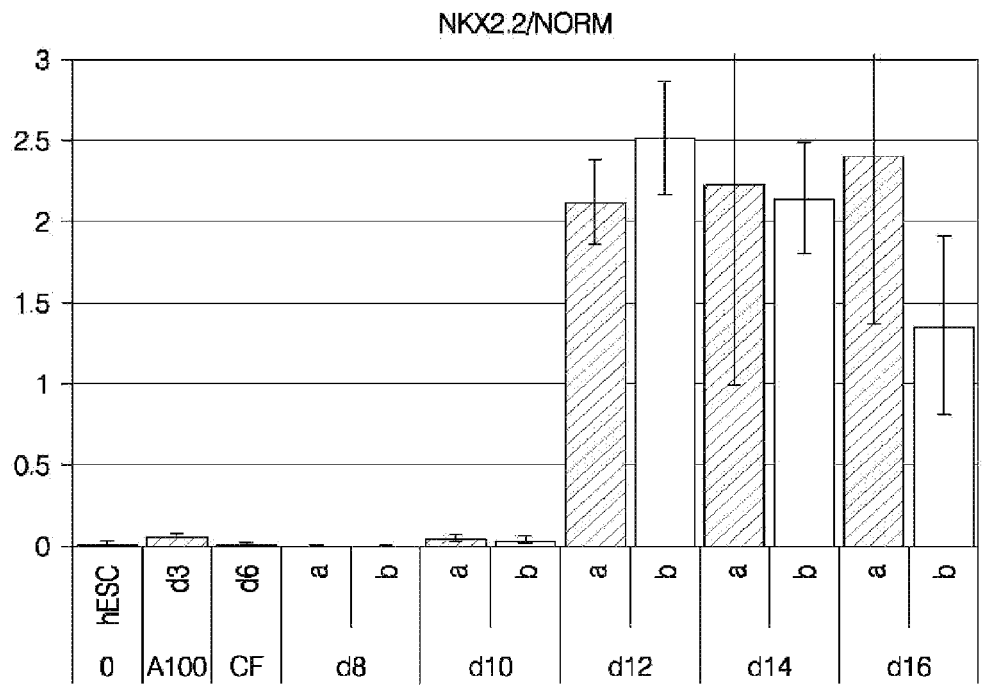
Figure 3H:
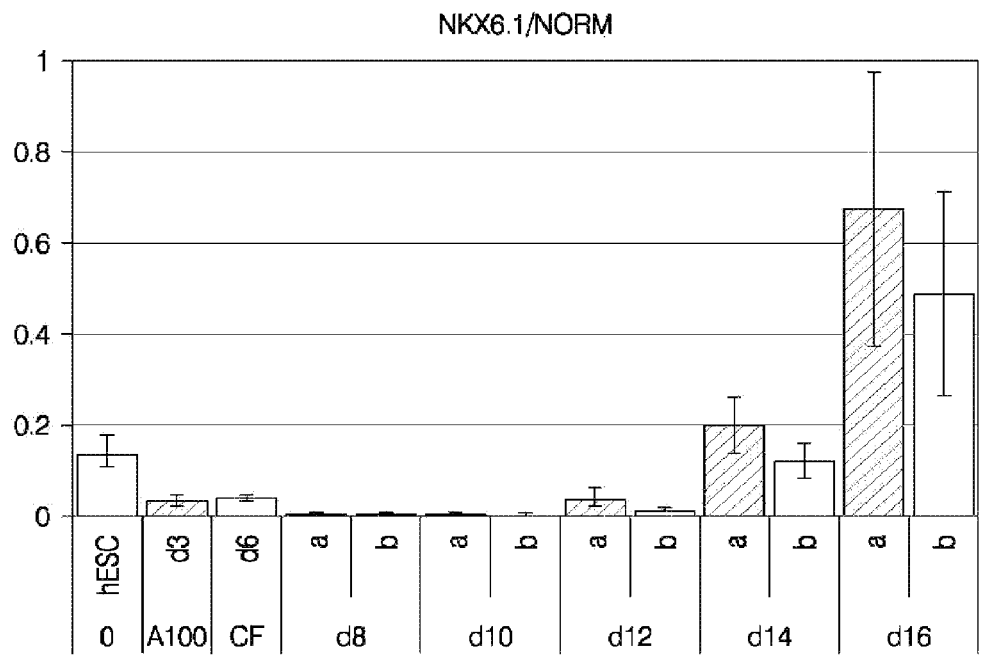
Figure 3I:
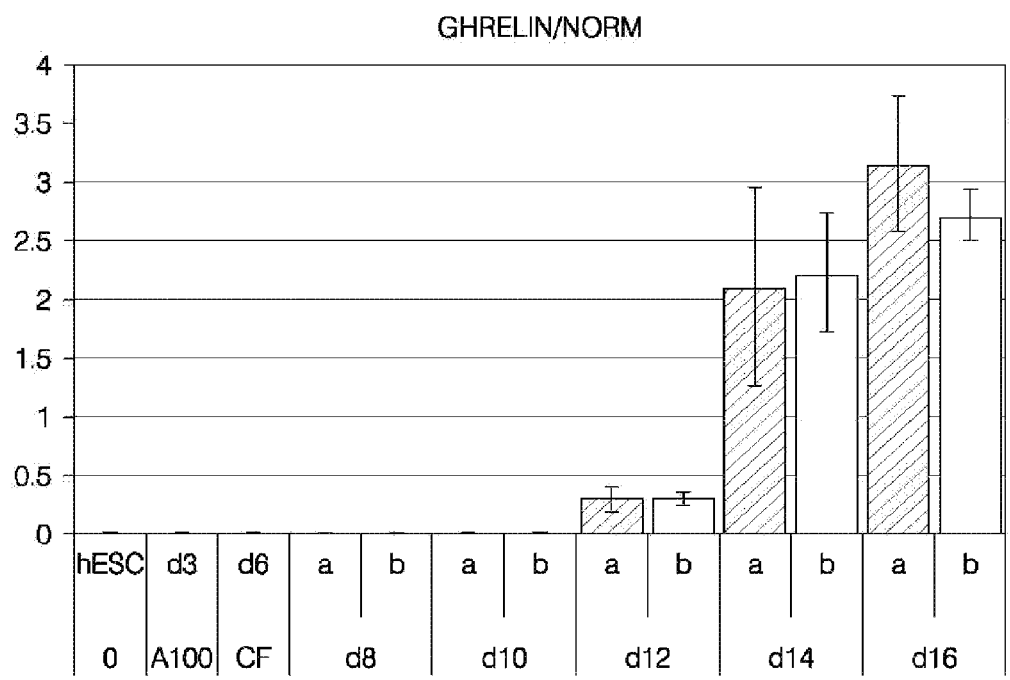
Figure 3J:
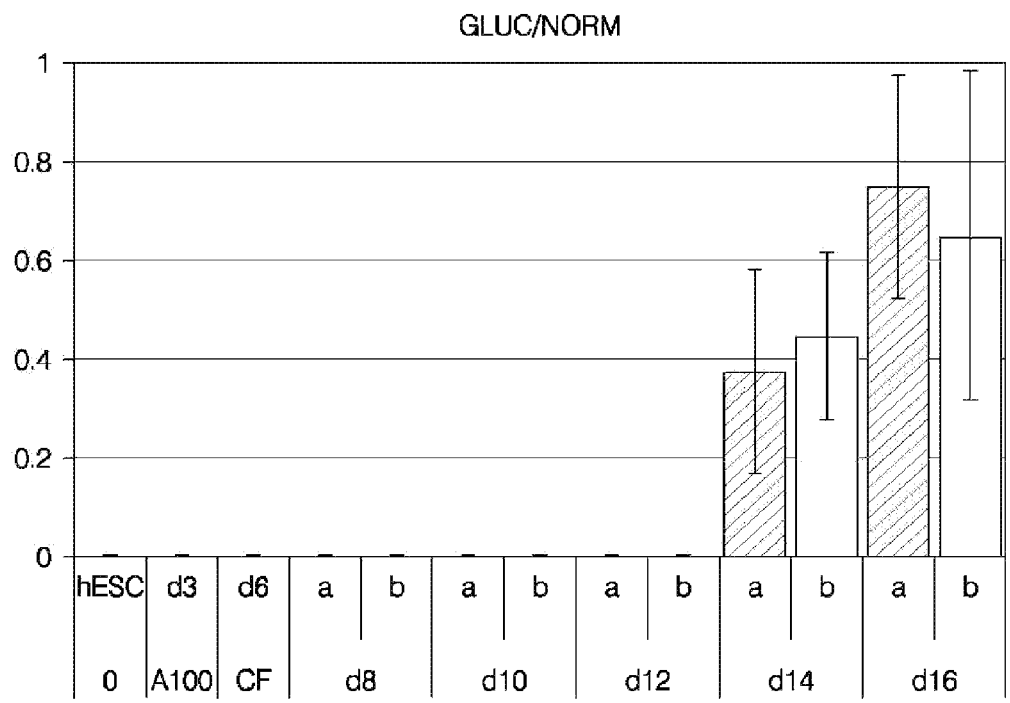
Figure 3K:
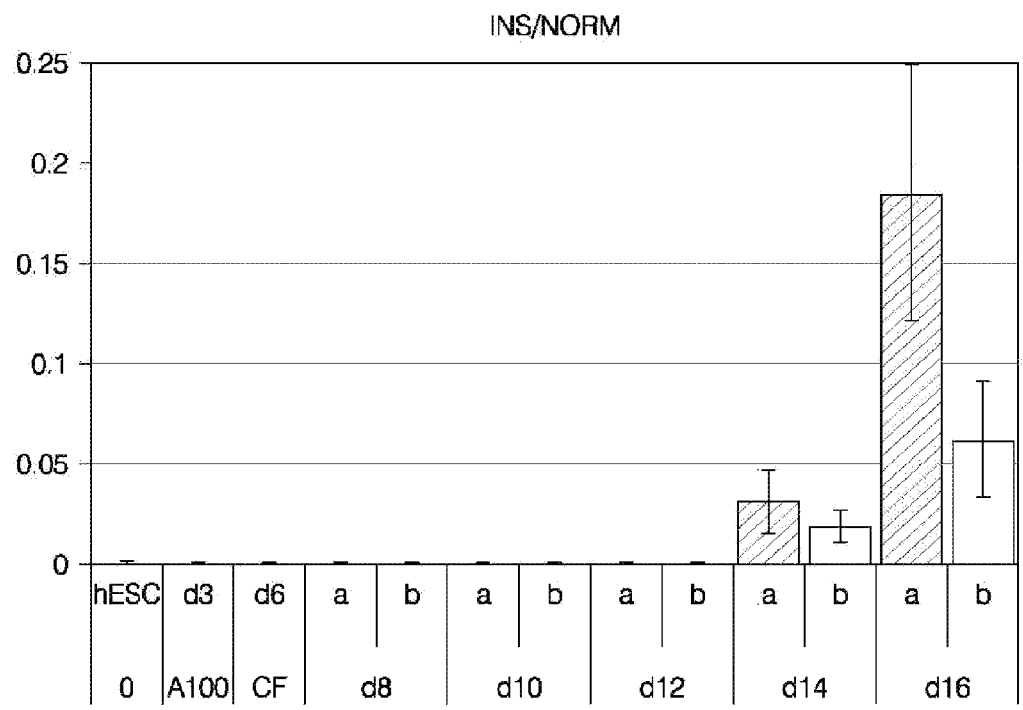
Figure 3L:
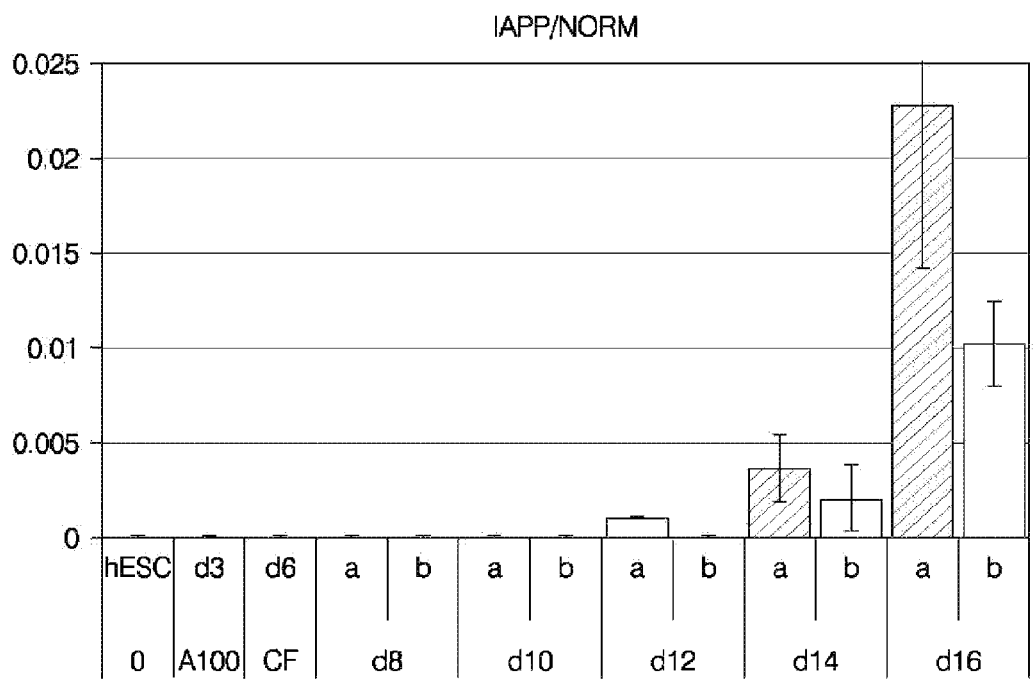

As depicted in FIG. 1, there was a temporal continuum of gene expression resulting in an invariant pattern of sequential transcription factor appearance leading to the production of pancreatic hormone producing cells. As shown in FIGS. 3A-3L, the temporal dynamic of gene expression indicated that the hESCs were transitioning through the same intermediates that occur during development of the pancreas in vivo. The first step of applying activin A in low FBS has been previously characterized to robustly produce DE (D'Amour, K., et al., *Nature Biotechnology* 23, 1534-1541, (2005)). Following the formation of DE, the expression of FOXA1 and HNF1b was significantly increased as a result of the treatment during step 2 (FIGS. 3A-3B). This step (2-4 days in length) likely represent a posteriorization of the endoderm and was further promoted by the removal of activin signaling. Furthermore, the addition of FGF10 (5-500 ng/ml) was beneficial together with the addition of KAAD-cyclopamine (0.1-2 µM, sonic hedgehog inhibitor) which further specified foregut cells into the pancreatic domain. The next step of differentiation involved the application of retinoic acid (RA) and resulted in robustly increased expression of HNF6 and PDX1 (FIGS. 3C-3D). To elicit further differentiation of PDX1-expressing pancreatic progenitors down the endocrine lineage it was beneficial to inhibit Notch signaling. This was achieved by the application of an inhibitor of gamma secretase. This class of drugs blocks the intramembrane cleavage of the Notch molecule, thereby precluding the release of the activated Notch intracellular domain. A 2-4 day application of the gamma secretase inhibitor DAPT, either in the terminal days of RA addition or immediately following RA withdrawal, resulted in a transient induction of NGN3 and PAX4 expression (FIGS. 3E-3F). These two genes were expressed in endocrine progenitor cells but not mature endocrine hormone producing cells. The expression of the transcription factors NKX2.2 and NKX6.1 as well as pancreatic hormones occurred subsequent to the induction of the endocrine precursor stage (FIGS. 3G-3L).

Example 8

Pancreatic Endocrine Hormone Expression

Human embryonic stem cells were differentiated in this experiment as described in Example 3 and Example 4 and then processed for immunocytochemistry to detect islet antigens. Cultures were fixed for 15 minutes at room temperature in 4% w/v paraformaldehyde in PBS, washed several times in TBS and blocked for 30 minutes in TBS++ (TBS containing 3% normal donkey serum (Jackson ImmunoResearch Laboratories) and 0.25% w/v Triton X-100 (Sigma)). Primary and secondary antibodies (Jackson ImmunoResearch Laboratories) were diluted in TBS++ and incubated for 24 hours at 4° C. or 2 hours at room temperature, respectively.

As shown in FIGS. 7A-7D, insulin, glucagon and somatostatin were expressed in individual cells within patches or isolated groups and also in cells expressing more than one hormone. As shown in FIGS. 8A-8D, following the sequential differentiation from hESC to pancreatic islet hormone-expressing cells, (ES/ME/DE/FE/PancE/PancEndocrine/Islet hormone), individual insulin, glucagon and somatostatin cells were produced. In addition, as shown in panel 8D, double and triple labeled hormone containing cells were also produced. During early fetal development of the human pancreas, there is initially an abundance of multiple hormone producing cells, which segregate with time to single hormone producing cells. In a typical cluster produced by the methods described herein, we observed both single, double and triple positive cells in a ratio of about 32% insulin, about 20% somatostatin, about 10% glucagon and about 38% double positive cells.

Example 9

C-Peptide/Insulin Release and Glucose Stimulated C-Peptide/Insulin Secretion (GSIS)

Human embryonic stem cells were differentiated as described in Example 3 first for the production of DE and ultimately on to islet hormone expression. Cells were fed fresh media each day and a sample of the media was collected from the plate after each successive day during step 4 of the differentiation. The levels of C-peptide in these media samples were measured by ELISA (see FIGS. 9A-9B).

Human embryonic stem cells were differentiated as described in Example 4. On day 22 the media was changed to CMRL with 10% FBS containing exendin 4 (50 ng/mL) and exchanged every other day. On day 26, a glucose stimulation assay was performed as follows. The cells were placed into media containing 1.6 mM glucose (g50) for 2 hours after which a media sample was collected. The media was replaced with fresh media containing 16 mM glucose (g400) and allowed to incubate 2 hours more after which media samples were collected. Duplicate samples were also taken from each plate and gene expression was analyzed by real-time quantitative PCR (see FIGS. 10A-10B).

As proof of function pancreatic beta cells must synthesize, store and release mature insulin. Insulin is initially synthesized as proinsulin after which it is folded via disulfide bonding. Within the golgi bodies the folded proinsulin molecule is specifically cleaved by prohormone convertase releasing the C "connecting"-peptide from the disulfide linked A and B chains. The mature insulin is stored in crystalline form (complexed with Zn) together with the C-peptide and released in a 1:1 molar ratio. Exposure to elevated glucose levels results in $Ca^{2+}$-mediated insulin and C-peptide release via granule fusion to the plasma membrane.

Figure 9A:
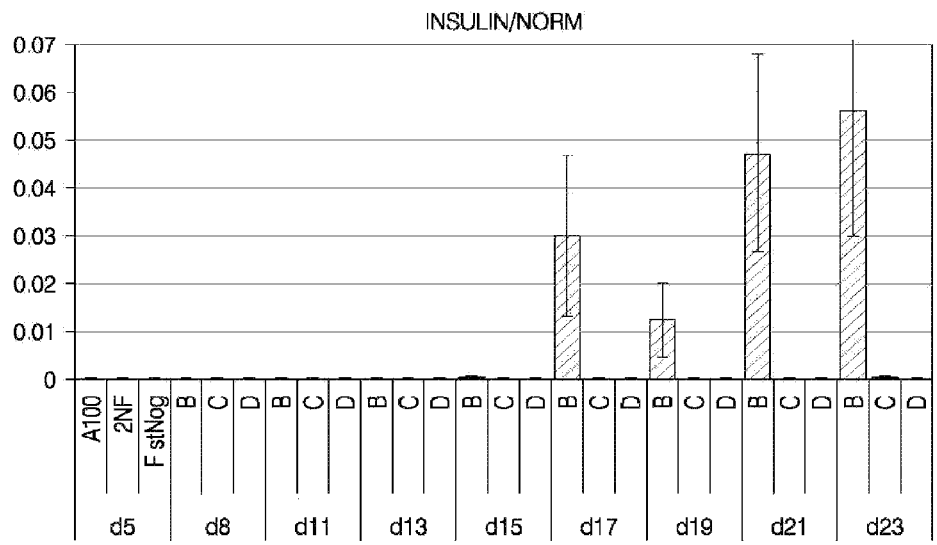
FIGS. 9A-9B are bar charts showing that insulin mRNA detection, panel FIG. 9A, correlates with the ability to measure C-peptide released into the culture media, panel FIG. 9B. Abbreviations are as follows: A100—100 ng/ml activin A; 2NF—2% fetal bovine serum (FBS) and no factors; Fstnog—50 ng/ml follistatin and 100 ng/ml noggin; "B"—cultures receiving A100 on days 1-5, "C"—cultures receiving 2% FBS and no factors on days 1-5; and "D"—cultures receiving 50 ng/ml follistatin and 100 ng/ml noggin on days 1-5.
Figure 9B:
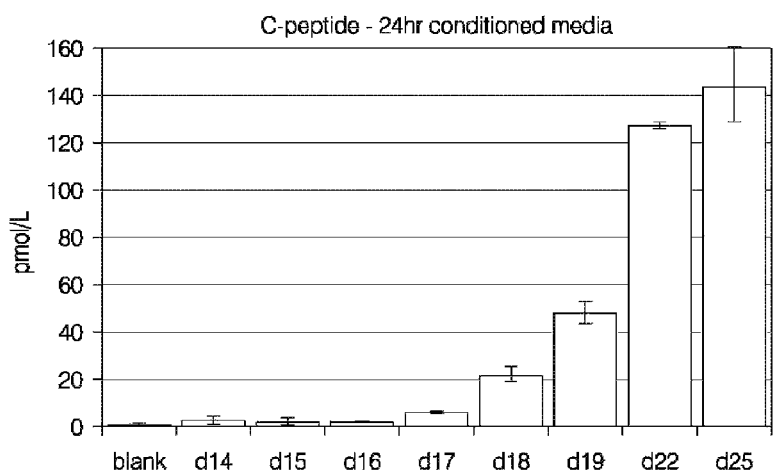
Figure 10A:
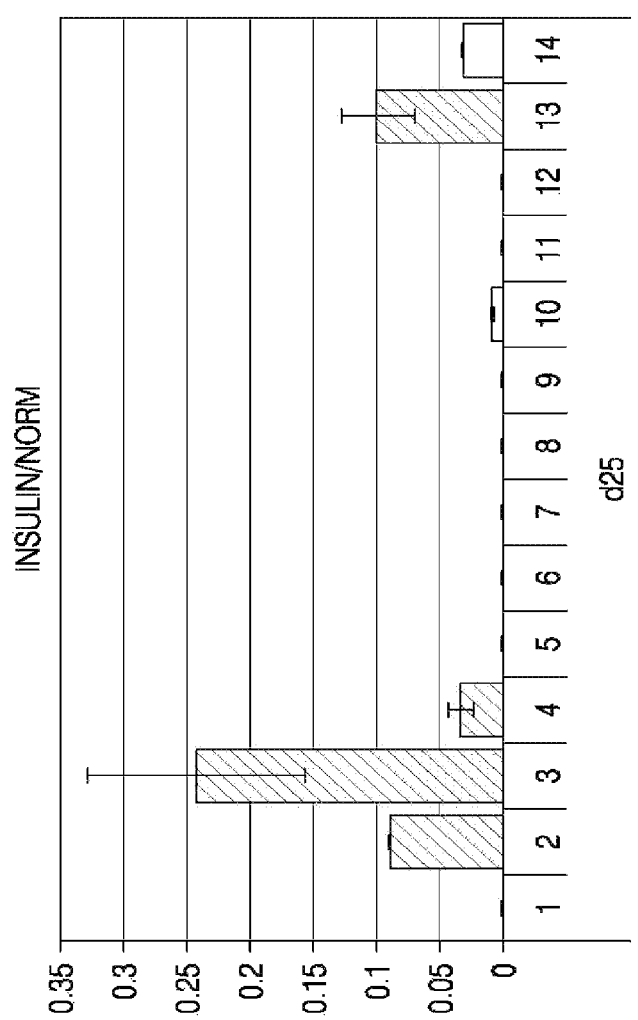
FIGS. 10A-10B are bar charts showing that conditions which display robust insulin mRNA detection, panel FIG. 10A also display glucose stimulated C-peptide secretion, panel FIG. 10B. Abbreviations are as follows: g50—1.6 mM glucose; g400-16 mM glucose.
Figure 10B:
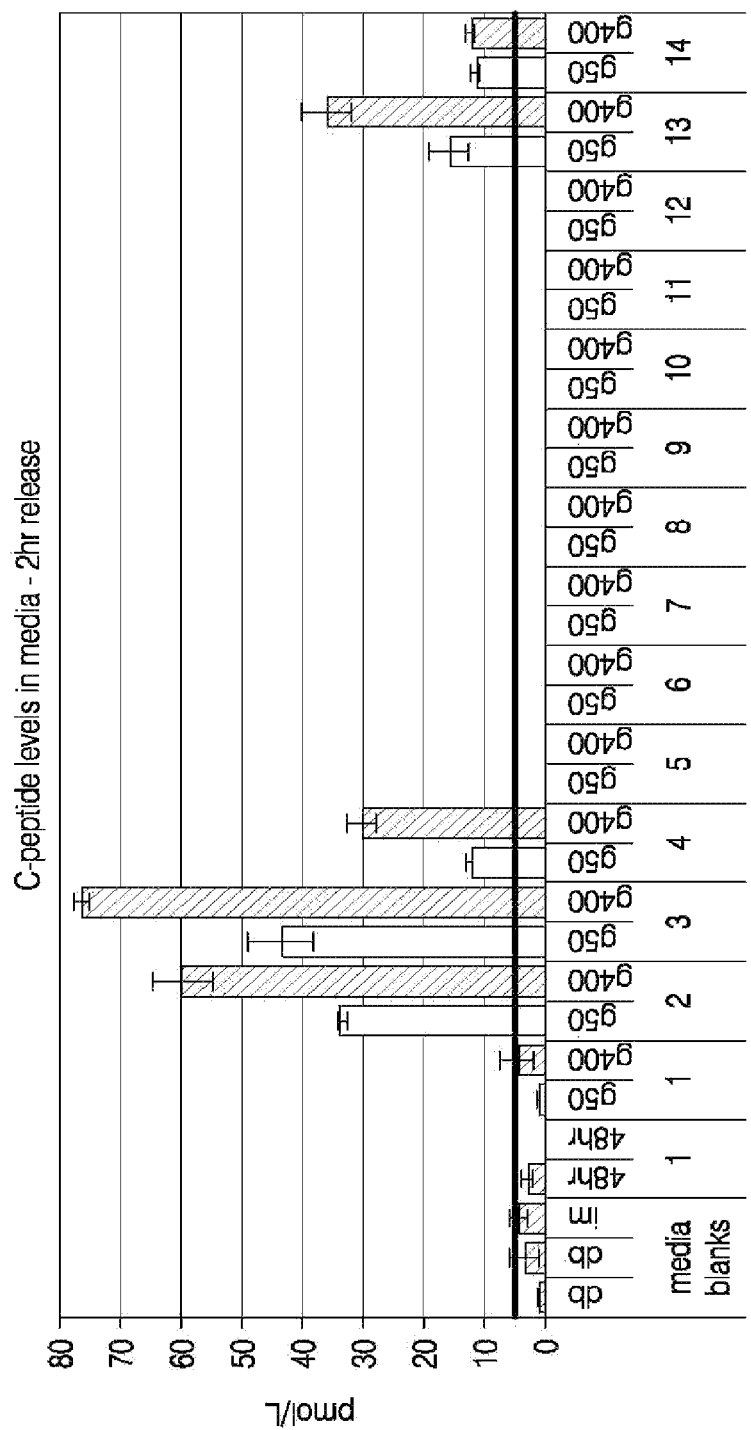
Figure 11A:
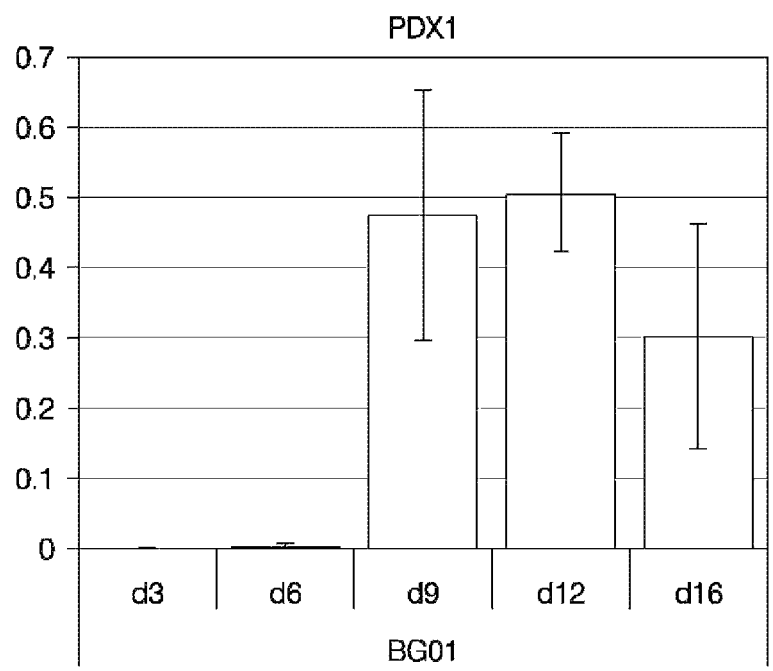
FIGS. 11A-11F are bar charts showing that hESC lines BG01 and BG02 are capable of differentiation to pancreatic islet hormone-expressing cells. Panels A and B show the upregulation of PDX1 mRNA for BG01 (FIG. 11A) and BG02 (FIG. 11B); panels
Figure 11B:
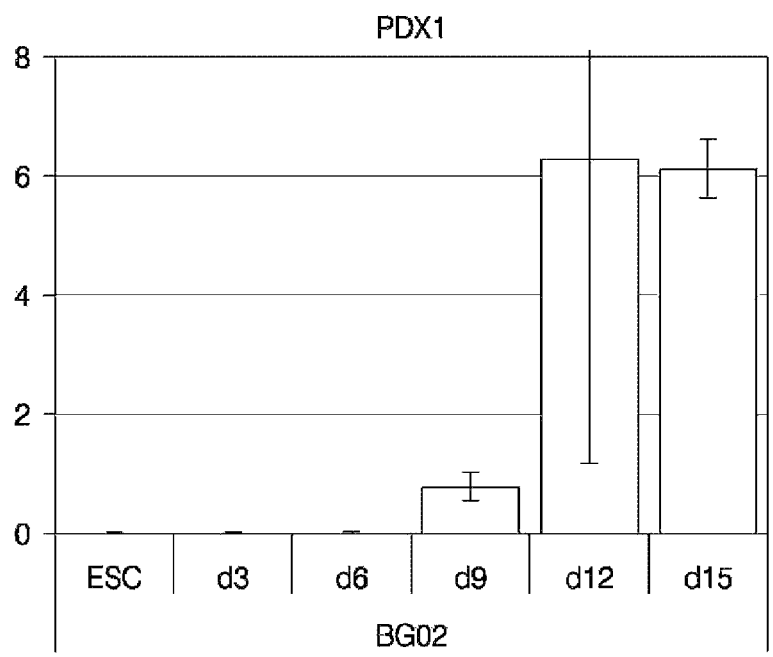
Figure 11C:
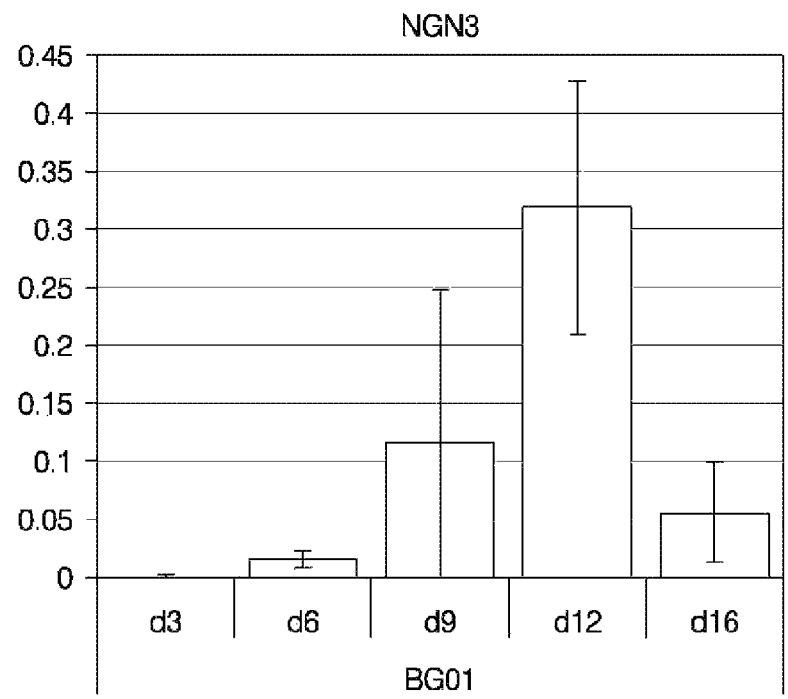
Figure 11D:
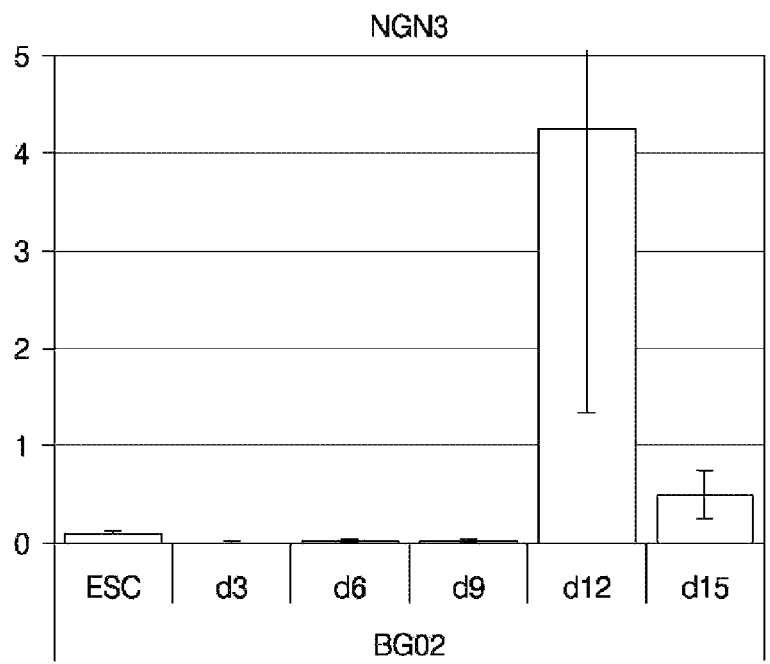
Figure 11E:
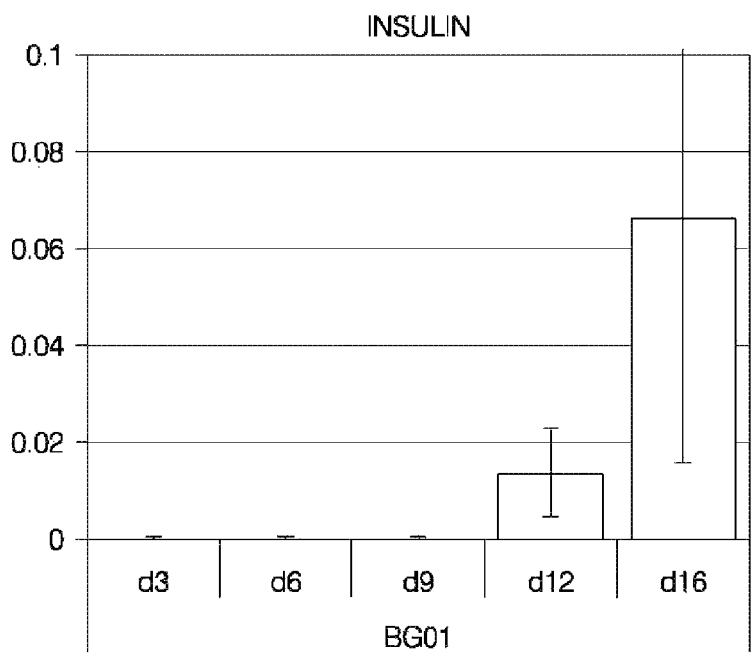
Figure 11F:
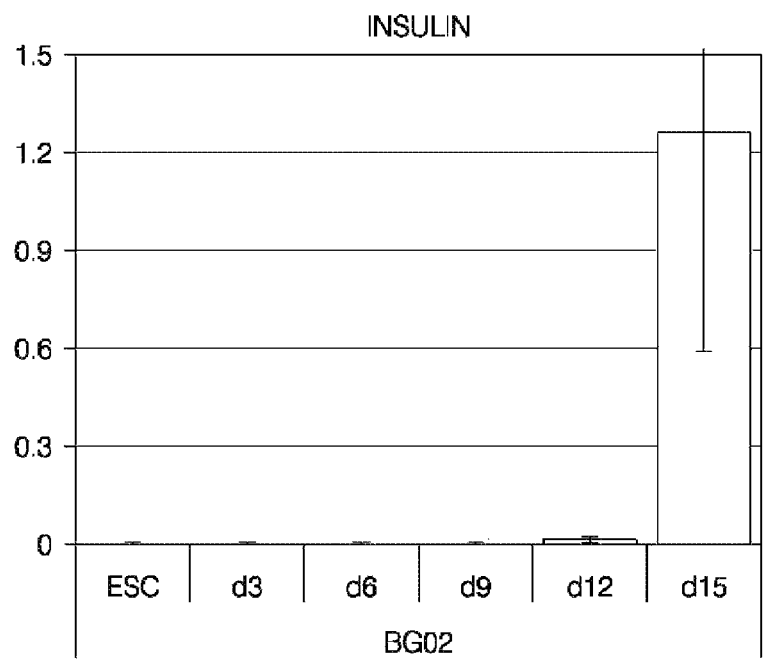
Figure 12A:
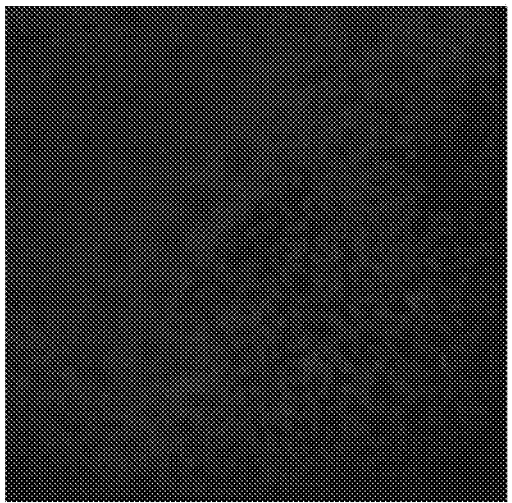
FIGS. 12A-12D are photomicrographs showing immunoreactivity of hESC-derived cells treated to differentiate to early pancreatic islet hormone-expressing cells for NCAM (FIG. 12C) and NKX2.2 (FIG. 12B). Total cell population is stained with DAPI (FIG. 12A). These micrographs indicate that NKX2.2-positive cells are also NCAM positive (FIG. 12D).
Figure 12B:
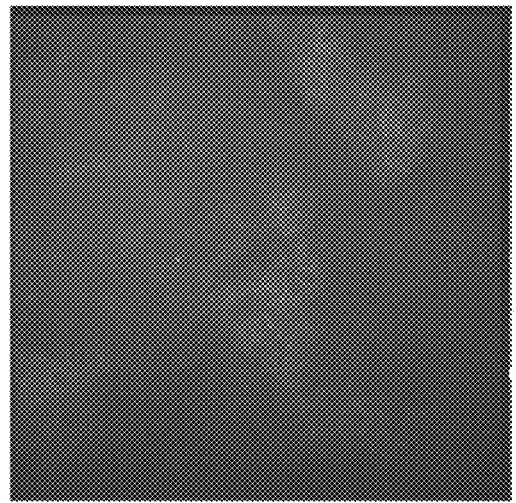
Figure 12C:
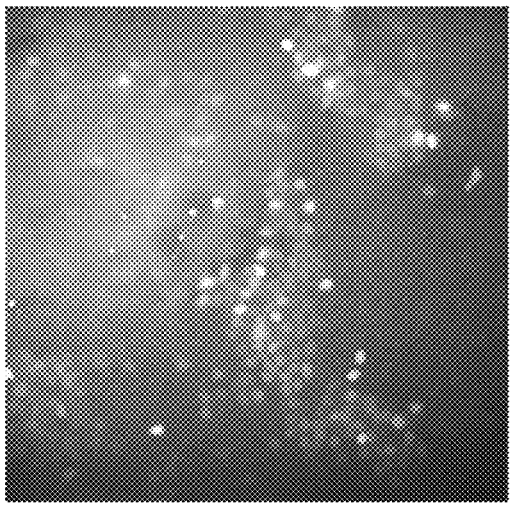
Figure 12D:
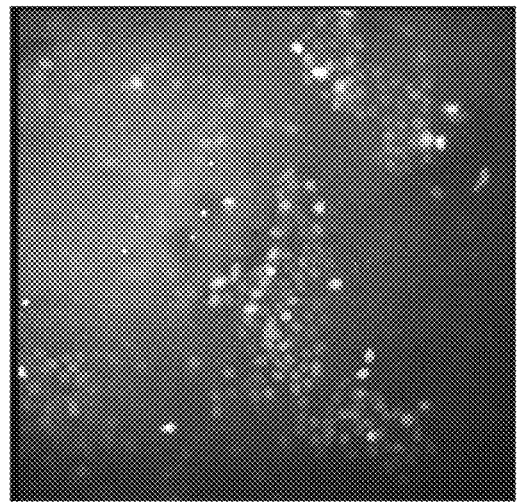
Figure 13A:
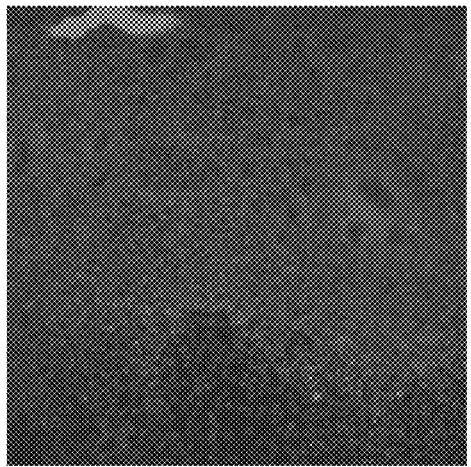
FIGS. 13A-13D are photomicrographs showing immunoreactivity of hESC-derived cells treated to differentiate to immature pancreatic islet hormone-expressing cells for NCAM (FIG. 13C) and insulin (FIG. 13B). Total cell population is stained with DAPI (FIG. 13A). These micrographs indicate that insulin-positive cells are also NCAM positive (FIG. 13D).
Figure 13B:
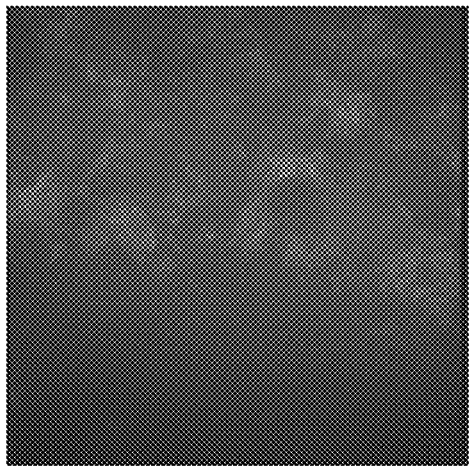
Figure 13C:
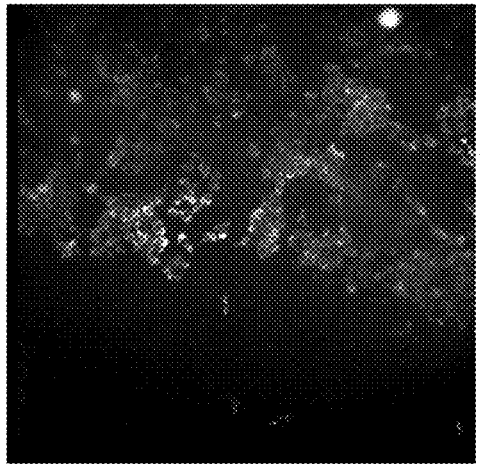
Figure 13D:
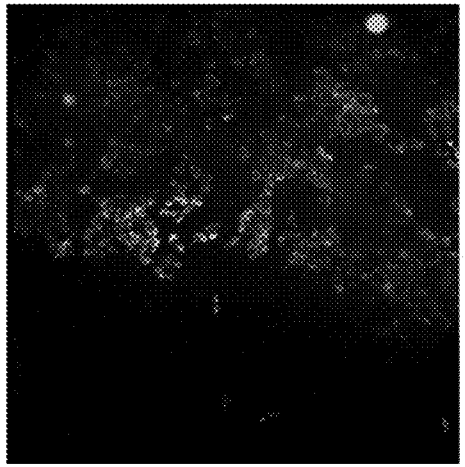

As shown in FIGS. 9A-9B, 1 day after insulin message was robustly expressed by QPCR, C-peptide/insulin could be measured by ELISA. The levels of C-peptide increased with time in culture and plateaued just after insulin mRNA plateaued. In FIGS. 10A-10B, 14 different conditions were evaluated for insulin production. Conditions 2-4 and 13 which had measurable insulin gene expression by QPCR also had (glucose stimulated insulin secretion) GSIS. These data strongly support the contention that bona fide GSIS is occurring in these cells and that these hESC-derived pancreatic insulin cells are functional.

Example 10

Differentiation of Additional Human Embryonic Stem Cell Lines to Pancreatic Islet Hormone-Expressing Cells Two additional human embryonic stem cell lines were differentiated for 15 or 16 days via a 5-step protocol to achieve pancreatic islet hormone-expressing cells. The first step comprised 3 days differentiation with activin A (100 ng/ml) to robustly produce DE (D'Amour, K., et al., Nature Biotechnology 23, 1534-1541, (2005)). Step 2 comprised 3 days differentiation in RPMI with 2% FBS containing FGF10 (50 ng/mL) and KAAD-cyclopamine (0.5 µM). Step 3 comprised 3 days differentiation in CMRL with B27 supplement (1:100) containing FGF10 (50 ng/mL), KAAD-cyclopamine (0.5 µM), and retinoic acid (2 µM). Step 4 comprised 3 days differentiation in DMEM (BG02) or CMRL (BG01) with B27 supplement (1:100) containing DAPT (1 uM) and exendin 4 (40 ng/mL). The fifth step comprised 4 days (BG02) or 5 days (BG01) differentiation in CMRL (BG02) or DMEM (BG01) with B27 supplement (1:100) containing exendin 4 (40 ng/mL). Duplicate samples were taken from each plate at multiple time points and gene expression was analyzed by real-time quantitative PCR.

As shown in FIGS. 11A-11F the differentiation protocol produced very similar transitions through cellular intermediates en route to production of insulin-expressing islet cells. PDX1-positive pancreatic endoderm was first induced by application of retinoic acid during stage 3 (day 9). Endocrine precursors expressing NGN3 were produced during step 4 as a result of inhibiting Notch signaling peaking at day 12. Subsequently, the NGN3 levels dropped as these endocrine precursors further differentiated to hormone-expressing phenotypes as indicated by the increases in insulin expression at days 12-16. This and similar differentiation protocols have also been applied to hESC lines BG03, Cyt-25, and Cyt-49 ESC lines. While there were quantitative differences between cell lines for the effectiveness of a given differentiation protocol, all cell lines qualitatively exhibited the same cellular transitions and ultimately yielded hormone-expressing cells.

Example 11

Comparison of Differentiation Conditions

We have identified a core set of differentiation conditions that may be minimally sufficient to produce pancreatic islet hormone-expressing cells from hESCs. In the simplest format, the differentiation method comprised applying a TGFβ growth factor to hESCs to induce the differentiation of definitive endoderm (D'Amour, K., et al., Nature Biotechnology 23, 1534-1541, (2005) followed by the activation of retinoid signaling in the endoderm cells. In building on this core set of conditions, various other growth factors were added exogenously that increased the effectiveness of the differentiation at one or more steps between the hESC and the insulin-expressing cells. Table 2 describes a core set of conditions (treatment #1) as well as various modifications that resulted in enhanced production of hormone-expressing islet cells.

Human embryonic stem cell lines were differentiated for 17 days via a 5-step protocol to produce pancreatic islet hormone-expressing cells. The first step comprised 3 days differentiation with activin A (100 ng/ml) to robustly produce DE (D'Amour, K., et al., Nature Biotechnology 23, 1534-1541, (2005)). Step 2 comprised 3 days differentiation in RPMI with 2% FBS containing one of the following: (a) 100 ng/mL activin A (treatment i), (b) no exogenous growth factors (treatment ii), or (c) 50 ng/mL FGF10 and 0.5 µM KAAD-cyclopamine (treatments iii and iv). Step 3 comprised 3 days differentiation in CMRL with B27 supplement (1:100) containing either (a) 2 µM retinoic acid (treatments i-iii) or (b) 2 µM retinoic acid and 0.5 µM KAAD-cyclopamine (treatment iv). Steps 4 and 5 were the same for all conditions (treatments i-iv). Step 4 comprised 2 days differentiation in CMRL with B27 supplement (1:100) containing 1 µM DAPT and 40 ng/mL exendin 4. Step 5 comprised 5 days differentiation in CMRL with B27 supplement (1:100) containing 40 ng/mL exendin 4. Duplicate samples were taken from each plate at multiple time points and gene expression was analyzed by real-time quantitative PCR.

The following table shows the relative expression levels of NGN3 at day 12 as well as insulin and glucagon at day 17 when normalized to the most minimal condition in this experiment (treatment i).

TABLE 2

| | Day 12 NGN3 | Day 17 INSULIN | Day 17 GLUCAGON |
|---|---|---|---|
| Treatment i | 1.00 | 1.00 | 1.00 |
| Treatment ii | 1.45 | 2.03 | 0.56 |
| Treatment ii | 256 | 166 | 59 |
| Treatment iv | 397 | 342 | 121 |

The removal of TGFB signaling during step 2 (treatment ii) resulted in modest improvements in NGN3 and insulin expression and a slight decrease in glucagon expression. The addition of FGF10 and KAAD-cyclopamine in the absence of activin A during step 2 resulted in significant increases in the performance of endocrine differentiation. The further modification of maintaining KAAD-cyclopamine in the presence of retinoic acid during step 3 further increased the performance 2-fold relative to treatment iii where retinoic acid was used alone.

Human embryonic stem cell lines were also differentiated for 15 days via a 6-step protocol to achieve islet hormone-expressing cells. The first step comprised 3 days differentiation with either; i) activin A (100 ng/ml) or ii) activin A (100 ng/ml) and Wnt3a (25 ng/mL) to robustly produce DE (D'Amour, K., et al., Nature Biotechnology 23, 1534-1541, (2005)). Step 2 comprised 3 days differentiation in RPMI with 2% FBS containing FGF10 (50 ng/mL) and KAAD-cyclopamine (0.5 µM). Step 3 comprised 2 days differentiation in CMRL with B27 supplement (1:100) containing FGF10 (50 ng/mL), KAAD-cyclopamine (0.5 µM) and retinoic acid (2 µM). Step 4 comprised 2 days differentiation in CMRL with B27 supplement (1:100) containing retinoic acid (2 µM) and DAPT (1 µM). Step 5 comprised 2 days differentiation in CMRL with B27 supplement (1:100) containing DAPT (1 µM) and exendin 4 (40 ng/mL). Step 6 comprised 3 days differentiation in CMRL with B27 supplement (1:100) containing exendin 4 (40 ng/mL). Duplicate samples were taken from each plate at multiple time points and gene expression was analyzed by real-time quantitative PCR.

Table 3 shows the relative expression levels of PDX1 at days 8 and 12, NGN3 at day 12 as well as insulin and glucagon at day 15 when normalized to the condition without added Wnt3a.

TABLE 3

| | Day 8 PDX1 | Day 12 PDX1 | Day 12 NGN3 | Day 15 INSULIN | Day 15 GLUCAGON |
|---|---|---|---|---|---|
| Treatment i | 1.00 | 1.00 | 1.00 | 1.00 | 1.00 |
| Treatment ii | 5.56 | 8.91 | 11.09 | 15.02 | 32.66 |

These data demonstrate that addition of Wnt3a during the first step resulted in marked enhancement of endocrine cell differentiation.

Example 12

Production and Characterization of Immature Pancreatic Hormone-Expressing Cells Derived from Human Embryonic Stem Cells Human embryonic stem cells (hESCs) were differentiated for 25 days via a 5-step protocol to achieve immature pancreatic islet hormone-expressing cells. The first step comprised 1 day differentiation in Wnt3a (25 ng/ml) Activin A (100 ng/ml) in serum-free media, followed by 2 days in activin A (100 ng/ml) in media supplemented with 0.2% FBS to robustly produce DE (D'Amour, K., et al., *Nature Biotechnology* 23, 1534-1541, (2005)). Step 2 comprised 3 days differentiation in DMEM with 2% FBS containing FGF10 (50 ng/ml) and KAAD-cyclopamine (0.25 µM). Step 3 comprised 2 days differentiation in DMEM with B27 supplement (1:100), with exogenously added KAAD-cyclopamine (0.2 µM), FGF10 (50 ng/ml), and retinoic acid (2 µM). The fourth step comprised 6 days treatment with DMEM with B27 supplement (1:100) with exogenously added KAAD-cyclopamine (0.2 µM) and FGF10 (50 ng/ml). Step 5 comprised 11 days treatment with DMEM with B27 supplement (1:100) containing exendin 4 (50 ng/ml) and glucagon-like peptide 1, amino acids 1-37 (50 ng/ml).

Figure 16A:
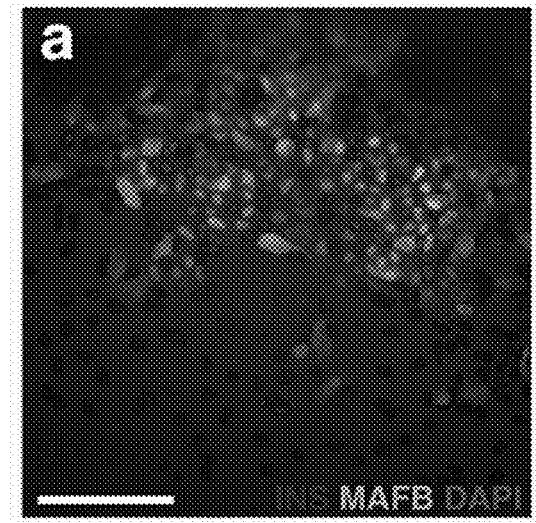
FIGS. 16A-16D are photomicrographs showing immunoreactivity of hESC-derived cells treated to differentiate to endocrine precursor cells for MAFB and INS.
Figure 16B:
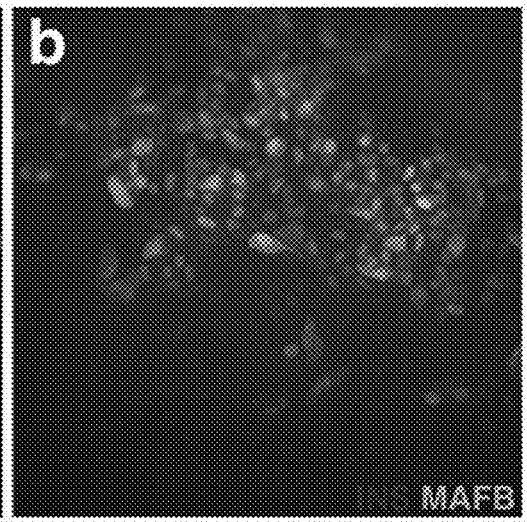

For the experimental data shown in FIG. 16A and FIG. 16B, the hESC cells were differentiated as described in Example 16.

To confirm the presence of human immature pancreatic islet hormone-expressing cells in the 23-day-old cultures, the cells were analyzed by immunocytochemistry for the expression of NCAM, NKX2.2, INS, and PAX6. Briefly, cultures were fixed for 15 minutes at 24° C. in 4% w/v paraformaldehyde in PBS, washed several times in PBS and blocked for 30 minutes in PBST (TBS/0.1% w/v Triton X-100 (Sigma)) containing 5% normal donkey serum (NDS, Jackson ImmunoResearch Laboratories). The cells were then incubated with primary antibodies to NCAM, NKX2.2, INS and/or PAX6. The primary antibodies were diluted in PBST/5% NDS. The cells were incubated with the primary antibodies were for 24 hours at 4° C. or 2 hours at 24° C. The cells were then washed and incubated with secondary antibodies for 1 hour at 24° C. Cy3 and Cy5 conjugated donkey antibodies against mouse rabbit, and guinea pig, as appropriate, were used at 1:500 (Jackson ImmunoResearch Laboratories). Alexa-488 and Alexa-555 conjugated donkey antibodies against mouse, rat, rabbit, guinea pig, and goat (Molecular Probes) were used at 1:500.

As shown in FIGS. 12A-12D, NCAM and NKX2.2 were co-expressed in hESC-derived immature pancreatic islet hormone-expressing cells. These data suggest that the timing of NCAM correlates with the "delamination" of nascent endocrine cells from the epithelium.

FIGS. 13A-13D and FIGS. 14A-14F show that NCAM, PAX6 and INS were co-expressed in hESC-derived cells treated to differentiate to immature pancreatic islet hormone-expressing cells. These data demonstrate that NCAM is a good marker for hESC-derived immature pancreatic islet hormone-expressing cells.

Figure 16C:
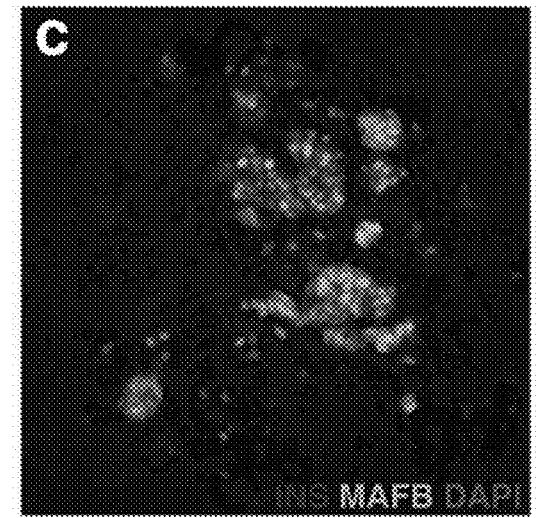
Figure 16D:
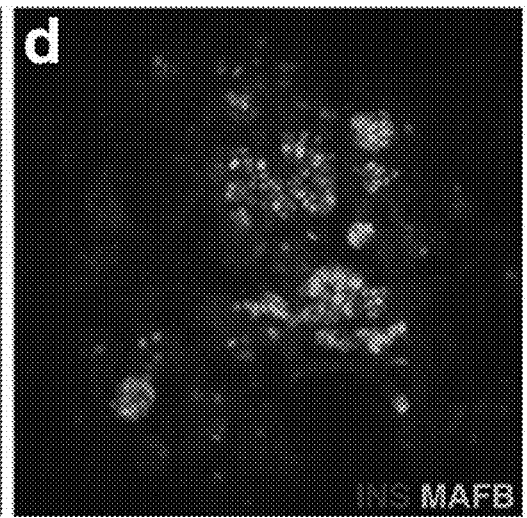

FIGS. 16A-16B demonstrate that MAFB was co-expressed with insulin expressing cells in hESC-derived immature pancreatic islet hormone-expressing cells. The cells shown in FIGS. 16A-16B were differentiated using the differentiation protocol described in Example 15, below, and processed for immunocytochemistry as above. FIGS. 16C-16D show the same pattern of MAFB and INS expression in cells derived from 13.5 week old human fetal pancreas.

Example 13

Expression of Synaptophysin by Pancreatic Hormone-Expressing Cells Derived from Human Embryonic Stem Cells Synaptophysin (SYP) is a known marker for endocrine cells from in vivo sources. (Protela-Gomez et al, 2004). To confirm the production of endocrine cells from hESCs, hESCs were differentiated using the following protocol and analyzed by immunocytochemistry for expression of SYP and NKX2.2.

Human embryonic stem cells were differentiated for 18 days via a 6-step protocol to achieve pancreatic islet hormone-expressing cells. The first step comprised 1 day differentiation in Wnt3a (25 ng/ml) Activin A (100 ng/ml) in serum-free media, followed by 1 day in activin A (100 ng/ml) alone, in media supplemented with 0.2% FBS and 3 days in Activin A (100 ng/ml) in media supplemented with 2.0% FBS to robustly produce DE (D'Amour, K., et al., *Nature Biotechnology* 23, 1534-1541, (2005)). Step 2 comprised 3 days differentiation in DMEM with 2% FBS containing FGF10 (50 ng/ml) and KAAD-cyclopamine (0.25 µM). Step 3 comprised 1 day differentiation in DMEM with B27 supplement (1:100) and retinoic acid (1 µM). The fourth step comprised 6 days treatment with DMEM with B27 supplement (1:100) with exogenously added KAAD-cyclopamine (0.2 µM) and FGF10 (50 ng/ml) and retinoic acid (1 µM). Step 5 comprised 1 day treatment with DMEM with B27 supplement (1:100) containing FGF10 (50 ng/ml) and KAAD-cyclopamine (0.25 µM). Step 6 comprised 4 days treatment with DMEM with B27 supplement (1:100) and exendin 4 (50 ng/ml).

Figure 15A:
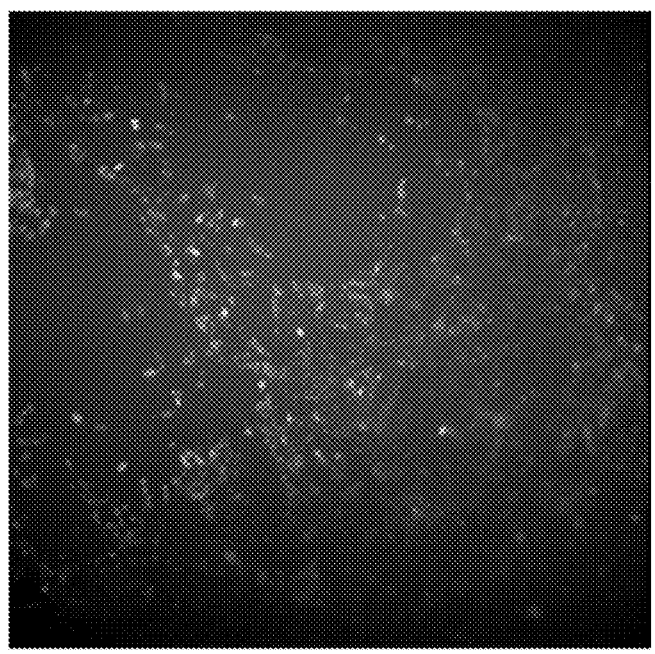
FIGS. 15A-15B are photomicrographs showing immunoreactivity of hESC-derived cells treated to differentiate to immature pancreatic islet hormone-expressing cells for NKX2.2 and synaptophysin. These micrographs indicate that synaptophysin-positive cells are also NKX2.2 positive (FIG. 15A and FIG. 15B).
Figure 15B:
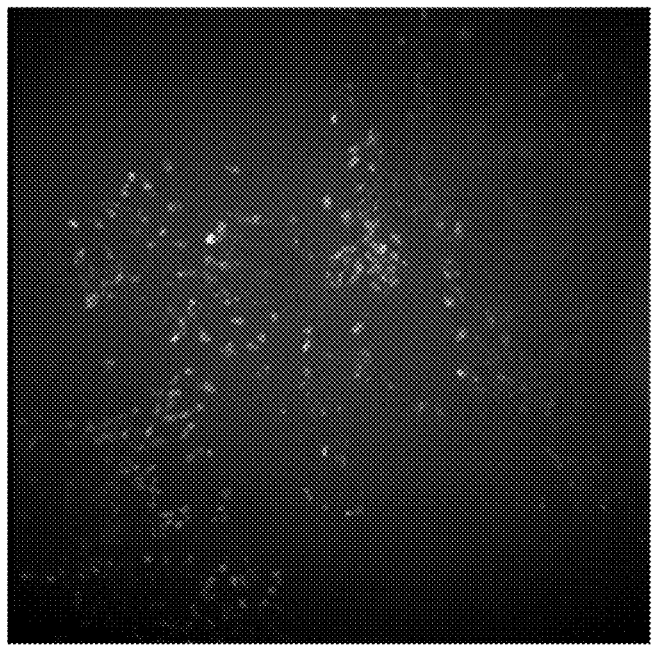

The cells were fixed and processed as described above, using anti-SYP, anti-NKX2.2 primary antibodies. FIGS. 15A-15B show the co-expression of SYP and NKX2.2, confirming the production of immature pancreatic islet hormone-expressing cells.

Example 14

Analysis of NCAM-Labeled hESC-Derived Immature Pancreatic Hormone-Expressing Cells Using Flow Cytometry Human embryonic stem cells (hESCs) were differentiated for 18 days via a 5-step protocol to achieve immature pancreatic islet hormone-expressing cells. The first step comprised 1 day differentiation in Wnt3a (25 ng/ml) activin A (100 ng/ml) in serum-free media, followed by 1 day in activin A (100 ng/ml) in media supplemented with 0.2% FBS and 1 day in activin A (100 ng/ml) in media supplemented with 2.0% FBS to robustly produce DE (D'Amour, K., et al., *Nature Biotechnology* 23, 1534-1541, (2005)). Step 2 comprised 3 days differentiation in DMEM with 2% FBS containing FGF10 (50 ng/ml) and KAAD-cyclopamine (0.25 µM). Step 3 comprised 4 days differentiation in DMEM with B27 supplement (1:100), with exogenously added KAAD-cyclopamine (0.2 µM), and retinoic acid (2 µM). The fourth step comprised 3 days treatment with DMEM with B27 supplement (1:100) with exogenously added KAAD-cyclopamine (0.2 µM) and exendin 4 (50 ng/ml). Step 5 comprised 5 days treatment with DMEM with B27 supplement (1:100) containing exendin 4 (50 ng/ml).

Single cell suspensions of hESC-derived cells treated as described above were obtained as follows: Cell cultures were dissociated with either TRYPLET™ (Invitrogen, Catalog. No. 12563-011) or ACCUTASE™ enzymes (Innovative Cell Technologies, Catalog No. AT104) at 37° C. according to the manufacturer's instructions. The cells were then washed with PBS/10% FBS collected by centrifugation and resuspended in PBS/3% FBS. Cells were incubated with anti-NCAM antibody directly conjugated to PE for 20 minutes on ice and then washed. Intracellular antibody staining was performed by treating the NCAM-PE stained cells from above with CYTOFIX/CYTOPERM™ fixation and permeability buffer and PERM/WASH™ wash buffer (Beckton Dickinson) according to the manufacturer's instructions. Cells were incubated anti-insulin (DakoCytomation, Catalog No. A0564), and anti-synaptophysin (DakoCytomation, Catalog No. A0010) primary antibodies for 20 minutes on ice. Cells were washed and incubated with either donkey anti-guinea pig Cy5 1:1000 (Jackson Immunoresearch 706-176-148), donkey anti-rabbit Alexa 488 1:2000 (Invitrogen A21206) secondary antibodies according to the manufacturer's instructions.

Flow cytometry was performed on a FACSARIA™ Fluorescence activated cell sorter (Becton Dickinson), according to the manufacturer's instructions and analyzed using FACSDIVA™ FACS analysis software (Becton Dickinson).

Figure 17B:
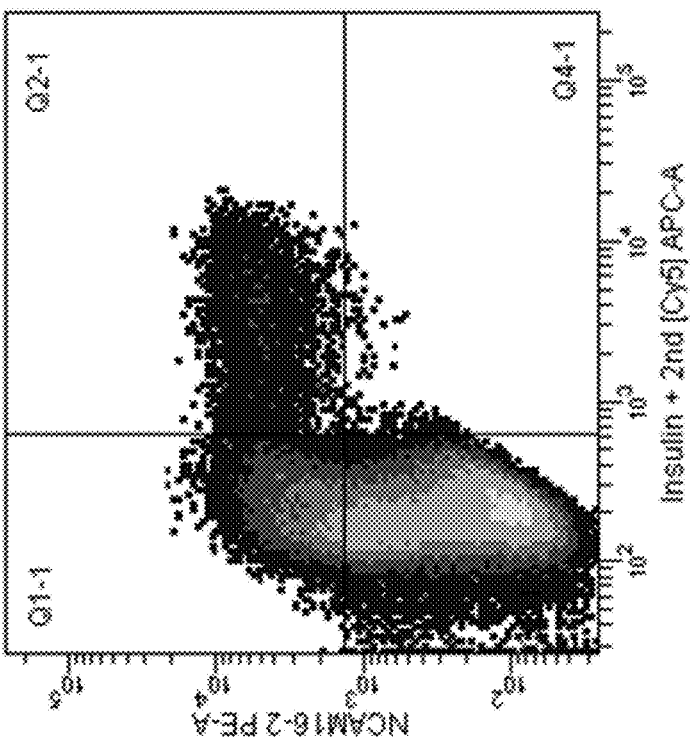
FIGS. 17A-17B are flow cytometry dot plots showing the co-segregation of immature pancreatic islet hormone-expressing cells expressing synaptophysin and NCAM (FIG. 17A) as well as the co-segregation of immature pancreatic islet hormone-expressing cells expressing INS and NCAM (FIG. 17B).
Figure 17A:
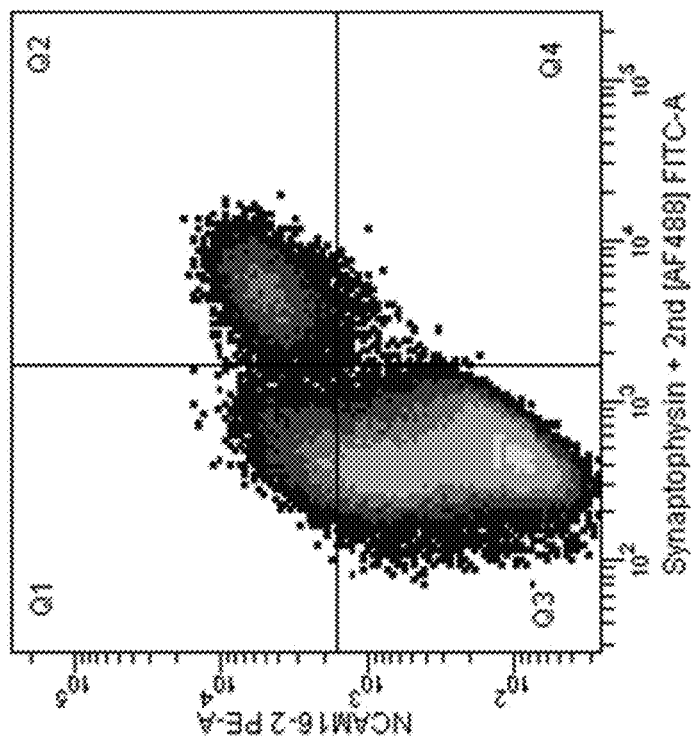

As shown in FIG. 17A, approximately 10% of the hESC-derived cells differentiated as described were SYP positive. Moreover, almost all of the SYP positive hESC-derived cells were also positive for NCAM. FIG. 17B shows that almost all of the NCAM positive hESC-derived cells were also positive for INS. These data confirm the immunocytochemistry data in FIGS. 12A-12D, 13A-13D, 14A-14F, 15A-15B and FIGS. 16A-16D, and demonstrate that NCAM is a useful marker for hESC-derived immature pancreatic islet hormone-expressing cells.

Example 15

Sorting NCAM Positive hESC-Derived Immature Pancreatic Islet Hormone-Expressing Cell Populations Enriches the Populations for Immature Pancreatic Islet Hormone-Expressing Cells In a second set of experiments, hESCs were differentiated for 19 days via a 6-step protocol to achieve immature pancreatic islet hormone-expressing cells. The first step comprised 1 day differentiation in Wnt3a (25 ng/ml) activin A (100 ng/ml) in serum-free media, followed by 1 day in activin A (100 ng/ml) alone in media supplemented with 0.2% FBS, and 1 day in activin A (100 ng/ml) in media supplemented with 2.0% FBS to robustly produce DE (D'Amour, K., et al., *Nature Biotechnology* 23, 1534-1541, (2005)). Step 2 comprised 3 days differentiation in DMEM with 2% FBS containing FGF10 (50 ng/mL) and KAAD-cyclopamine (0.25 µM). Step 3 comprised 4 days differentiation in DMEM with B27 supplement (1:100), with exogenously added KAAD-cyclopamine (0.2 µM), and retinoic acid (2 µM). The fourth step comprised 1 day treatment with DMEM with B27 supplement (1:100) with exogenously added KAAD-cyclopamine (0.2 µM) and glucagon-like peptide 1, amino acid 1-37 (50 ng/ml). Step 5 comprised 3 days treatment with DMEM with B27 supplement (1:100) with exogenously added exendin 4 (50 ng/mL) and glucagon-like peptide 1, amino acids 1-37 (50 ng/ml). Step 6 comprised 5 days treatment with DMEM with B27 supplement (1:100) containing exendin 4 (50 ng/ml).

Differentiation protocols were modified as follows for particular experiments. For the experimental data shown in FIGS. 19A-19D, Step 3 of the protocol above included treatment with noggin (100 ng/ml). In Step 4, instead of treatment with glucagon-like peptide 1, cells were treated with exendin 4 (50 ng/ml) Step 5 comprised a 5 day treatment that did not include glucagon-like peptide 1. Finally, Step 6 was replaced by a 4-day treatment in CMRL media with B27 supplement (1:100) containing exendin 4 (50 ng/ml).

For the experimental data shown in FIGS. 20A-20C, Step 3 was modified to a 3 day treatment that included noggin (100 ng/ml). Step 4 was modified to include nicotinamide (10 mM). Step 5 was modified to a 4 day treatment that included nicotinamed (10 mM), and that did not include exendin 4. Step 6 was modified to comprise a 1 day treatment that included glucagon-like peptide 1, 1-37 (50 ng/ml) and nicotinamide 10 mM. The cell differentiation protocol also included a seventh step, comprising 4 days treatment in CMRL media with B27 supplement (1:100), glucagon-like peptide 1, 1-37 (50 ng/ml) and nicotinamide (10 mM).

For the experimental data shown in FIGS. 25A-25F, Step 3 of the differentiation protocol was modified to include treatment with retinoic acid at 1 µM, and included treatment with noggin (50 ng/ml) and nicotinamide (10 mM). Step 4 was modified to include nicotinamide (10 mM) and to exclude treatment with glucagon-like peptide 1, 1-37. Step was modified to include nicotinamide (10 mM) and to exclude treatment with glucagon-like peptide 1, 1-37, and exclude exendin 4. Step 6 was modified to only be a 1 day treatment and excluded exendin 4. The cell differentiation also included a seventh step, comprising 7 days treatment in CMRL supplemented with B27 (1:100).

Single cell suspensions of the cells were obtained as described above. The cells were then washed with PBS/10% FBS collected by centrifugation and resuspended in PBS/3% FBS. Cells were incubated with anti-NCAM directly conjugated to PE (NCAM16.2, Becton Dickinson, Catalog No. 340363) for 20 minutes on ice. Cells were subsequently washed with PBS/3% FBS collected by centrifugation and resuspended in Hanks balanced salt solution, 2% FBS, 20 mM HEPES. Cells were sorted with a FACS Aria machine (Becton Dickinson), and collected in Hanks balanced salt solution with 10% FBS. Intracellular antibody staining was performed by treating either the pre-sorted population of cells or the NCAM-positive sorted population of cells with CYTOFIX/CYTOPERM™ fixation and permeability buffer and PERM/WASH™ wash buffer (Beckton Dickinson) according to the manufacturer's instructions. Cells were washed and incubated with either donkey anti-guinea pig Cy5 1:1000 (Jackson Immunoresearch 706-176-148), donkey anti-rabbit Alexa 488 1:2000 (Invitrogen A21206) secondary antibodies according to the manufacturer's instructions.

Flow cytometry was performed on a FACSARIA™ Fluorescence activated cell sorter (Becton Dickinson), according to the manufacturer's instructions and analyzed using FACSDIVA™ FACS analysis software (Becton Dickinson).

Figure 18A:
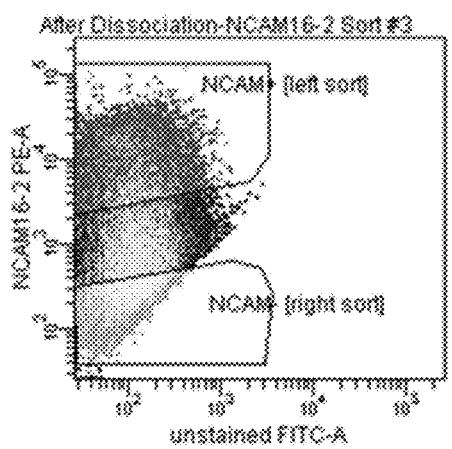
FIGS. 18A-18D are flow cytometry dot plots of hESC-derived cells treated to differentiate to immature pancreatic islet hormone-expressing cells.

NCAM positive and NCAM negative cells were collected and then reanalyzed by flow cytometry using the protocol above for NCAM, SYP, PAX6 and CHGA. In one experiment, following sorting (shown in FIG. 18A), NCAM positive cells were aggregated in inverted hanging drops. These cells were collected and analyzed in cryosections using immunocytochemistry for PAX6, INS, and GCG. Approximately 7,000 NCAM positive sorted cells were seeded per drop, cultured in RPMI media containing 10% FBS, Fibronectin, Laminin, Collagen, HGF and EGF and incubated for 72 hours. The cell aggregates were collected and processed for immunocytochemical analysis as described above.

Figure 18B:
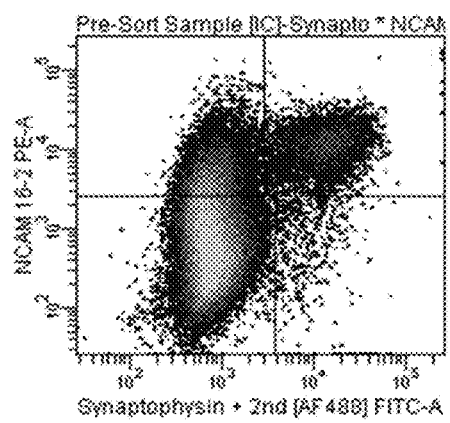
Figure 18C:
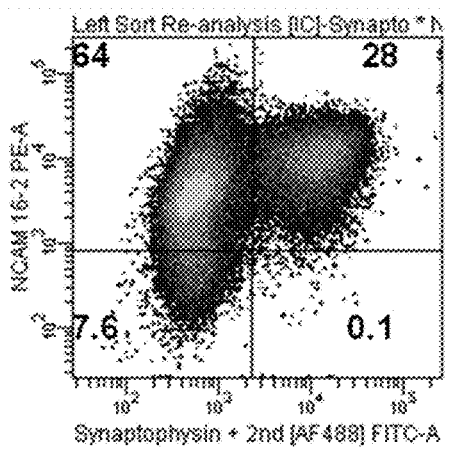
Figure 18D:
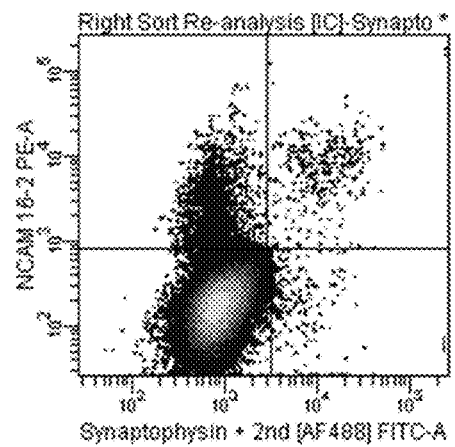
Figure 19A:
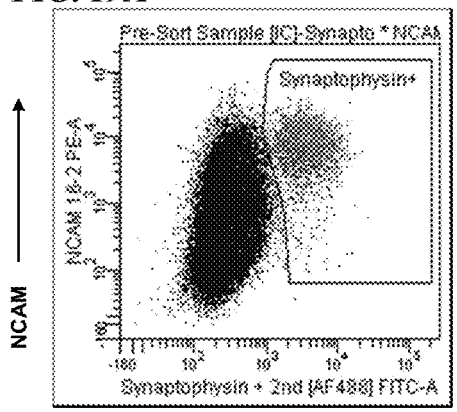
FIGS. 19A-19D are flow cytometry dot plots of hESC-derived cells that have been treated to differentiate to immature pancreatic islet hormone-expressing cells. The treated cells that have (FIG. 19B, FIG. 19D) or have not (FIG. 19A, FIG. 19C) been sorted for NCAM positive cells.
Figure 19B:
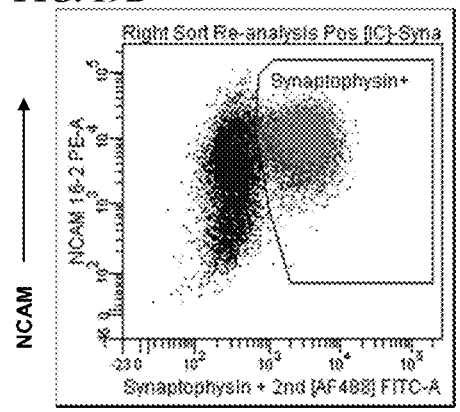
Figure 19C:
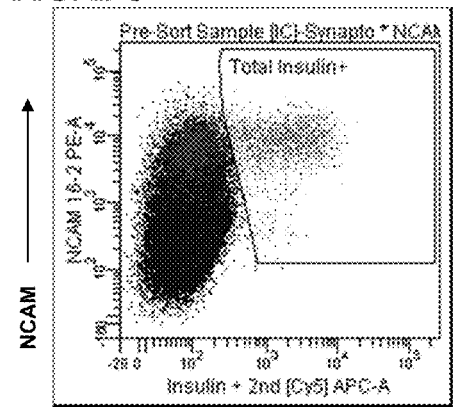
Figure 19D:
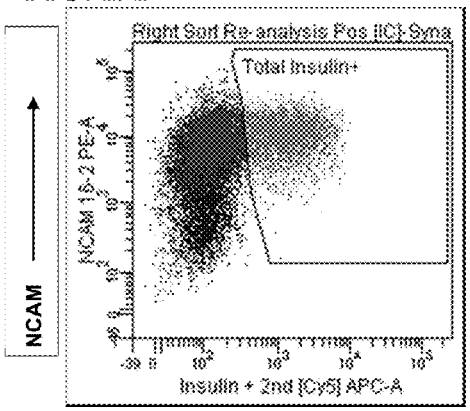

As shown in FIG. 18B, when cells were analyzed by flow cytometry prior to sorting for NCAM, approximately 7% of the cell population was both NCAM positive and SYP positive. Sorting NCAM positive cells (FIG. 18A, "left sort") resulted in an approximately 4-fold enrichment for NCAM positive/SYP positive cells compared to cells that were not sorted (FIG. 18B). As shown in FIG. 18D, the population of NCAM negative cells was depleted for SYP positive cells. FIG. 19A and FIG. 19D show that an hESC-derived cell population differentiated as described above and analyzed by flow cytometry for NCAM comprised approximately 4% and 2% NCAM positive/SYP positive and NCAM positive/INS positive cells. FIG. 19B shows that sorting the same population of NCAM positive hESC-derived cells resulted in a greater than 10-fold enrichment of NCAM positive/SYP positive cells, producing a cell population comprising 47% NCAM positive/SYP positive cells. FIG. 19D shows that sorting the same population of hESC-derived cells resulted in a greater than 8-fold enrichment of NCAM positive/INS positive cells. As shown in FIGS. 20A-20C, sorting NCAM positive hESC-derived cells differentiated as described above produced an enriched cell population that comprised 72% NCAM positive/SYP positive cells.

Figure 25E:
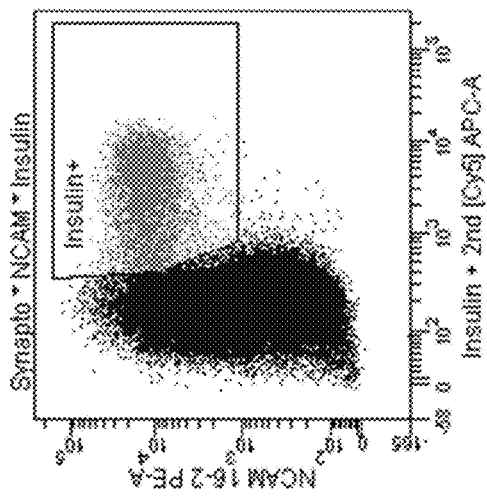
FIGS. 25A-25F are flow cytometry dot plots of hESC-derived cells that have been treated to differentiate to immature pancreatic islet hormone-expressing cells.
Figure 25F:
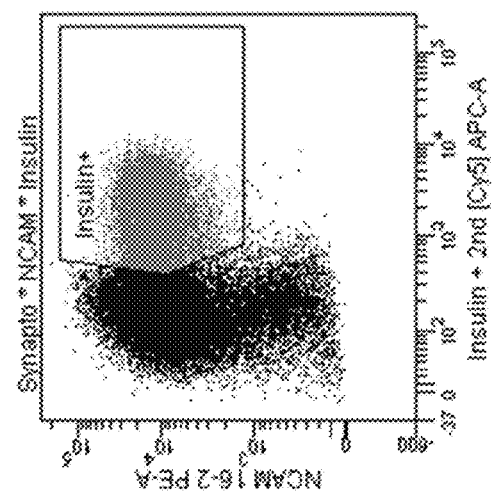
Figure 25C:
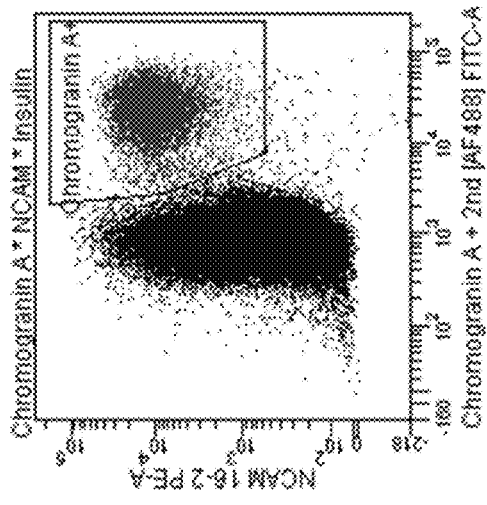
Figure 25D:
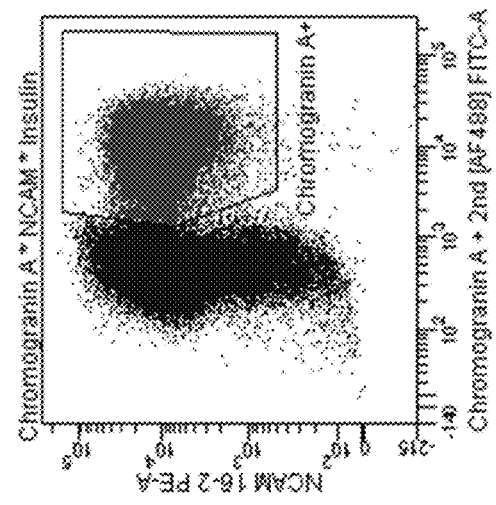
Figure 25A:
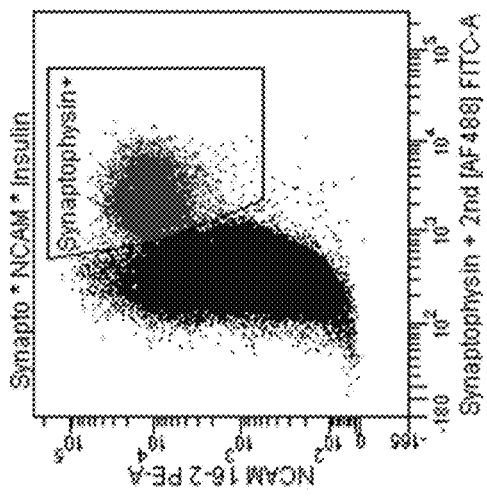
Figure 25B:
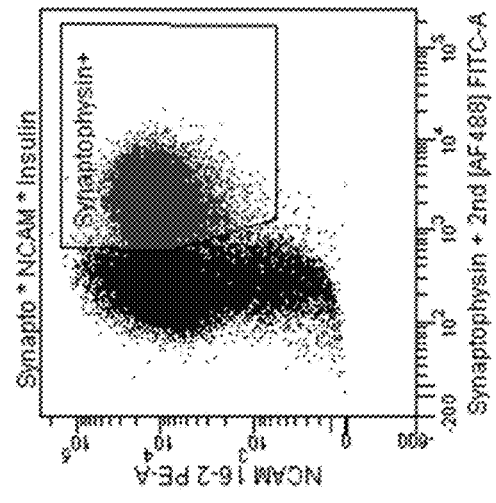

FIGS. 25A-25F show the results of an independent experiment. As shown in FIGS. 25A-25F, NCAM positive/SYP positive cells represented about 7.4% of the cell population prior to sorting. Sorting of NCAM positive cells resulted in a population that is about 42% SYP positive, a greater than 5-fold enrichment (FIGS. 25A-25B). Similarly, sorting of NCAM positive cells enriched the cell population for CHGA-expressing cells from about 8.7% of the cell population to about 42% of the cell population (FIGS. 25C-25D). Likewise, the NCAM sorting enriched the cell population for INS-expressing cells from about 6% of the total cell population to about 24% of the cell population (FIGS. 25E-25F).

FIGS. 27A-27D and 28A-28D show that hanging drop aggregates of NCAM positive sorted cells contained a significant proportion of cells that co-expressed PAX6 and INS. FIGS. 28A-28D show that NCAM positive sorted cells contained a significant proportion of cells that co-expressed GCG and INS.

The data demonstrate that NCAM is useful for sorting cells using FACS. As such, NCAM can be used to enrich, isolate and/or purify hESC-derived immature pancreatic hormone-expressing cells.

Example 16

Enrichment of NCAM Positive/SYP Positive hESC-Derived Immature Pancreatic Islet Hormone-Expressing Cell Populations Using a Negative Selection for CD133

In a third set of experiments, hESCs were differentiated for 19 days via a 6-step protocol to achieve immature pancreatic islet hormone-expressing cells. The first step comprised 1 day differentiation in Wnt3a (25 ng/ml) activin A (100 ng/ml) in serum-free media, followed by 1 day in activin A (100 ng/ml) alone in media supplemented with 0.2% FBS, and 1 day in activin A (100 ng/ml) in media supplemented with 2.0% FBS to robustly produce DE (D'Amour, K., et al., Nature Biotechnology 23, 1534-1541, (2005)). Step 2 comprised 3 days differentiation in DMEM with 2% FBS containing FGF10 (50 ng/mL) and KAAD-cyclopamine (0.25 μM). Step 3 comprised 3 days differentiation in DMEM with B27 supplement (1:100), with exogenously added KAAD-cyclopamine (0.2 μM), retinoic acid (2 μM), and exendin 4 (50 ng/ml). The fourth step comprised 1 day treatment with DMEM with B27 supplement (1:100) with exogenously added KAAD-cyclopamine (0.2 μM) and exendin 4 (50 ng/ml). Step 5 comprised 9 days treatment with DMEM with B27 supplement (1:100) containing exendin 4 (50 ng/ml).

Cell cultures were processed for flow cytometry analysis as described above, using NCAM, SYP and CD133 primary antibodies as described in Example 14, or sorted using NCAM and CD133 antibodies as described in Example 15.

As shown in FIG. 21B, approximately 7.5% of the cells in the hESC-derived cell population differentiated as described in Example 14 were NCAM positive/CD133 negative. Counterstaining of these cells for SYP, showed that 93% of the NCAM positive/CD133 negative cells were positive for SYP.

Figure 26A:
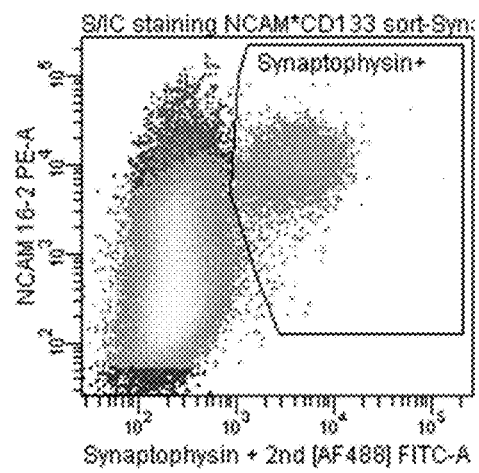
FIGS. 26A-26C are flow cytometry dot plots of hESC-derived cells that have been treated to differentiate to immature pancreatic islet hormone-expressing cells.
Figure 26B:
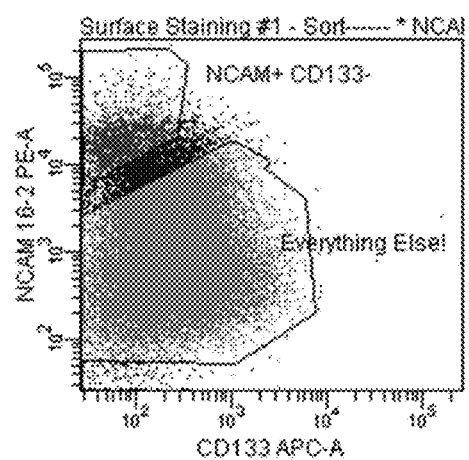
Figure 26C:
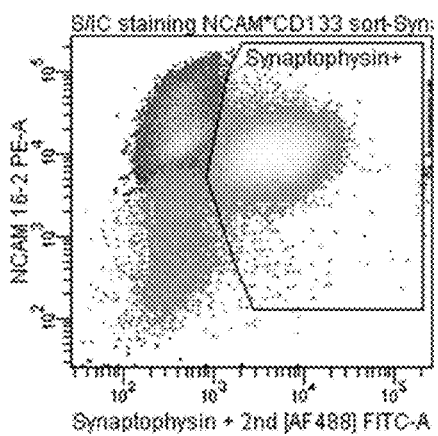
Figure 28A:
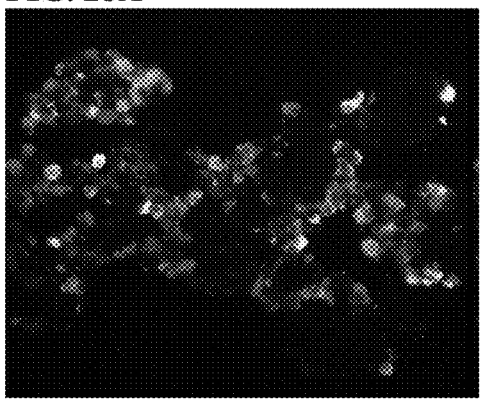
FIGS. 28A-28D are photomicrographs showing immunoreactivity of immature pancreatic islet hormone-expressing cells expressing INS (FIG. 28C) or GCG (FIG. 28D). The cells are hESC-derived stem cells treated to differentiate to immature pancreatic islet hormone-expressing cells and sorted using Fluorescence Activated Cell Sorting technology. The cells represented in the micrographs also stained brightly for NCAM.
Figure 28B:
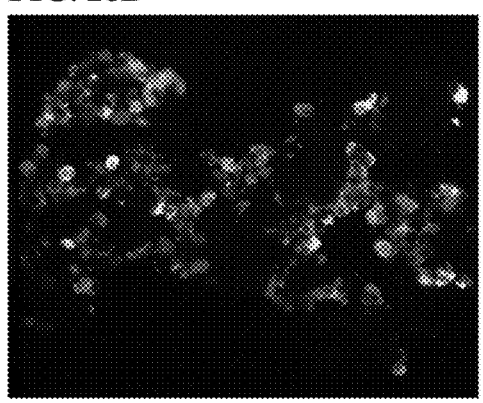
Figure 28C:
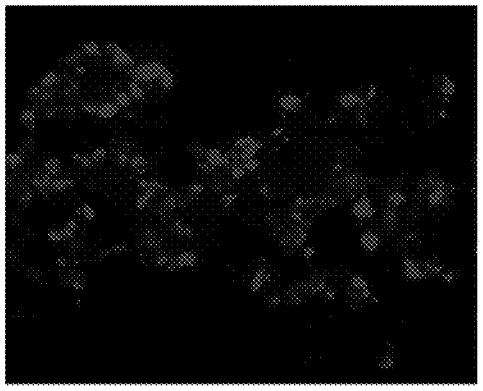
Figure 28D:
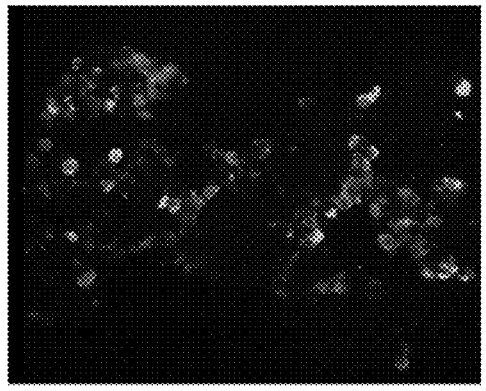

As shown in FIGS. 26A and 26B, approximately 4.6% of the cell population differentiated as described above stained positively for SYP, and approximately 5.3% of the cell population stained positively for NCAM and negative for CD133. By contrast, approximately 66.5% of the subpopulation of NCAM positive/CD133 negative cells stained positively for SYP (FIG. 26C). These data demonstrate that sorting for NCAM positive and CD133 negative cells can be used to enrich, isolate and/or purify hESC-derived immature pancreatic hormone-expressing cells.

Example 17

Differentiation of hESCs to Endocrine Precursor Cells and Immature Pancreatic Islet Hormone-Expressing Cells hESCs were differentiated for 19 days via a 6-step protocol to achieve immature pancreatic islet hormone-expressing cells. The first step comprised 1 day differentiation in Wnt3a (25 ng/ml) activin A (100 ng/ml) in serum-free media, followed by 1 day in activin A (100 ng/ml) alone in media supplemented with 0.2% FBS, and 1 day in activin A (100 ng/ml) in media supplemented with 2.0% FBS to robustly produce DE (D'Amour, K., et al., Nature Biotechnology 23, 1534-1541, (2005)). Step 2 comprised 3 days differentiation in DMEM with 2% FBS containing FGF10 (50 ng/mL) and KAAD-cyclopamine (0.25 μM). Step 3 comprised 4 days differentiation in DMEM with B27 supplement (1:100), with exogenously added KAAD-cyclopamine (0.2 μM), retinoic acid (2 μM), glucagon-like peptide 1, amino acid 1-37 (50 ng/ml), and NOGGIN (50 ng/ml). The fourth step comprised a 3 day treatment with DMEM with B27 supplement (1:100) and glucagon-like peptide 1, amino acid 1-37 (50 ng/ml). Step 5 comprised 6 days treatment with DMEM with B27 supplement (1:100) containing exendin 4 (50 ng/ml). On days 12, 15 and 1919, cells were sorted using FACS as described in Example 14 to separate NCAM positive cells from NCAM negative cells. Duplicate samples of pre-sorted cells, NCAM positive cells and NCAM negative cells were taken from each culture and gene expression was analyzed by real-time quantitative PCR.

Figure 22A:
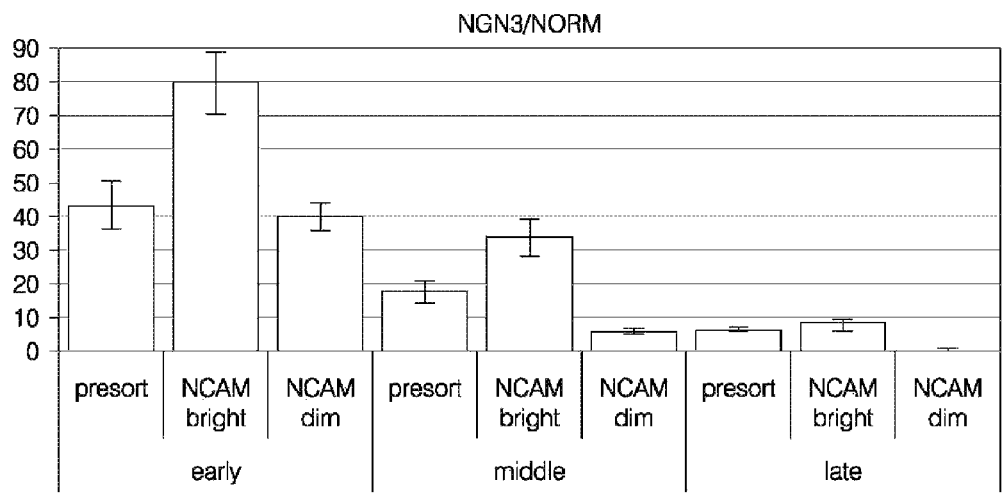
FIGS. 22A-22K are bar charts showing the mRNA levels of certain markers as detected by QPCR in hESC-derived cells that have been treated to differentiate to endocrine precursor cells ("early") or that have been treated to differentiate to immature pancreatic islet hormone-expressing cells ("middle" and "late"). The data labeled "Presort" represent marker mRNA levels in cells that have not been processed and sorted through a FACS machine. The data labeled "NCAM bright" represent marker mRNA levels in cells that are NCAM positive. The data labeled "NCAM dim" represent marker mRNA levels in cells that are NCAM negative. Specifically shown are the mRNA levels of NGN3 (FIG. 22A), PAX4 (FIG. 22B), INS (FIG. 22C), Pancreatic polypeptide (FIG. 2D), PAX6 (FIG. 22E), GCG (FIG. 22F), GHRL (FIG. 22G), GCK (FIG. 22H), SST (FIG. 22I), NXK2.2 (FIG. 22J) and SYP (FIG. 22K).
Figure 22B:
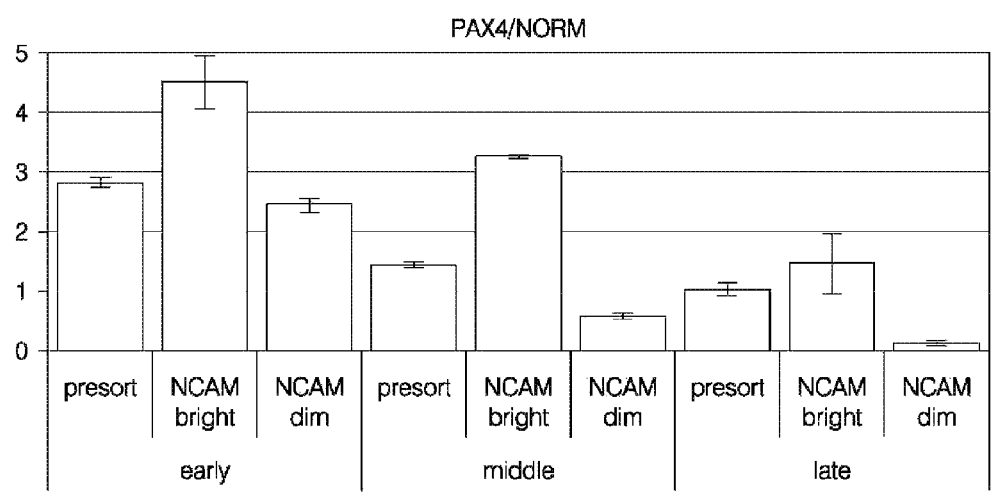
Figure 22C:
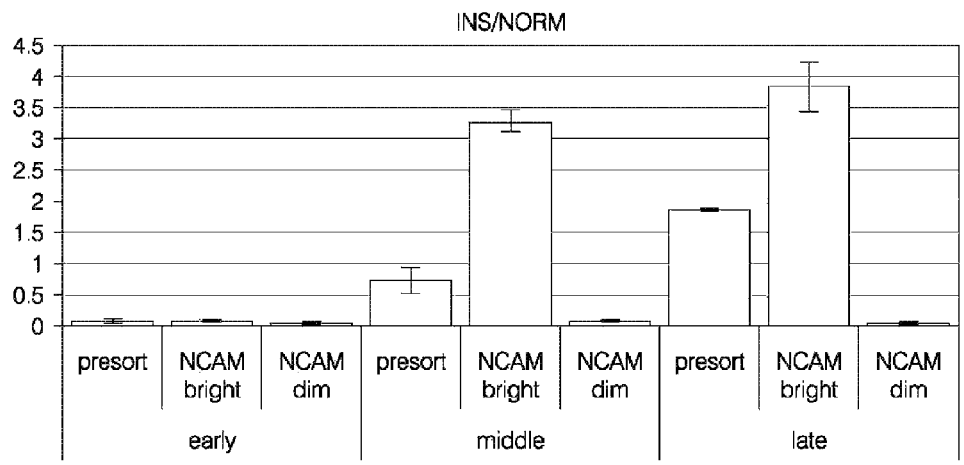
Figure 22D:
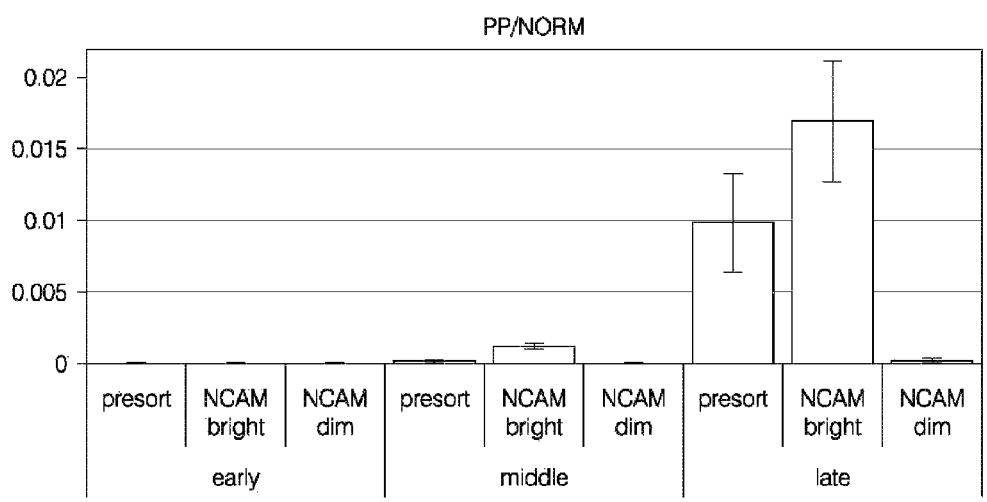
Figure 22E:
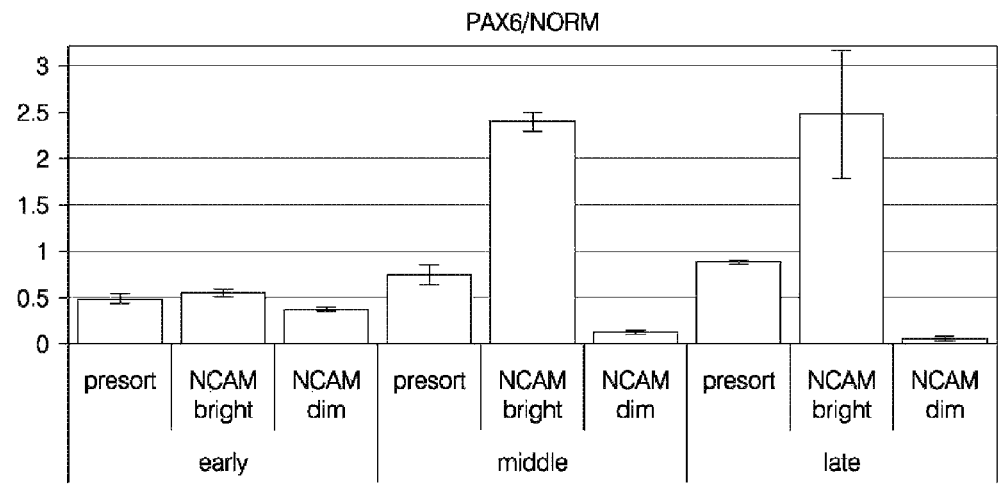
Figure 22F:
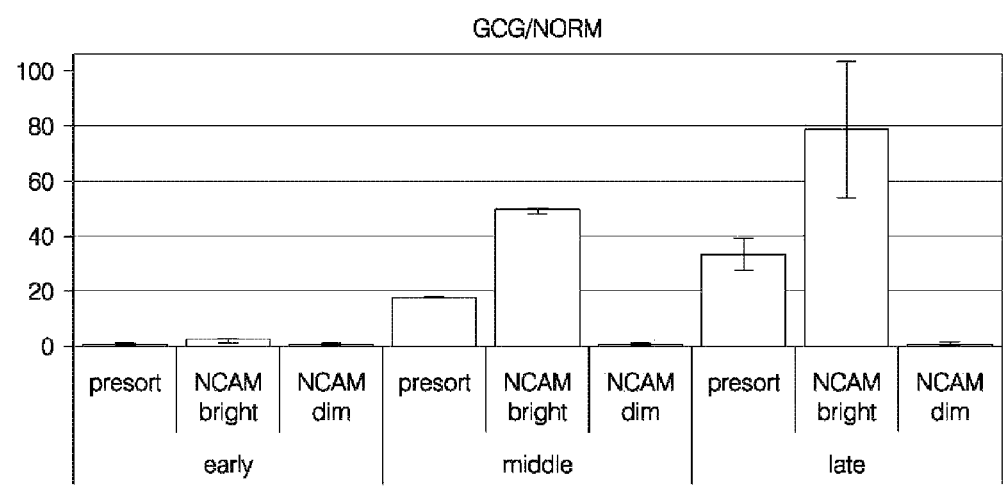
Figure 22G:
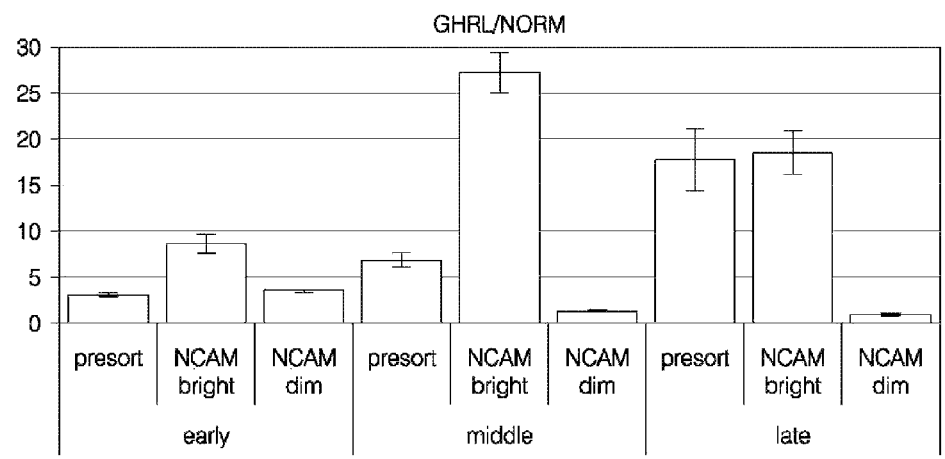
Figure 22H:
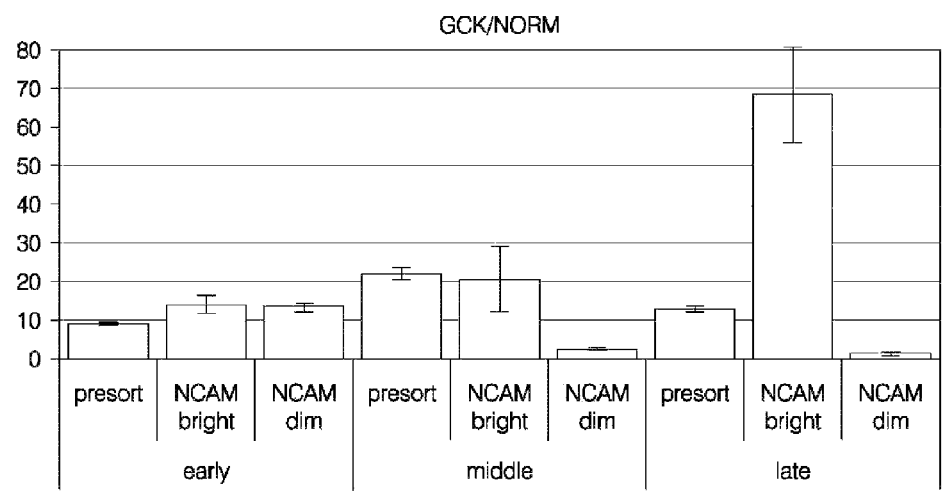
Figure 22I:
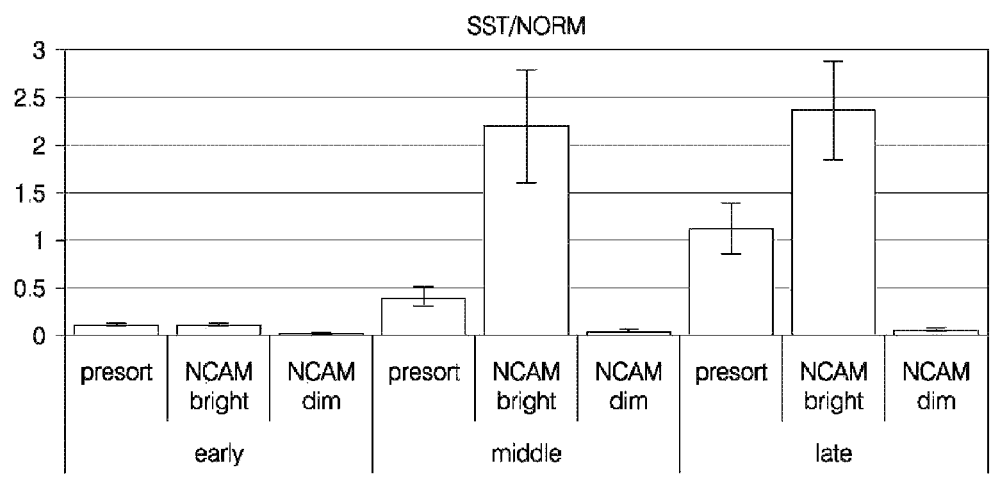
Figure 22J:
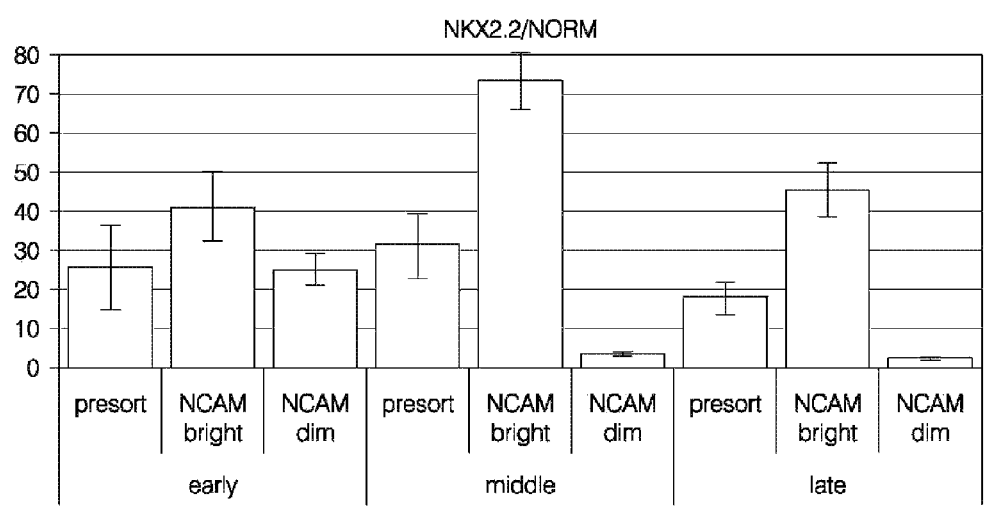
Figure 22K:
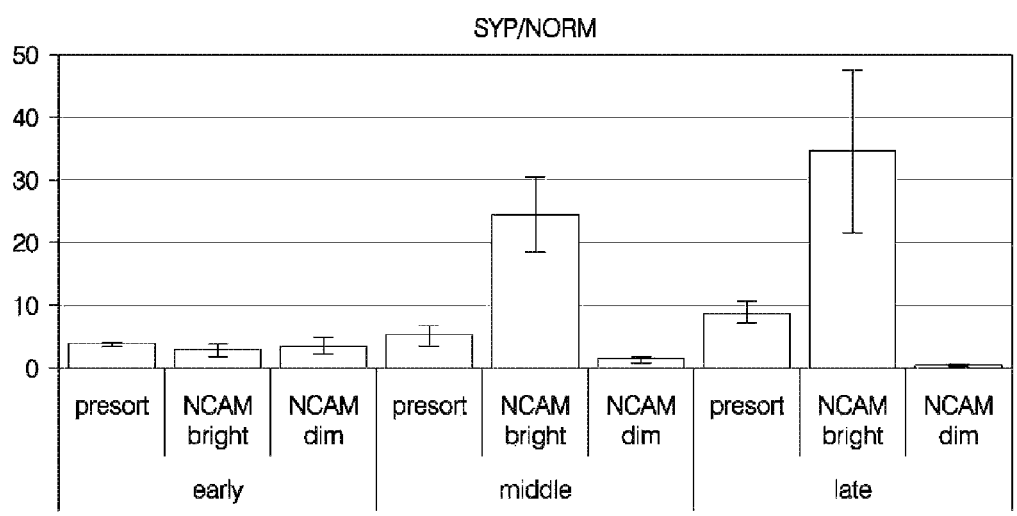

As shown in FIGS. 22A-22K, there was a temporal continuum of gene expression as cells progressed from endocrine precursor cells ("early") to immature pancreatic islet hormone-expressing cells ("middle" and "late"). FIGS. 22A and 22B show that NCAM positive cells were enriched for NGN3 and PAX4. The expression of NGN3 and PAX4 decreased as the hESCs differentiated into immature pancreatic islet hormone-expressing cells. As shown in FIGS. 22C-22K, NCAM-positive cells were also highly enriched for cells expressing markers indicative of immature pancreatic islet hormone-expressing cells, including INS, PP, PAX6, GCG, GHRL, GCK, SST, NKX2.2, and SYP, compared to NCAM negative cells. Endocrine precursor cells did not substantially express INS, PP, PAX6, GCG, GHRL, GCK, and SYP, whereas cells that were further differentiated towards pancreatic islet hormone-expressing cells exhibited increased expression of the same markers, which are characteristic of pancreatic endocrine cells.

Figure 23A:
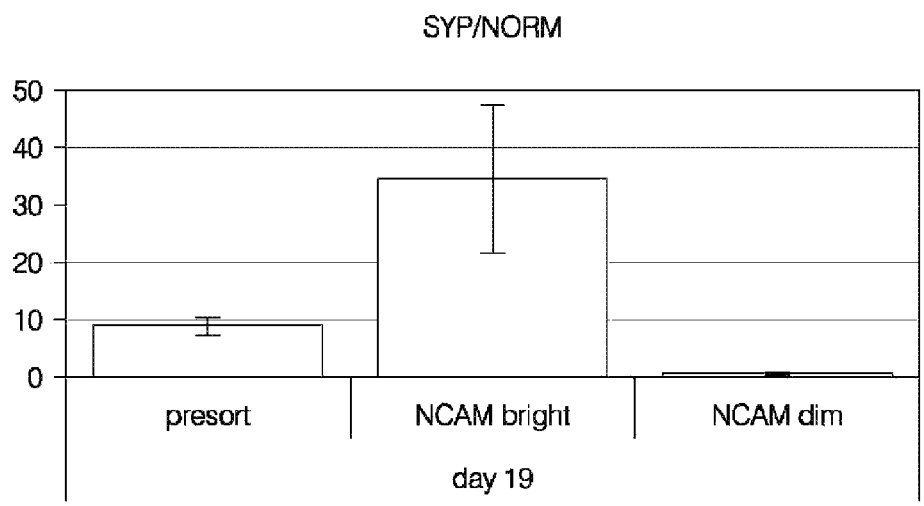
FIGS. 23A-23E are bar charts showing the mRNA levels of certain markers as detected by QPCR in hESC derived cells that have been treated to differentiate to immature pancreatic islet hormone-expressing cells (day 19). The data labeled "Presort" represent marker mRNA levels in cells that have not been processed and sorted through a FACS machine. The data labeled "NCAM bright" represent marker mRNA levels in cells that are NCAM positive. The data labeled "NCAM dim" represent marker mRNA levels in cells that are NCAM negative. Specifically shown are the mRNA levels of NEUROD (FIG. 23A), ISL1 (FIG. 23B), GAS (FIG. 23C), KIR6.2 (FIG. 23D), and SUR1 (FIG. 23E).
Figure 23B:
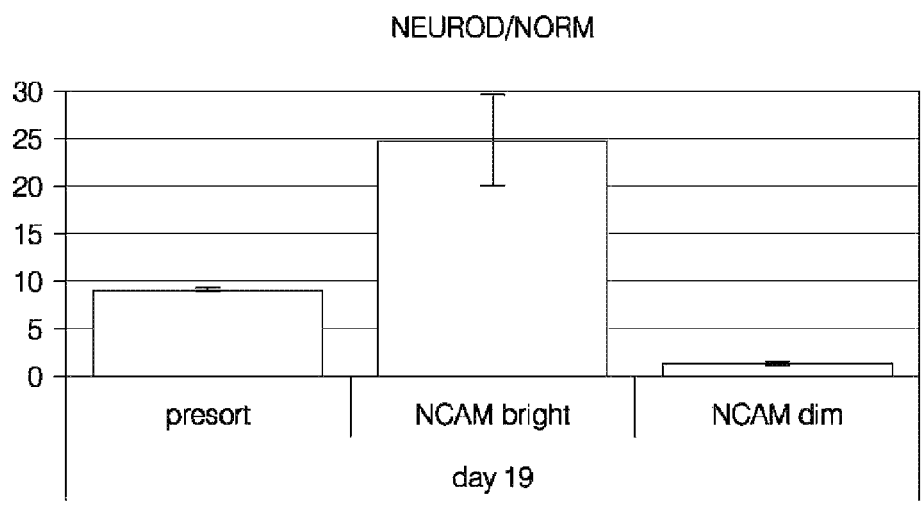
Figure 23C:
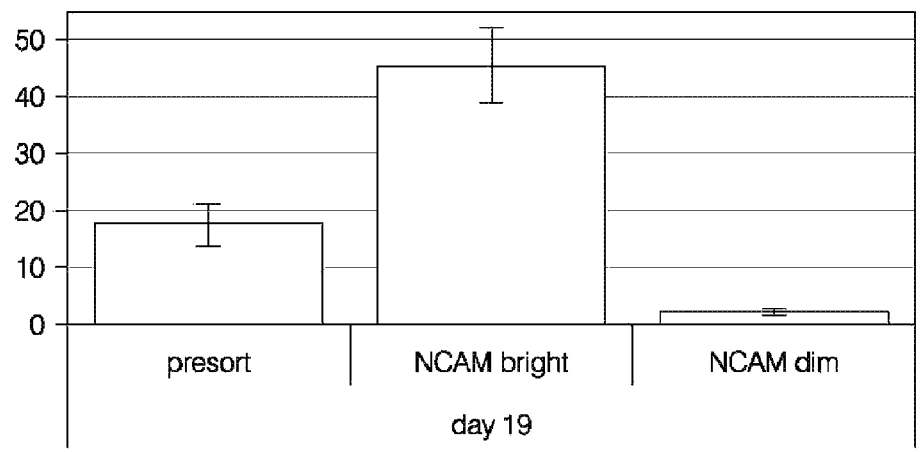
Figure 23D:
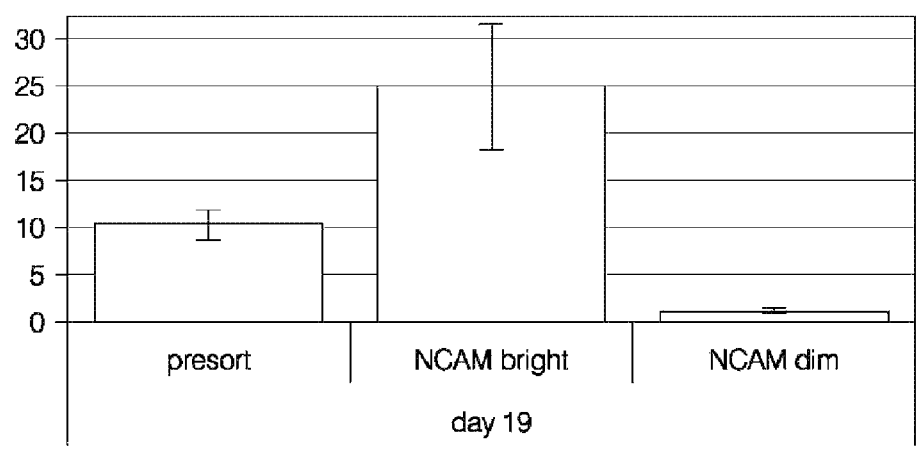
Figure 23E:
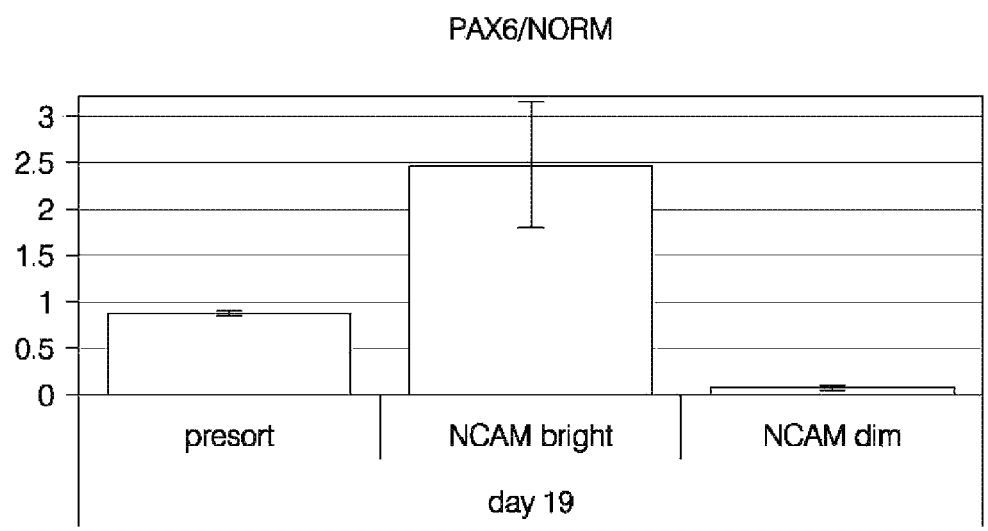

FIGS. 23A-23E show additional QPCR data hESC cells that were differentiated and sorted on day 19 as described above. Sorting the hESC-derived cell population for NCAM positive cells produced a population of cells that was highly enriched for endocrine markers such as NEUROD (FIG. 23A), ISL1 (FIG. 23B), GAS (FIG. 23C), KIR6.2 (FIG. 23D), and SUR1 (FIG. 23E).

Figure 24A:
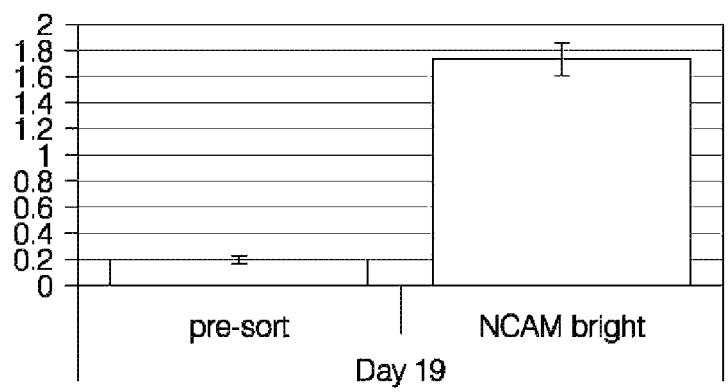
FIGS. 24A-24K are bar charts showing the mRNA levels of certain markers as detected by QPCR in hESC derived cells that have been treated to differentiate to immature pancreatic islet hormone-expressing cells (day 19). The data labeled "Presort" represent marker mRNA levels in cells that have not been passed through but not sorted in a FACS machine (live, gated cells). The data labeled "NCAM bright" represent marker mRNA levels in cells that are NCAM positive. Specifically shown are the mRNA levels of NCAM1 (FIG. 24A), NKX2.2 (FIG. 24B), SYP (FIG. 24C), PAX6 (FIG. 24D), NEUROD (FIG. 24E), ISL1 (FIG. 24F), INS (FIG. 24G), GCG (FIG. 24H), GHRL (FIG. 24I), SST (FIG. 24J) and PP (FIG. 24K).
Figure 24B:
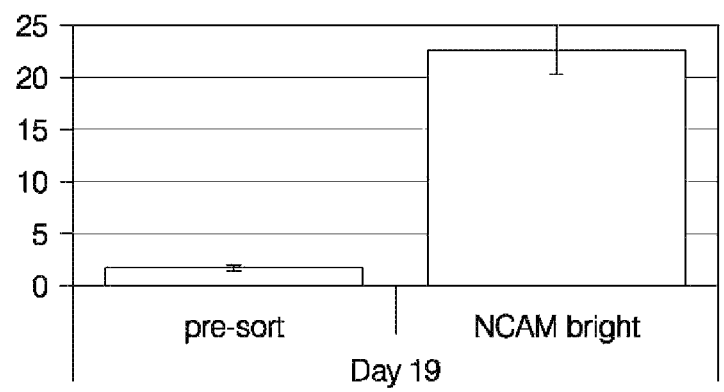
Figure 24C:
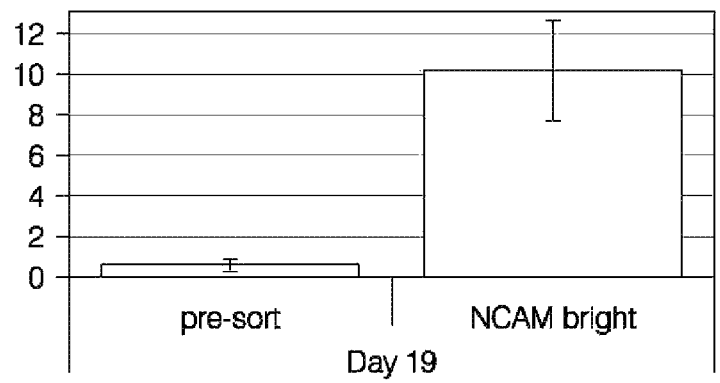
Figure 24D:
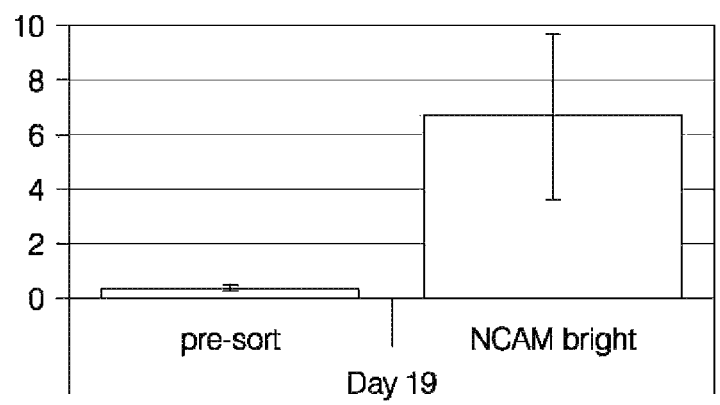
Figure 24E:
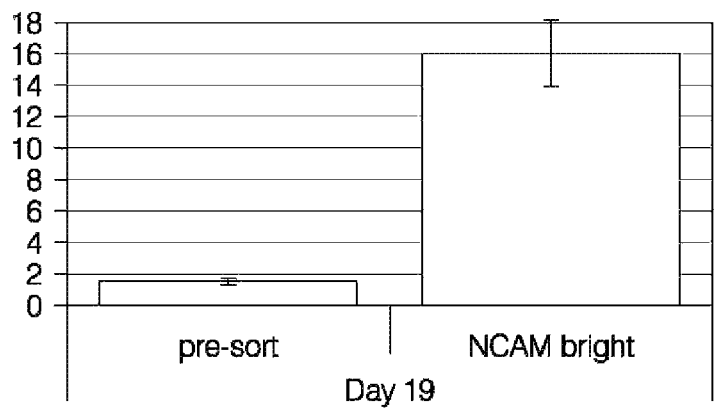
Figure 24F:
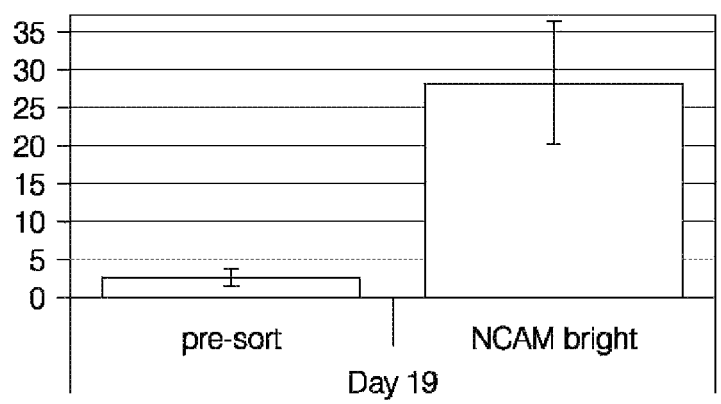
Figure 24G:
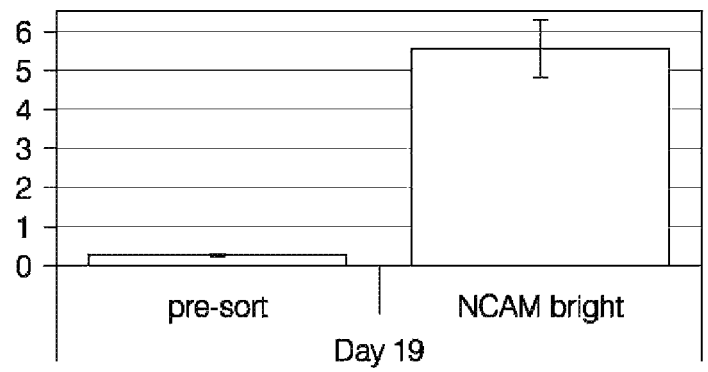
Figure 24H:
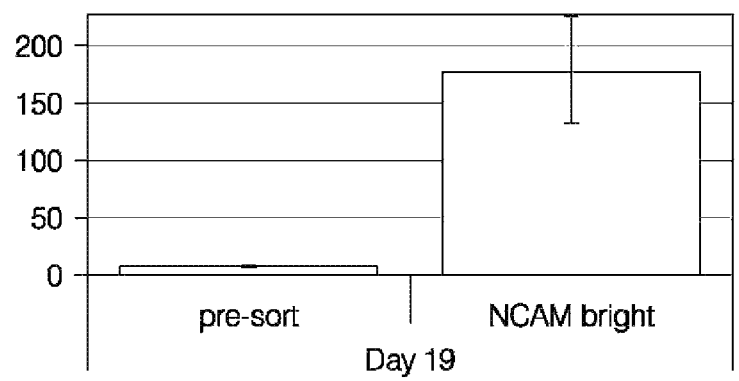
Figure 24I:
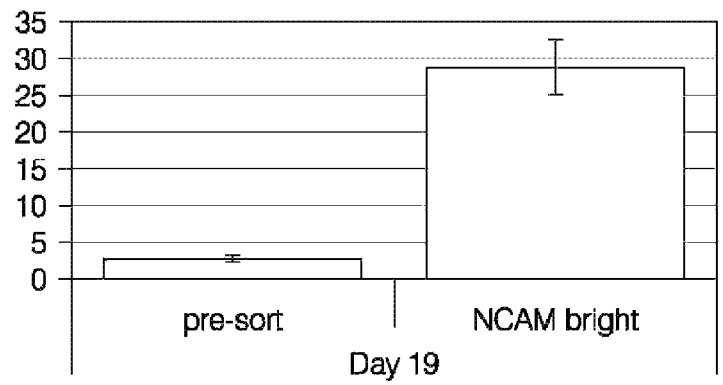
Figure 24J:
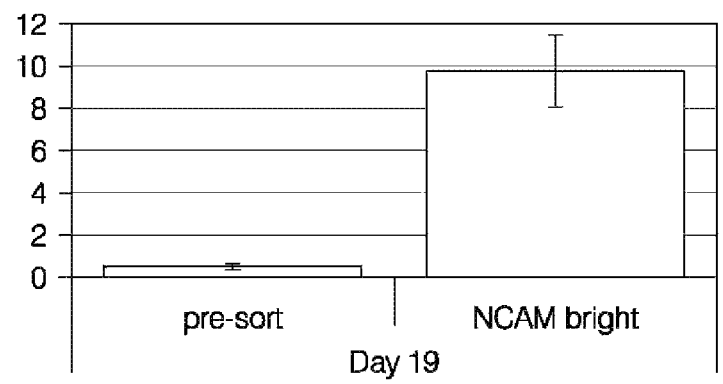
Figure 24K:
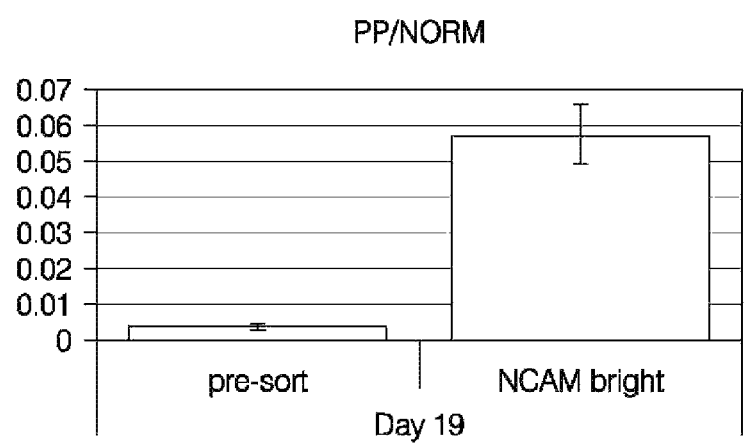

FIGS. 24A-24K represent an independent experiment performed on hESC-derived cells that were differentiated and sorted on day 19 as described above. In this experiment, data labeled "Pre-sort" was obtained from hESC differentiated as described above that had been gated, but not sorted using FACS. The figures show that sorting the cell population for NCAM produces a population of cells that was highly enriched for NCAM (FIG. 24A), as expected, as well as the following markers that are characteristic of endocrine cells: NKX2.2 (FIG. 24B), SYP (FIG. 24C), PAX6 (FIG. 24D), NEUROD (FIG. 24E), ISL1 (FIG. 24F), INS (FIG. 24G), GCG (FIG. 24H), GHRL (FIG. 24I), SST (FIG. 24J), and PP (FIG. 24K). These data confirm that NCAM is useful for the enrichment, isolation and purification of immature endocrine cells.

Example 18

Method of Obtaining Insulin-Expressing Cells Using Noggin without Exogenous Retinoids This example demonstrates an alternative method for differentiating hESCs to insulin-expressing cells using noggin treatment without the addition of an exogenous retinoid source, for example retinol (vitamin A) which may be present in media supplements such as B27.

Human ESCs were differentiated to definitive endoderm cells via treatment with activin A (100 ng/ml) and Wnt3a (25 ng/ml) in RPMI+0% FBS for the first day and then for 2 more days with activin A (100 ng/ml) alone in RPMI+0.2% v/v FBS. Definitive endoderm was differentiated to foregut endoderm by treatment with KGF (50 ng/ml) and KAAD-cyclopamine (0.25 µM) for 3 days in RPMI+2% v/v FBS. Differentiation then proceeded in DMEM+1% v/v B27 supplement containing KGF (50 ng/ml) and KAAD-cyclopamine (0.25 µM) for one day followed by 5 additional days of the same with or without the addition of noggin (100 ng/ml). The B27 supplement used was either with (B27+) or without (B27-) vitamin A. On days 13, 14 and 15 of differentiation, the KGF was removed but the KAAD-cyclopamine (0.25 µM) and noggin (when used) remained in the culture medium. The differentiation medium for days 16-19 consisted of CMRL+1% v/v B27 (with or without vitamin A as in previous conditions) with no additional factors. Cultures were sampled in duplicate on days 3, 6, 9, 12, 15 and 19 of differentiation and analyzed for expression of pancreatic markers using real-time PCR.

Figure 29A:
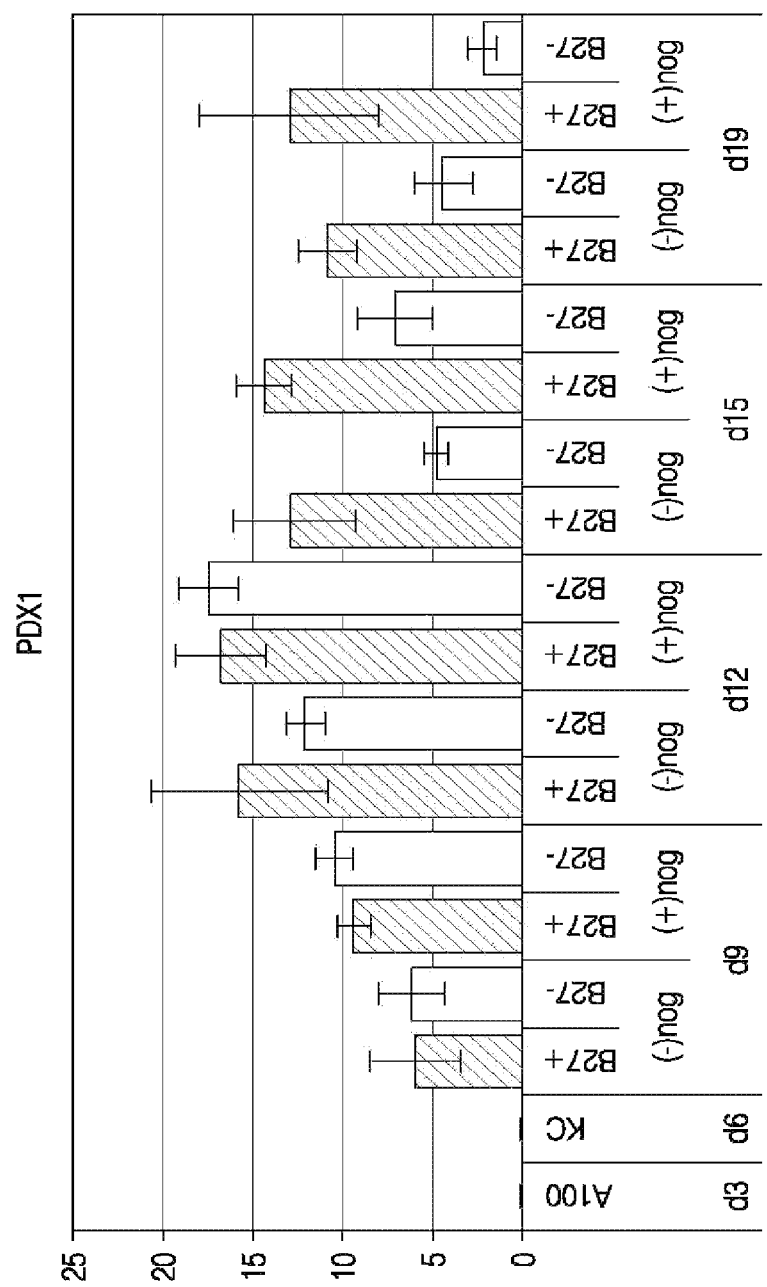
FIGS. 29A-29F are bar charts showing the mRNA levels of certain markers as detected by QPCR in hESC derived cells that have been treated to differentiate to pancreatic insulin-expressing cells (day 19). Specifically shown are the mRNA levels of PDX1 (FIG. 29A), NGN3 (FIG. 29B), INS (FIG. 29C), SST (FIG. 29D), GCG (FIG. 29E) and GHRL (FIG. 29F). The abbreviations are indicated as follows: A100—100 ng/ml activin A; KC—50 ng/ml KGF and 0.25 µM KAAD cyclopamine; and nog—noggin.
Figure 29B:
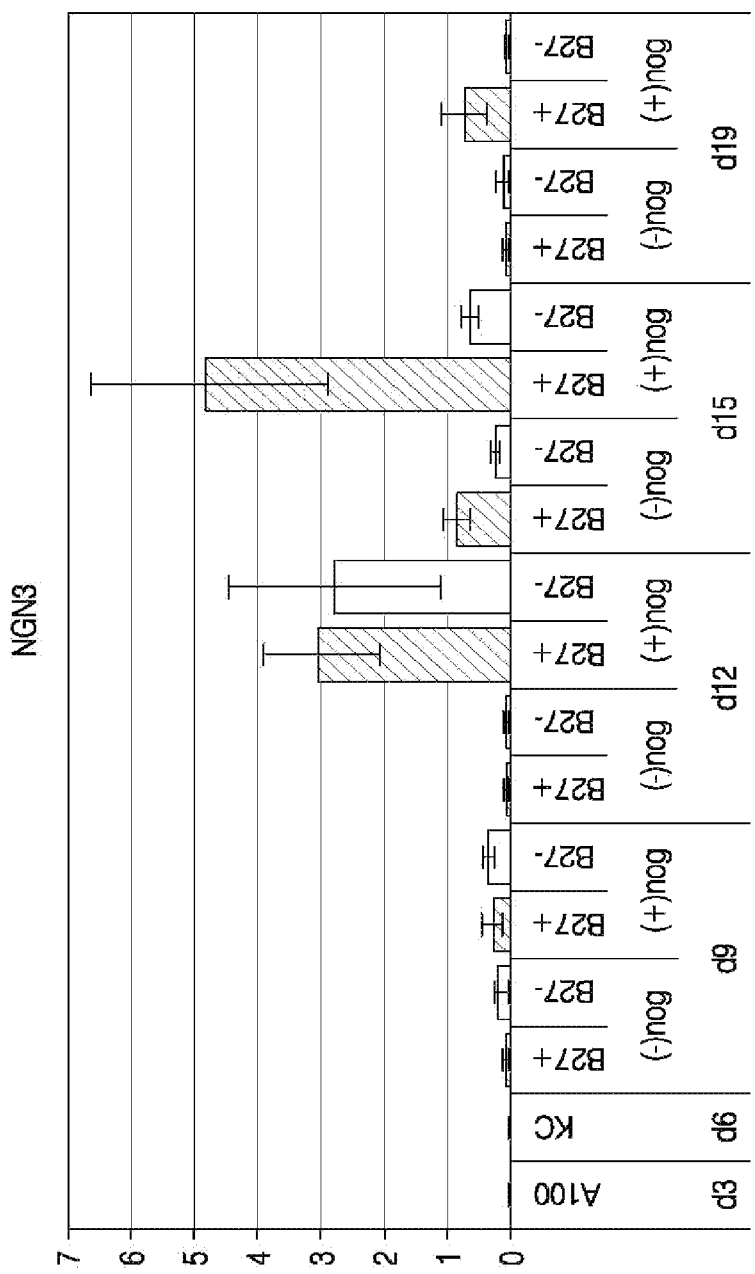
Figure 29C:
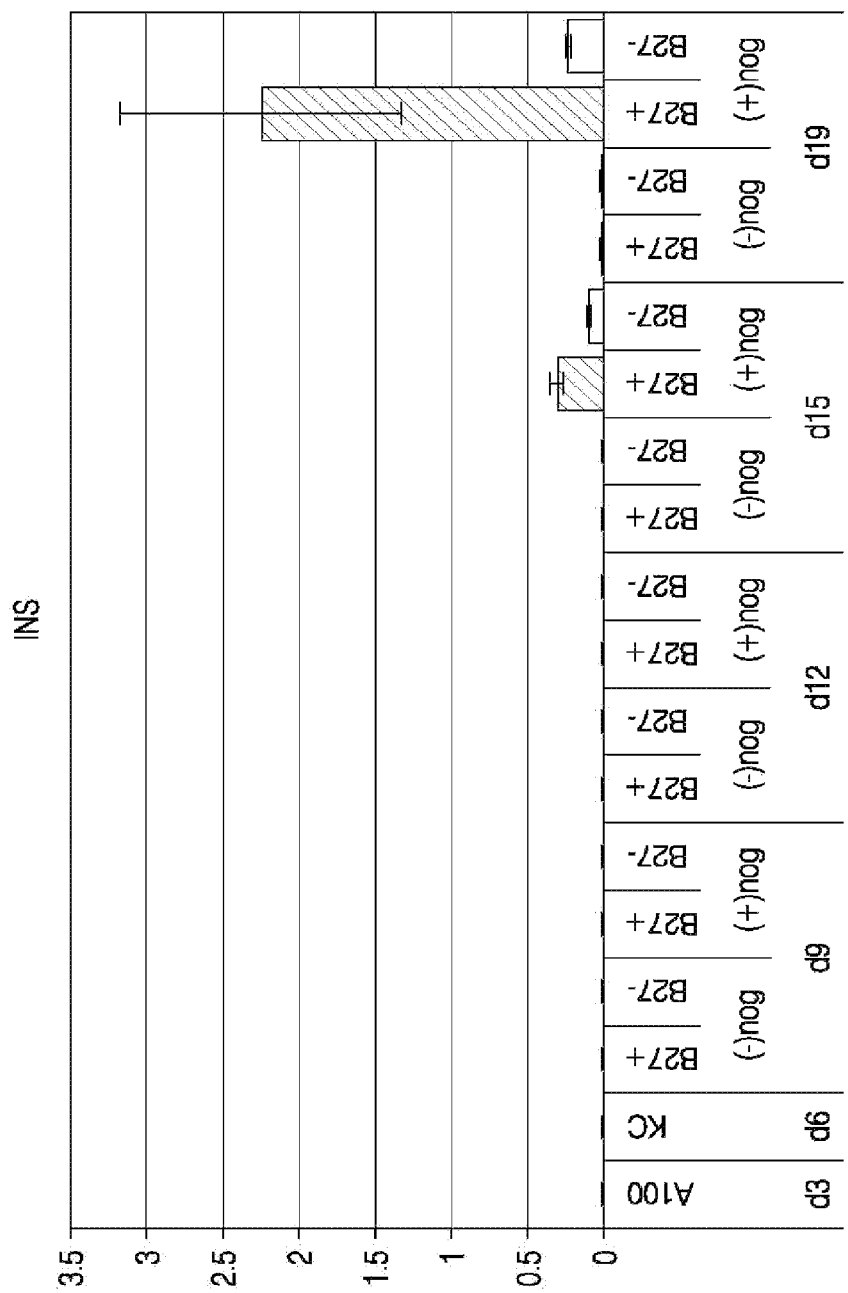
Figure 29D:
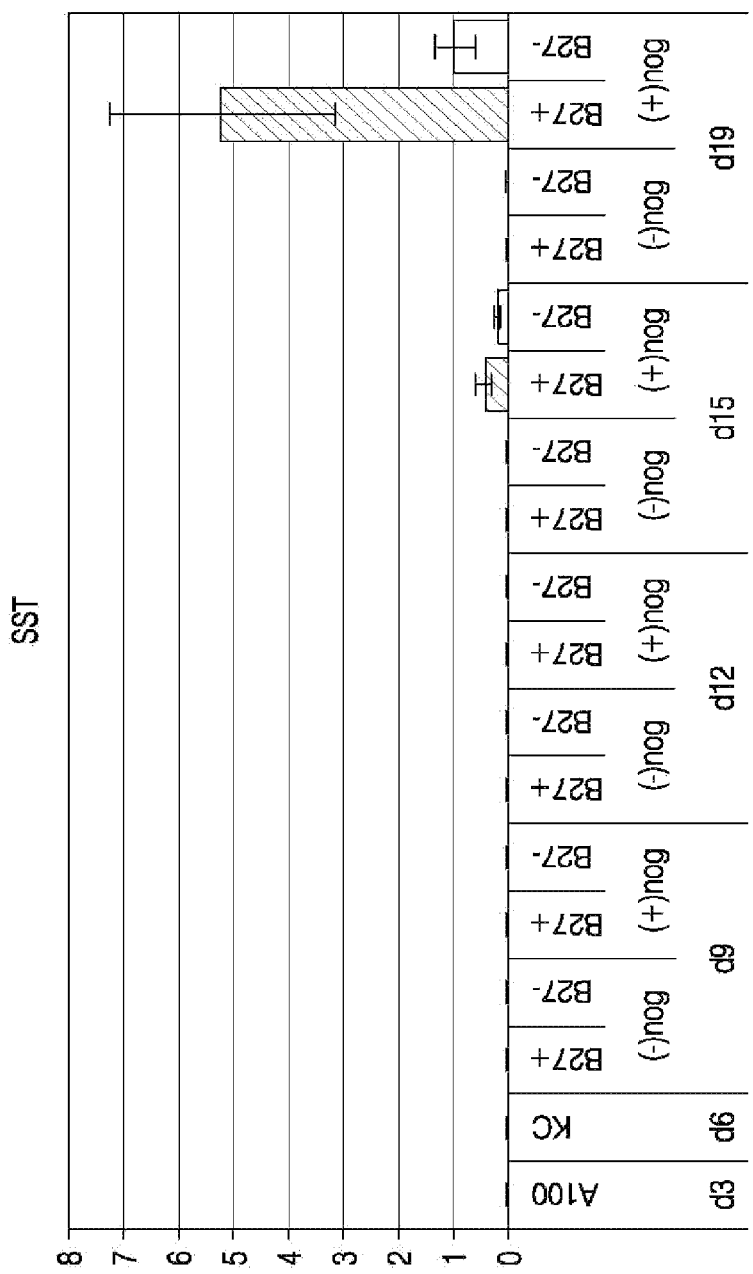
Figure 29E:
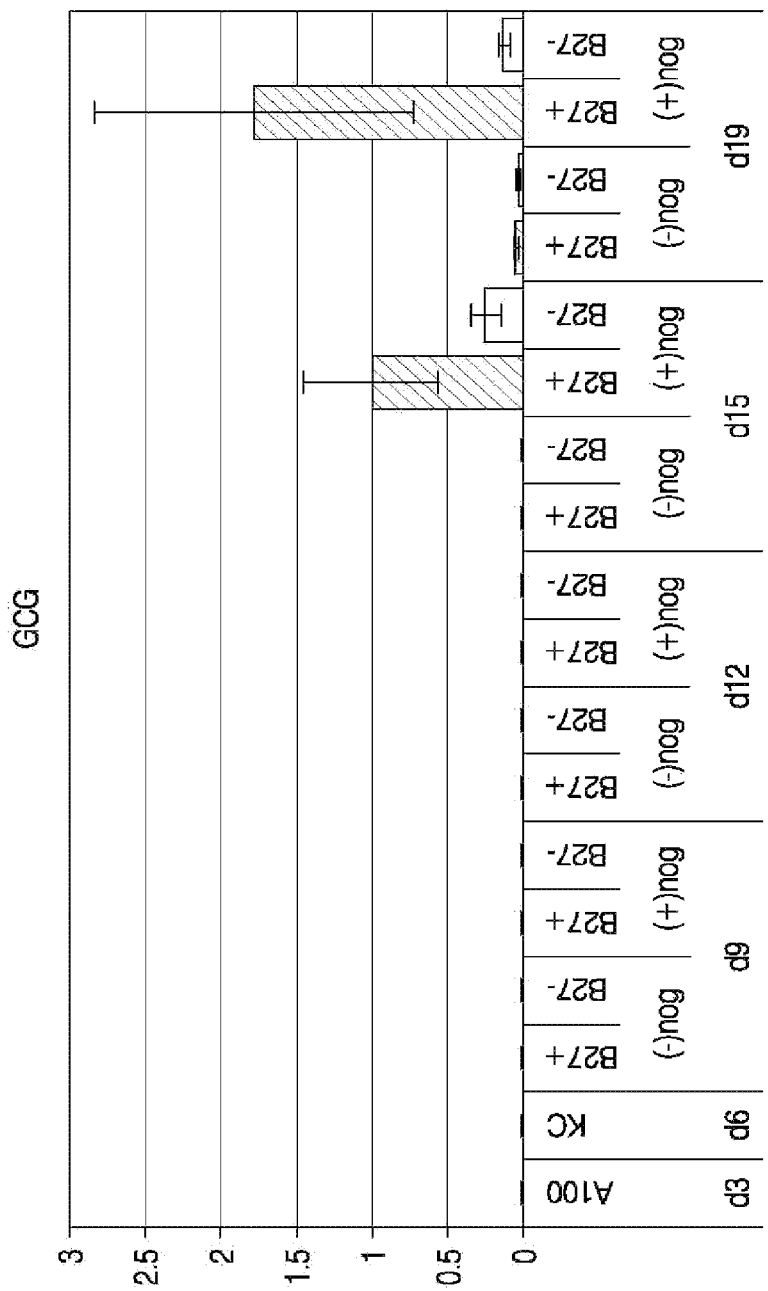
Figure 29F:
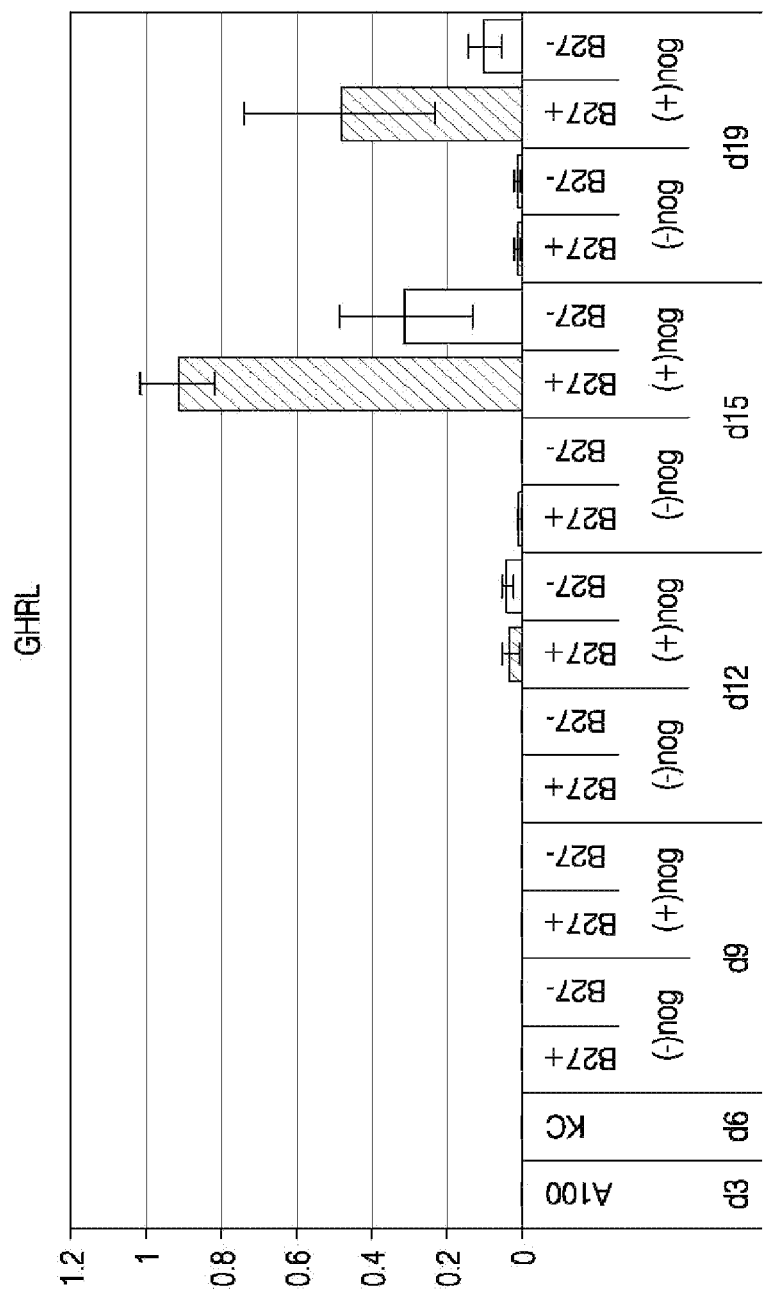

Induction of PDX1 gene expression was not dependent on either noggin treatment or the presence or absence of vitamin A in the B27 supplement (FIG. 29A). In contrast, the induction of pancreatic endocrine differentiation, as evidenced by NGN3 expression induced at day 12, was highly dependent on the presence of noggin (FIG. 29B). Subsequent to the induction of NGN3 expression, the expression of pancreatic hormones INS, GCG, SST, and GHRL was also dependent on the presence of noggin (FIGS. 29C-29F). The ability for noggin to maintain NGN3 expression beyond day 12 was enhanced by the presence of vitamin A in the B27 supplement. In addition, the magnitude of pancreatic hormone expression was also enhanced by the presence of vitamin A in the B27 supplement, however, in the complete absence of exogenous retinoid application noggin treatment was still sufficient to induce differentiation to insulin-expressing cells.

Example 19

Method of Obtaining Insulin-Expressing Cells Using Combination of Noggin and Retinoic Acid This example demonstrates that noggin and retinoic acid can be used in conjunction for differentiating hESCs to insulin-expressing cells and that the addition of noggin to retinoic acid potentiates the action of the retinoic acid, particularly when retinoic acid is used at lower concentrations.

Human ESCs were differentiated to definitive endoderm via treatment with activin A (100 ng/ml) and Wnt3a (25 ng/ml) in RPMI+0% FBS for the first day and then for 2 more days with activin A (100 ng/ml) alone in RPMI+0.2% v/v FBS. Definitive endoderm was differentiated to foregut endoderm by treatment with KGF (50 ng/ml) and KAAD-cyclopamine (0.25 µM) for 3 days in RPMI+2% v/v FBS. Differentiation then proceeded for 3 days in DMEM+1% v/v B27 supplement containing KAAD-cyclopamine (0.25 µM) and all-trans retinoic acid (0.1 µM or 2 µM) with or without the addition of noggin (0, 30 or 100 ng/ml). This was followed by a 2 day treatment period with the gamma-secretase inhibitor DAPT (1 µM) provided in DMEM+1% v/v B27 and subsequently the cells were cultured in CMRL+1% v/v B27 with no additional growth factors.

Figure 30A:
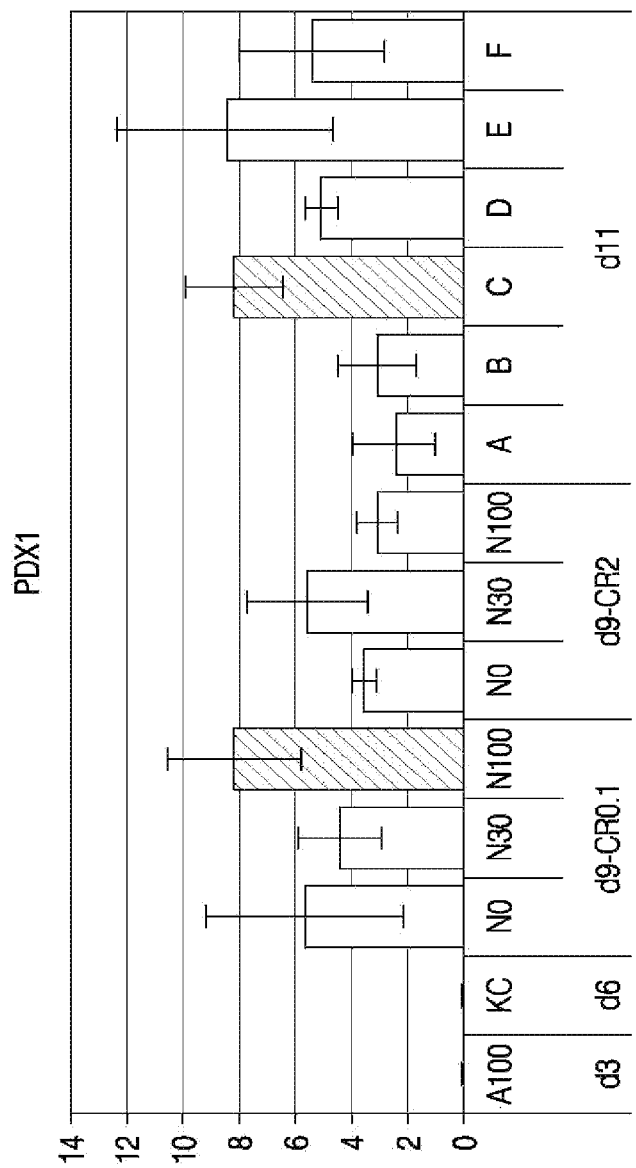
FIGS. 30A-30F are bar charts showing the mRNA levels of certain markers as detected by QPCR in hESC derived cells that have been treated to differentiate to hormone-expressing cells (day 11). Specifically shown are the mRNA levels of PDX1 (FIG. 30A), NGN3 (FIG. 30B), PTF1A (FIG. 30C), NKX6.1 (FIG. 30D), INS (FIG. 30E) and GCG (FIG. 30F). The abbreviations are indicated as follows: A100—100 ng/ml activin A; KC—50 ng/ml KGF and 0.25 µM KAAD cyclopamine; N—noggin; CR0.1—0.25 µM KAAD cyclopamine and 0.1 µM retinoic acid; CR 2—0.25 µM KAAD cyclopamine and 2 µM retinoic acid; "A"—0 ng/ml noggin and 0.1 µM retinoic acid; "B"—30 ng/ml noggin and 0.1 µM retinoic acid; "C"—100 ng/ml noggin and 0.1 µM retinoic acid; "D"—0 ng/ml noggin and 2 µM retinoic acid; "E"—30 ng/ml noggin and 2 µM retinoic acid and "F" 100 ng/ml noggin and 2 µM retinoic acid.
Figure 30B:
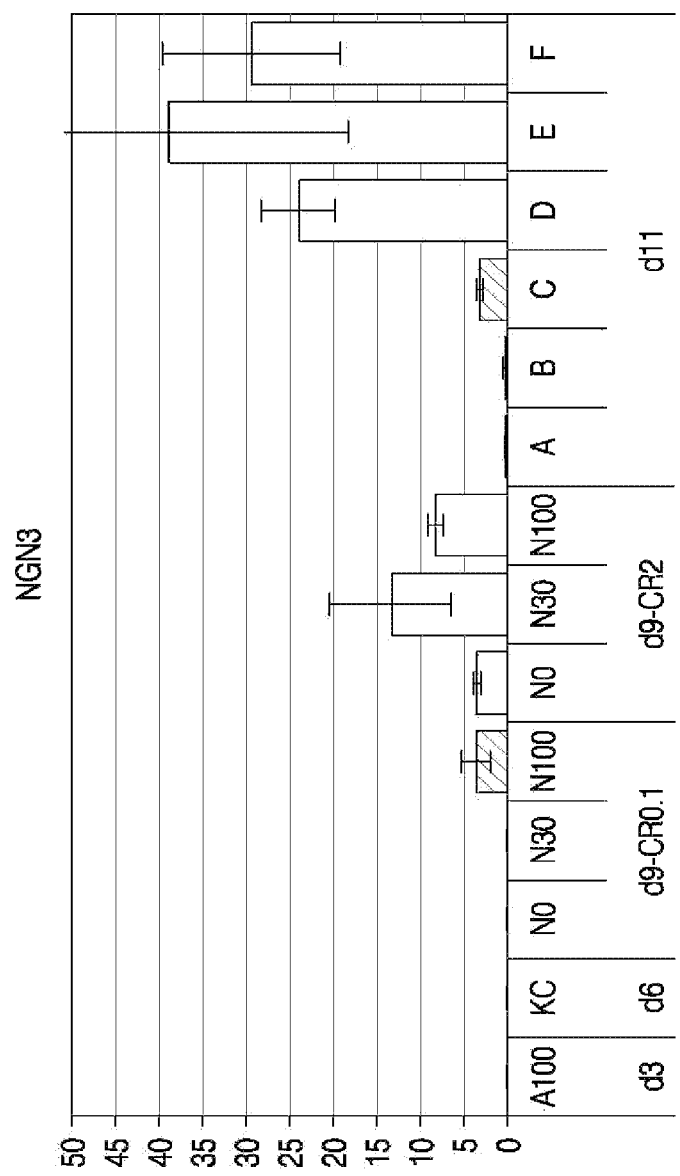
Figure 30C:
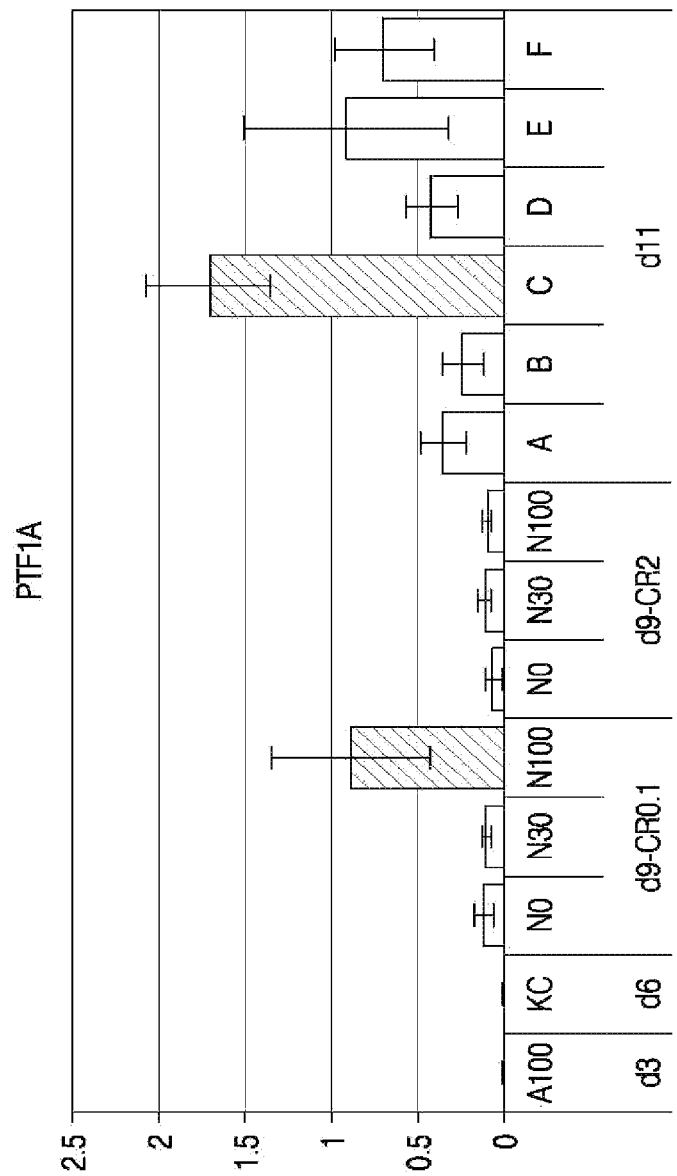
Figure 30D:
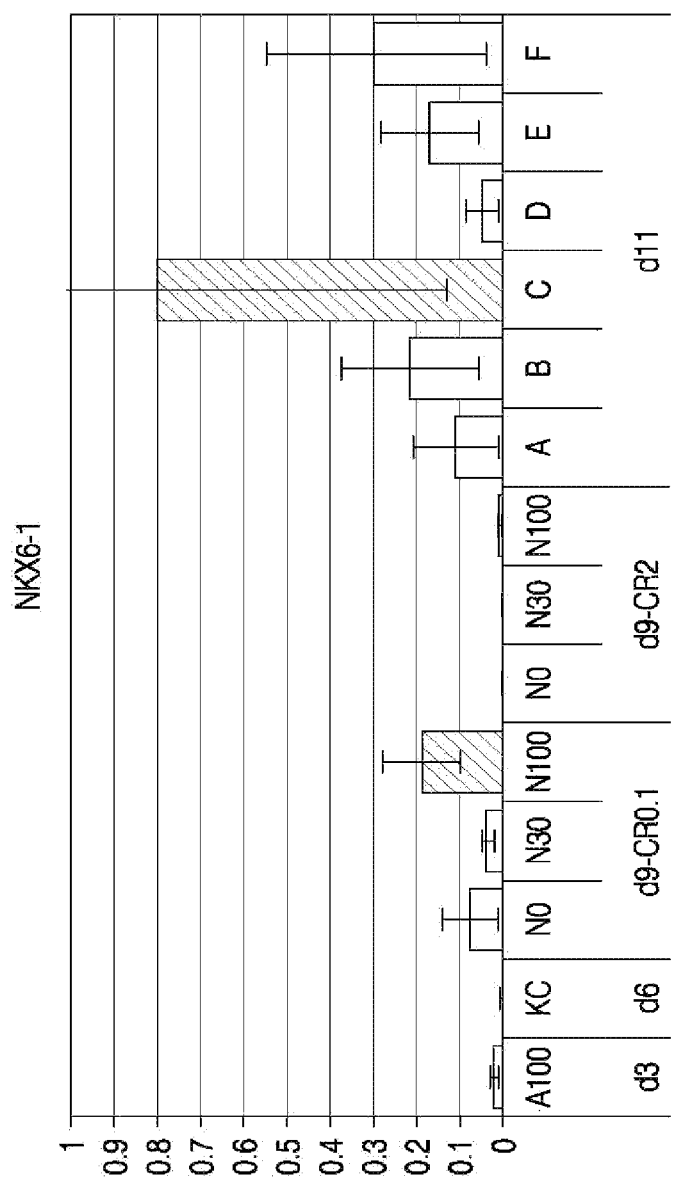
Figure 30E:
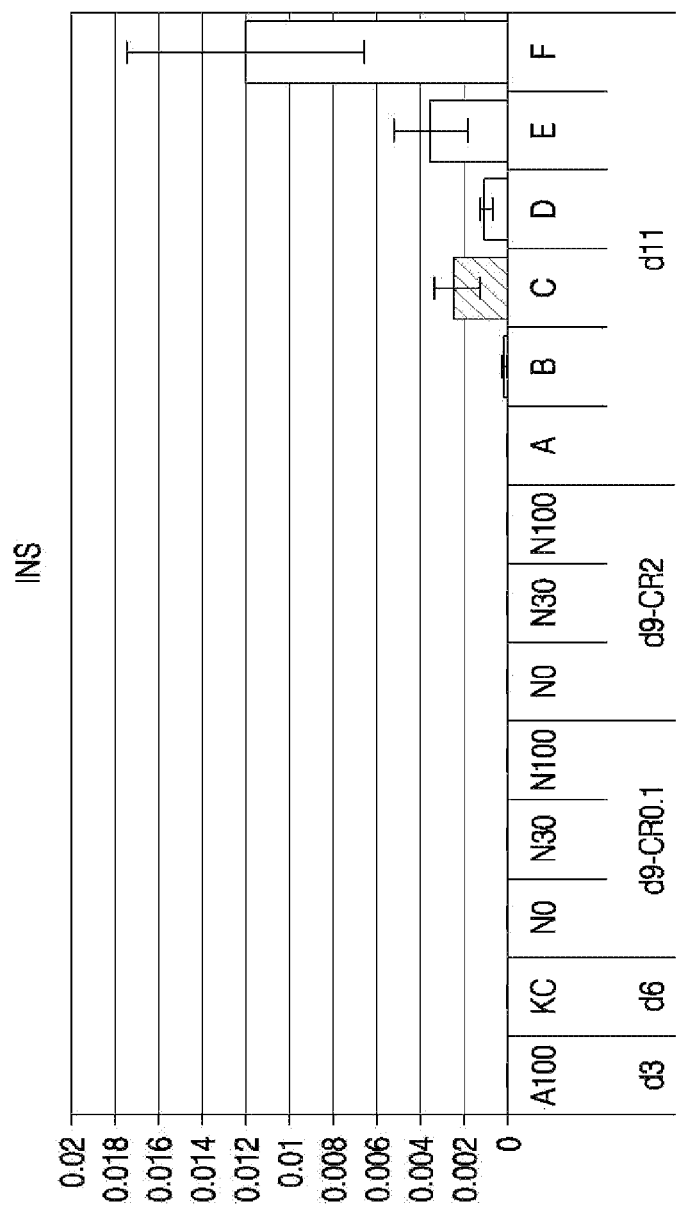
Figure 30F:
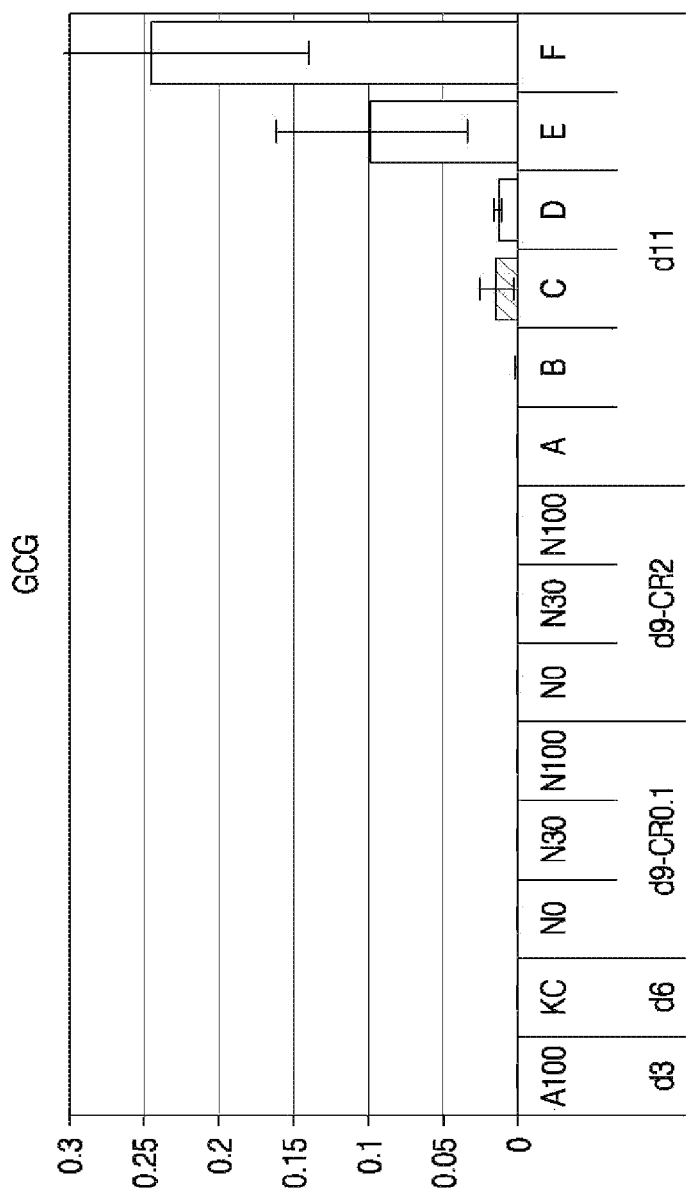

The concentration of retinoic acid and the addition of noggin had very little effect on the expression levels of PDX1 at days 9 or 11 (FIG. 30A). However, the addition of noggin to low dose RA (0.1 µM) dramatically enhanced the expression of the endocrine progenitor marker NGN3 at day 9 (FIG. 30B) as well as the initial appearance of INS and GCG gene expression at day 11 (FIGS. 30E and 30F). This result may be due to an enhancement of differentiation to pancreatic epithelium as indicated by the enhanced expression of PTF1A (FIG. 30C) and NKX6-1 (FIG. 30D), particularly in condition "C" using lower RA concentration (0.1 µM) and high noggin concentration (100 ng/ml). These results demonstrated that the combination of noggin and retinoid signaling acts synergistically to specify pancreatic epithelium and ultimately pancreatic endocrine differentiation from foregut endoderm derived from hESCs.

Example 20

In Vivo Maturation of Pancreatic Epithelium

In order to further study the potential of hESC-derived material to further differentiate into functional insulin-producing cells, we transplanted in vitro differentiated cells into immunocompromised mice (SCID/Bg). To achieve this, confluent cells at various stages of the differentiation process were mechanically scored using a modified McIlwain tissue chopper (see Joannides et al., (2006). *Stem Cells* 24:230-235, the disclosure of which is incorporated herein by reference in its entirety) and subsequently transferred to nonadherent plates for culture. The resultant aggregates were pipetted onto gelatin sponge scaffolds (Gelfoam; Pharmacia) and overlaid with Matrigel (BD). Each 8 mm diameter×2 mm scaffold was loaded with 25-40 µl of aggregates. Two of these tissue constructs were subsequently transplanted into the epididymal fat pad of each mouse.

Grafted material was allowed to differentiate and mature in vivo. Every two weeks, functionality of the insulin-producing cells in these grafts was tested by injecting animals with arginine to induce insulin secretion. Blood was collected 4 minutes after arginine injection and tested for human C-peptide. Human C-peptide was detected in animal serum as early as 5 weeks after transplantation and increased over time. Ten to sixteen weeks post-transplant, two animals contained grafts that were responsive to glucose. These data suggest that the number of functional insulin-producing cells in the grafts is increasing over time probably through a combination of progenitor proliferation and maturation.

Histological examination of grafts harvested at different time points revealed the presence of expanding and maturing pancreatic epithelium. Grafts harvested at later time points had larger amounts of this epithelium. Pancreatic epithelium was identified by morphology and expression of typical developmental markers such as Pdx1 and Nkx6.1. Examination of hormone markers revealed that islet-like cell clusters budded off of the pancreatic epithelium in a manner analogous to normal pancreatic development. These clusters contained singly-positive hormonal cells including insulin-cells that are also Nkx6.1-positive and Pdx1-positive. The cell cluster architecture resembled that of normal fetal islets.

Example 21

Transplanted hESC-Derived Grafts Develop into Hormone-Expressing Pancreatic Islets Engrafted cells from pancreatic-like epithelium give rise to endocrine cells expressing markers characteristic of functioning pancreatic hormone-secreting cells. Histological examination of grafts harvested from animals receiving transplants were performed substantially as described in Example 20.

Briefly, the grafts were dissected from the animals and washed with PBS$^{+/+}$ (containing Mg$^{++}$ and Ca$^{++}$, Invitrogen) twice, and then transferred to freshly prepared 4% paraformaldehyde/PBS and fixed for about 2-3 hours with mild agitation at 4° C. The grafts were again washed in PBS(−) for another 2-3 hours with mild agitation at 4° C., and the PBS(−) was changed after 1 hour. The grafts were then equilibrated in 30% sucrose/PBS(−) overnight at 4° C. with mild agitation and mounted into OCT compound (VWR, cat. #25608-930) and frozen with dry ice/iso-pentane. The graft tissues were cut into various thickness, e.g., 10 µl, using a cryostat, and sections were dried overnight at room temperature, and stored in the freezer. To determine hormone-secreting cell types, immunohistochemistry was performed by allowing the frozen sections to thaw at room temperature, and once thawed the sections were washed with PBS 2 times for 10 minutes each, or what ever time is appropriate to remove the OCT compound from the tissue sections. The tissue sections were permeabilized with PBS+0.2% Tween20 for about 15 minutes. The sections were first incubated with a blocking solution containing 5% normal donkey serum/PBS+0.1% Triton-X. The incubation was done in a humidified chamber for about 1 hour at room temperature. The blocking solution was then carefully aspirated off and the sections were incubated again in a humidified chamber overnight at 4° C. with the primary antibodies, which were diluted in 1% BSA/PBS+0.1% Triton-X. After incubation with the primary antibodies the sections were then washed with PBS+0.2% Tween-20 three times for about 10 minutes each. The sections were again incubated in a humidified chamber at room temperature with the appropriate secondary antibodies as recommended by the supplier (Invitrogen, Carlsbad, Calif.), diluted in 1% BSA/PBS+0.1% Triton-X. After about one hour, the sections were washed with PBS+0.2% Tween-20 twice for about 10 minutes each, and then rinsed with PBS once for about 10 minutes before they were mounted on the Vectashield and stained with 4',6-diamidino-2-phenylindole (Dapi). Additional antibodies to other markers typical of pancreatic hormone secreting cells were analyzed including transcription factors Nkx2.2, Nkx6.1 and Pdx1. See Table 4 below.

TABLE 4

Antibodies to pancreatic hormones and transcription factors for identification of mature in vivo cells

| Antibody | Host | Dilution | Provider |
|---|---|---|---|
| Insulin | Guinea Pig | 500 | Dako: A0564 |
| Nkx2.2 | Mouse | 20 | Developmental Studies Hybridoma Bank: 74.5A5 |
| Nkx6.1 | Rabbit | 1200 | Gift from Dr. Ole Madsen |
| Glucagon | Rabbit | 200 | Invitrogen(Zymed): 18-0064 |
| Glucagon | Mouse | 500 | Sigma: G2654 |
| Somatostatin | Goat | 200 | Santa Cruz: sc-7819 |
| Pdx1 | Goat | 2000 | Gift from Dr. Chris Wright |

Figure 31A:
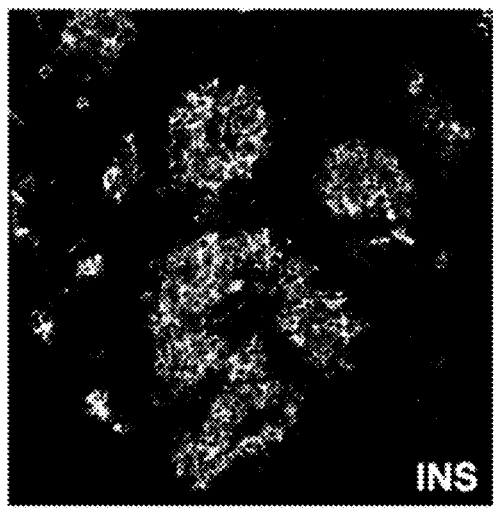
FIGS. 31A-31D are photomicrographs showing monochromatic immunoreactivity of mature pancreatic islet hormone-expressing cells for insulin, INS (FIG. 31A), glucagon, GCG (FIG. 31B), somatostatin, SST (FIG. 31C), and DAPI (FIG. 31D).
Figure 31B:
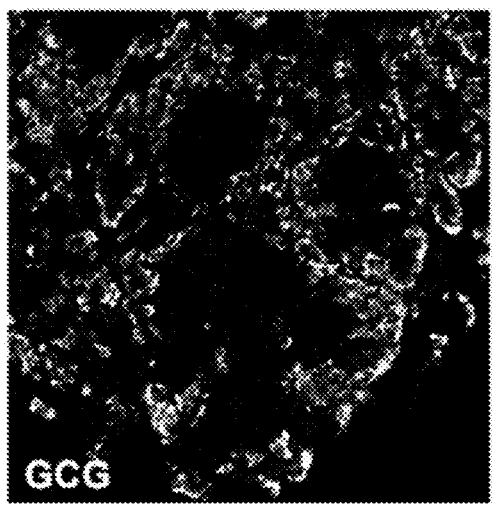
Figure 31C:
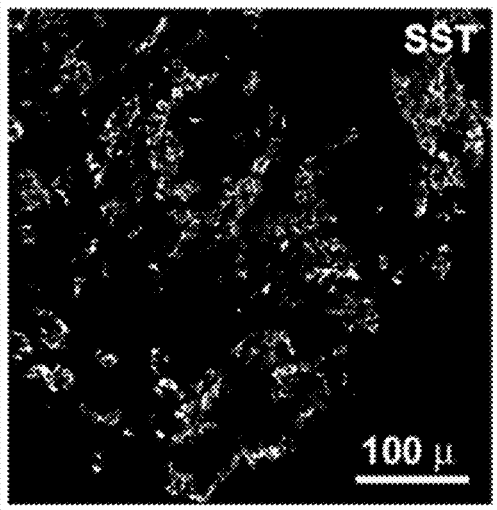
Figure 31D:
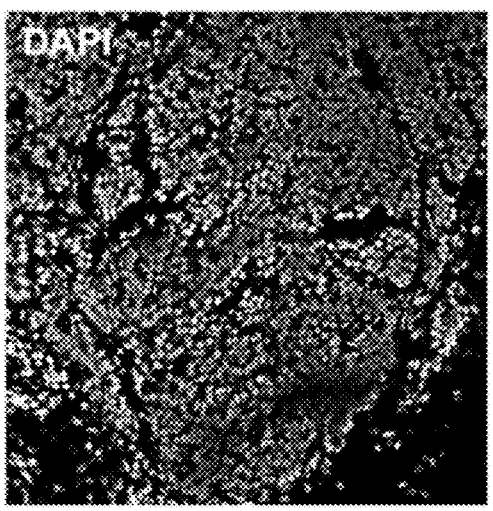

Examination of at least insulin, glucagon and somatostatin hormone markers indicate that the mature in vivo grafted cells were pancreatic hormone-expressing cells which budded off of the pancreatic epithelium to form islet cell clusters (FIGS. 31A-31D). As shown in FIGS. 31A-31D (Animal No. 205), the maturation of the grafted cells is in a manner analogous to normal pancreatic development of normal fetal islets. For example, the insulin-secreting cells form the central core of the islet (INS; FIG. 31A), and are surrounded by somatostatin-secreting cells (SST; FIG. 31C) and glucagon-secreting cells (GCG; FIG. 31B). Further, as shown in FIGS. 31A-31D, the islet cell clusters express one hormone per cell type. It has also been shown that at least the insulin-secreting cells were Nkx6.1 and Pdx1—positive. Table 5 shows the total number of insulin positive cells which co-localized with each or a combination of the transcription factors (markers) typical of pancreatic epithelium including PDX1, NKX6-1 and NKX2-2. These studies demonstrate that the grafted cells mature into pancreatic islet clusters in vivo, and express markers typical of hormone secreting cells.

TABLE 5

Grafted transplants contain insulin-expressing cells and have typical pancreatic epithelial markers

| | CELL COUNTS | | |
|---|---|---|---|
| | Total Insulin | Double Positive | Percent Double positive |
| PDX1 | 141 | 137 | 97 |
| NKX6-1 | 141 | 134 | 95 |
| NKX2-2 | 114 | 106 | 93 |

Example 22

Glucose Responsive Endocrine Cells in In Vivo Transplants

In order to further examine the potential of hESC-derived material to form functioning insulin-producing cells, in vitro differentiated human cells were transplanted at various stages into immunocompromised mice (SCID/Bg) and later assayed for human C-peptide release after the glucose administration in the grafted animals.

The culture, passaging and differentiation of hESCs were performed substantially as described in d'Amour et al 2005 and 2006, which are herein incorporated in their entirety. Briefly, undifferentiated cells were maintained on mouse embryo fibroblasts feeder layers (Specialty Media) in DMEM/F12 (Mediatech) supplemented with 20% Knock-Out serum replacement (KOSR, GIBCO BRL), 1 mM nonessential amino acids (GIBCO BRL), Glutamax (GIBCO BRL), penicillin/streptomycin (GIBCO BRL), 0.55 mM of 2-mercaptoethanol (GIBCO BRL) and 4 ng/mL recombinant human FGF2 (R&D Systems) and alternatively supplemented in 10-20 ng/mL of Activin A (R&D Systems). hESC cultures were manually passaged at about 1:4 to 1:8, 1:9, or 1:10 split ratio every 5 to 7 days. Before the cells were differentiated, they were given a brief wash in PBS$^{+/+}$ (containing Mg$^{++}$ and Ca$^{++}$, Invitrogen).

Figure 32A:
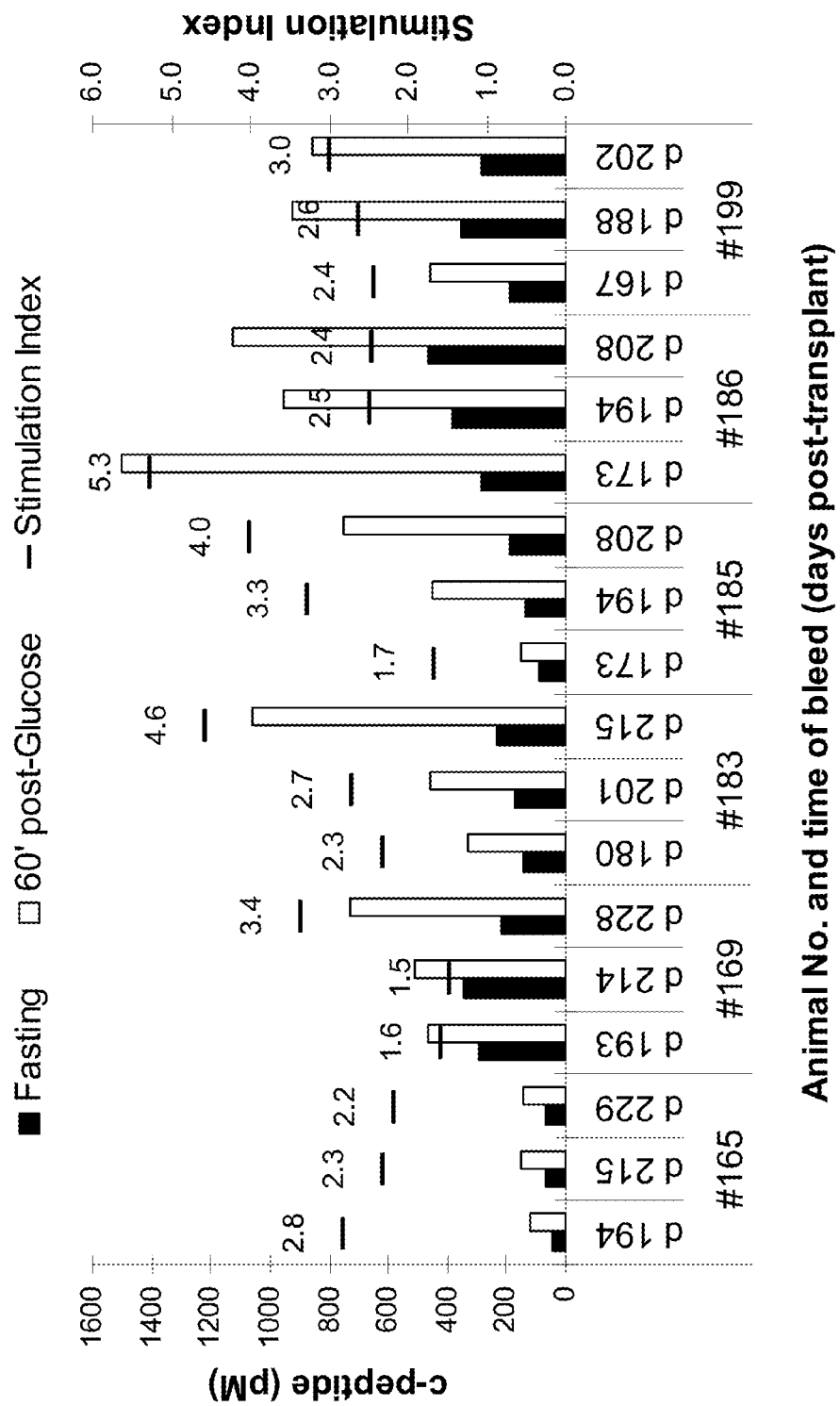
FIGS. 32A-32D are bar charts showing glucose responsiveness of human C-peptide release kinetics of transplanted hESC-derived pancreatic cells. Specifically shown are the levels of human C-peptide (y axis) after glucose administration. The x-axis indicates the Animal No. and the day of the bleed. The days are based on the number of days post-transplant. The Animal No. and differentiation protocol are also described in Examples 22 and Tables 6 and 7.
Figure 32B:
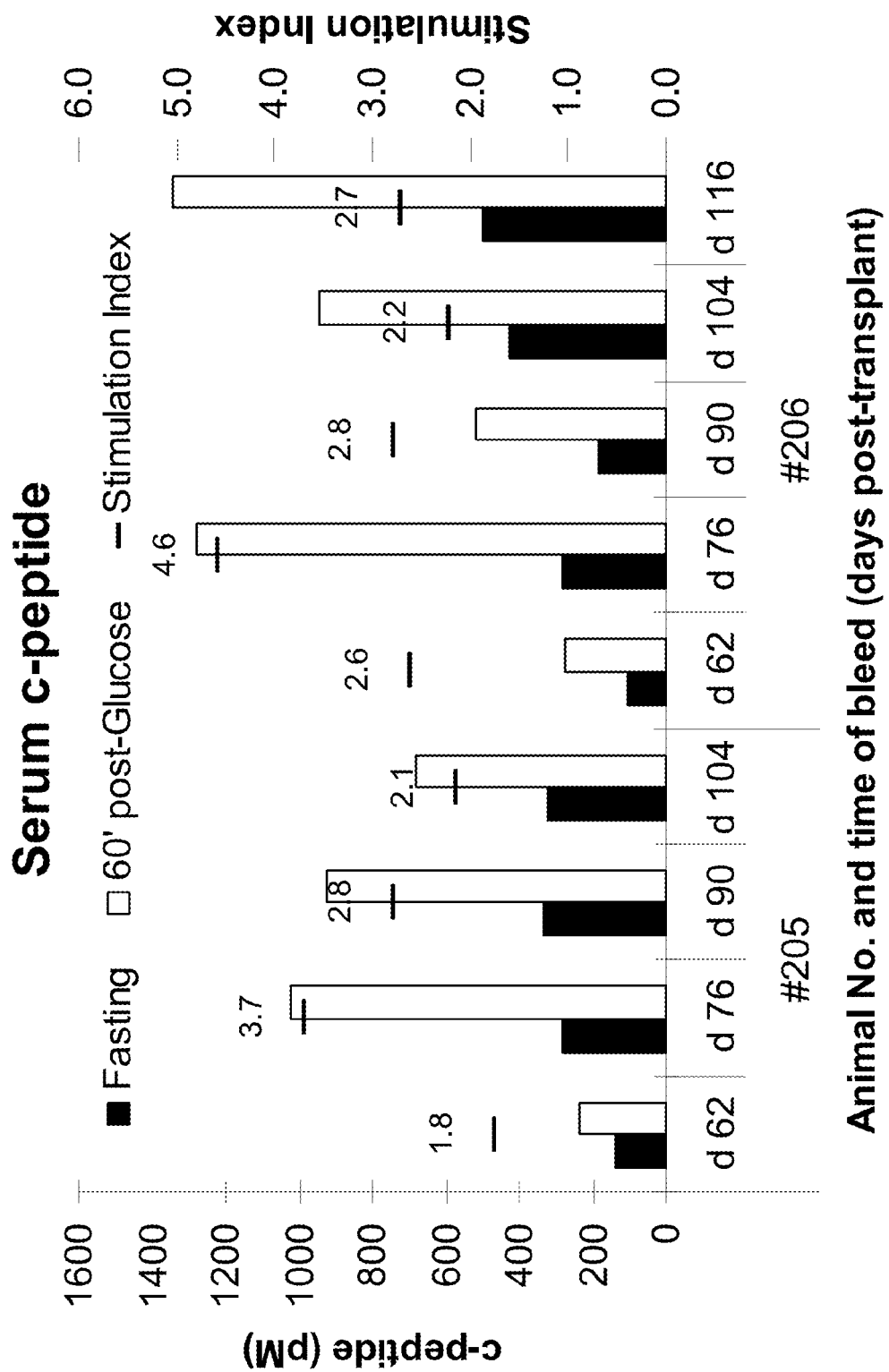

The differentiation culture conditions were substantially similar to that described in d'Amour et al. 2006. d'Amour et al. 2006 describe a 5 step differentiation protocol: stage 1 (definitive endoderm; d 1-d 4), stage 2 (primitive gut tube or foregut endoderm; d 5 to d 8), stage 3 (posterior foregut or Pdx1 endoderm; d 9 to d 12), stage 4 (pancreatic endoderm, or pancreatic epithelium and endocrine precursor; d 13 to d 15) and stage 5 (hormone expressing endocrine cell, d 16 or more). As in d'Amour et al. 2006, the undifferentiated cells were cultured for one day (d 1) in RPMI containing 100 ng/ml Activin A (R&D Systems) and 25 ng/ml recombinant human WNT3a (R&D Systems), two days (d 2 and d 3) in RPMI medium containing 0.2% fetal bovine serum (FBS, Specialty Media) and 100 ng/ml Activin A. The embodiments described herein were slightly modified beginning at day 3 (d 3). The cells from day 3 (definitive endoderm) were cultured for three days (d 4 to d 6; foregut endoderm) in RPMI medium containing 2% FBS, 50 ng/ml recombinant human KGF/FGF7 (R&D Systems), and 0.25 µM KAAD-cyclopamine (Toronto Research Chemicals). Activin is removed from cells at this stage. The cells were then cultured for another three days (d 7 to d 9) in DMEM (Hyclone) medium containing 1% B27 supplement (Invitrogen), 0.25 µM KAAD-cyclopamine, 2 µM all-trans retinoic acid (Sigma), and 50 ng/ml recombinant human Noggin (R&D Systems), three days (Pdx1 endoderm; d 10 to d 12) in DMEM medium containing 1% B27 supplement, and then cultured in CMRL medium (Invitrogen) containing 1% B27 supplement for up to 11 days (hormone expressing endocrine cells; d 13 to d 23). This method of culturing the cells in vitro was used for transplants in Animal Nos. 165, 169, 205 and 206; FIGS. 32A-32B, and Tables 6 and 7, (■). Other embodiments of the invention are substantially similar to these culture conditions; however, where they are different they are described accordingly, below.

Figure 32C:
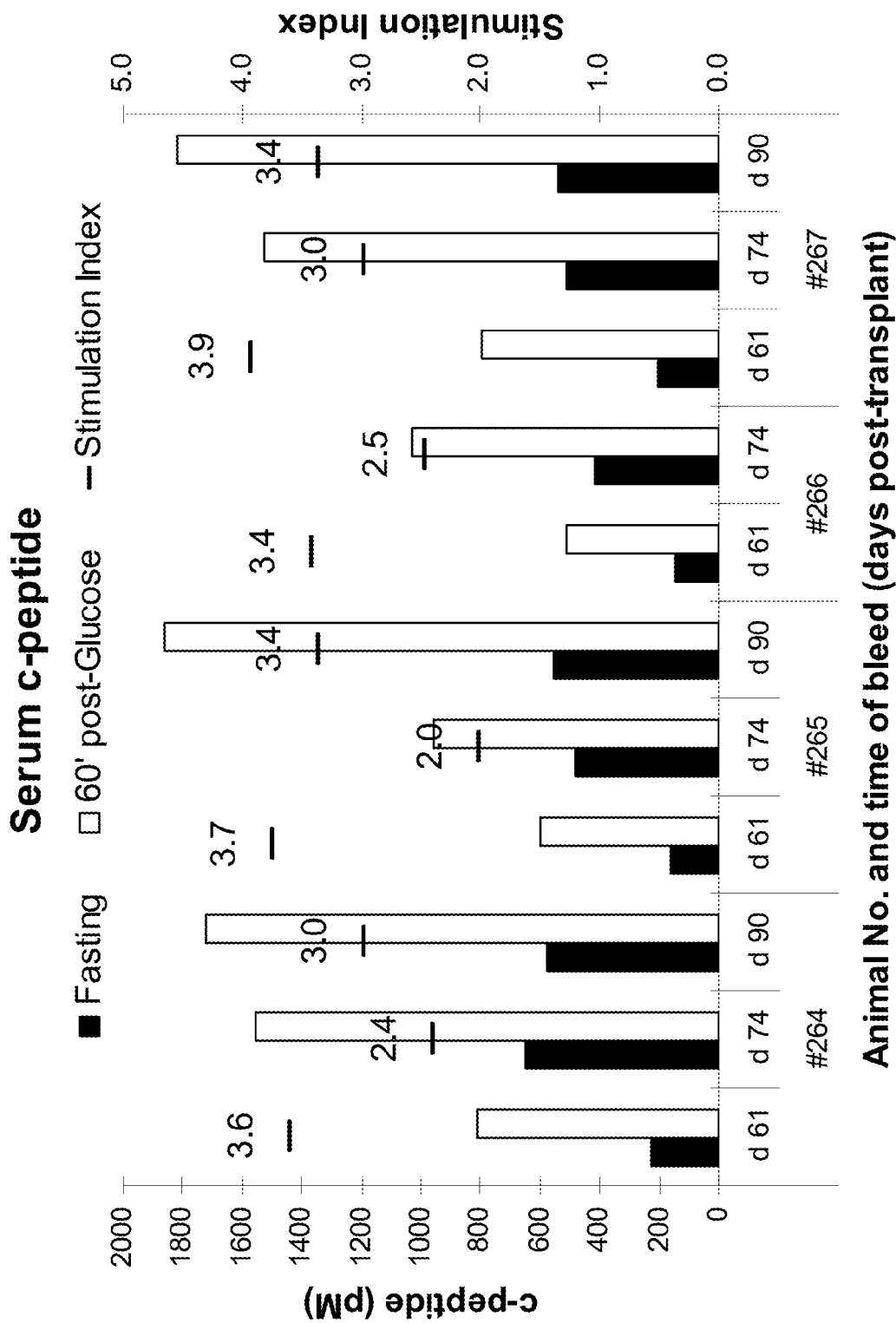

In another embodiment of the invention the culture conditions varied from that described above from day 4 through day 6, where 25 ng/mL of KGF/FGF7 was used instead of 50 ng/ml and no KAAD-cyclopamine. This method of culturing the cells in vitro was used for the transplants in Animal Nos. 264, 265, 266 and 267; FIG. 32C, and Tables 6 and 7, (○).

Still in another embodiment, the culture conditions were substantially identical to that described above for the first 6 days (d 1 to d 6), but were then followed by culturing the cells for six days (d 7 to d 12) in DMEM medium containing 1% B27 supplement, 50 ng/ml of KGF/FGF7, 0.25 µM KAAD-cyclopamine, and 200 ng/ml of Noggin, and then three days (d 13 to d 15) in DMEM medium containing 1% B27 supplement, 2 µM all-trans retinoic acid, 0.25 µM KAAD-cyclopamine, 200 ng/ml Noggin, followed by culturing the cells up to eight days (d 16 to d 23) in CMRL medium containing 1% B27 supplement. This method of culturing the cells in vitro was used for the transplants in Animal Nos. 183 and 185; FIG. 32A, and Tables 6 and 7, (◇).

In another embodiment of the invention, the culture conditions were substantially identical to that described above for the first 6 days (d 1 to d 6), but the cells were cultured for five days (d 7 to d 11) instead of 6 days in DMEM medium containing 1% B27 supplement, 50 ng/ml of KGF/FGF7, 0.25 µM KAAD-cyclopamine, and 100 ng/ml of Noggin (instead of 200 ng/ml as described above), and then three days (d 12 to d 14) in DMEM medium containing 1% B27 supplement, 2 µM all-trans retinoic acid, 0.25 µM KAAD-cyclopamine, 100 ng/ml Noggin (instead of 200 ng/ml as described above), and followed by culturing the cells up to nine days (d 15 to d 23) in CMRL medium containing 1% B27 supplement. This method of culturing the cells in vitro was used for the transplants in Animal Nos. 186 and 199; FIG. 32A, and Tables 6 and 7, (▲).

Figure 32D:
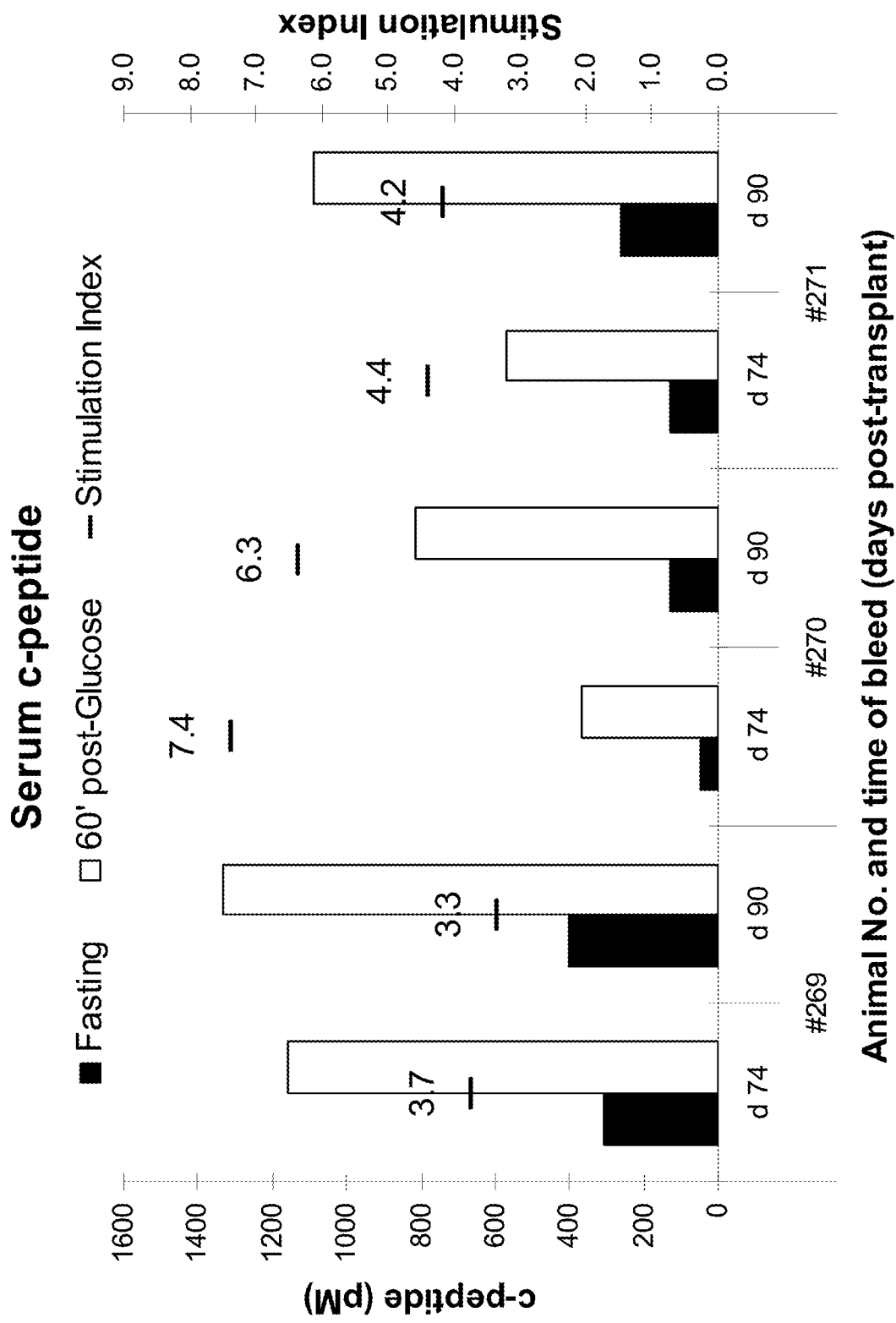

In yet another embodiment of the invention, the culture conditions were substantially similar to that described above for day 1 to day 3 (d 1 to d 3), then the cells were cultured for three days (d 4 to d 6) in RPMI medium containing 2% FBS and 25 ng/ml recombinant human KGF/FGF7 (R&D Systems), minus KAAD-cyclopamine, followed by nine days (d 7 to d 15) in DMEM medium containing 1% B27 supplement and 100 ng/ml of Noggin, and up to eight days (d 16 to d 23) in CMRL medium containing 1% B27 supplement. This method of culturing the cells in vitro was used for the transplants in Animal Nos. 269, 270, and 271; FIG. 32D, and Tables 6 and 7, (●).

Alternatively, at stage 2, whereby activin is removed or not included in the culture media, an agent which inhibits members of the TGF-beta receptor family can also be used. For example, SB-431542 is a specific inhibitor of the activin receptor-like (ALK) receptor and when added to the cell cultures at about 2.5, 5 and 10 µM amounts potentiated cell differentiation.

Confluent cells from cultures from the embodiments as described herein were mechanically scored at various stages of the differentiation process using the modified McIlwain tissue chopper. See Table 6, "Day of making transplant cell clusters". These cells at day 14 contained substantially no insulin secreting cells as demonstrated by real time quantitative PCR using insulin primers as described in d'Amour et al., 2006, Supplementary Table 1 (Forward primer: 5'-AAGAGGCCATCAAGCAGATCA (SEQ ID NO: 1); Reverse primer: 5'-CAGGAGGCGCATCCACA (SEQ ID NO: 2)). Cells were transferred to nonadherent plates for continued culturing until they were transplanted into the animals as indicated (Table 6). The resultant clusters, each about 100 to 400 microns in size were allowed to gravity settle and about 20 to 50 µl total of the gravity-settled volume was pipetted onto gelatin sponge scaffolds and overlaid with Matrigel substantially as described in Example 20. The clusters were surgically transplanted into either one or both epididymal fat pads of a mouse. Almost all the animals were implanted with two clusters, except Animal Nos. 205 and 206, which received just one. The following table summarizes the transplantation parameters:

TABLE 6

Transplantation of differentiated in vitro cell clusters

| Animal No. | hESC Line | Differentiation Protocol | Day of making transplant cell clusters* | Day of Transplant* |
|---|---|---|---|---|
| 165 | Cyt203 | (■) | 14 | 19 |
| 169 | Cyt203 | (■) | 12 | 14 |
| 183 | Cyt203 | (◇) | 15 | 22 |
| 185 | Cyt203 | (◇) | 6 | 21 |
| 186 | Cyt203 | (▲) | 6 | 16 |
| 199 | Cyt203 | (▲) | 7 | 14 |
| 205 | Cyt49 | (■) | 11 | 19 |
| 206 | Cyt49 | (■) | 11 | 19 |
| 264 | Cyt49 | (○) | 6 | 14 |
| 265 | Cyt49 | (○) | 6 | 14 |
| 266 | Cyt49 | (○) | 6 | 14 |
| 267 | Cyt49 | (○) | 6 | 14 |
| 269 | Cyt49 | (( )) | 6 | 14 |
| 270 | Cyt49 | (( )) | 6 | 14 |
| 271 | Cyt49 | (( )) | 6 | 14 |

*based on total number of days in the differentiation protocol

Figure 33:
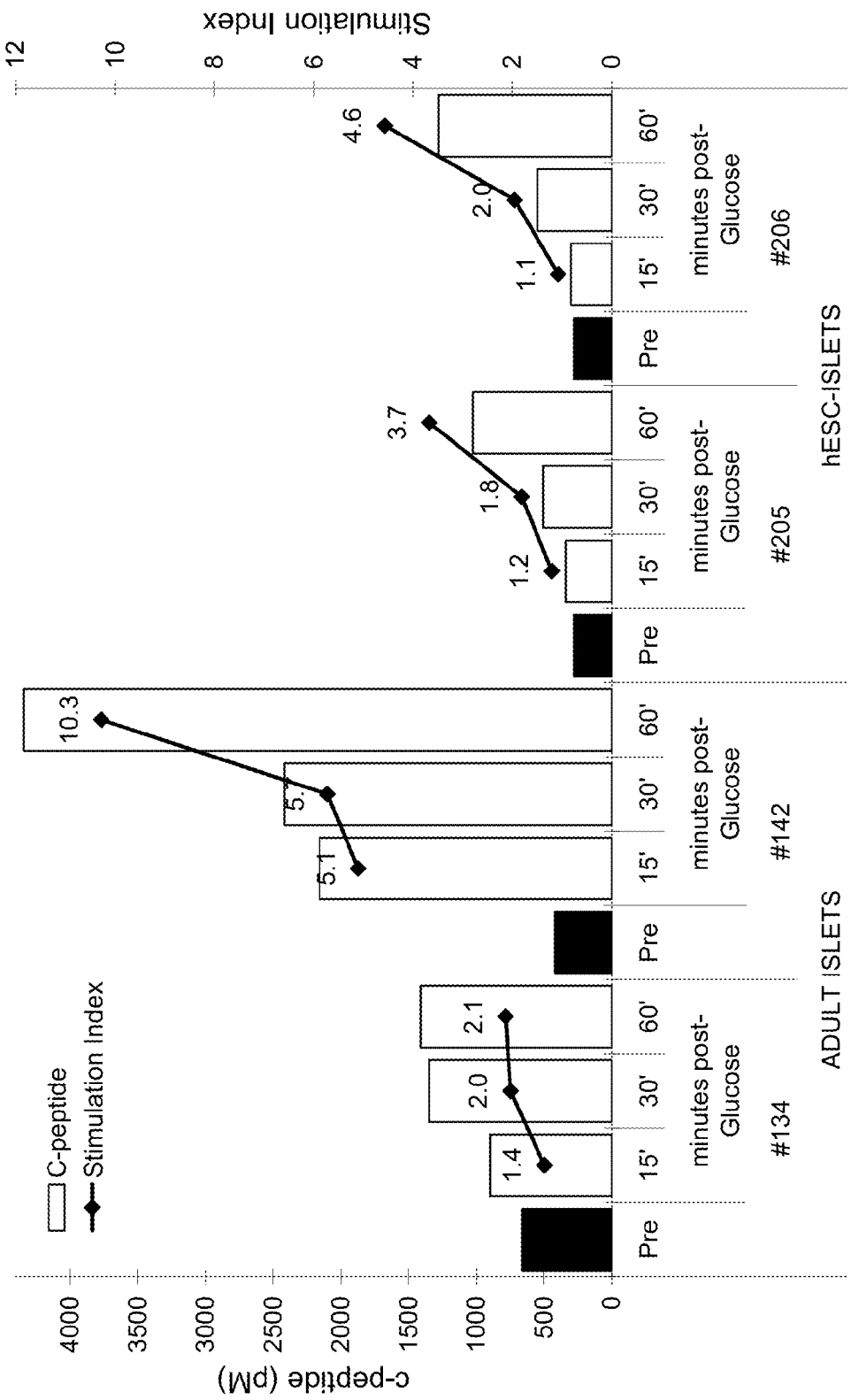
FIG. 33 is a bar chart showing glucose responsiveness of human C-peptide release kinetics of transplanted grafts derived from human islets (left panel) as compared to human ES-derived pancreatic cells (right panel).

After transplant, the grafted cells were allowed to differentiate and further mature in vivo. Glucose stimulated human C-peptide secretion of the grafted cells in serum was measured at various time points post transplant substantially similar to that described in Example 20, e.g. at least 30, 35, 40, 45, 50, 55, 60, 65 and more days. Additionally, to determine the optimum period(s) to measure and detect human C-peptide secretion in serum post-glucose administration, studies were performed using control human adult islets transplanted in an identical manner (FIG. 33, left panel). About 3000 human islets (or about 3-4 million cells) were transplanted into the epididymal fat pad of a mouse. Each human islet contained about 40-80% beta cells (or about 1.2-3.2 million beta cells). Glucose stimulated human C-peptide levels could be acutely measured in the serum as early as about 15 minutes post-glucose administration. In these animals, human C-peptide levels were highest at about 60 minutes post-glucose administration (FIG. 33, left panel). Hence, about 60 minutes post-glucose administration was the time period selected for measuring serum human C-peptide secretion in those animals receiving the hES-derived grafts.

Methods for determining glucose responsiveness in vivo in those animals with the grafted cells were performed substantially as described in Example 20. The animals were fasted for about 15-20 hrs, after which a blood sample ("pre-bleed") of about 50 µl was withdrawn from the tail. Each animal then received an intraperitoneal injection dose of about 3 g/kg of glucose in a 30% dextrose solution; and blood was withdrawn at about 15, 30 and 60 minutes time intervals post glucose infusion (FIGS. 32A-32D show the human C-peptide measurement at 60 minutes post-glucose administration). The serum was separated from the blood cells through centrifugation in micro-containers as described by the manufacturer (Becton Dickinson). The ELISA analysis was performed on about 5-25 µl of serum using ultrasensitive human specific C-peptide ELISA plates (Alpco). The detection of human C-peptide, and not endogenous mouse C-peptide, indicates that insulin secretion is derived from the grafted (exogenous) cells.

There were detectable levels of human C-peptide in the serum after about 30 minutes post-glucose administration (FIG. 33, right panel). Similar to the human islet transplants, animals with the transplanted hES-derived grafts had maximum glucose-stimulated serum human C-peptide levels at about 60 minutes post-glucose administration (FIG. 33). Increased serum C-peptide levels were observed at all graft implant dates (d 14, d 19, d 21 and d 22), as shown in Table 7. In general, those animals receiving cell cluster grafts from day 14 (d 14) responded earlier to glucose as compared to those grafts from day 19 (d 19) or more (Table 7). The following table summarizes the glucose stimulated c-peptide release in animals receiving grafted cells:

TABLE 7

Levels of glucose response in animals with differentiated in vitro hESC-derived transplants

| Animal No. | Day of Transplant* | Number of times glucose responsive | Range of graft age (days post-transplant) | Range of glucose stimulation index | Range of glucose-stimulated serum c-peptide (pM) | Figures |
|---|---|---|---|---|---|---|
| 165 | 19 | 3/3 | 194-229 | 2.3-2.8 | 122-152 | FIG. 32A |
| 169 | 14 | 3/3 | 193-228 | 1.5-3.4 | 462-731 | |
| 183 | 22 | 3/3 | 180-215 | 2.3-4.6 | 334-1056 | |
| 185 | 21 | 3/3 | 173-208 | 1.7-4.0 | 153-750 | |
| 186 | 16 | 3/3 | 173-208 | 2.4-5.3 | 954-1503 | |
| 199 | 14 | 3/3 | 167-202 | 2.4-3.0 | 455-921 | |
| 205 | 19 | 4/4 | 62-104 | 1.8-3.7 | 239-1026 | FIG. 32B |
| 206 | 19 | 4/4 | 62-104 | 2.6-4.6 | 274-1278 | |
| 264 | 14 | 3/3 | 61-90 | 2.4-3.6 | 776-1719 | FIG. 32C |
| 265 | 14 | 3/3 | 61-90 | 2.0-3.7 | 366-1862 | |
| 266 | 14 | 2/2 | 61-74 | 2.5-3.4 | 508-514 | |
| 267 | 14 | 3/3 | 61-90 | 2.6-3.9 | 763-1814 | |
| 269 | 14 | 2/2 | 74-90 | 3.3-3.7 | 1156-1335 | FIG. 32D |
| 270 | 14 | 2/2 | 74-90 | 6.3-7.4 | 364-814 | |
| 271 | 14 | 2/2 | 74-90 | 4.2-4.4 | 572-1087 | |

*based on total number of days in the differentiation protocol

The methods, compositions, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

As used in the claim below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

REFERENCES

Numerous literature and patent references have been cited in the present patent application. Each and every reference that is cited in this patent application is incorporated by reference herein in its entirety.

For some references, the complete citation is in the body of the text. For other references the citation in the body of the text is by author and year, the complete citation being as follows:

D'Amour, K., et al., Nature Biotechnology 23, 1534-1541, (2005).
Bocian-Sobkowska, J., et al. Histochem. Cell Biol. 112, 147-153, (1999).
Rahier J., et al., Cell Tissue Res. 200 (3), 359-366, (1979).
Malaisse-Langae F., et al., Diabetologia 17(6), 361-365, (1979).
Fiocca R., et al., Histochemistry, 77(4), 511-523, (1983).
Stefan Y., et al., Diabetologica, 23(2), 141-142, (1982).
Kelly, O. G. and Melton, D. A., Dev. Dyn. 218, 615-627, (2000).
Chen, Y., et al., Dev. Biol. 271(1), 144-160, (2004).
Field, H. A., et al., Dev. Biol. 263, 197-208 (2003).
Spooner, B. S., et al., J. Cell Biology, 47, 235-246, (1970).
Li, H., et al., Nature 23, 67-70, (1999).
Stafford, D. and Prince, Curr. Biol., 12, 1-20, (2002).
Moriya, N., et al., Develop. Growth Differ., 42, 175-185, (2000).
Chen, Y., et al. Dev. Biol. 271, 144-160, (2004).
Stafford, D., et al Development, 133(5), 949-956, (2006).
Martin, M., et al Dev. Biol. (2005).
Molotkov, A., Devel. Dyn. 232, 950-957 (2005).
Gao, R. et al., Diabeltologia, 48:2296-2304 (2005)
Ronn, L. et al. Eur J Neurosci., 16(9):1720-30 (2002)

What is claimed is:

1. A method for producing hormone secreting cells in vivo, said method comprising the steps of:
   a) producing human PDX-1 positive pancreatic hormone expressing cells in vitro; and
   b) transplanting the human PDX-1 positive pancreatic hormone expressing cells into a mammalian subject, wherein the PDX-1 positive pancreatic hormone expressing cells secrete a hormone in vivo.

2. A method for producing hormone secreting cells, said method comprising the steps of:
   a) obtaining a population of human pluripotent stem cells;
   b) differentiating the population of step (a) into human definitive endoderm cells;
   c) differentiating the population of human definitive endoderm cells into a population of human PDX-1 expressing pancreatic endoderm cells; and
   d) transplanting the population of human PDX-1 expressing pancreatic endoderm cells into a mammal, wherein the transplanted cells of step (c) are matured into hormone producing pancreatic endocrine cells.

3. The method of claim 1, wherein the hormone secreting cells secrete insulin.

4. The method of claim 1, wherein the hormone secreting cells express NKX6.1.

5. The method of claim 1, wherein the hormone secreting cells secrete glucagon.

6. The method of claim 1, wherein the mammalian subject is a human subject.

7. The method of claim 6, wherein the human subject has been identified as having a condition which limits the ability of the subject to produce sufficient levels of insulin in response to physiologically high blood glucose concentrations.

8. The method of claim 1, wherein the PDX-1 positive pancreatic cells are pancreatic endoderm cells, pancreatic progenitor cells, or endocrine precursor cells.

9. The method of claim 3, wherein insulin secretion is detected by measuring C-peptide levels.

10. The method of claim 9, wherein C-peptide levels increase over time.

11. The method of claim 3, wherein the insulin secreting cells are responsive to blood glucose.

12. The method of claim 3, wherein the number of insulin secreting cells increases over time.

13. The method of claim 3, wherein the insulin secreting cells form islet like cell clusters.

14. The method of claim 1, wherein the transplanted PDX-1 positive pancreatic cells form pancreatic epithelium.

15. The method of claim 14, wherein the pancreatic epithelium expresses NKX6.1.

16. The method of claim 14, wherein the pancreatic epithelium expands over time.

17. The method of claim 2, wherein the hormone secreting cells secrete insulin.

18. The method of claim 2, wherein the hormone secreting cells express NKX6.1.

19. The method of claim 2, wherein the hormone secreting cells secrete glucagon.

20. The method of claim 2, wherein the mammal is a human subject.

21. The method of claim 20, wherein the human subject has been identified as having a condition which limits the ability of the subject to produce sufficient levels of insulin in response to physiologically high blood glucose concentrations.

22. The method of claim 2, wherein the PDX-1 expressing pancreatic cells are pancreatic endoderm cells, pancreatic progenitor cells, or endocrine precursor cells.

23. The method of claim 11, wherein insulin secretion is detected by measuring C-peptide levels.

24. The method of claim 23, wherein C-peptide levels increase over time.

25. The method of claim 17, wherein the insulin secreting cells are responsive to blood glucose.

26. The method of claim 17, wherein the number of insulin secreting cells increases over time.

27. The method of claim 17, wherein the insulin secreting cells form islet like cell clusters.

28. The method of claim 2, wherein the transplanted PDX-1 expressing pancreatic cells form pancreatic epithelium.

29. The method of claim 28, wherein the pancreatic epithelium expresses NKX6.1.

30. The method of 28, wherein the pancreatic epithelium expands over time.

* * * * *